US012709620B2

(12) United States Patent
Gu et al.

(10) Patent No.: US 12,709,620 B2
(45) Date of Patent: Aug. 18, 2026

(54) COMPOUND FOR ADJUSTING ACTIVITY OF NMDA RECEPTOR, AND PHARMACEUTICAL COMPOSITION AND USE THEREOF

(71) Applicant: BEIJING GREATWAY PHARMACEUTICAL TECHNOLOGY CO., LTD., Beijing (CN)

(72) Inventors: Wei Gu, Beijing (CN); Zhaoji Dong, Beijing (CN); Ruiluan Wang, Beijing (CN)

(73) Assignee: BEIJING GREATWAY PHARMACEUTICAL TECHNOLOGY CO. LTD., Beijing (CN)

( * ) Notice: Subject to any disclaimer, the term of this patent is extended or adjusted under 35 U.S.C. 154(b) by 773 days.

(21) Appl. No.: 17/998,626

(22) PCT Filed: May 12, 2021

(86) PCT No.: PCT/CN2021/093264

§ 371 (c)(1),
(2) Date: Nov. 11, 2022

(87) PCT Pub. No.: WO2021/228123

PCT Pub. Date: Nov. 18, 2021

(65) Prior Publication Data

US 2023/0348493 A1 Nov. 2, 2023

(30) Foreign Application Priority Data

May 12, 2020 (CN) ......................... 202010397265.5

(51) Int. Cl.

| | |
|---|---|
| ***C07D 513/10*** | (2006.01) |
| ***A61P 25/00*** | (2006.01) |
| ***A61P 25/22*** | (2006.01) |
| ***A61P 25/24*** | (2006.01) |
| ***A61P 25/28*** | (2006.01) |

(52) U.S. Cl.
CPC .................................. *C07D 513/10* (2013.01)

(58) Field of Classification Search
CPC .................................................. C07D 513/10
See application file for complete search history.

(56) References Cited

U.S. PATENT DOCUMENTS

| | | | |
|---|---|---|---|
| 3,932,423 | A | 1/1976 | Arimura et al. |
| 4,587,250 | A | 5/1986 | Klauser et al. |
| 6,384,065 | B1 | 5/2002 | Chaki et al. |
| 2005/0256166 | A1 | 11/2005 | Nakai et al. |
| 2014/0113895 | A1 | 4/2014 | Burns Barbier et al. |

FOREIGN PATENT DOCUMENTS

| | | | |
|---|---|---|---|
| CN | 1129942 | A | 8/1996 |
| CN | 1244528 | A | 2/2000 |
| CN | 1662506 | A | 8/2005 |
| CN | 105408336 | A | 3/2016 |
| CN | 109937204 | A | 6/2019 |
| CN | 110198944 | A | 9/2019 |
| EP | 1076056 | A1 | 2/2001 |
| GB | 1429906 | A | 3/1976 |
| IN | 2966/DEL/2005 | | 7/2009 |
| JP | S49124075 | A | 11/1974 |
| JP | H06293761 | A | 10/1994 |
| JP | 2000026466 | A | 1/2000 |
| JP | 2005530742 | A | 10/2005 |
| JP | 2016506959 | A | 3/2016 |
| JP | 2019527233 | A | 9/2019 |
| JP | 2020506903 | A | 3/2020 |
| WO | 2004016587 | A1 | 2/2004 |
| WO | 2005003128 | A1 | 1/2005 |
| WO | 2008064218 | A2 | 5/2008 |
| WO | 2010084499 | A2 | 7/2010 |

OTHER PUBLICATIONS

"STN Registry", CAS RN 66924-89-8, Nov. 16, 1984.
"STN Registry", CAS RN 100454-83-9, Feb. 22, 1986.
"STN Registry", CAS RN 663178-70-9, Mar. 15, 2004.
"STN Registry", CAS RN 1172553-20-6, Aug. 4, 2009.
"STN Registry", CAS RN 2382684-70-8, Nov. 25, 2019.
Ozdowska et al: "3-piperidone derivatives. Part 1", Polish Journal of Chemistry, Polskie Towarzystwo Chemiczne, Polish Chemical Society, PL, vol. 52, Jan. 1, 1978 (Jan. 1, 1978), pp. 385-388, XP009555368, ISSN: 0137-5083.
Li Ying et al.: "Synthesis of 4,8-diaza-1-thia-spiro [4.5] decane-3-carboxylic acid derivatives", Yingyong-Huagong = Applied Chemical Industry, Yingyong Huagong Zazhishe, CN, vol. 43, No. 3, Mar. 1, 2014 (Mar. 1, 2014), pp. 404-407, XP009555493, ISSN: 1671-3206, DOI: 10.16581/J.CNKI.ISSN1671-3206.2014.03.017.
Extended European Search Report for European Application No. 21804453.5, dated Jul. 22, 2024, 18 pages.
First Office Action for Japanese Application No. 2022-569218, dated Jul. 2, 2024, 7 pages.

(Continued)

*Primary Examiner* — Sahar Javanmard
(74) *Attorney, Agent, or Firm* — Ryan L. Marshall; William R. Boudreaux; Barnes & Thornburg LLP

(57) ABSTRACT

Provided are a compound for adjusting the activity of an NMDA receptor, and a pharmaceutical composition and the use thereof. In particular, provided are a compound as represented by formula I, a pharmaceutically acceptable salt or ester, a stereoisomer, or a solvate thereof. The compound has the effect of enhancing the activity of the NMDA receptor, and can be used to prepare drugs for preventing/treating depression, anxiety disorder, tension, learning and cognitive defects, neuropathic pain and other diseases,

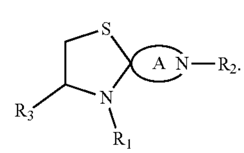

18 Claims, No Drawings

(56) References Cited

OTHER PUBLICATIONS

Office Action for Canadian Application No. 3,183,111, dated May 1, 2024, 23 pages.
"STN Registry", CAS RN 1214181-64-2, Mar. 24, 2010 (Mar. 24, 2010).
"STN Registry", CAS RN 1214842-69-9 et al., Nov. 25, 2019 (Nov. 25, 2019).
"STN Registry", CAS RN 1214078-42-8 et al., Mar. 24, 2010 (Mar. 24, 2010).
Registry entries from chemical abstract services (CAS) with various dates.
Lu, Y., Freeland, S. On the evolution of the standard amino-acid alphabet . Genome Biol 7, 102 (2006). https://doi.org/10.1186/GB-2006-7-1-102.
Third Office Action for JP Application No. 2022-569218, mailed Nov. 5, 2024, with English translation, 5 pages.

COMPOUND FOR ADJUSTING ACTIVITY OF NMDA RECEPTOR, AND PHARMACEUTICAL COMPOSITION AND USE THEREOF

CROSS-REFERENCE TO RELATED APPLICATIONS

The present application is a U.S. nationalization under 35 U.S.C. § 371 of International Application No. PCT/CN2021/093264, filed 12 May 2021, which claims priority from Chinese patent application number 202010397265.5 filed on 12 May 2020. The disclosures of these priority applications are incorporated herein in their entirety.

TECHNICAL FIELD

The invention belongs to the field of pharmaceutical and chemical industry, which relates to a compound for adjusting the activity of an NMDA receptor, and a pharmaceutical composition and the use thereof. Specifically, the present invention relates to the compound capable of enhancing the activity of the NMDA receptor and use of the compound in preparation of medicaments for preventing/treating depression, anxiety, tension, learning and cognitive deficits, neuropathic pain and other diseases.

BACKGROUND ART

N-methyl-D-aspartic acid (NMDA) receptor is an ionotropic receptor for an excitatory neurotransmitter glutamate and is involved in many complex physiological and pathological mechanisms. The NMDA receptor can mediate $Ca^{2+}$ influx, enhance synaptic plasticity, and participate in learning-memory and nervous system development; when excitatory amino acid of the body is increased sharply, a large influx of $Ca^{2+}$ can be induced by stimulating the NMDA receptors, resulting in cell death. The imbalance of NMDA receptor activity regulation has been considered to be an important reason of central nervous system diseases such as neurodegenerative diseases, depression, epilepsy and ischemic brain injury.

The NMDA receptor has an important role during excitatory neurotoxic process. The excitatory neurotoxic process is characterized in that the excessive release of extracellular glutamate results in excessive activation of NMDA receptor, causes influx of $Ca^{2+}$ and $Na^+$ and $K^+$ efflux, causes activation of intracellular signaling pathway, intracellular $Ca^{2+}$ overload, and cell dysfunction, induces apoptosis or initiates cell death signal transduction pathway, and ultimately leads to neuronal death, resulting in neurodegenerative diseases, depression and other diseases, while an NMDA receptor antagonist can reduce the excitatory neurotoxic effect of cells by inhibiting the activity of NMDA receptor. In addition, by mediating $Ca^{2+}$ influx, NMDA receptor can also enhance synaptic plasticity and neuronal excitability, induce long term promotion (LTP), and promote neural cell development, and NMDA receptor plays an important role in the treatment of cognitive dysfunction caused by the diseases such as neurodegenerative diseases, depression and schizophrenia. Therefore, reasonable regulation of the activity of NMDA receptor plays an important role in the treatment of neurological diseases.

Studies show that the NMDA receptor antagonist has rapid antidepressant effects, and an NMDA receptor agonist can also regulate the sensitivity of postsynaptic AMPA by increasing the release of the neurotransmitter mediated by NMDA receptor to generate the antidepressant effects. An NMDA receptor partial agonist can exert dual (antagonist/agonist) effects on NMDA receptor through allosteric sites.

In the field of antidepressant research, an NMDA receptor modulator which is designed and synthesized, such as the NMDA partial agonist/antagonist, is of great significance for the treatment of depression by exerting partial agonistic and/or antagonistic effects on NMDA receptors.

CONTENTS OF INVENTION

After intensive research and creative labor, inventors of the invention obtain a compound represented by formula I. The inventors are surprised to find that the compound of formula I or a pharmaceutically acceptable salt, a solvate thereof, or a mixture thereof can be the agonist of NMDA receptor, especially the partial agonist, and has a high affinity with NMDA receptor; while reflected in animal models, the compound can rapidly, effectively and persistently prevent and treat depression and anxiety states of the model animals.

COMPOUND OF THE PRESENT INVENTION

One aspect of the present invention relates to a compound represented by formula I, a pharmaceutically acceptable salt or ester, stereoisomer or solvate thereof,

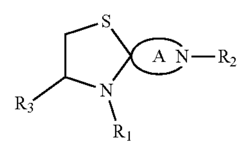

I wherein,

Ring A is 3- to 8-membered aliphatic heterocycle;

$R_1$ is selected from H, C1-C6 alkyl, aryl-C1-C4 alkyl, C2-C6 acyl, —CONRR' and natural amino acid fragments;

$R_2$ is selected from H, C1-C6 alkyl, C1-C6 alkoxycarbonyl, C2-C6 acyl, —CONRR' and natural amino acid fragments;

$R_3$ is selected from H, cyano, 3- to 8-membered nitrogen-containing aliphatic heterocycle-C1-C4 acyl, C1-C6 alkoxycarbonyl and —$CONHR_4$;

R and R' are each independently selected from H and C1-C6 alkyl;

$R_4$ is selected from H, C1-C6 alkyl, natural amino acid fragments and carboxylic acid derivatives of the said natural amino acid fragments;

optionally, the C1-C6 alkyl, aryl-C1-C4 alkyl, C2-C6 acyl, 3- to 8-membered nitrogen-containing aliphatic heterocycle-C1-C4 acyl, C1-C6 alkoxycarbonyl, —CONRR', —$CONHR_4$ and natural amino acid fragments are each independently substituted by one or more substituents selected from: halogen, amino, hydroxyl, cyano, carboxyl, nitro, C1-C6 alkyl, and C1-C6 alkoxy;

and, $R_1$, $R_2$ and $R_3$ satisfy:

(1) $R_1$, $R_2$ and $R_3$ are not H at the same time;

(2) when $R_1$ and $R_3$ are H, $R_2$ is not Boc;

(3) when the formula I is
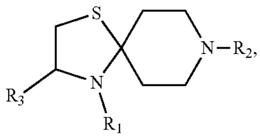
$R_1$ is
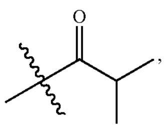 [SMILES: *C(=O)C(C)C],
and $R_3$ is H; $R_2$ is not H,
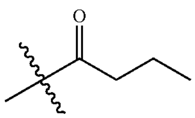, 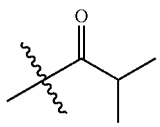,
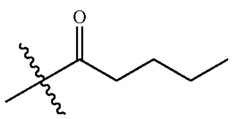, 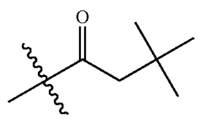,
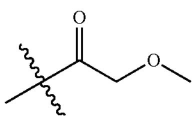, 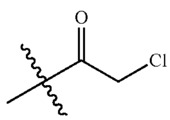,
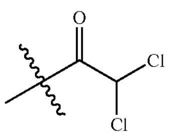, 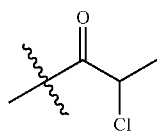,
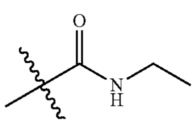, 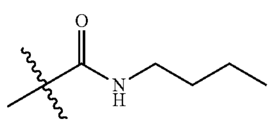,
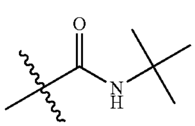 or 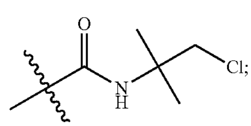
(4) when the formula I is
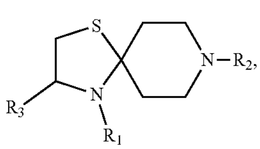
$R_1$ is
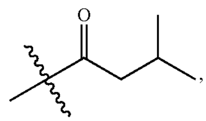 [SMILES: *C(=O)CC(C)C],
and $R_3$ is H; $R_2$ is not C2-C6 acyl or —CONRR';
(5) when the formula I is
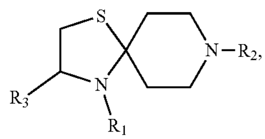
$R_1$ and $R_3$ are H; $R_2$ is not C1-C4 alkyl, acetyl,
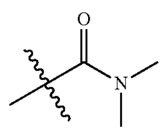 or 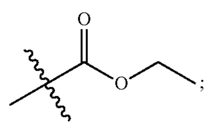;
(6) the compound of the formula I is not
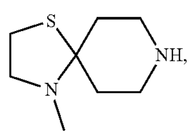 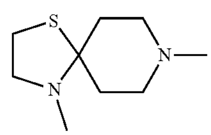,
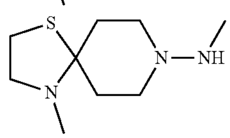, 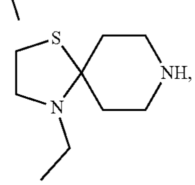
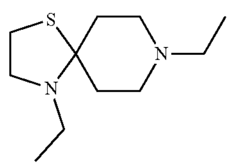, 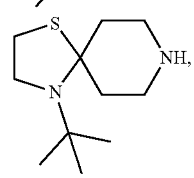
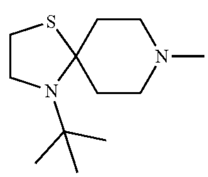, 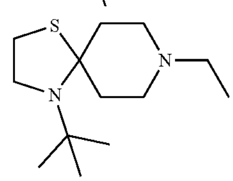,
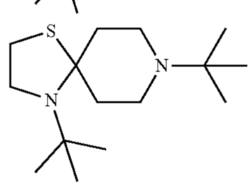, 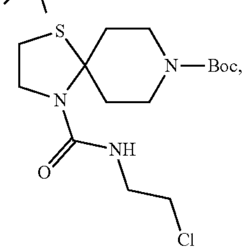

-continued

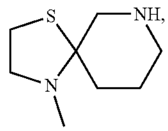

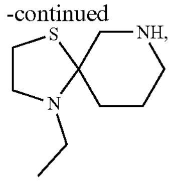

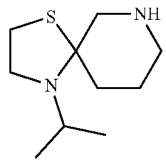

or

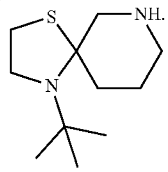

In some embodiments, Ring A is selected from 4- to 7-membered aliphatic heterocycle, and preferably 4- to 6-membered aliphatic heterocycle.

In some embodiments, Ring A is selected from 4- to 7-membered nitrogen-containing aliphatic heterocycle, and preferably 4- to 6-membered nitrogen-containing aliphatic heterocycle.

In some embodiments, Ring A is selected from

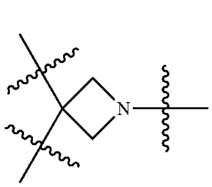

,

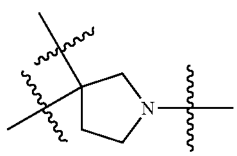

,

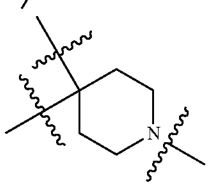

,

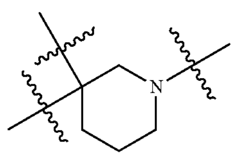

,

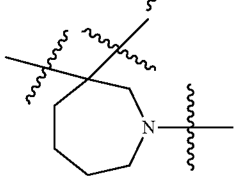

and

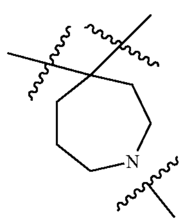

.

In some embodiments, Ring A is selected from

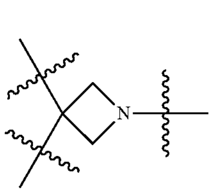

,

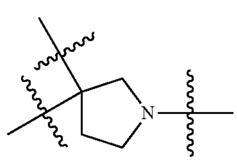

,

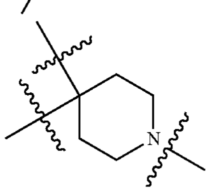

and

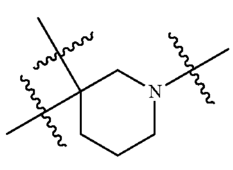

,

In some embodiments, $R_1$ is selected from H, C1-C6 alkyl, phenyl-C1-C4 alkyl, C2-C6 acyl and natural amino acid fragments.

In some embodiments, $R_1$ is selected from H, C1-C6 alkyl and C2-C6 acyl.

In some embodiments, $R_1$ is H.

In some embodiments, $R_1$ is selected from carboxyl residues of natural amino acids.

In some embodiments, $R_1$ is selected from H, acetyl, methyl,

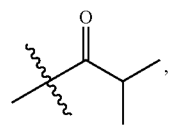

,

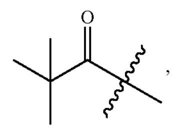

,

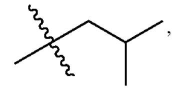

,

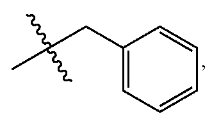

,

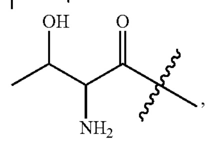

,

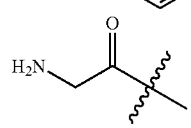

,

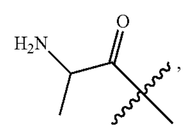

,

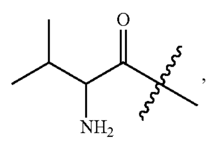

,

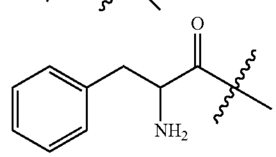

,

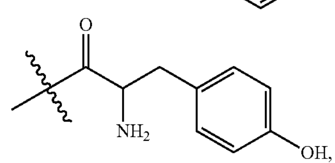

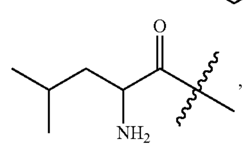

,

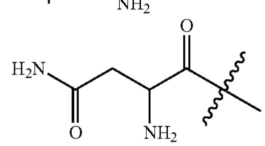

and

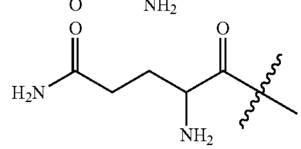

.

In some embodiments, $R_1$ is selected from H, acetyl, methyl,

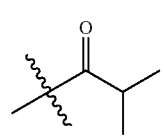

,

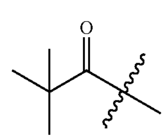

,

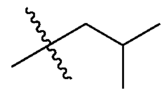

,

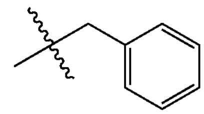

,

-continued

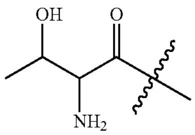, 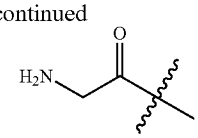,

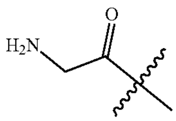, 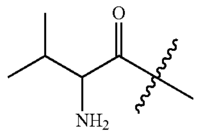,

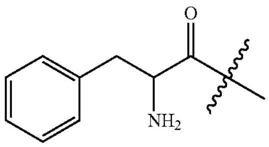,

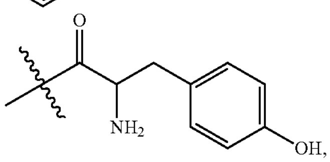

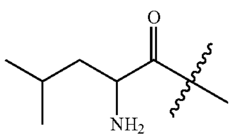 and

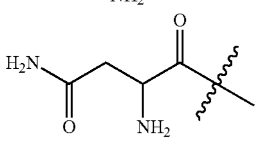.

In some embodiments, $R_1$ is selected from H, acetyl, methyl,

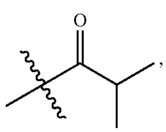, 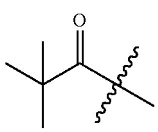, 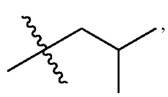,

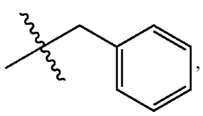, 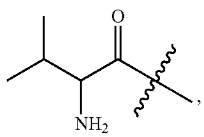,

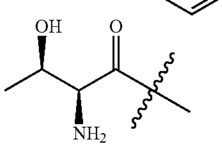 and 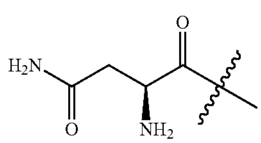.

In some embodiments, $R_2$ is selected from H, C1-C6 alkyl, C1-C6 alkoxycarbonyl, C2-C6 acyl, and natural amino acid fragments; optionally, the C1-C6 alkyl, phenyl-C1-C4 alkyl, C2-C6 acyl and natural amino acid fragments are each independently substituted by one or more substituents selected from: halogen, amino, hydroxyl, cyano, carboxyl, nitro, C1-C6 alkyl and C1-C6 alkoxy.

In some embodiments, $R_2$ is selected from H, C1-C4 alkoxycarbonyl, C2-C6 acyl and carboxyl residues of the natural amino acids.

In some embodiments, $R_2$ is selected from H, C1-C6 alkyl, C2-C6 acyl and carboxyl residues of natural amino acids.

In some embodiments, $R_2$ is selected from H, C1-C6 alkyl and C2-C6 acyl.

In some embodiments, $R_2$ is selected from carboxyl residues of natural amino acids.

In some embodiments, $R_2$ is selected from H, methyl, ethyl, propyl, butyl, tert-butoxycarbonyl, acetyl,

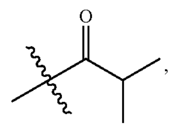, 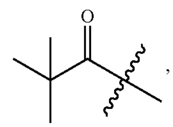,

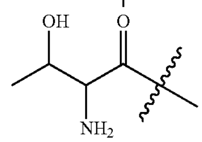, 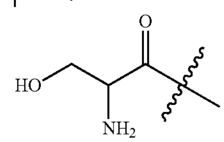,

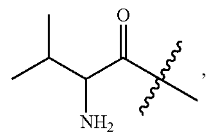, 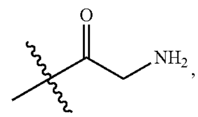

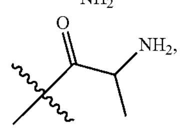 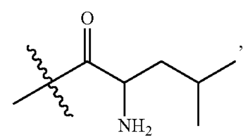,

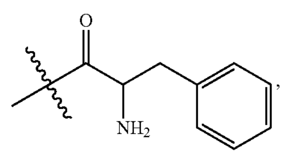

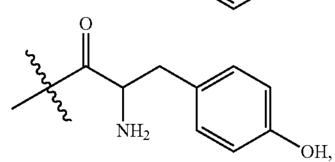 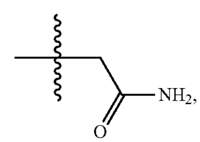

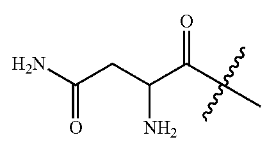 and

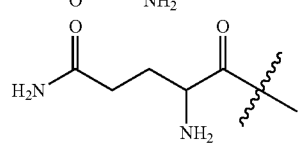.

In some embodiments, $R_2$ is selected from H, methyl, ethyl, tert-butoxycarbonyl, acetyl,

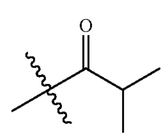, 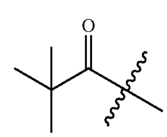,

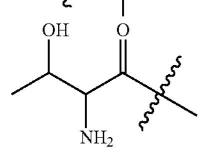, 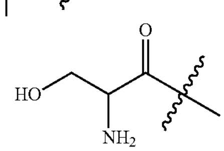,

-continued

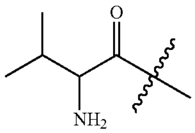 , 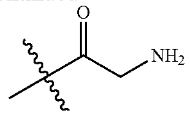 ,

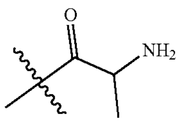 , 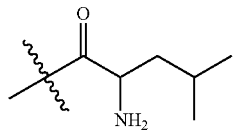 ,

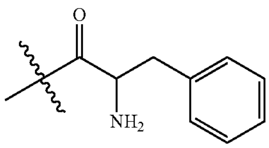 ,

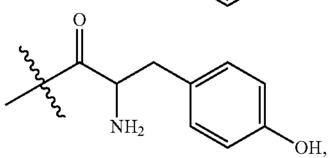 ,

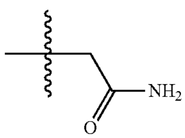 and 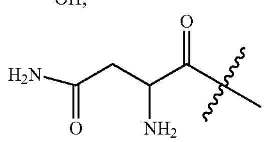 .

In some embodiments, $R_2$ is selected from H methyl, tert-butoxycarbonyl, acetyl,

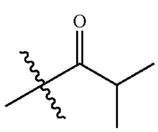 , 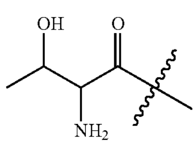 ,

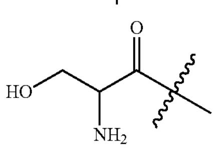 and 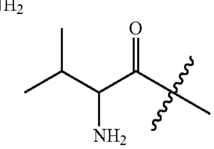 .

In some embodiments, $R_3$ is selected from H, cyano, 5- to 7-membered (e.g. 6-membered) nitrogen-containing aliphatic heterocycle-C1-C3 acyl (e.g. formyl), C1-C4 alkoxycarbonyl and —CONHR$_4$; $R_4$ is selected from H, natural amino acid fragments, amide derivatives of the said natural amino acid fragments and cyano derivatives of the said natural amino acid fragments.

In some embodiments, $R_3$ is selected from H, cyano, 5- to 7-membered nitrogen-containing aliphatic heterocycle-C1-C3 acyl, C1-C4 alkoxycarbonyl and —CONHR$_4$; $R_4$ is selected from H, natural amino acid fragments and amide derivatives of the said natural amino acid fragments.

In some embodiments, $R_3$ is selected from H, cyano, 5- to 7-membered nitrogen-containing aliphatic heterocycle-C1-C3 acyl, C1-C4 alkoxycarbonyl and —CONHR$_4$; $R_4$ is selected from H and natural amino acid fragments.

In some embodiments, $R_3$ is selected from H, cyano, 5- to 7-membered nitrogen-containing aliphatic heterocycle-C1-C3 acyl, C1-C4 alkoxycarbonyl and —CONHR$_4$; $R_4$ is selected from H and amide derivatives of natural amino acid fragments.

In some embodiments, $R_3$ is H.

In some embodiments, $R_3$ is —CONHR$_4$; $R_4$ is selected from amino residues of natural amino acids, and amide derivatives of the said amino residue of natural amino acids.

In some embodiments, RA s selected from H, cyano,

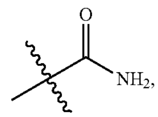 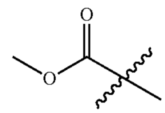 ,

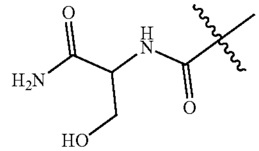 , 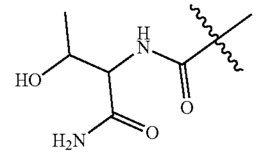 ,

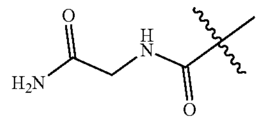 , 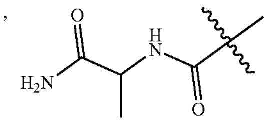 ,

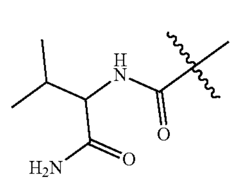 , 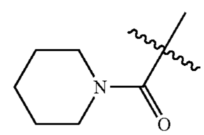 ,

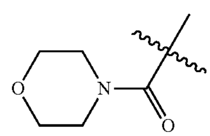 , 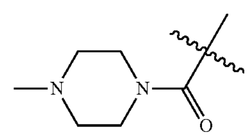 ,

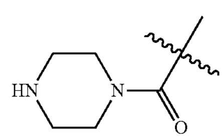 and 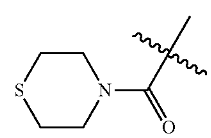 .

In some embodiments, $R_3$ is selected from H, cyano,

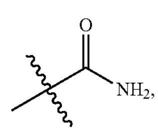 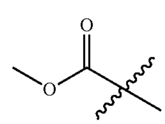 ,

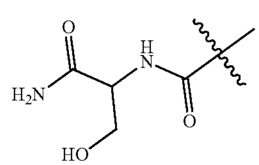 , 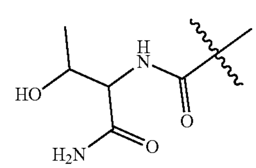 ,

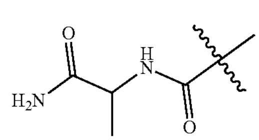 , 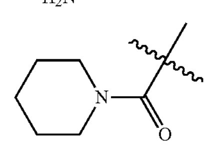 ,

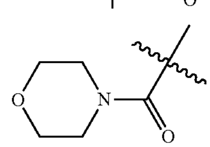 , 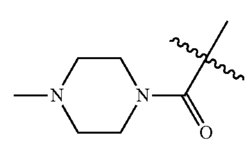 ,

-continued

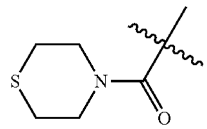

and

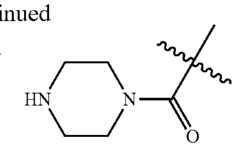

.

In some embodiments, $R_3$ is selected from H, cyano, C1-C4 alkoxycarbonyl and —$CONHR_4$; $R_4$ is selected from H, natural amino acid fragments, amide derivatives of the said natural amino acid fragments, and cyano derivatives of the said natural amino acid fragments.

In some embodiments, $R_3$ is selected from H, cyano, C1-C4 alkoxycarbonyl and —$CONHR_4$; $R_4$ is selected from H, natural amino acid fragments and amide derivatives of the said natural amino acid fragments.

In some embodiments, $R_3$ is selected from H, cyano, C1-C4 alkoxycarbonyl and —$CONHR_4$; $R_4$ is selected from H and natural amino acid fragments.

In some embodiments, $R_3$ is selected from H, cyano, C1-C4 alkoxycarbonyl and —$CONHR_4$; $R_4$ is selected from H and amide derivatives of natural amino acid fragments.

In some embodiments, Ring A is selected from

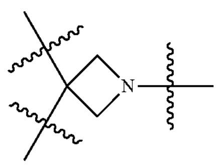,

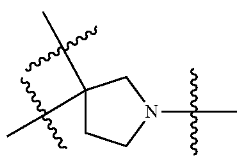,

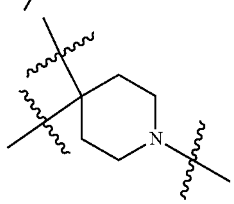,

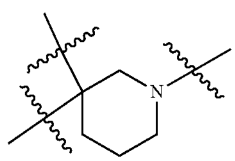,

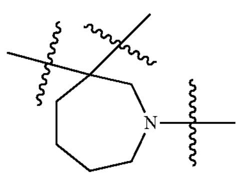,

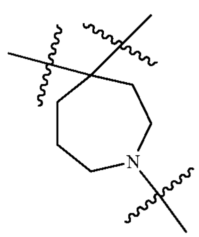;

$R_1$ is independently selected from —H, C1-C6 alkyl and C2-C6 acyl;

$R_2$ is selected from H, Boc, C2-C6 acyl and natural amino acid fragments;

$R_3$ is H.

In some embodiments, Ring A is selected from

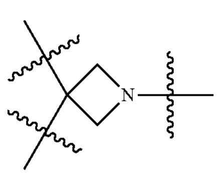,

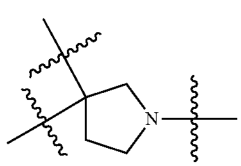,

-continued

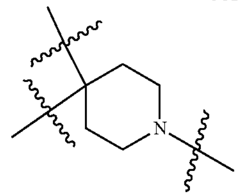,

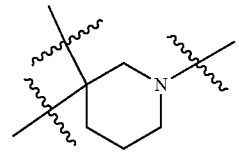,

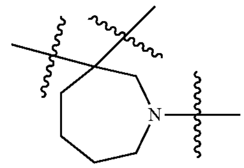,

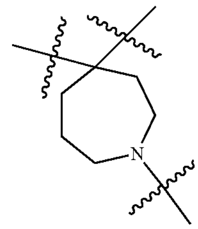;

$R_1$ is selected from natural amino acid fragments;

$R_2$ is selected from H, C1-C6 alkyl, C2-C6 acyl and natural amino acid fragments;

$R_3$ is H.

In some embodiments, Ring A is selected from

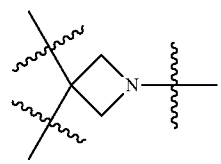,

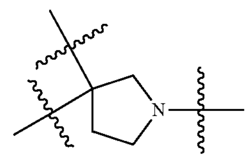,

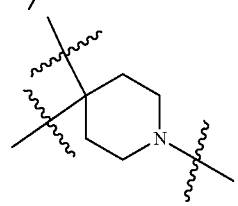,

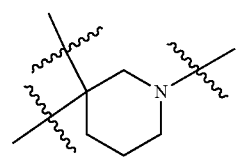,

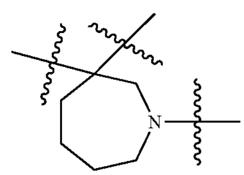,

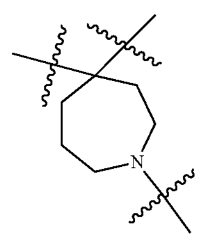;

$R_1$ is H;

$R_2$ is selected from natural amino acid fragments;

$R_3$ is selected from methyl ester, ethyl ester, propyl ester, isopropyl ester, formamide, cyano and $CONHR_4$;

$R_4$ is selected from natural amino acid fragments and carboxylic acid derivatives of the said natural amino acid fragments.

In some embodiments, Ring A is selected from

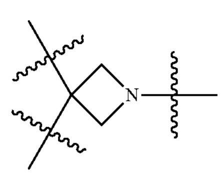,

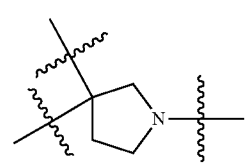,

-continued

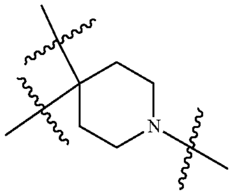
,
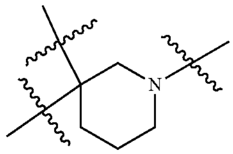
,
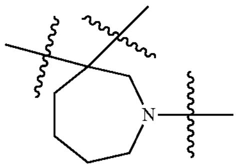
,
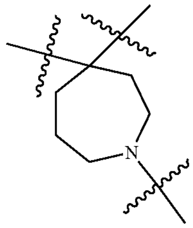
;

$R_1$ is H;

$R_2$ is selected from H, C1-C6 alkyl, C2-C6 acyl;

$R_3$ is selected from $CONHR_4$;

$R_4$ is selected from natural amino acid fragments and carboxylic acid derivatives of the said natural amino acid fragments.

In some embodiments, the said natural amino acid fragments are selected from the carboxyl residues of the following amino acids: Thr, Ser, Val, Gly, Ala, Ile, Phe, Gln and Tyr.

In some embodiments, the said natural amino acid fragments are selected from the amino residues of the following amino acids: Thr, Ser, Val, Gly, Ala, Ile, Phe, Gln and Tyr.

In some embodiments, natural amino acid fragments are selected from

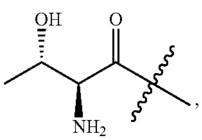
,
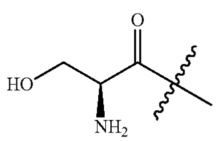
,
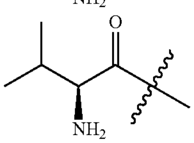
,
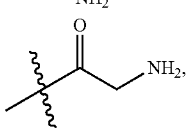

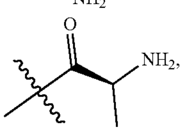

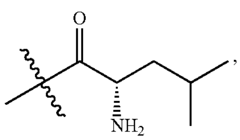
,
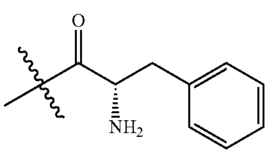
,
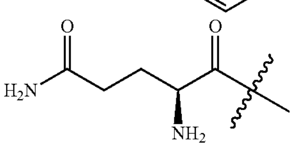
and
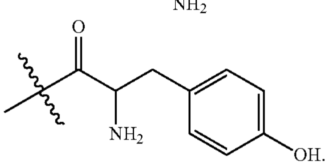

In some embodiments, natural amino acid fragments are selected form

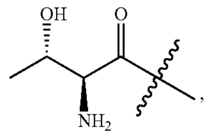
,
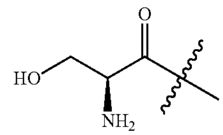
,
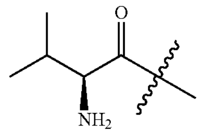
,
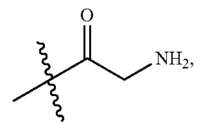

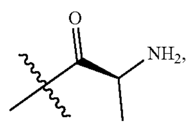

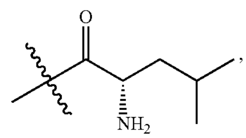
,
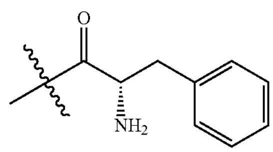
and
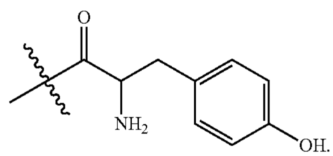

In some embodiments, natural amino acid fragments are selected from

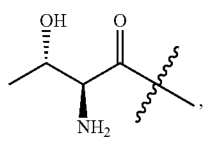
,
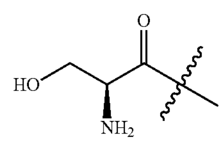
and
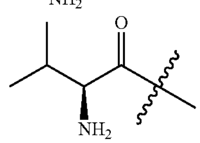

In some embodiments, natural amino acid fragments are selected from

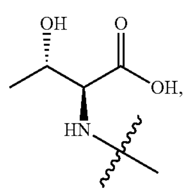

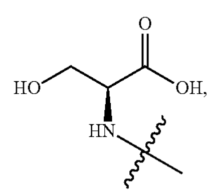

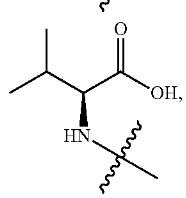

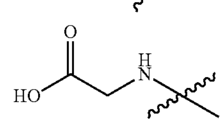
,

-continued

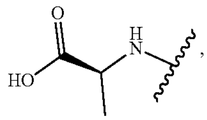,

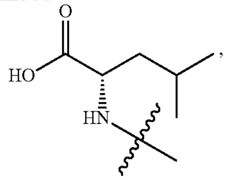,

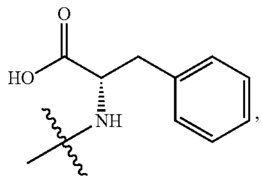,

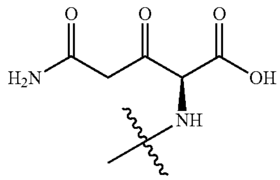

and

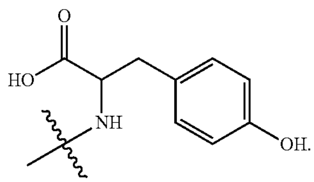

In the embodiments of the present invention, the carboxylic acid derivative of the natural amino acid fragments is formed by replacing a part of carboxyl group in the natural amino acid fragment with other atomic group and hydrolyzed to obtain the carboxylic acid. Amide derivatives, cyano derivatives and carboxylate derivatives of the said natural amino acid fragments are included. In some embodiments, the carboxylic acid derivatives of the natural amino acid fragments include, but are not limited to, amide derivatives, cyano derivatives and carboxylate derivatives of the following amino acid fragments: Thr, Ser, Val, Gly, Ala, Ile, Phe, Gln and Tyr. In some embodiments, the carboxylic acid derivative of the natural amino acid fragments is, for example:

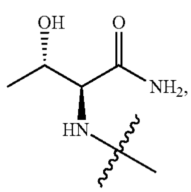

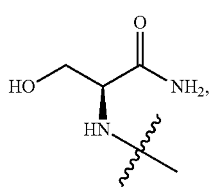

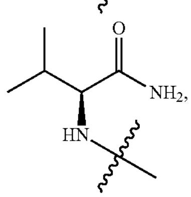

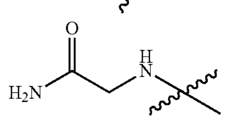,

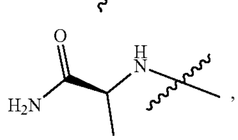,

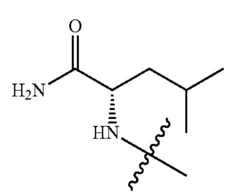,

-continued

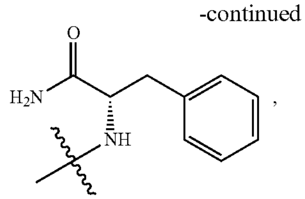,

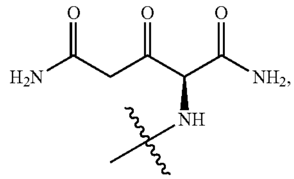

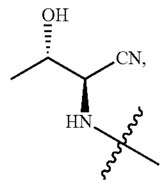

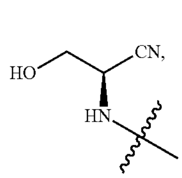

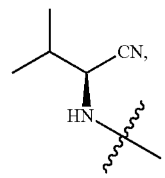

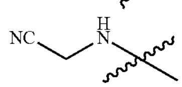,

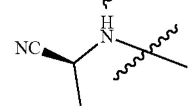,

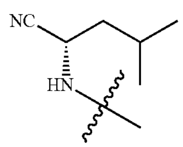,

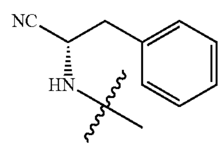

or

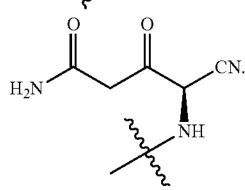

In some embodiments, Ring A is 3- to 8-membered aliphatic heterocycle;

$R_1$ is selected from H, C1-C6 alkyl, aryl-C1-C4 alkyl, C2-C6 acyl, —CONRR' and natural amino acid fragments;

$R_2$ is selected from H, C1-C6 alkyl, C1-C6 alkoxycarbonyl, C2-C6 acyl, —CONRR' and natural amino acid fragments;

$R_3$ is selected from H, cyano, C1-C6 alkoxycarbonyl and —$CONHR_4$;

R and R' are each independently selected from H and C1-C6 alkyl;

$R_4$ is selected from H, C1-C6 alkyl, natural amino acid fragments and carboxylic acid derivatives of the said natural amino acid fragments;

optionally, the C1-C6 alkyl, aryl-C1-C4 alkyl, C2-C6 acyl, C1-C6 alkoxycarbonyl, —CONRR', —$CONHR_4$ and natural amino acid fragments are each independently substituted by one or more substituents selected from: halogen, amino, hydroxyl, cyano, carboxyl, nitro, C1-C6 alkyl and C1-C6 alkoxy.

In some embodiments, $R_1$, $R_2$ and $R_3$ satisfy:

(1) $R_1$, $R_2$ and $R_3$ are not H at the same time;

(2) when $R_1$ and $R_3$ are H, $R_2$ is not Boc;

(3) when the formula I is
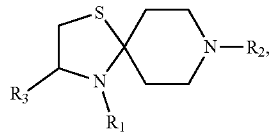
R1 is 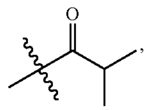
and $R_3$ is H; $R_2$ is not H,
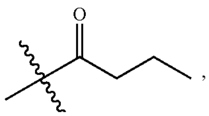, 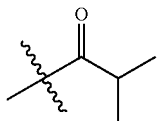,
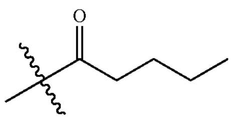, 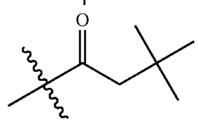,
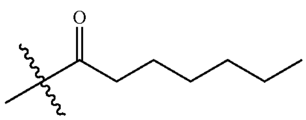,
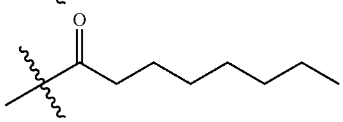,
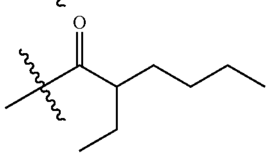,
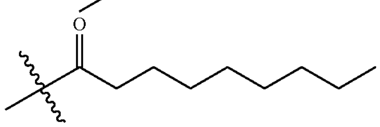,
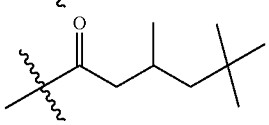,
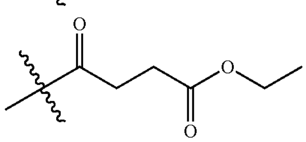,
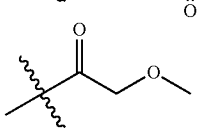, 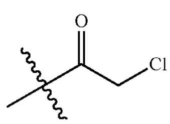,
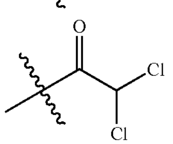, 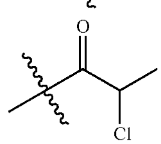,
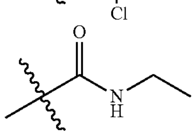, 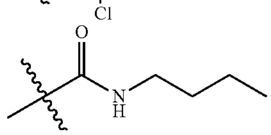,
-continued
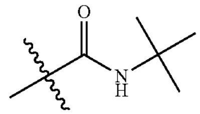 or 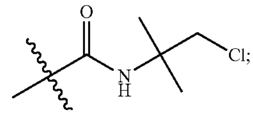
(4) when the formula I is
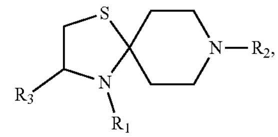
$R_1$ is
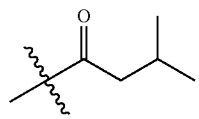
and $R_3$ is H; $R_2$ is not C2-C6 acyl or —CONRR';
(5) when the formula I is
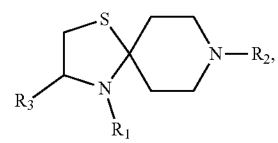
$R_1$ and $R_3$ are H; $R_2$ is not C1-C4 alkyl, acetyl,
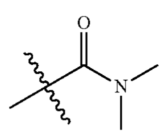 or 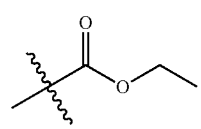;
(6) the compound of the formula I is not
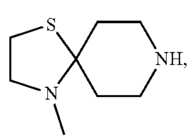 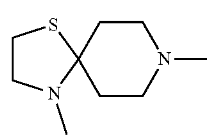,
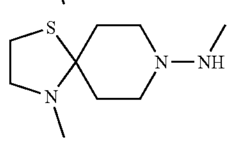, 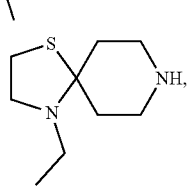

-continued

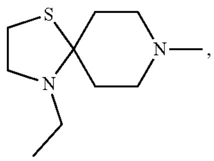, 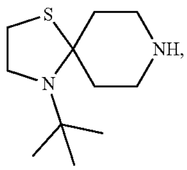

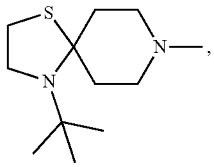, 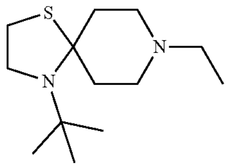,

-continued

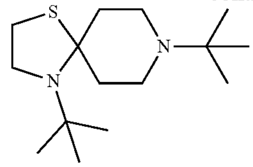 or 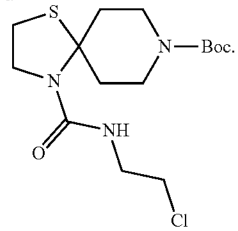.

In some embodiments, $R_3$ is selected from H, cyano, C1-C4 alkoxycarbonyl and —CONHR$_4$; $R_4$ is selected from H, natural amino acid fragments, amide derivatives of the said natural amino acid fragments, and cyano derivatives of the said natural amino acid fragments.

In some embodiments, the present invention provides the following compounds or salts thereof.

| Number | Structural formula | Number | Structural formula |
|---|---|---|---|
| A-001 | 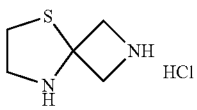 | A-002 | 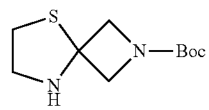 [SMILES: CC(C)(C)OC(=O)N1CC2(C1)NCCS2] |
| A-003 | 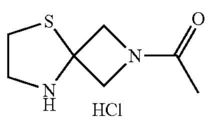 | A-004 | 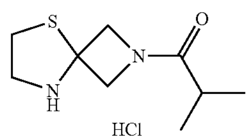 |
| A-005 | 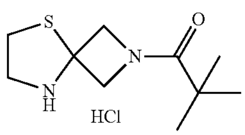 | A-006 | 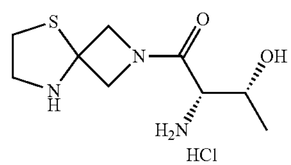 |
| A-007 | 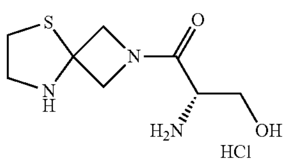 [SMILES: N[C@@H](CO)C(=O)N1CC2(C1)NCCS2 ; Cl] | A-007-1 | 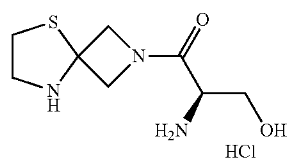 [SMILES: N[C@H](CO)C(=O)N1CC2(C1)NCCS2 ; Cl] |
| A-008 | 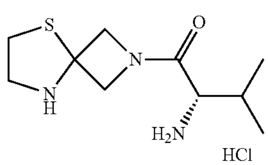 | A-008-1 | 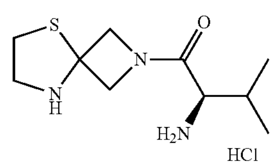 |
| A-009 | 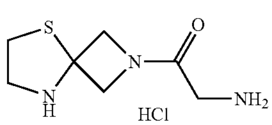 [SMILES: NCC(=O)N1CC2(C1)NCCS2 ; Cl] | A-010 | 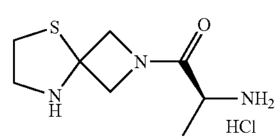 |

-continued
| Number | Structural formula | Number | Structural formula |
|---|---|---|---|
| A-011 | 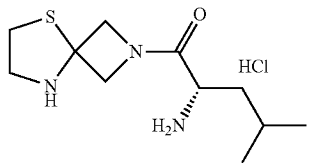 [SMILES: CC(C)C[C@H](N)C(=O)N1CC2(C1)NCCS2 ; Cl] | A-012 | 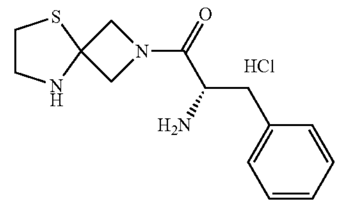 [SMILES: N[C@@H](Cc1ccccc1)C(=O)N1CC2(C1)NCCS2 ; Cl] |
| A-013 | 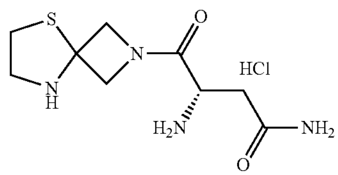 [SMILES: NC(=O)C[C@H](N)C(=O)N1CC2(C1)NCCS2 ; Cl] | A-014 | 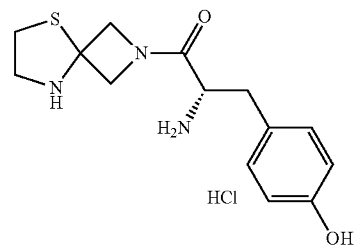 [SMILES: N[C@@H](Cc1ccc(O)cc1)C(=O)N1CC2(C1)NCCS2 ; Cl] |
| A-015 | 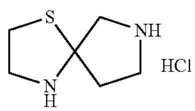 | A-016 | 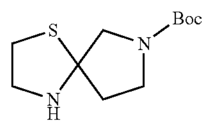 [SMILES: CC(C)(C)OC(=O)N1CCC2(C1)NCCS2] |
| A-017 | 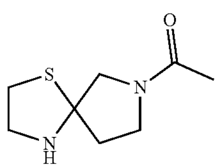 | A-018 | 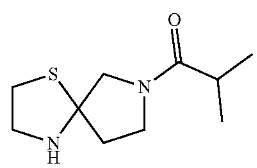 |
| A-019 | 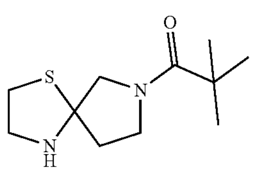 | A-020 | 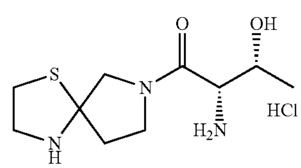 [SMILES: C[C@@H](O)[C@H](N)C(=O)N1CCC2(C1)NCCS2 ; Cl] |
| A-021 | 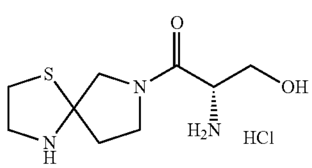 [SMILES: N[C@@H](CO)C(=O)N1CCC2(C1)NCCS2 ; Cl] | A-022 | 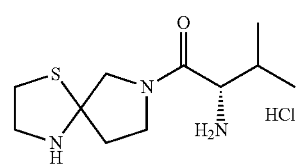 [SMILES: CC(C)[C@H](N)C(=O)N1CCC2(C1)NCCS2 ; Cl] |
| A-023 | 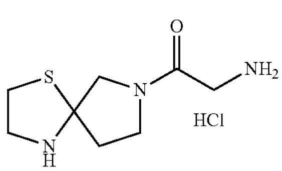 [SMILES: NCC(=O)N1CCC2(C1)NCCS2 ; Cl] | A-024 | 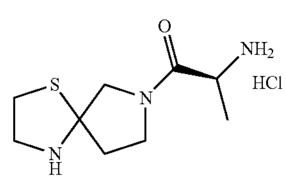 |
| A-025 | 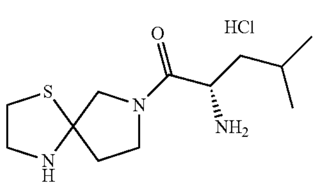 [SMILES: Cl ; CC(C)C[C@H](N)C(=O)N1CCC2(C1)NCCS2] | A-026 | 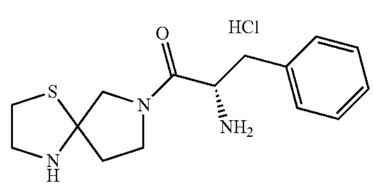 [SMILES: Cl ; N[C@@H](Cc1ccccc1)C(=O)N1CCC2(C1)NCCS2] |

-continued
| Number | Structural formula | Number | Structural formula |
|---|---|---|---|
| A-027 | 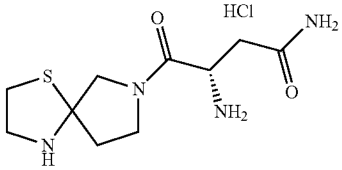 [SMILES: Cl ; NC(=O)C[C@H](N)C(=O)N1CCC2(C1)NCCS2] | A-028 | 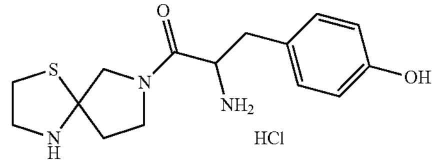 [SMILES: NC(Cc1ccc(O)cc1)C(=O)N1CCC2(C1)NCCS2 ; Cl] |
| A-029 | 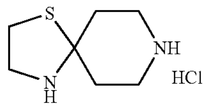 | A-030 | 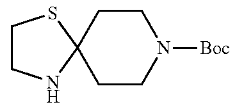 [SMILES: CC(C)(C)OC(=O)N1CCC2(CC1)NCCS2] |
| A-031 | 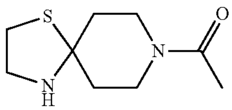 | A-032 | 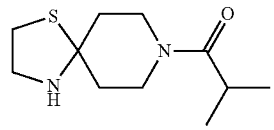 |
| A-033 | 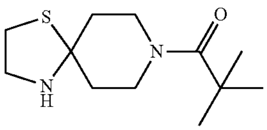 [SMILES: CC(C)(C)C(=O)N1CCC2(CC1)NCCS2] | A-034 | 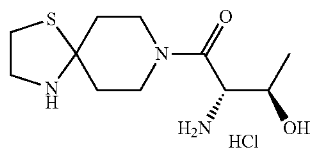 [SMILES: C[C@@H](O)[C@H](N)C(=O)N1CCC2(CC1)NCCS2 ; Cl] |
| A-035 | 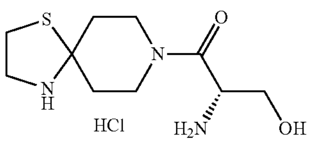 [SMILES: N[C@@H](CO)C(=O)N1CCC2(CC1)NCCS2 ; Cl] | A-036 | 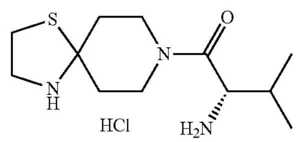 [SMILES: CC(C)[C@H](N)C(=O)N1CCC2(CC1)NCCS2 ; Cl] |
| A-037 | 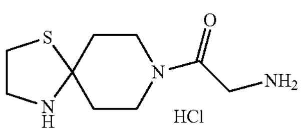 [SMILES: NCC(=O)N1CCC2(CC1)NCCS2 ; Cl] | A-038 | 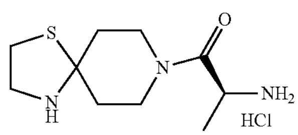 |
| A-039 | 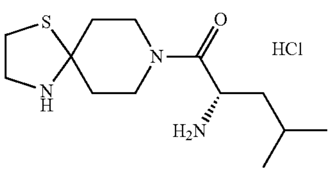 [SMILES: CC(C)C[C@H](N)C(=O)N1CCC2(CC1)NCCS2 ; Cl] | A-040 | 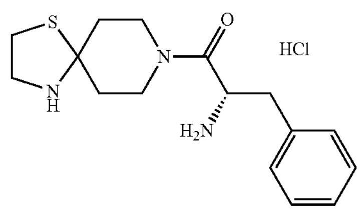 [SMILES: N[C@@H](Cc1ccccc1)C(=O)N1CCC2(CC1)NCCS2 ; Cl] |
| A-041 | 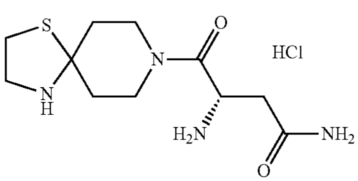 [SMILES: NC(=O)C[C@H](N)C(=O)N1CCC2(CC1)NCCS2 ; Cl] | A-042 | 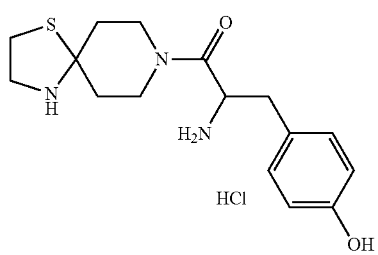 [SMILES: NC(Cc1ccc(O)cc1)C(=O)N1CCC2(CC1)NCCS2 ; Cl] |
| A-043 | 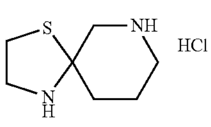 | A-044 | 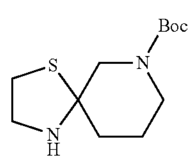 [SMILES: CC(C)(C)OC(=O)N1CCCC2(C1)NCCS2] |

-continued
| Number | Structural formula | Number | Structural formula |
| --- | --- | --- | --- |
| A-045 | 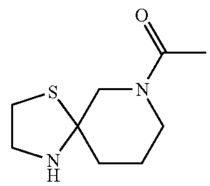 | A-046 | 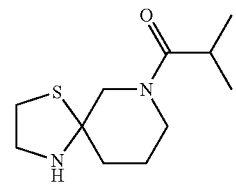 |
| A-047 | 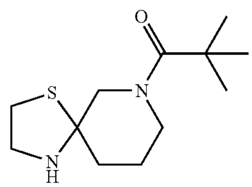 [SMILES: CC(C)(C)C(=O)N1CCCC2(C1)NCCS2] | A-048 | 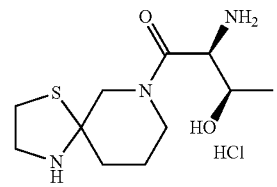 [SMILES: C[C@@H](O)[C@H](N)C(=O)N1CCCC2(C1)NCCS2 ; Cl] |
| A-049 | 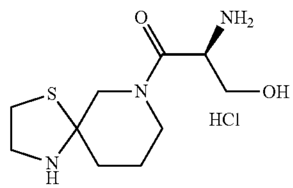 [SMILES: N[C@@H](CO)C(=O)N1CCCC2(C1)NCCS2 ; Cl] | A-050 | 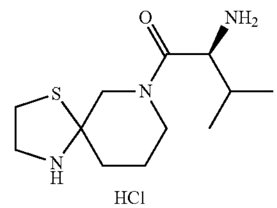 [SMILES: CC(C)[C@H](N)C(=O)N1CCCC2(C1)NCCS2 ; Cl] |
| A-051 | 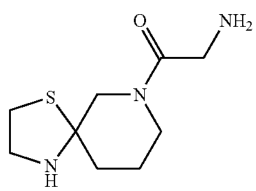 [SMILES: NCC(=O)N1CCCC2(C1)NCCS2] | A-052 | 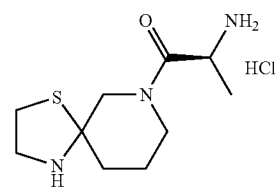 |
| A-053 | 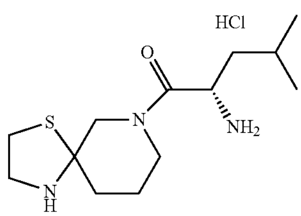 [SMILES: CC(C)C[C@H](N)C(=O)N1CCCC2(C1)NCCS2 ; Cl] | A-054 | 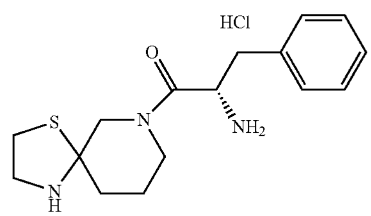 [SMILES: N[C@@H](Cc1ccccc1)C(=O)N1CCCC2(C1)NCCS2 ; Cl] |
| A-055 | 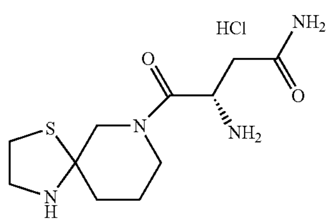 [SMILES: NC(=O)C[C@H](N)C(=O)N1CCCC2(C1)NCCS2 ; Cl] | A-056 | 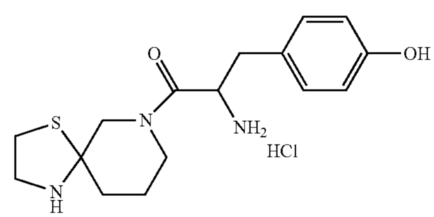 [SMILES: NC(Cc1ccc(O)cc1)C(=O)N1CCCC2(C1)NCCS2 ; Cl] |
| A-057 | 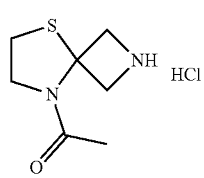 | A-058 | 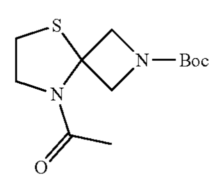 [SMILES: CC(=O)N1CCSC12CN(C(=O)OC(C)(C)C)C2] |
| A-059 | 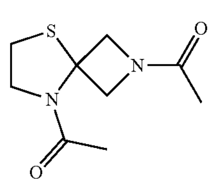 | A-060 | 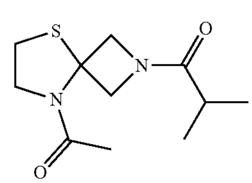 [SMILES: CC(=O)N1CCSC12CN(C(=O)C(C)C)C2] |

-continued
| Number | Structural formula | Number | Structural formula |
|---|---|---|---|
| A-061 | 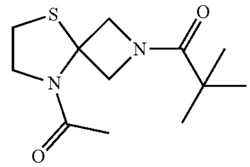 [SMILES: CC(=O)N1CCSC12CN(C(=O)C(C)(C)C)C2] | A-062 | 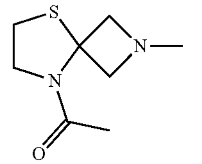 |
| A-063 | 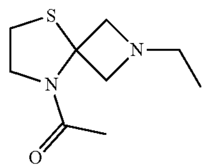 | A-064 | 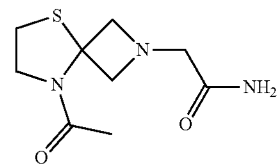 |
| A-065 | 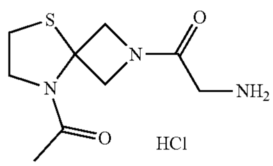 HCl | A-066 | 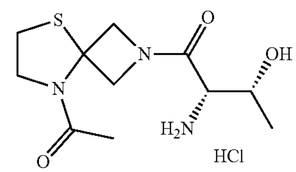 [SMILES: CC(=O)N1CCSC12CN(C(=O)[C@@H](N)[C@@H](C)O)C2 ; Cl] HCl |
| A-067 | 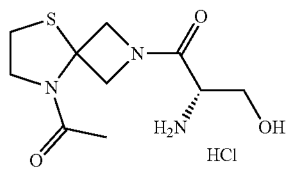 [SMILES: CC(=O)N1CCSC12CN(C(=O)[C@@H](N)CO)C2 ; Cl] HCl | A-068 | 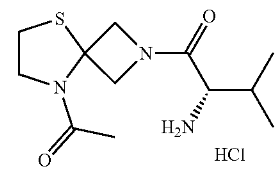 [SMILES: CC(=O)N1CCSC12CN(C(=O)[C@@H](N)C(C)C)C2 ; Cl] HCl |
| A-069 | 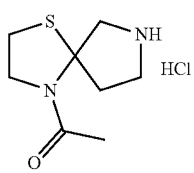 HCl | A-070 | 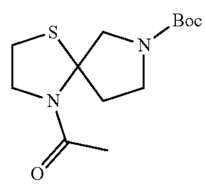 [SMILES: CC(=O)N1CCSC12CCN(C(=O)OC(C)(C)C)C2] |
| A-071 | 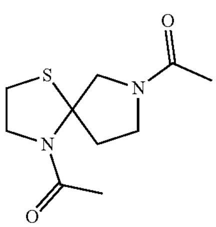 | A-072 | 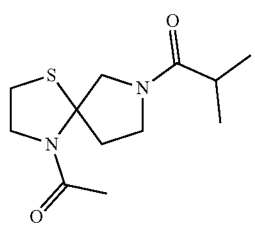 [SMILES: CC(=O)N1CCSC12CCN(C(=O)C(C)C)C2] |
| A-073 | 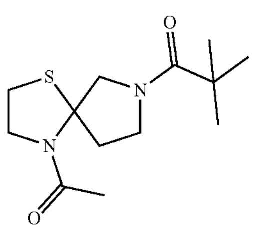 [SMILES: CC(=O)N1CCSC12CCN(C(=O)C(C)(C)C)C2] | A-074 | 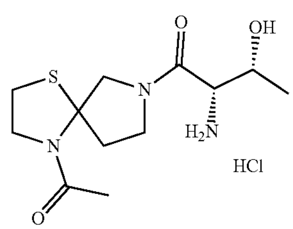 [SMILES: CC(=O)N1CCSC12CCN(C(=O)[C@@H](N)[C@@H](C)O)C2 ; Cl] HCl |
| A-075 | 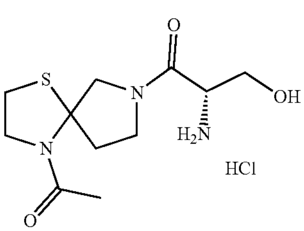 [SMILES: CC(=O)N1CCSC12CCN(C(=O)[C@@H](N)CO)C2 ; Cl] HCl | A-076 | 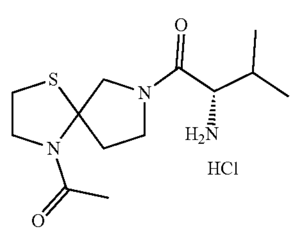 [SMILES: CC(=O)N1CCSC12CCN(C(=O)[C@@H](N)C(C)C)C2 ; Cl] HCl |

-continued
| Number | Structural formula | Number | Structural formula |
|---|---|---|---|
| A-077 | 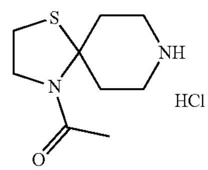 | A-078 | 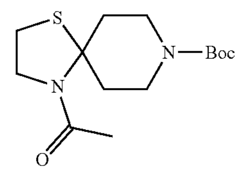 [SMILES: CC(=O)N1CCSC12CCN(C(=O)OC(C)(C)C)CC2] |
| A-079 | 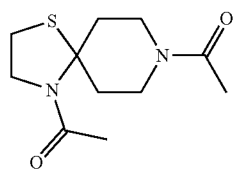 | A-080 | 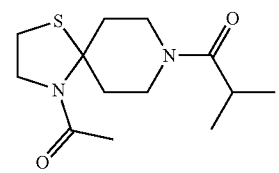 [SMILES: CC(=O)N1CCSC12CCN(C(=O)C(C)C)CC2] |
| A-081 | 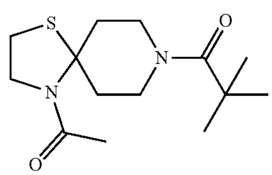 [SMILES: CC(=O)N1CCSC12CCN(C(=O)C(C)(C)C)CC2] | A-082 | 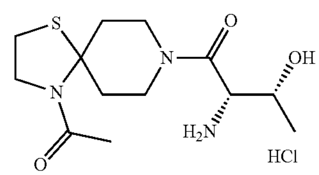 [SMILES: CC(=O)N1CCSC12CCN(C(=O)[C@@H](N)[C@@H](C)O)CC2 ; Cl] |
| A-083 | 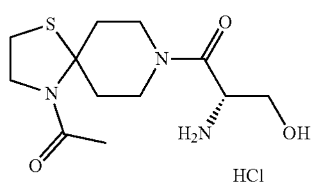 [SMILES: CC(=O)N1CCSC12CCN(C(=O)[C@@H](N)CO)CC2 ; Cl] | A-084 | 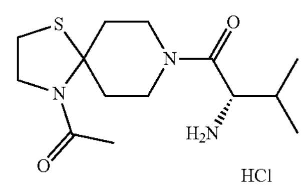 [SMILES: CC(=O)N1CCSC12CCN(C(=O)[C@@H](N)C(C)C)CC2 ; Cl] |
| A-085 | 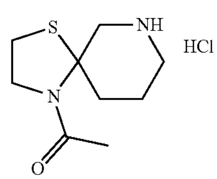 | A-086 | 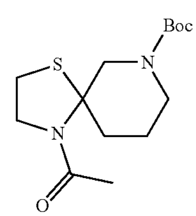 [SMILES: CC(=O)N1CCSC12CCCN(C(=O)OC(C)(C)C)C2] |
| A-087 | 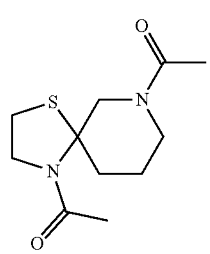 [SMILES: CC(=O)N1CCCC2(C1)SCCN2C(C)=O] | A-088 | 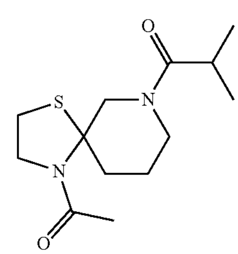 [SMILES: CC(=O)N1CCSC12CCCN(C(=O)C(C)C)C2] |
| A-089 | 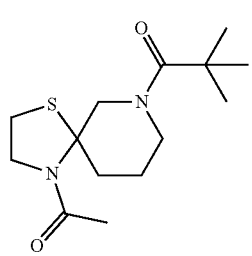 [SMILES: CC(=O)N1CCSC12CCCN(C(=O)C(C)(C)C)C2] | A-090 | 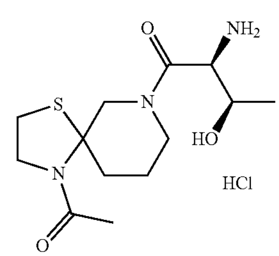 [SMILES: CC(=O)N1CCSC12CCCN(C(=O)[C@@H](N)[C@@H](C)O)C2 ; Cl] |

-continued
| Number | Structural formula | Number | Structural formula |
|---|---|---|---|
| A-091 | 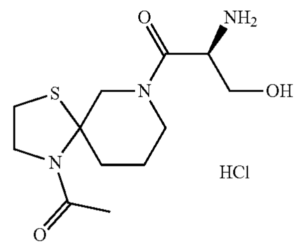 [SMILES: CC(=O)N1CCSC12CCCN(C(=O)[C@@H](N)CO)C2 ; Cl] | A-092 | 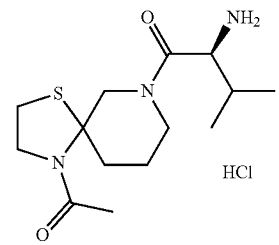 [SMILES: CC(=O)N1CCSC12CCCN(C(=O)[C@@H](N)C(C)C)C2 ; Cl] |
| A-093 | 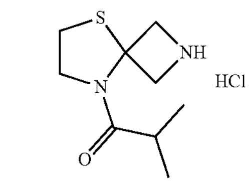 | A-094 | 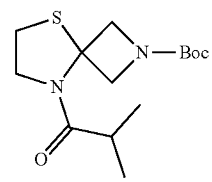 [SMILES: CC(C)C(=O)N1CCSC12CN(C(=O)OC(C)(C)C)C2] |
| A-095 | 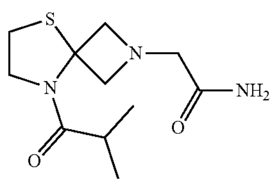 [SMILES: CC(C)C(=O)N1CCSC12CN(CC(N)=O)C2] | A-096 | 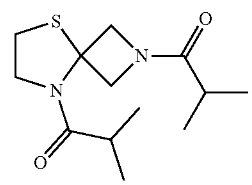 [SMILES: CC(C)C(=O)N1CC2(C1)SCCN2C(=O)C(C)C] |
| A-097 | 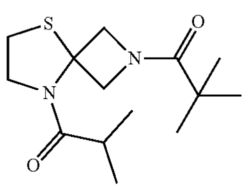 [SMILES: CC(C)C(=O)N1CCSC12CN(C(=O)C(C)(C)C)C2] | A-098 | 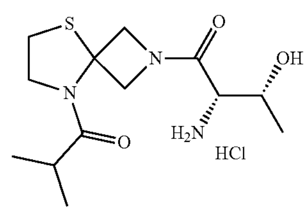 [SMILES: CC(C)C(=O)N1CCSC12CN(C(=O)[C@@H](N)[C@@H](C)O)C2 ; Cl] |
| A-099 | 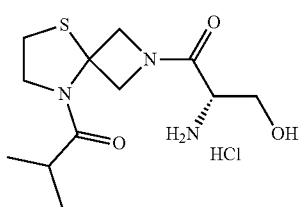 [SMILES: CC(C)C(=O)N1CCSC12CN(C(=O)[C@@H](N)CO)C2 ; Cl] | A-100 | 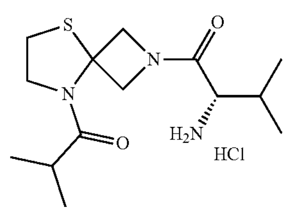 [SMILES: CC(C)C(=O)N1CCSC12CN(C(=O)[C@@H](N)C(C)C)C2 ; Cl] |
| A-101 | 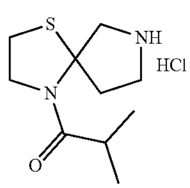 | A-102 | 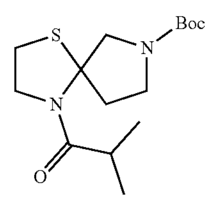 [SMILES: CC(C)C(=O)N1CCSC12CCN(C(=O)OC(C)(C)C)C2] |
| A-103 | 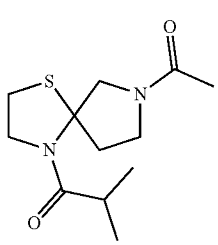 [SMILES: CC(=O)N1CCC2(C1)SCCN2C(=O)C(C)C] | A-104 | 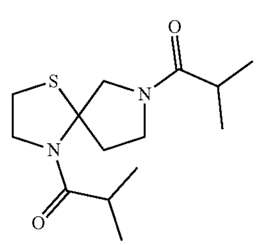 [SMILES: CC(C)C(=O)N1CCC2(C1)SCCN2C(=O)C(C)C] |

-continued
| Number | Structural formula | Number | Structural formula |
|---|---|---|---|
| A-105 | 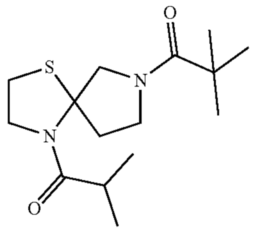 [SMILES: CC(C)C(=O)N1CCSC12CCN(C(=O)C(C)(C)C)C2] | A-106 | 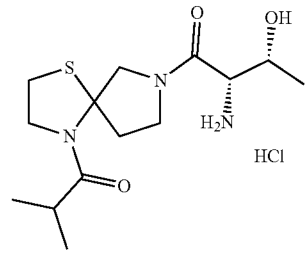 [SMILES: CC(C)C(=O)N1CCSC12CCN(C(=O)[C@@H](N)[C@@H](C)O)C2 ; Cl] |
| A-107 | 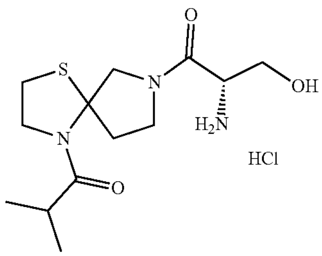 [SMILES: CC(C)C(=O)N1CCSC12CCN(C(=O)[C@@H](N)CO)C2 ; Cl] | A-108 | 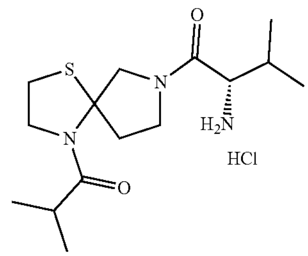 [SMILES: CC(C)C(=O)N1CCSC12CCN(C(=O)[C@@H](N)C(C)C)C2 ; Cl] |
| A-109 | 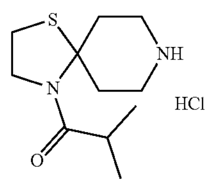 | A-110 | 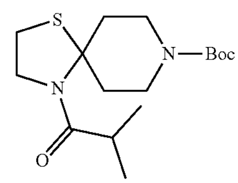 [SMILES: CC(C)C(=O)N1CCSC12CCN(C(=O)OC(C)(C)C)CC2] |
| A-111 | 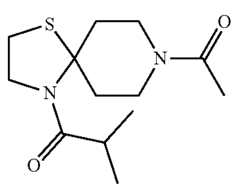 [SMILES: CC(=O)N1CCC2(CC1)SCCN2C(=O)C(C)C] | A-112 | 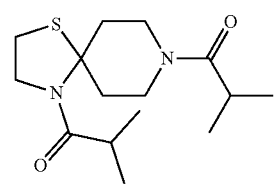 [SMILES: CC(C)C(=O)N1CCC2(CC1)SCCN2C(=O)C(C)C] |
| A-113 | 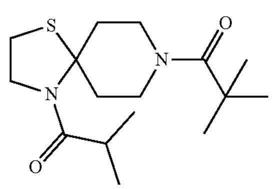 [SMILES: CC(C)C(=O)N1CCSC12CCN(C(=O)C(C)(C)C)CC2] | A-114 | 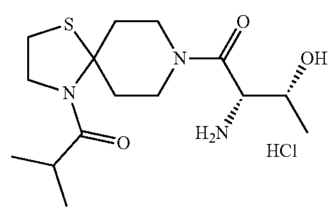 [SMILES: CC(C)C(=O)N1CCSC12CCN(C(=O)[C@@H](N)[C@@H](C)O)CC2 ; Cl] |
| A-115 | 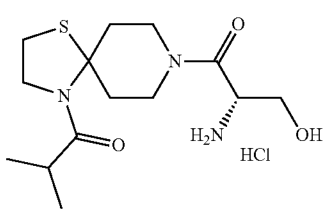 [SMILES: CC(C)C(=O)N1CCSC12CCN(C(=O)[C@@H](N)CO)CC2 ; Cl] | A-116 | 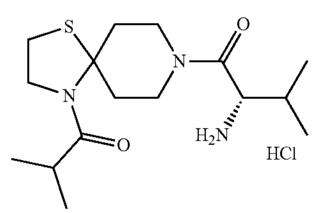 [SMILES: CC(C)C(=O)N1CCSC12CCN(C(=O)[C@@H](N)C(C)C)CC2 ; Cl] |
| A-117 | 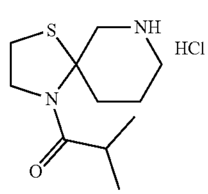 | A-118 | 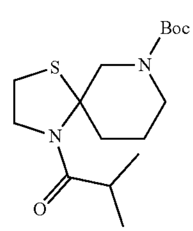 [SMILES: CC(C)C(=O)N1CCSC12CCCN(C(=O)OC(C)(C)C)C2] |

-continued
| Number | Structural formula | Number | Structural formula |
|---|---|---|---|
| A-119 | 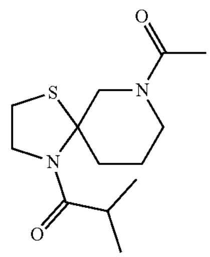 | A-120 | 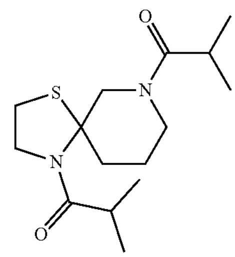 [SMILES: CC(C)C(=O)N1CCCC2(C1)SCCN2C(=O)C(C)C] |
| A-121 | 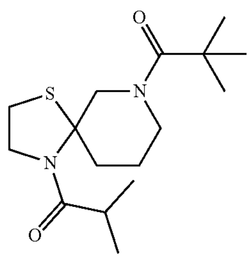 [SMILES: CC(C)C(=O)N1CCSC12CCCN(C(=O)C(C)(C)C)C2] | A-122 | 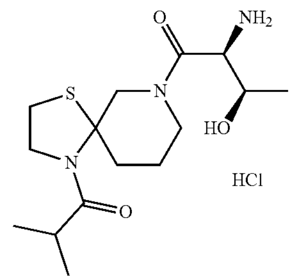 [SMILES: CC(C)C(=O)N1CCSC12CCCN(C(=O)[C@@H](N)[C@@H](C)O)C2 ; Cl] HCl |
| A-123 | 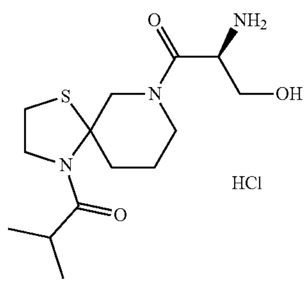 [SMILES: CC(C)C(=O)N1CCSC12CCCN(C(=O)[C@@H](N)CO)C2 ; Cl] HCl | A-124 | 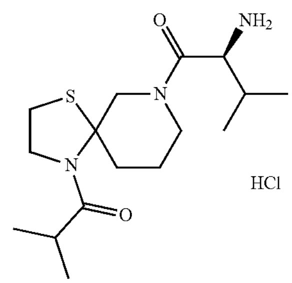 [SMILES: CC(C)C(=O)N1CCSC12CCCN(C(=O)[C@@H](N)C(C)C)C2 ; Cl] HCl |
| A-125 | 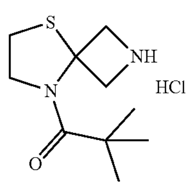 HCl | A-126 | 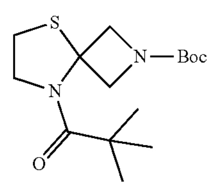 [SMILES: CC(C)(C)OC(=O)N1CC2(C1)SCCN2C(=O)C(C)(C)C] |
| A-127 | 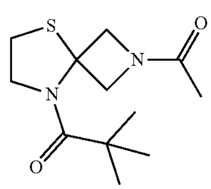 [SMILES: CC(=O)N1CC2(C1)SCCN2C(=O)C(C)(C)C] | A-128 | 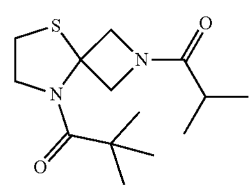 [SMILES: CC(C)C(=O)N1CC2(C1)SCCN2C(=O)C(C)(C)C] |
| A-129 | 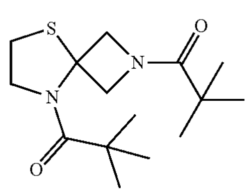 [SMILES: CC(C)(C)C(=O)N1CC2(C1)SCCN2C(=O)C(C)(C)C] | A-130 | 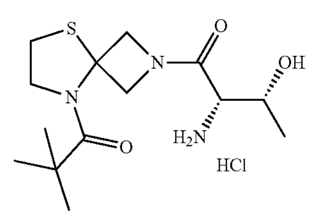 [SMILES: C[C@@H](O)[C@H](N)C(=O)N1CC2(C1)SCCN2C(=O)C(C)(C)C ; Cl] HCl |

-continued
| Number | Structural formula | Number | Structural formula |
|---|---|---|---|
| A-131 | 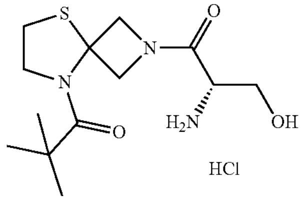 [SMILES: CC(C)(C)C(=O)N1CCSC12CN(C(=O)[C@@H](N)CO)C2 ; Cl] | A-132 | 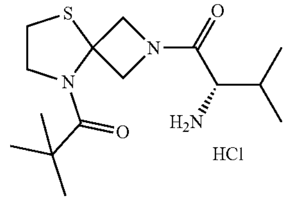 [SMILES: CC(C)[C@H](N)C(=O)N1CC2(C1)SCCN2C(=O)C(C)(C)C ; Cl] |
| A-133 | 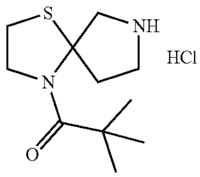 | A-134 | 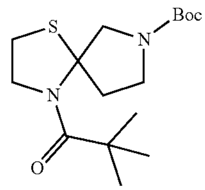 [SMILES: CC(C)(C)OC(=O)N1CCC2(C1)SCCN2C(=O)C(C)(C)C] |
| A-135 | 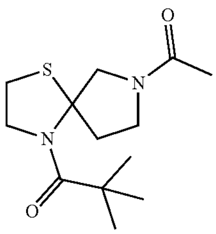 [SMILES: CC(=O)N1CCC2(C1)SCCN2C(=O)C(C)(C)C] | A-136 | 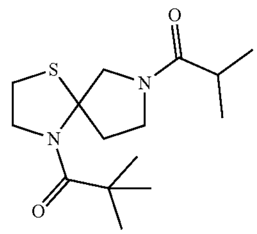 [SMILES: CC(C)C(=O)N1CCC2(C1)SCCN2C(=O)C(C)(C)C] |
| A-137 | 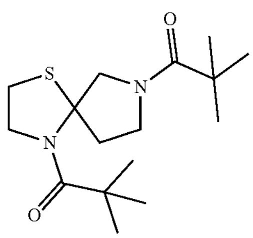 [SMILES: CC(C)(C)C(=O)N1CCC2(C1)SCCN2C(=O)C(C)(C)C] | A-138 | 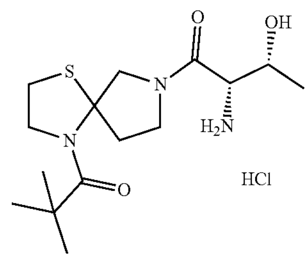 [SMILES: C[C@@H](O)[C@H](N)C(=O)N1CCC2(C1)SCCN2C(=O)C(C)(C)C ; Cl] |
| A-139 | 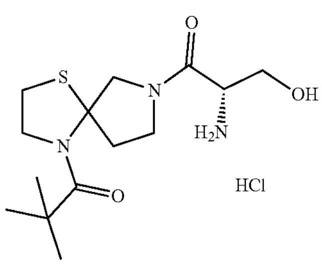 [SMILES: CC(C)(C)C(=O)N1CCSC12CCN(C(=O)[C@@H](N)CO)C2 ; Cl] | A-140 | 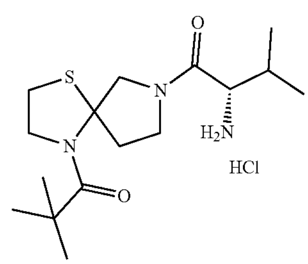 [SMILES: CC(C)[C@H](N)C(=O)N1CCC2(C1)SCCN2C(=O)C(C)(C)C ; Cl] |
| A-141 | 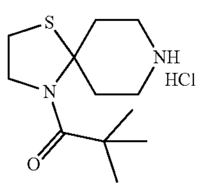 [SMILES: CC(C)(C)C(=O)N1CCSC12CCNCC2 ; Cl] | A-142 | 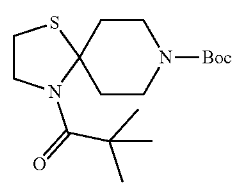 [SMILES: CC(C)(C)OC(=O)N1CCC2(CC1)SCCN2C(=O)C(C)(C)C] |
| A-143 | 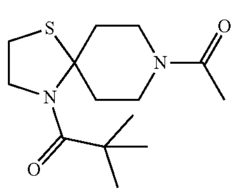 [SMILES: CC(=O)N1CCC2(CC1)SCCN2C(=O)C(C)(C)C] | A-144 | 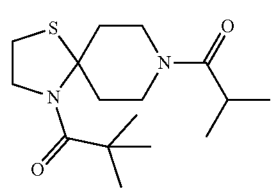 [SMILES: CC(C)C(=O)N1CCC2(CC1)SCCN2C(=O)C(C)(C)C] |

-continued
| Number | Structural formula | Number | Structural formula |
| --- | --- | --- | --- |
| A-145 | 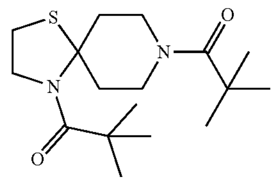 [SMILES: CC(C)(C)C(=O)N1CCC2(CC1)SCCN2C(=O)C(C)(C)C] | A-146 | 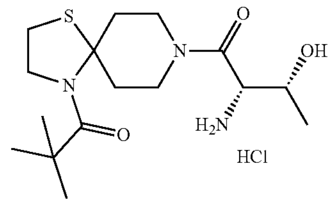 [SMILES: C[C@@H](O)[C@H](N)C(=O)N1CCC2(CC1)SCCN2C(=O)C(C)(C)C ; Cl] |
| A-147 | 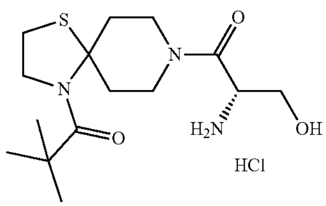 [SMILES: CC(C)(C)C(=O)N1CCSC12CCN(C(=O)[C@@H](N)CO)CC2 ; Cl] | A-148 | 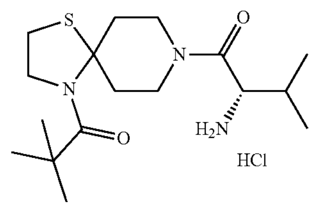 [SMILES: CC(C)[C@H](N)C(=O)N1CCC2(CC1)SCCN2C(=O)C(C)(C)C ; Cl] |
| A-149 | 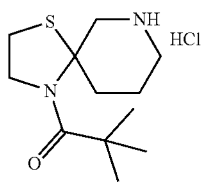 [SMILES: CC(C)(C)C(=O)N1CCSC12CCCNC2 ; Cl] | A-150 | 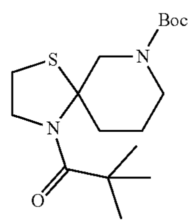 [SMILES: CC(C)(C)OC(=O)N1CCCC2(C1)SCCN2C(=O)C(C)(C)C] |
| A-151 | 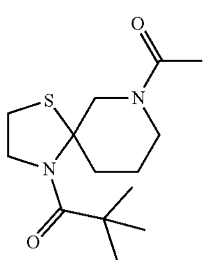 [SMILES: CC(=O)N1CCCC2(C1)SCCN2C(=O)C(C)(C)C] | A-152 | 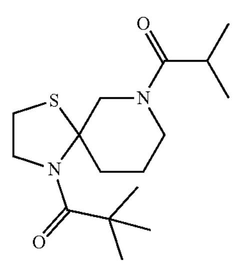 [SMILES: CC(C)C(=O)N1CCCC2(C1)SCCN2C(=O)C(C)(C)C] |
| A-153 | 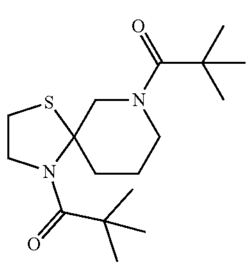 [SMILES: CC(C)(C)C(=O)N1CCCC2(C1)SCCN2C(=O)C(C)(C)C] | A-154 | 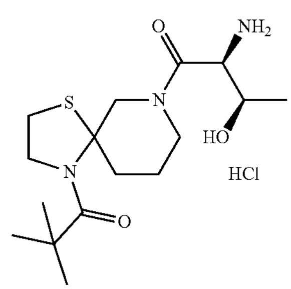 [SMILES: C[C@@H](O)[C@H](N)C(=O)N1CCCC2(C1)SCCN2C(=O)C(C)(C)C ; Cl] |
| A-155 | 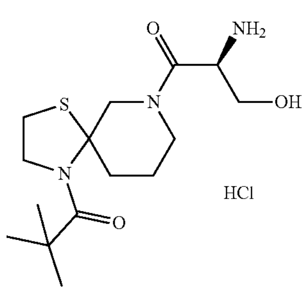 [SMILES: CC(C)(C)C(=O)N1CCSC12CCCN(C(=O)[C@@H](N)CO)C2 ; Cl] | A-156 | 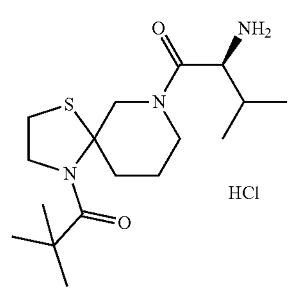 [SMILES: CC(C)[C@H](N)C(=O)N1CCCC2(C1)SCCN2C(=O)C(C)(C)C ; Cl] |

-continued
| Number | Structural formula | Number | Structural formula |
|---|---|---|---|
| A-157 | 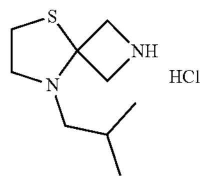 | A-158 | 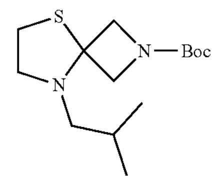 [SMILES: CC(C)CN1CCSC12CN(C(=O)OC(C)(C)C)C2] |
| A-159 | 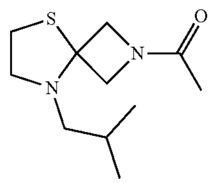 | A-160 | 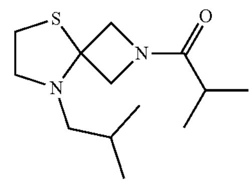 [SMILES: CC(C)CN1CCSC12CN(C(=O)C(C)C)C2] |
| A-161 | 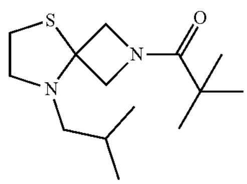 [SMILES: CC(C)CN1CCSC12CN(C(=O)C(C)(C)C)C2] | A-162 | 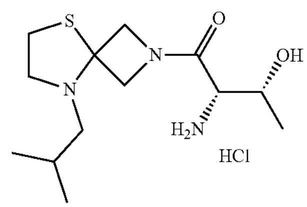 [SMILES: CC(C)CN1CCSC12CN(C(=O)[C@@H](N)[C@@H](C)O)C2 ; Cl] |
| A-163 | 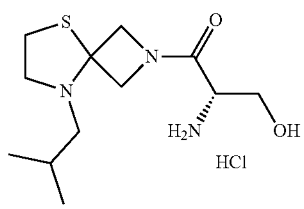 [SMILES: CC(C)CN1CCSC12CN(C(=O)[C@@H](N)CO)C2 ; Cl] | A-164 | 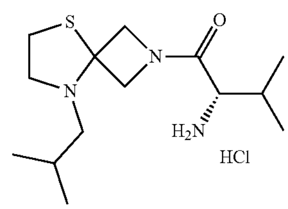 [SMILES: CC(C)CN1CCSC12CN(C(=O)[C@@H](N)C(C)C)C2 ; Cl] |
| A-165 | 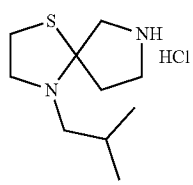 | A-166 | 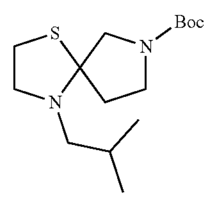 [SMILES: CC(C)CN1CCSC12CCN(C(=O)OC(C)(C)C)C2] |
| A-167 | 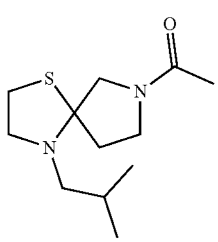 [SMILES: CC(=O)N1CCC2(C1)SCCN2CC(C)C] | A-168 | 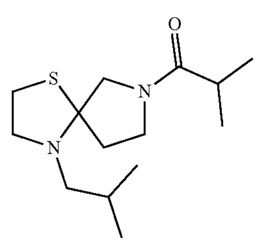 [SMILES: CC(C)CN1CCSC12CCN(C(=O)C(C)C)C2] |
| A-169 | 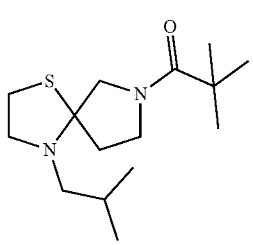 [SMILES: CC(C)CN1CCSC12CCN(C(=O)C(C)(C)C)C2] | A-170 | 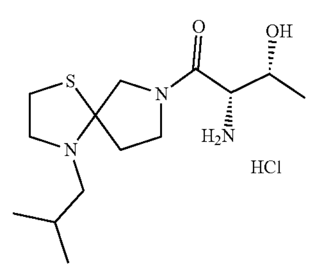 [SMILES: CC(C)CN1CCSC12CCN(C(=O)[C@@H](N)[C@@H](C)O)C2 ; Cl] |

-continued
| Number | Structural formula | Number | Structural formula |
|---|---|---|---|
| A-171 | 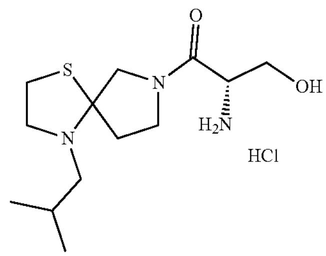 [SMILES: CC(C)CN1CCSC12CCN(C(=O)[C@@H](N)CO)C2 ; Cl] | A-172 | 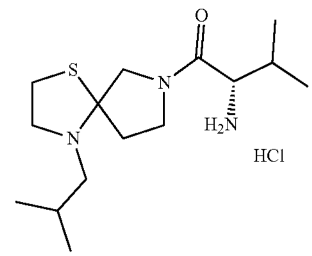 [SMILES: CC(C)CN1CCSC12CCN(C(=O)[C@@H](N)C(C)C)C2 ; Cl] |
| A-173 | 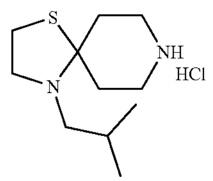 | A-174 | 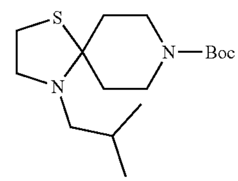 [SMILES: CC(C)CN1CCSC12CCN(C(=O)OC(C)(C)C)CC2] |
| A-175 | 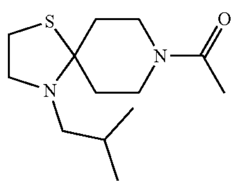 [SMILES: CC(=O)N1CCC2(CC1)SCCN2CC(C)C] | A-176 | 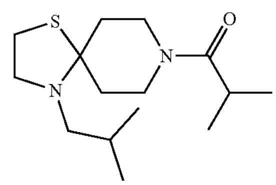 [SMILES: CC(C)CN1CCSC12CCN(C(=O)C(C)C)CC2] |
| A-177 | 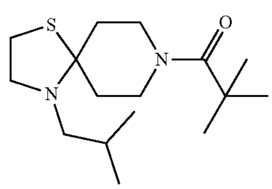 [SMILES: CC(C)CN1CCSC12CCN(C(=O)C(C)(C)C)CC2] | A-178 | 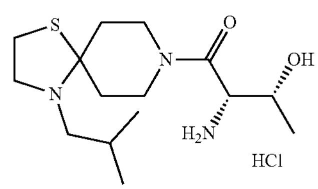 [SMILES: CC(C)CN1CCSC12CCN(C(=O)[C@@H](N)[C@@H](C)O)CC2 ; Cl] |
| A-179 | 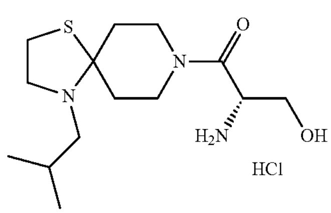 [SMILES: CC(C)CN1CCSC12CCN(C(=O)[C@@H](N)CO)CC2 ; Cl] | A-180 | 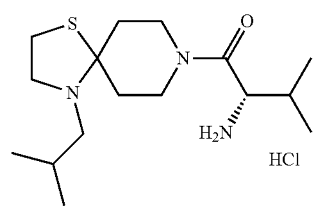 [SMILES: CC(C)CN1CCSC12CCN(C(=O)[C@@H](N)C(C)C)CC2 ; Cl] |
| A-181 | 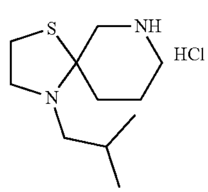 | A-182 | 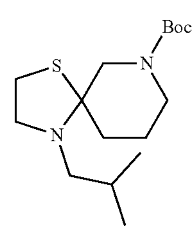 [SMILES: CC(C)CN1CCSC12CCCN(C(=O)OC(C)(C)C)C2] |
| A-183 | 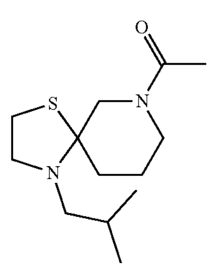 [SMILES: CC(=O)N1CCCC2(C1)SCCN2CC(C)C] | A-184 | 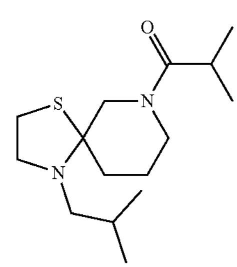 [SMILES: CC(C)CN1CCSC12CCCN(C(=O)C(C)C)C2] |

-continued
| Number | Structural formula | Number | Structural formula |
|---|---|---|---|
| A-185 | 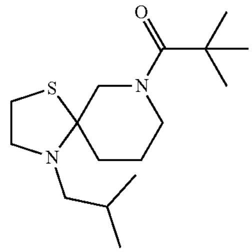 [SMILES: CC(C)CN1CCSC12CCCN(C(=O)C(C)(C)C)C2] | A-186 | 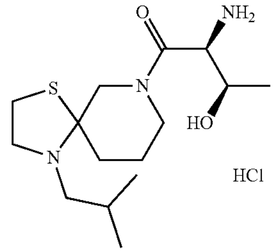 [SMILES: CC(C)CN1CCSC12CCCN(C(=O)[C@@H](N)[C@@H](C)O)C2 ; Cl] |
| A-187 | 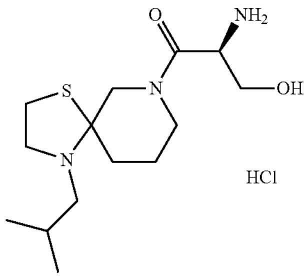 [SMILES: CC(C)CN1CCSC12CCCN(C(=O)[C@@H](N)CO)C2 ; Cl] | A-188 | 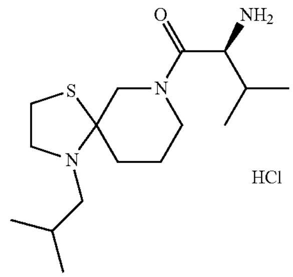 [SMILES: CC(C)CN1CCSC12CCCN(C(=O)[C@@H](N)C(C)C)C2 ; Cl] |
| A-189 | 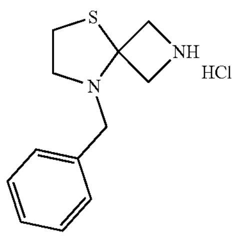 [SMILES: c1ccc(CN2CCSC23CNC3)cc1 ; Cl] | A-190 | 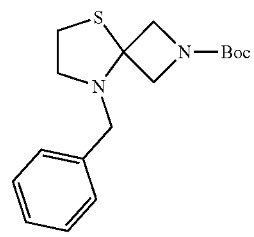 [SMILES: CC(C)(C)OC(=O)N1CC2(C1)SCCN2Cc1ccccc1] |
| A-191 | 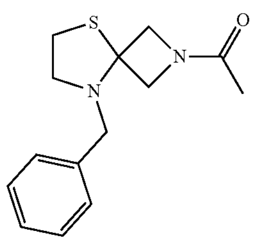 [SMILES: CC(=O)N1CC2(C1)SCCN2Cc1ccccc1] | A-192 | 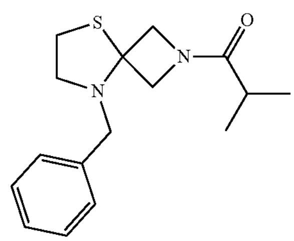 [SMILES: CC(C)C(=O)N1CC2(C1)SCCN2Cc1ccccc1] |
| A-193 | 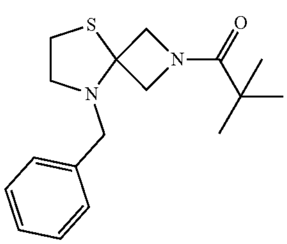 [SMILES: CC(C)(C)C(=O)N1CC2(C1)SCCN2Cc1ccccc1] | A-194 | 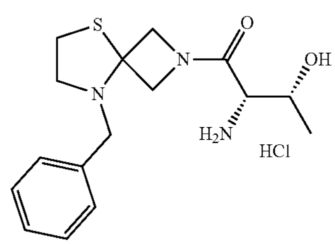 [SMILES: C[C@@H](O)[C@H](N)C(=O)N1CC2(C1)SCCN2Cc1ccccc1 ; Cl] |
| A-195 | 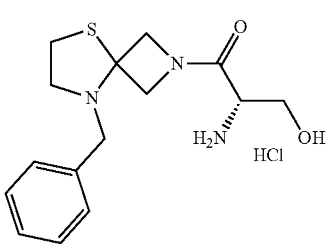 [SMILES: N[C@@H](CO)C(=O)N1CC2(C1)SCCN2Cc1ccccc1 ; Cl] | A-196 | 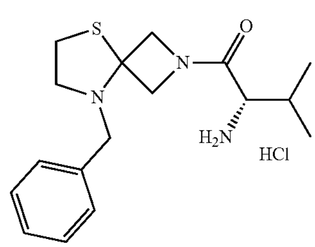 [SMILES: CC(C)[C@H](N)C(=O)N1CC2(C1)SCCN2Cc1ccccc1 ; Cl] |

-continued
| Number | Structural formula | Number | Structural formula |
|---|---|---|---|
| A-197 | 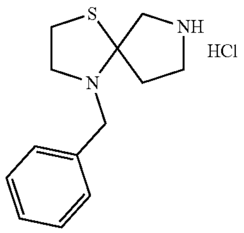 [SMILES: c1ccc(CN2CCSC23CCNC3)cc1 ; Cl] | A-198 | 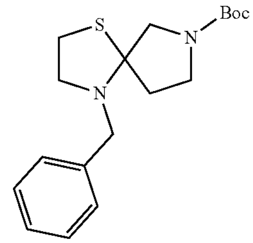 [SMILES: CC(C)(C)OC(=O)N1CCC2(C1)SCCN2Cc1ccccc1] |
| A-199 | 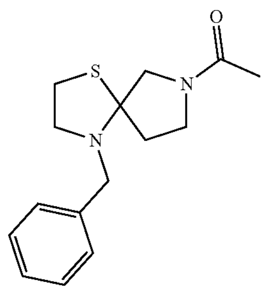 [SMILES: CC(=O)N1CCC2(C1)SCCN2Cc1ccccc1] | A-200 | 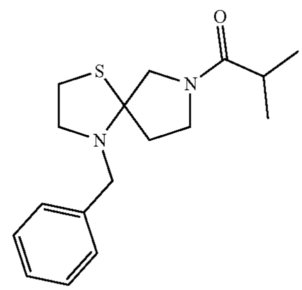 [SMILES: CC(C)C(=O)N1CCC2(C1)SCCN2Cc1ccccc1] |
| A-201 | 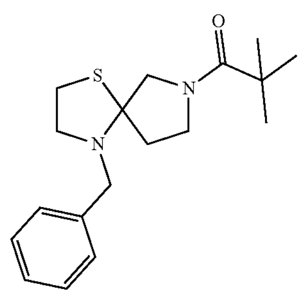 [SMILES: CC(C)(C)C(=O)N1CCC2(C1)SCCN2Cc1ccccc1] | A-202 | 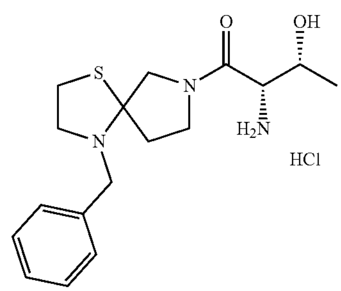 [SMILES: C[C@@H](O)[C@H](N)C(=O)N1CCC2(C1)SCCN2Cc1ccccc1 ; Cl] |
| A-203 | 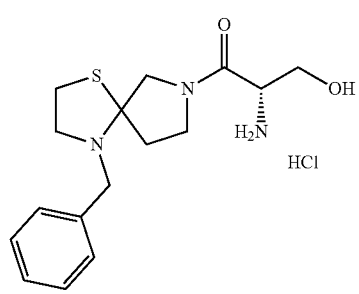 [SMILES: N[C@@H](CO)C(=O)N1CCC2(C1)SCCN2Cc1ccccc1 ; Cl] | A-204 | 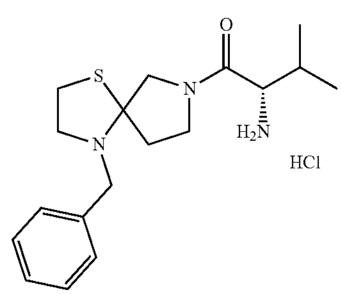 [SMILES: CC(C)[C@H](N)C(=O)N1CCC2(C1)SCCN2Cc1ccccc1 ; Cl] |
| A-205 | 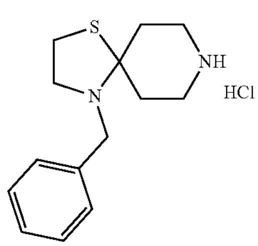 [SMILES: c1ccc(CN2CCSC23CCNCC3)cc1 ; Cl] | A-206 | 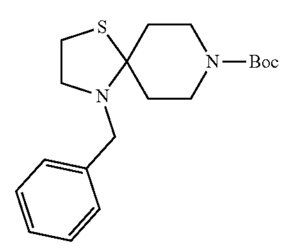 [SMILES: CC(C)(C)OC(=O)N1CCC2(CC1)SCCN2Cc1ccccc1] |
| A-207 | 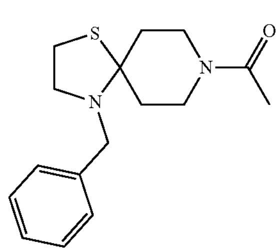 [SMILES: CC(=O)N1CCC2(CC1)SCCN2Cc1ccccc1] | A-208 | 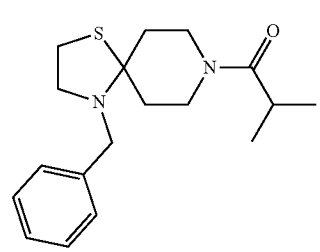 [SMILES: CC(C)C(=O)N1CCC2(CC1)SCCN2Cc1ccccc1] |

-continued
| Number | Structural formula | Number | Structural formula |
| --- | --- | --- | --- |
| A-209 | 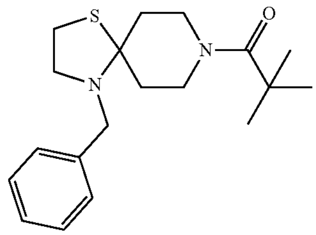 [SMILES: CC(C)(C)C(=O)N1CCC2(CC1)SCCN2Cc1ccccc1] | A-210 | 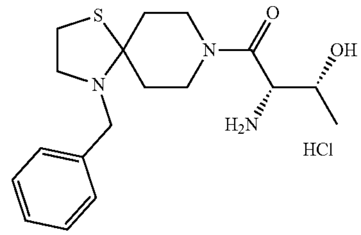 [SMILES: C[C@@H](O)[C@H](N)C(=O)N1CCC2(CC1)SCCN2Cc1ccccc1 ; Cl] |
| A-211 | 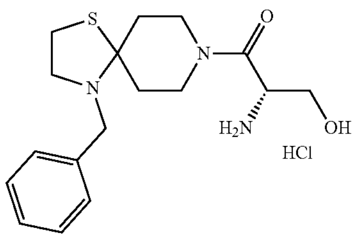 [SMILES: N[C@@H](CO)C(=O)N1CCC2(CC1)SCCN2Cc1ccccc1 ; Cl] | A-212 | 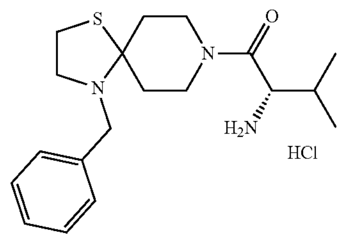 [SMILES: CC(C)[C@H](N)C(=O)N1CCC2(CC1)SCCN2Cc1ccccc1 ; Cl] |
| A-213 | 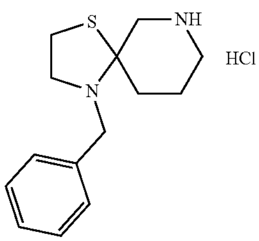 [SMILES: c1ccc(CN2CCSC23CCCNC3)cc1 ; Cl] | A-214 | 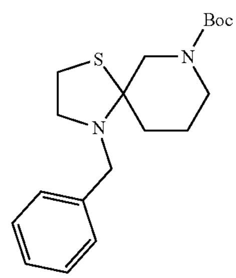 [SMILES: CC(C)(C)OC(=O)N1CCCC2(C1)SCCN2Cc1ccccc1] |
| A-215 | 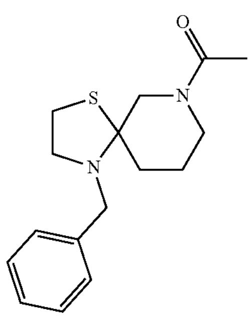 [SMILES: CC(=O)N1CCCC2(C1)SCCN2Cc1ccccc1] | A-216 | 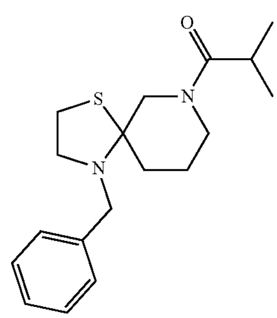 [SMILES: CC(C)C(=O)N1CCCC2(C1)SCCN2Cc1ccccc1] |
| A-217 | 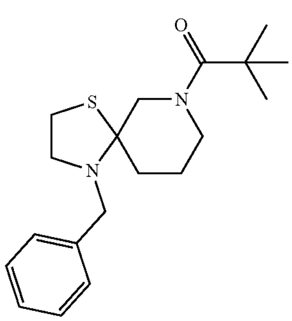 [SMILES: CC(C)(C)C(=O)N1CCCC2(C1)SCCN2Cc1ccccc1] | A-218 | 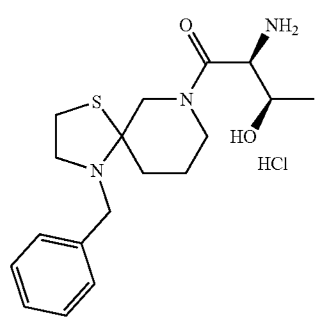 [SMILES: C[C@@H](O)[C@H](N)C(=O)N1CCCC2(C1)SCCN2Cc1ccccc1 ; Cl] |

-continued
| Number | Structural formula | Number | Structural formula |
|---|---|---|---|
| A-219 | 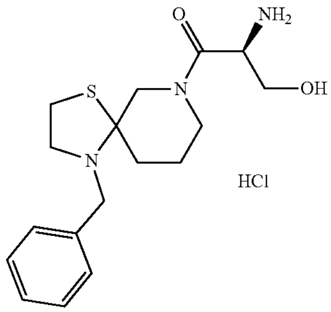 [SMILES: N[C@@H](CO)C(=O)N1CCCC2(C1)SCCN2Cc1ccccc1 ; Cl] HCl | A-220 | 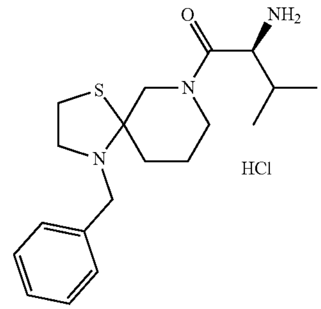 [SMILES: CC(C)[C@H](N)C(=O)N1CCCC2(C1)SCCN2Cc1ccccc1 ; Cl] HCl |
| A-221 | 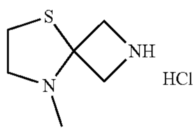 HCl | A-222 | 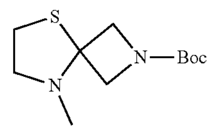 [SMILES: CN1CCSC12CN(C(=O)OC(C)(C)C)C2] |
| A-223 | 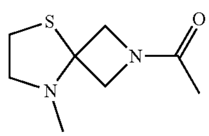 | A-224 | 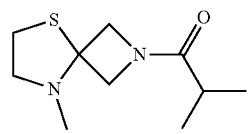 |
| A-225 | 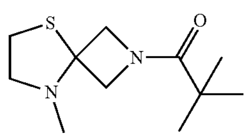 | A-226 | 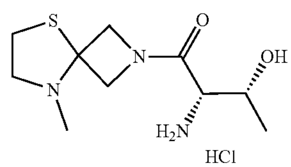 [SMILES: C[C@@H](O)[C@H](N)C(=O)N1CC2(C1)SCCN2C ; Cl] HCl |
| A-227 | 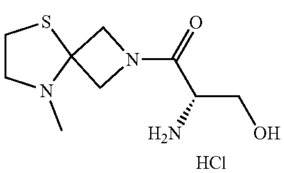 HCl | A-228 | 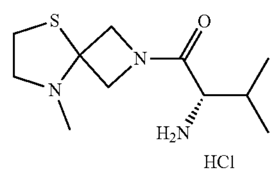 [SMILES: CC(C)[C@H](N)C(=O)N1CC2(C1)SCCN2C ; Cl] HCl |
| A-229 | 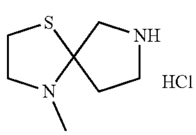 HCl | A-230 | 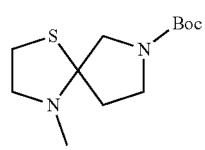 [SMILES: CN1CCSC12CCN(C(=O)OC(C)(C)C)C2] |
| A-231 | 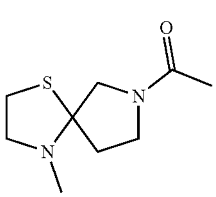 | A-232 | 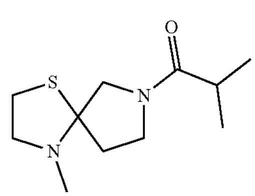 |
| A-233 | 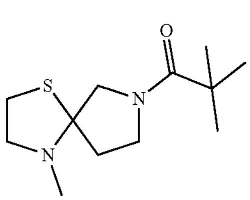 [SMILES: CN1CCSC12CCN(C(=O)C(C)(C)C)C2] | A-234 | 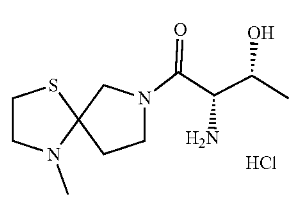 [SMILES: C[C@@H](O)[C@H](N)C(=O)N1CCC2(C1)SCCN2C ; Cl] HCl |

-continued
| Number | Structural formula | Number | Structural formula |
|---|---|---|---|
| A-235 | 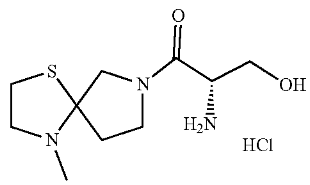 [SMILES: CN1CCSC12CCN(C(=O)[C@@H](N)CO)C2 ; Cl] | A-236 | 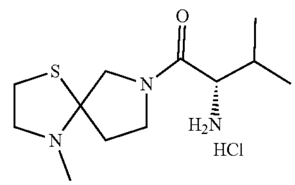 [SMILES: CC(C)[C@H](N)C(=O)N1CCC2(C1)SCCN2C ; Cl] |
| A-237 | 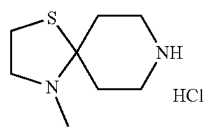 | A-238 | 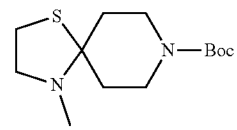 [SMILES: CN1CCSC12CCN(C(=O)OC(C)(C)C)CC2] |
| A-239 | 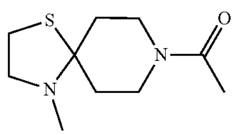 | A-240 | 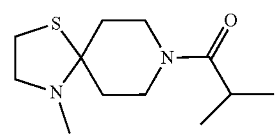 [SMILES: CC(C)C(=O)N1CCC2(CC1)SCCN2C] |
| A-241 | 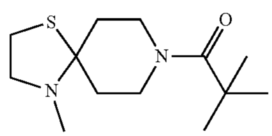 [SMILES: CN1CCSC12CCN(C(=O)C(C)(C)C)CC2] | A-242 | 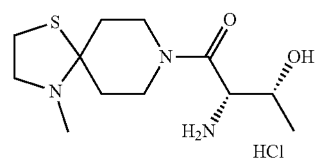 [SMILES: C[C@@H](O)[C@H](N)C(=O)N1CCC2(CC1)SCCN2C ; Cl] |
| A-243 | 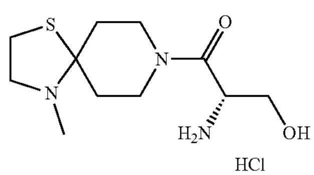 [SMILES: CN1CCSC12CCN(C(=O)[C@@H](N)CO)CC2 ; Cl] | A-244 | 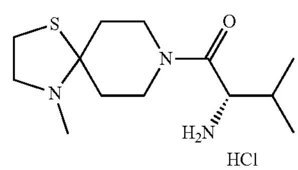 [SMILES: CC(C)[C@H](N)C(=O)N1CCC2(CC1)SCCN2C ; Cl] |
| A-245 | 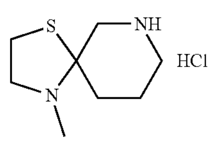 | A-246 | 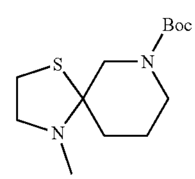 [SMILES: CN1CCSC12CCCN(C(=O)OC(C)(C)C)C2] |
| A-247 | 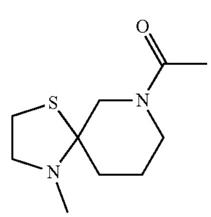 | A-248 | 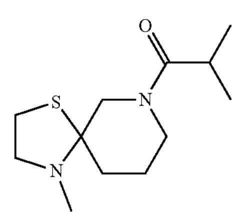 [SMILES: CC(C)C(=O)N1CCCC2(C1)SCCN2C] |
| A-249 | 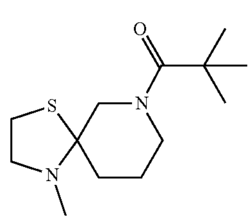 [SMILES: CN1CCSC12CCCN(C(=O)C(C)(C)C)C2] | A-250 | 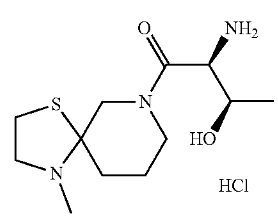 [SMILES: C[C@@H](O)[C@H](N)C(=O)N1CCCC2(C1)SCCN2C ; Cl] |

-continued
| Number | Structural formula | Number | Structural formula |
|---|---|---|---|
| A-251 | 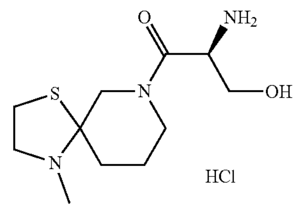 [SMILES: CN1CCSC12CCCN(C(=O)[C@@H](N)CO)C2 ; Cl] | A-252 | 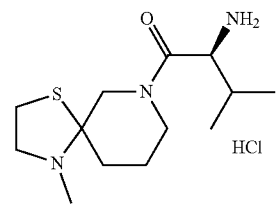 [SMILES: CC(C)[C@H](N)C(=O)N1CCCC2(C1)SCCN2C ; Cl] |
| A-253 | 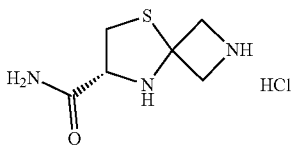 [SMILES: NC(=O)[C@@H]1CSC2(CNC2)N1 ; Cl] | A-254 | 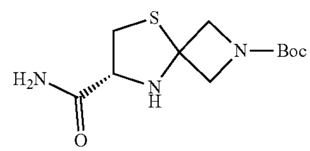 [SMILES: CC(C)(C)OC(=O)N1CC2(C1)N[C@H](C(N)=O)CS2] |
| A-255 | 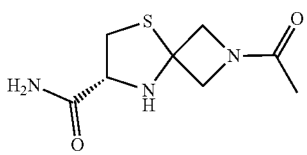 | A-256 | 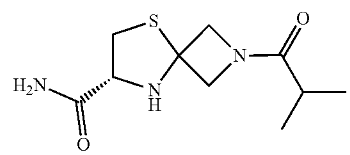 [SMILES: CC(C)C(=O)N1CC2(C1)N[C@H](C(N)=O)CS2] |
| A-257 | 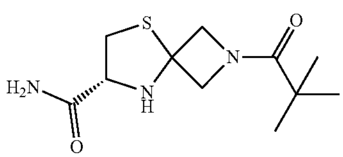 [SMILES: CC(C)(C)C(=O)N1CC2(C1)N[C@H](C(N)=O)CS2] | A-258 | 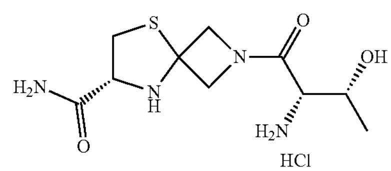 [SMILES: C[C@@H](O)[C@H](N)C(=O)N1CC2(C1)N[C@H](C(N)=O)CS2 ; Cl] |
| A-259 | 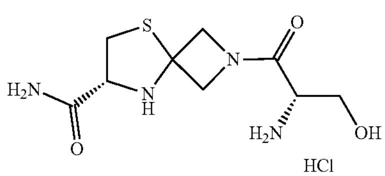 [SMILES: NC(=O)[C@@H]1CSC2(CN(C(=O)[C@@H](N)CO)C2)N1 ; Cl] | A-260 | 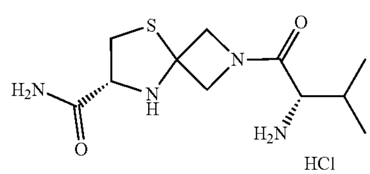 [SMILES: CC(C)[C@H](N)C(=O)N1CC2(C1)N[C@H](C(N)=O)CS2 ; Cl] |
| A-261 | 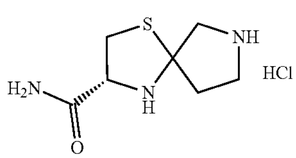 [SMILES: NC(=O)[C@@H]1CSC2(CCNC2)N1 ; Cl] | A-262 | 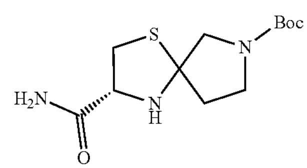 [SMILES: CC(C)(C)OC(=O)N1CCC2(C1)N[C@H](C(N)=O)CS2] |
| A-263 | 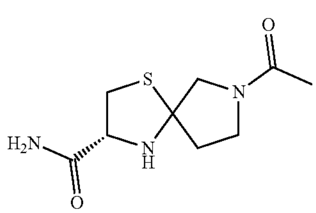 | A-264 | 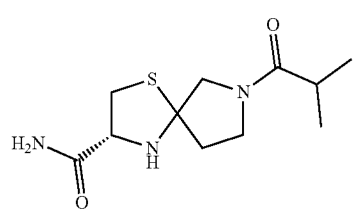 [SMILES: CC(C)C(=O)N1CCC2(C1)N[C@H](C(N)=O)CS2] |
| A-265 | 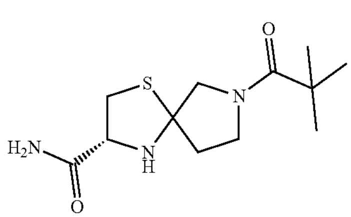 [SMILES: CC(C)(C)C(=O)N1CCC2(C1)N[C@H](C(N)=O)CS2] | A-266 | 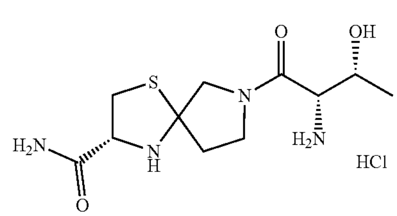 [SMILES: C[C@@H](O)[C@H](N)C(=O)N1CCC2(C1)N[C@H](C(N)=O)CS2 ; Cl] |

-continued
| Number | Structural formula | Number | Structural formula |
| --- | --- | --- | --- |
| A-267 | 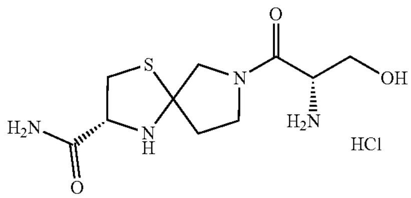 [SMILES: NC(=O)[C@@H]1CSC2(CCN(C(=O)[C@@H](N)CO)C2)N1 ; Cl] | A-268 | 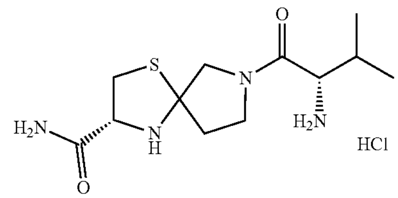 [SMILES: CC(C)[C@H](N)C(=O)N1CCC2(C1)N[C@H](C(N)=O)CS2 ; Cl] |
| A-269 | 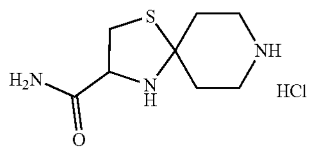 [SMILES: NC(=O)C1CSC2(CCNCC2)N1 ; Cl] | A-270 | 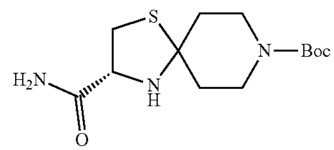 [SMILES: CC(C)(C)OC(=O)N1CCC2(CC1)N[C@H](C(N)=O)CS2] |
| A-271 | 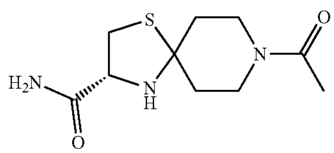 [SMILES: CC(=O)N1CCC2(CC1)N[C@H](C(N)=O)CS2] | A-272 | 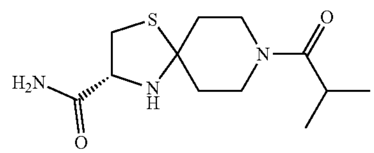 |
| A-273 | 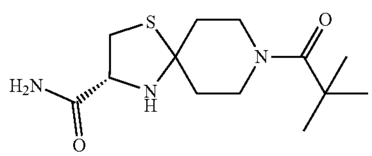 [SMILES: CC(C)(C)C(=O)N1CCC2(CC1)N[C@H](C(N)=O)CS2] | A-274 | 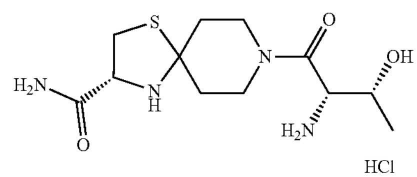 [SMILES: C[C@@H](O)[C@H](N)C(=O)N1CCC2(CC1)N[C@H](C(N)=O)CS2 ; Cl] |
| A-275 | 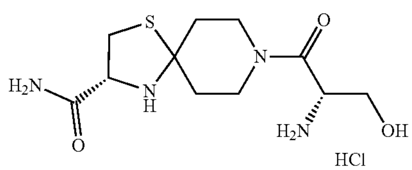 [SMILES: NC(=O)[C@@H]1CSC2(CCN(C(=O)[C@@H](N)CO)CC2)N1 ; Cl] | A-276 | 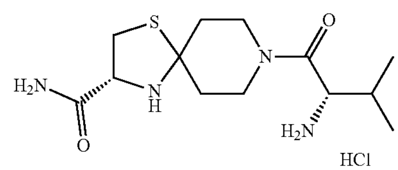 [SMILES: CC(C)[C@H](N)C(=O)N1CCC2(CC1)N[C@H](C(N)=O)CS2 ; Cl] |
| A-277 | 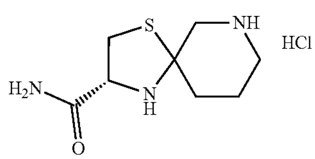 [SMILES: NC(=O)[C@@H]1CSC2(CCCNC2)N1 ; Cl] | A-278 | 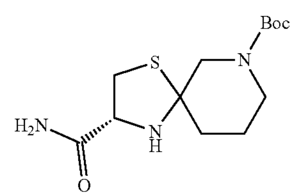 [SMILES: CC(C)(C)OC(=O)N1CCCC2(C1)N[C@H](C(N)=O)CS2] |
| A-279 | 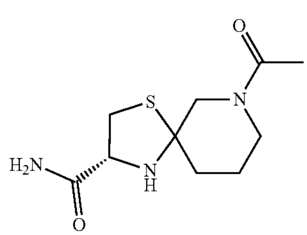 [SMILES: CC(=O)N1CCCC2(C1)N[C@H](C(N)=O)CS2] | A-280 | 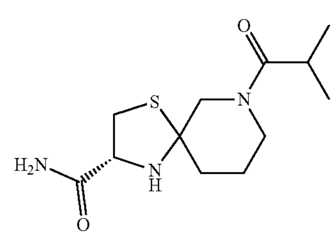 [SMILES: CC(C)C(=O)N1CCCC2(C1)N[C@H](C(N)=O)CS2] |
| A-281 | 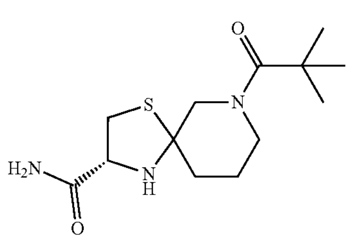 [SMILES: CC(C)(C)C(=O)N1CCCC2(C1)N[C@H](C(N)=O)CS2] | A-282 | 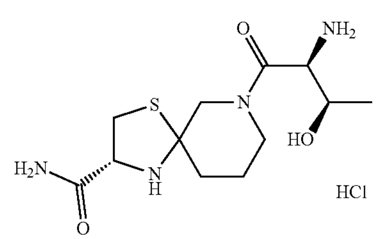 [SMILES: C[C@@H](O)[C@H](N)C(=O)N1CCCC2(C1)N[C@H](C(N)=O)CS2 ; Cl] |

-continued
| Number | Structural formula | Number | Structural formula |
|---|---|---|---|
| A-283 | 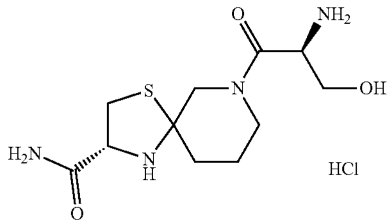 [SMILES: NC(=O)[C@@H]1CSC2(CCCN(C(=O)[C@@H](N)CO)C2)N1 ; Cl] | A-284 | 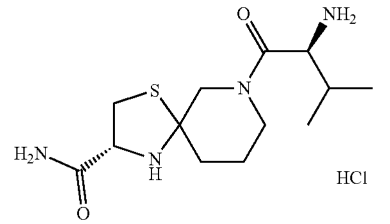 [SMILES: CC(C)[C@H](N)C(=O)N1CCCC2(C1)N[C@H](C(N)=O)CS2 ; Cl] |
| A-285 | 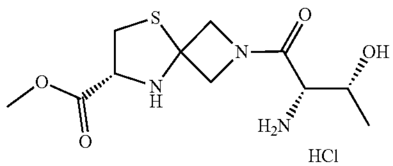 [SMILES: COC(=O)[C@@H]1CSC2(CN(C(=O)[C@@H](N)[C@@H](C)O)C2)N1 ; Cl] | A-286 | 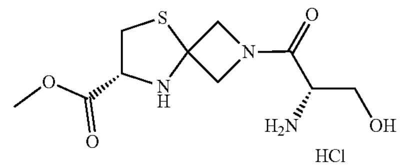 [SMILES: COC(=O)[C@@H]1CSC2(CN(C(=O)[C@@H](N)CO)C2)N1 ; Cl] |
| A-287 | 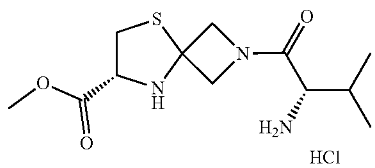 [SMILES: COC(=O)[C@@H]1CSC2(CN(C(=O)[C@@H](N)C(C)C)C2)N1 ; Cl] | A-288 | 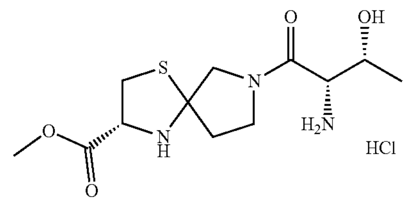 [SMILES: COC(=O)[C@@H]1CSC2(CCN(C(=O)[C@@H](N)[C@@H](C)O)C2)N1 ; Cl] |
| A-289 | 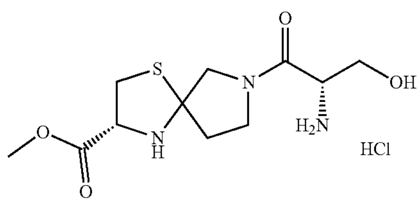 [SMILES: COC(=O)[C@@H]1CSC2(CCN(C(=O)[C@@H](N)CO)C2)N1 ; Cl] | A-290 | 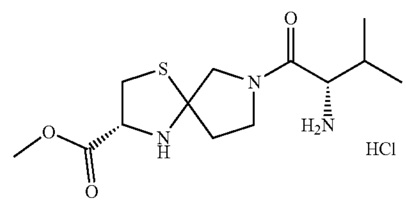 [SMILES: COC(=O)[C@@H]1CSC2(CCN(C(=O)[C@@H](N)C(C)C)C2)N1 ; Cl] |
| A-291 | 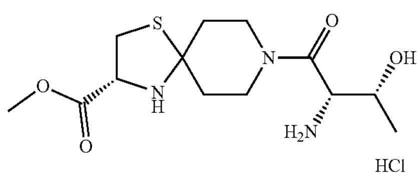 [SMILES: COC(=O)[C@@H]1CSC2(CCN(C(=O)[C@@H](N)[C@@H](C)O)CC2)N1 ; Cl] | A-292 | 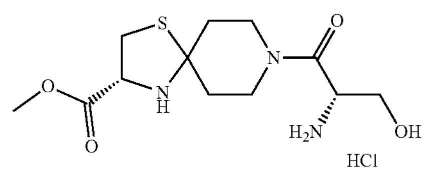 [SMILES: COC(=O)[C@@H]1CSC2(CCN(C(=O)[C@@H](N)CO)CC2)N1 ; Cl] |
| A-293 | 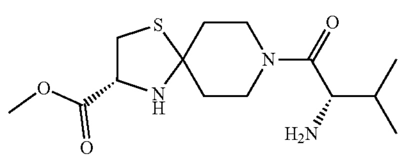 | A-294 | 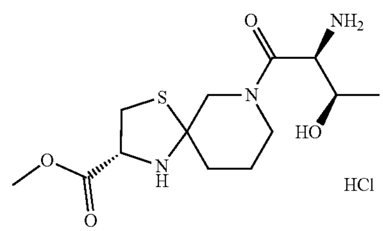 [SMILES: COC(=O)[C@@H]1CSC2(CCCN(C(=O)[C@@H](N)[C@@H](C)O)C2)N1 ; Cl] |
| A-295 | 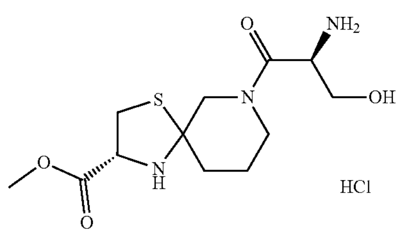 [SMILES: COC(=O)[C@@H]1CSC2(CCCN(C(=O)[C@@H](N)CO)C2)N1 ; Cl] | A-296 | 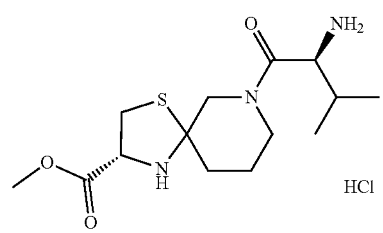 [SMILES: COC(=O)[C@@H]1CSC2(CCCN(C(=O)[C@@H](N)C(C)C)C2)N1 ; Cl] |
| A-297 | 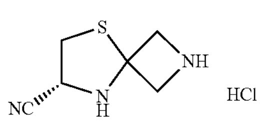 | A-298 | 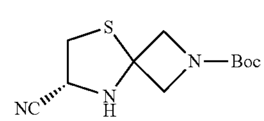 [SMILES: CC(C)(C)OC(=O)N1CC2(C1)N[C@H](C#N)CS2] |

-continued
| Number | Structural formula | Number | Structural formula |
|---|---|---|---|
| A-299 | 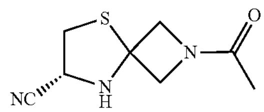 | A-300 | 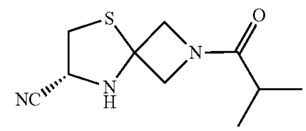 |
| A-301 | 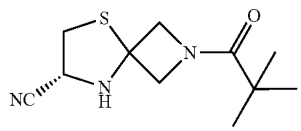 [SMILES: CC(C)(C)C(=O)N1CC2(C1)N[C@H](C#N)CS2] | A-302 | 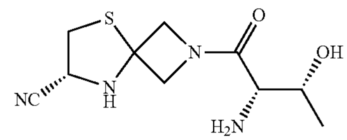<br>HCl |
| A-303 | 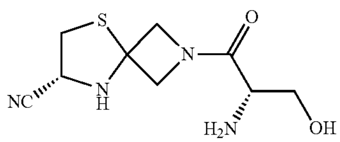<br>HCl | A-304 | 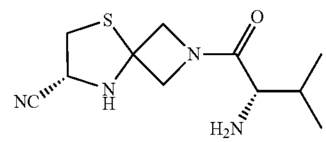<br>HCl |
| A-305 | 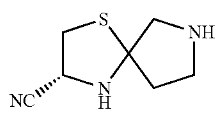 HCl | A-306 | 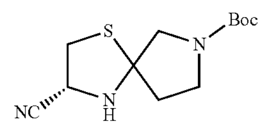 [SMILES: CC(C)(C)OC(=O)N1CCC2(C1)N[C@H](C#N)CS2] |
| A-307 | 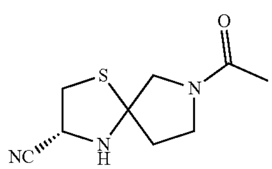 | A-308 | 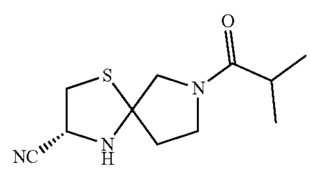 [SMILES: CC(C)C(=O)N1CCC2(C1)N[C@H](C#N)CS2] |
| A-309 | 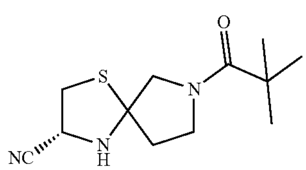 [SMILES: CC(C)(C)C(=O)N1CCC2(C1)N[C@H](C#N)CS2] | A-310 | 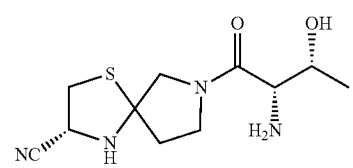 [SMILES: C[C@@H](O)[C@H](N)C(=O)N1CCC2(C1)N[C@H](C#N)CS2] |
| A-311 | 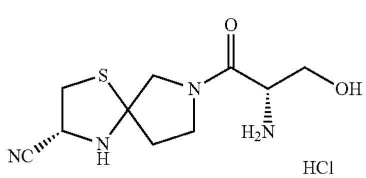 [SMILES: N#C[C@@H]1CSC2(CCN(C(=O)[C@@H](N)CO)C2)N1 ; Cl]<br>HCl | A-312 | 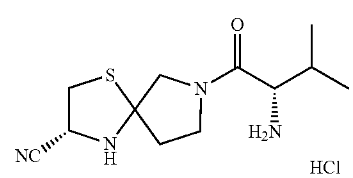 [SMILES: CC(C)[C@H](N)C(=O)N1CCC2(C1)N[C@H](C#N)CS2 ; Cl]<br>HCl |
| A-313 | 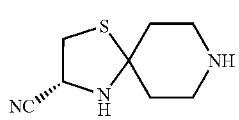<br>HCl | A-314 | 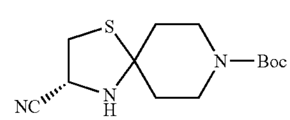 [SMILES: CC(C)(C)OC(=O)N1CCC2(CC1)N[C@H](C#N)CS2] |
| A-315 | 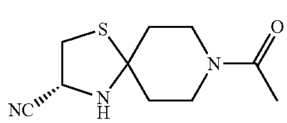 | A-316 | 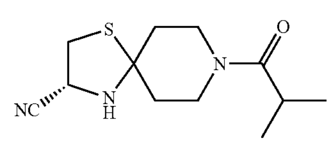 [SMILES: CC(C)C(=O)N1CCC2(CC1)N[C@H](C#N)CS2] |
| A-317 | 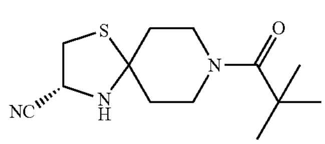 [SMILES: CC(C)(C)C(=O)N1CCC2(CC1)N[C@H](C#N)CS2] | A-318 | 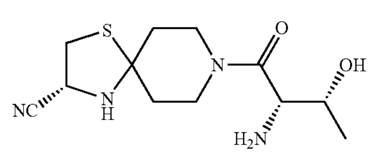<br>HCl |

-continued
| Number | Structural formula | Number | Structural formula |
|---|---|---|---|
| A-319 | 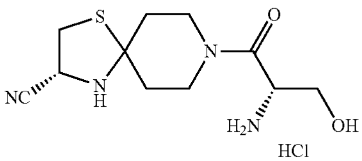 [SMILES: N#C[C@@H]1CSC2(CCN(C(=O)[C@@H](N)CO)CC2)N1 ; Cl] | A-320 | 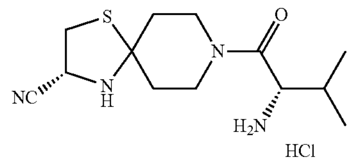 [SMILES: CC(C)[C@H](N)C(=O)N1CCC2(CC1)N[C@H](C#N)CS2 ; Cl] |
| A-321 | 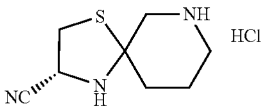 [SMILES: N#C[C@@H]1CSC2(CCCNC2)N1 ; Cl] | A-322 | 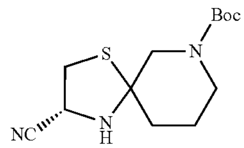 [SMILES: CC(C)(C)OC(=O)N1CCCC2(C1)N[C@H](C#N)CS2] |
| A-323 | 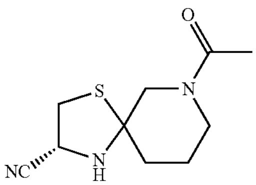 | A-324 | 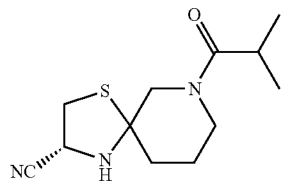 [SMILES: CC(C)C(=O)N1CCCC2(C1)N[C@H](C#N)CS2] |
| A-325 | 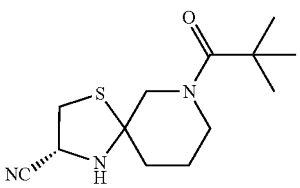 [SMILES: CC(C)(C)C(=O)N1CCCC2(C1)N[C@H](C#N)CS2] | A-326 | 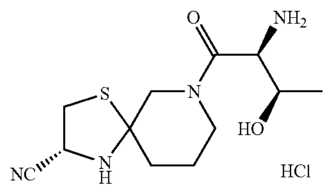 [SMILES: C[C@@H](O)[C@H](N)C(=O)N1CCCC2(C1)N[C@H](C#N)CS2 ; Cl] |
| A-327 | 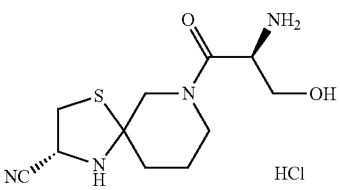 [SMILES: N#C[C@@H]1CSC2(CCCN(C(=O)[C@@H](N)CO)C2)N1 ; Cl] | A-328 | 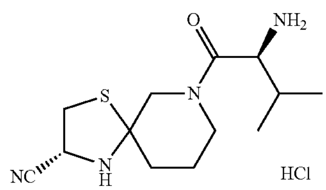 [SMILES: CC(C)[C@H](N)C(=O)N1CCCC2(C1)N[C@H](C#N)CS2 ; Cl] |
| A-329 | 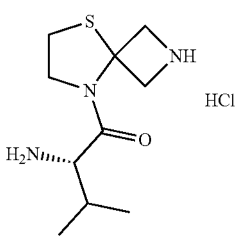 | A-330 | 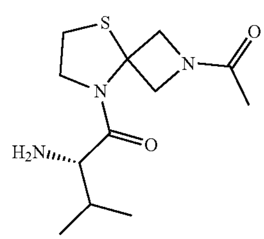 [SMILES: CC(=O)N1CC2(C1)SCCN2C(=O)[C@@H](N)C(C)C] |
| A-331 | 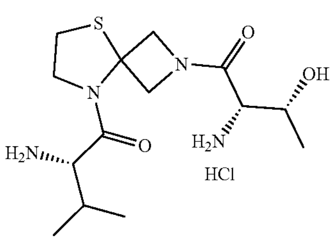 [SMILES: CC(C)[C@H](N)C(=O)N1CCSC12CN(C(=O)[C@@H](N)[C@@H](C)O)C2 ; Cl] | A-332 | 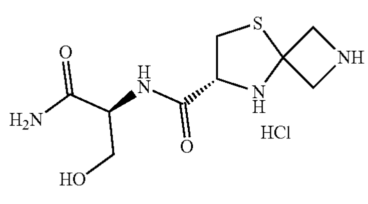 [SMILES: NC(=O)[C@H](CO)NC(=O)[C@@H]1CSC2(CNC2)N1 ; Cl] |
| A-333 | 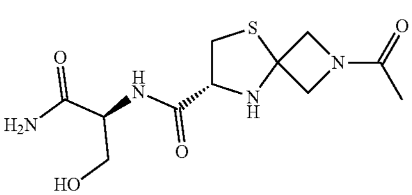 [SMILES: CC(=O)N1CC2(C1)N[C@H](C(=O)N[C@@H](CO)C(N)=O)CS2] | A-334 | 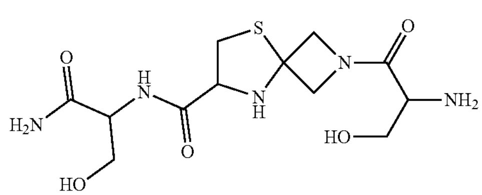 [SMILES: NC(=O)C(CO)NC(=O)C1CSC2(CN(C(=O)C(N)CO)C2)N1] |

-continued
| Number | Structural formula | Number | Structural formula |
|---|---|---|---|
| A-335 | 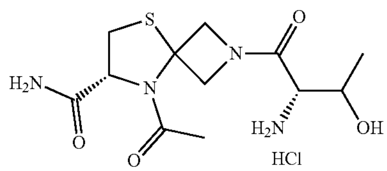 [SMILES: CC(=O)N1[C@H](C(N)=O)CSC12CN(C(=O)[C@@H](N)C(C)O)C2 ; Cl] | A-336 | 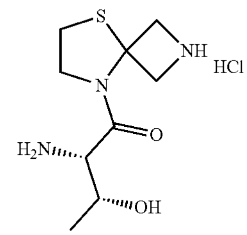 |
| A-337 | 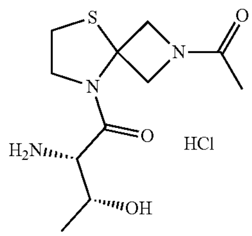 [SMILES: CC(=O)N1CC2(C1)SCCN2C(=O)[C@@H](N)[C@@H](C)O ; Cl] | A-338 | 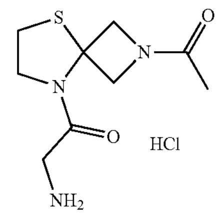 |
| A-339 | 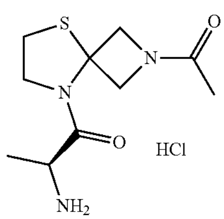 [SMILES: CC(=O)N1CC2(C1)SCCN2C(=O)[C@H](C)N ; Cl] | A-340 | 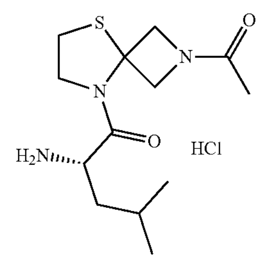 [SMILES: CC(=O)N1CC2(C1)SCCN2C(=O)[C@@H](N)CC(C)C ; Cl] |
| A-341 | 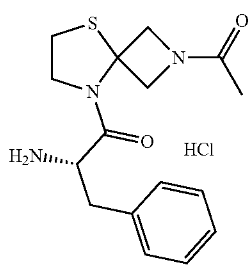 [SMILES: CC(=O)N1CC2(C1)SCCN2C(=O)[C@@H](N)Cc1ccccc1 ; Cl] | A-342 | 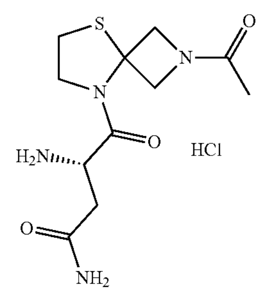 [SMILES: CC(=O)N1CC2(C1)SCCN2C(=O)[C@@H](N)CC(N)=O ; Cl] |
| A-343 | 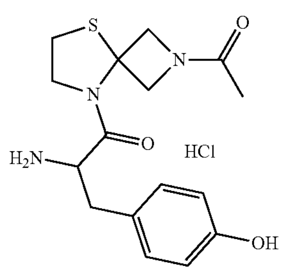 [SMILES: CC(=O)N1CC2(C1)SCCN2C(=O)C(N)Cc1ccc(O)cc1 ; Cl] | A-344 | 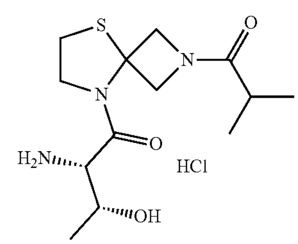 [SMILES: CC(C)C(=O)N1CC2(C1)SCCN2C(=O)[C@@H](N)[C@@H](C)O ; Cl] |
| A-345 | 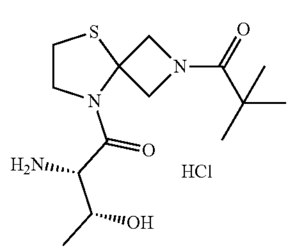 [SMILES: C[C@@H](O)[C@H](N)C(=O)N1CCSC12CN(C(=O)C(C)(C)C)C2 ; Cl] | A-346 | 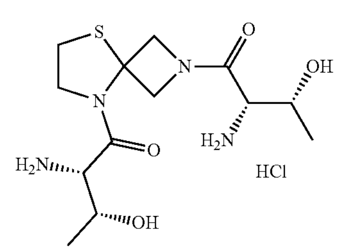 [SMILES: C[C@@H](O)[C@H](N)C(=O)N1CC2(C1)SCCN2C(=O)[C@@H](N)[C@@H](C)O ; Cl] |

-continued
| Number | Structural formula | Number | Structural formula |
|---|---|---|---|
| A-347 | 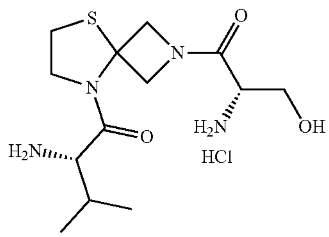 [SMILES: CC(C)[C@H](N)C(=O)N1CCSC12CN(C(=O)[C@@H](N)CO)C2 ; Cl] | A-348 | 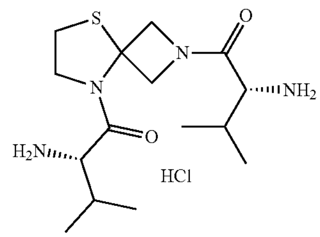 [SMILES: CC(C)[C@H](N)C(=O)N1CCSC12CN(C(=O)[C@H](N)C(C)C)C2 ; Cl] |
| A-349 | 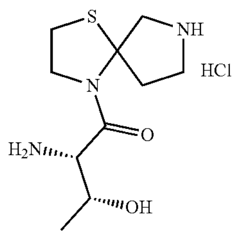 [SMILES: C[C@@H](O)[C@H](N)C(=O)N1CCSC12CCNC2 ; Cl] | A-350 | 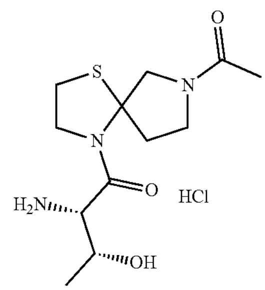 [SMILES: CC(=O)N1CCC2(C1)SCCN2C(=O)[C@@H](N)[C@@H](C)O ; Cl] |
| A-351 | 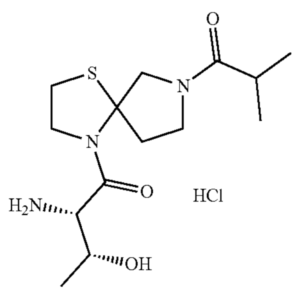 [SMILES: CC(C)C(=O)N1CCC2(C1)SCCN2C(=O)[C@@H](N)[C@@H](C)O ; Cl] | A-352 | 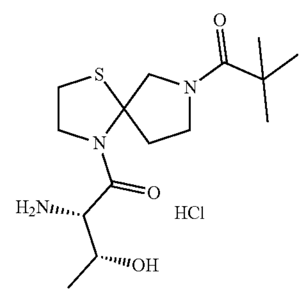 [SMILES: C[C@@H](O)[C@H](N)C(=O)N1CCSC12CCN(C(=O)C(C)(C)C)C2 ; Cl] |
| A-353 | 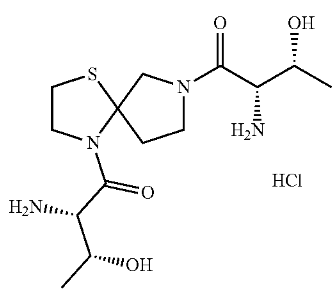 [SMILES: C[C@@H](O)[C@H](N)C(=O)N1CCC2(C1)SCCN2C(=O)[C@@H](N)[C@@H](C)O ; Cl] | A-354 | 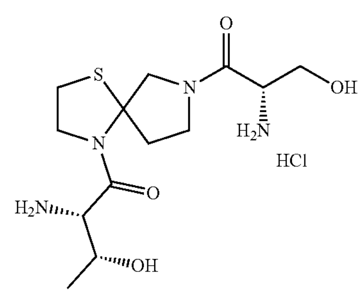 [SMILES: C[C@@H](O)[C@H](N)C(=O)N1CCSC12CCN(C(=O)[C@@H](N)CO)C2 ; Cl] |
| A-355 | 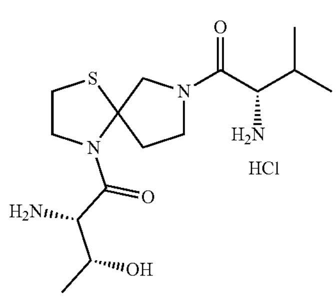 [SMILES: CC(C)[C@H](N)C(=O)N1CCC2(C1)SCCN2C(=O)[C@@H](N)[C@@H](C)O ; Cl] | A-356 | 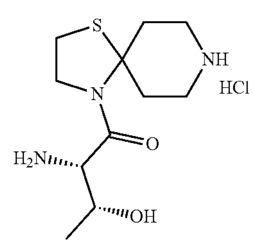 [SMILES: C[C@@H](O)[C@H](N)C(=O)N1CCSC12CCNCC2 ; Cl] |

-continued
| Number | Structural formula | Number | Structural formula |
|---|---|---|---|
| A-357 | 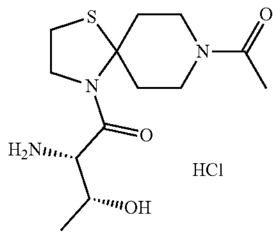 [SMILES: CC(=O)N1CCC2(CC1)SCCN2C(=O)[C@@H](N)[C@@H](C)O ; Cl] | A-358 | 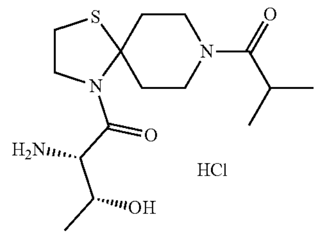 [SMILES: CC(C)C(=O)N1CCC2(CC1)SCCN2C(=O)[C@@H](N)[C@@H](C)O ; Cl] |
| A-359 | 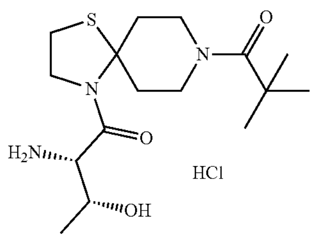 [SMILES: C[C@@H](O)[C@H](N)C(=O)N1CCSC12CCN(C(=O)C(C)(C)C)CC2 ; Cl] | A-360 | 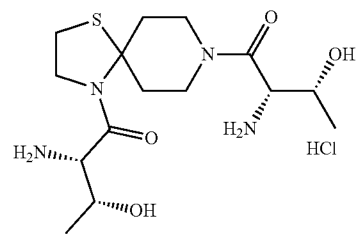 [SMILES: C[C@@H](O)[C@H](N)C(=O)N1CCC2(CC1)SCCN2C(=O)[C@@H](N)[C@@H](C)O ; Cl] |
| A-361 | 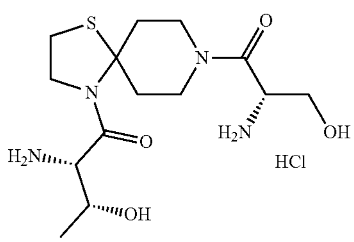 [SMILES: C[C@@H](O)[C@H](N)C(=O)N1CCSC12CCN(C(=O)[C@@H](N)CO)CC2 ; Cl] | A-362 | 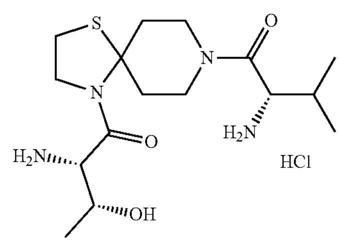 [SMILES: CC(C)[C@H](N)C(=O)N1CCC2(CC1)SCCN2C(=O)[C@@H](N)[C@@H](C)O ; Cl] |
| A-363 | 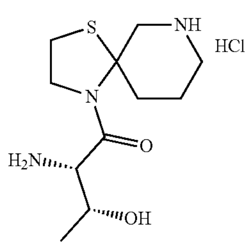 [SMILES: C[C@@H](O)[C@H](N)C(=O)N1CCSC12CCCNC2 ; Cl] | A-364 | 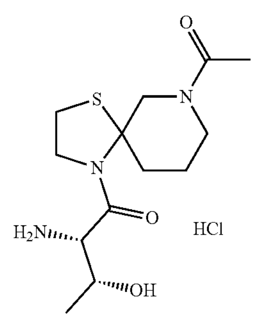 [SMILES: CC(=O)N1CCCC2(C1)SCCN2C(=O)[C@@H](N)[C@@H](C)O ; Cl] |
| A-365 | 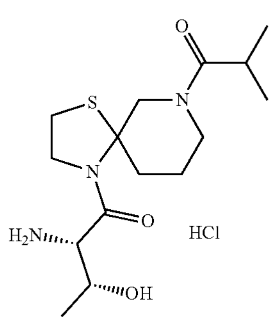 [SMILES: CC(C)C(=O)N1CCCC2(C1)SCCN2C(=O)[C@@H](N)[C@@H](C)O ; Cl] | A-366 | 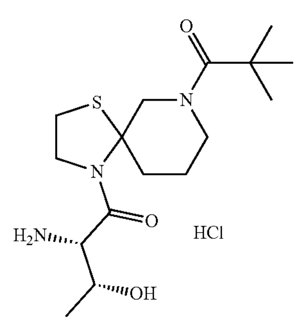 [SMILES: C[C@@H](O)[C@H](N)C(=O)N1CCSC12CCCN(C(=O)C(C)(C)C)C2 ; Cl] |

-continued
| Number | Structural formula | Number | Structural formula |
|---|---|---|---|
| A-367 | 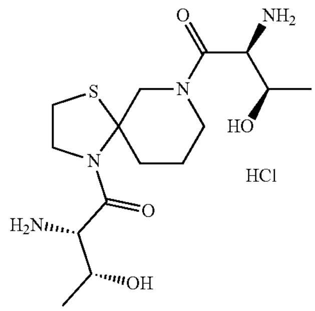 [SMILES: C[C@@H](O)[C@H](N)C(=O)N1CCCC2(C1)SCCN2C(=O)[C@@H](N)[C@@H](C)O ; Cl] | A-368 | 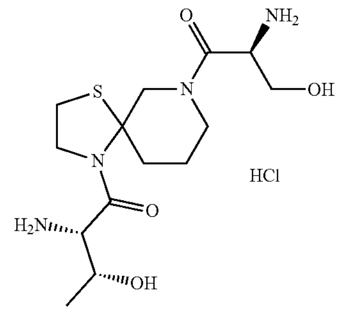 [SMILES: C[C@@H](O)[C@H](N)C(=O)N1CCSC12CCCN(C(=O)[C@@H](N)CO)C2 ; Cl] |
| A-369 | 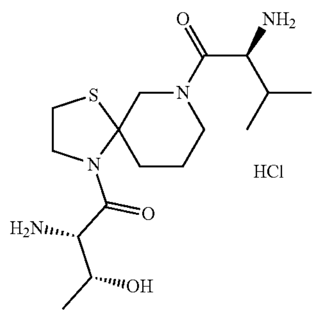 [SMILES: CC(C)[C@H](N)C(=O)N1CCCC2(C1)SCCN2C(=O)[C@@H](N)[C@@H](C)O ; Cl] | A-370 | 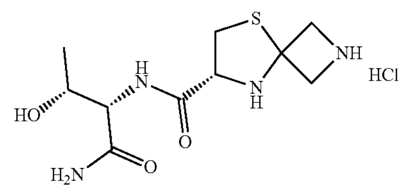 [SMILES: C[C@@H](O)[C@H](NC(=O)[C@@H]1CSC2(CNC2)N1)C(N)=O ; Cl] |
| A-371 | 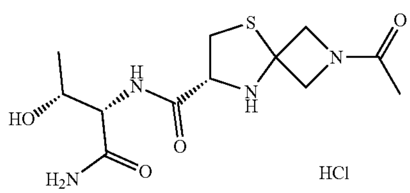 [SMILES: CC(=O)N1CC2(C1)N[C@H](C(=O)N[C@H](C(N)=O)[C@@H](C)O)CS2 ; Cl] | A-372 | 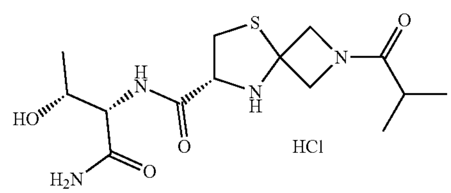 [SMILES: CC(C)C(=O)N1CC2(C1)N[C@H](C(=O)N[C@H](C(N)=O)[C@@H](C)O)CS2 ; Cl] |
| A-373 | 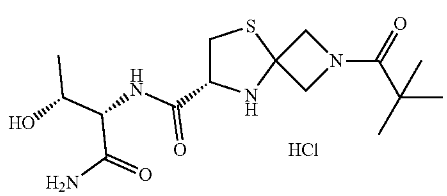 [SMILES: C[C@@H](O)[C@H](NC(=O)[C@@H]1CSC2(CN(C(=O)C(C)(C)C)C2)N1)C(N)=O ; Cl] | A-374 | 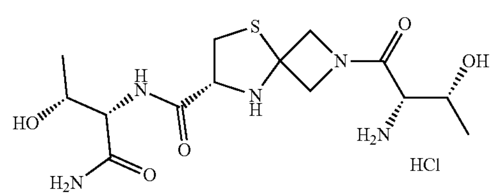 [SMILES: C[C@@H](O)[C@H](N)C(=O)N1CC2(C1)N[C@H](C(=O)N[C@H](C(N)=O)[C@@H](C)O)CS2 ; Cl] |
| A-375 | 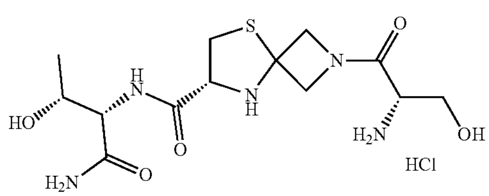 [SMILES: C[C@@H](O)[C@H](NC(=O)[C@@H]1CSC2(CN(C(=O)[C@@H](N)CO)C2)N1)C(N)=O ; Cl] | A-376 | 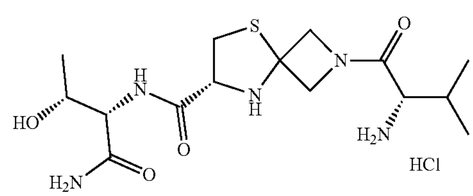 [SMILES: CC(C)[C@H](N)C(=O)N1CC2(C1)N[C@H](C(=O)N[C@H](C(N)=O)[C@@H](C)O)CS2 ; Cl] |
| A-377 | 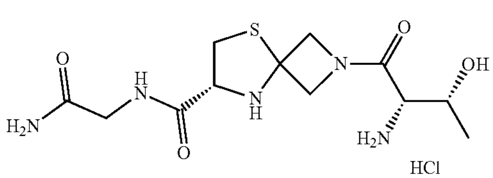 [SMILES: C[C@@H](O)[C@H](N)C(=O)N1CC2(C1)N[C@H](C(=O)NCC(N)=O)CS2 ; Cl] | A-378 | 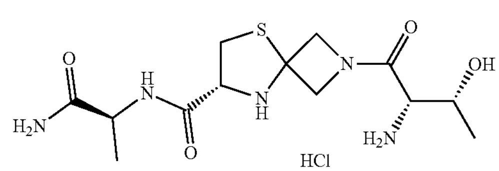 [SMILES: C[C@H](NC(=O)[C@@H]1CSC2(CN(C(=O)[C@@H](N)[C@@H](C)O)C2)N1)C(N)=O ; Cl] |
| A-379 | 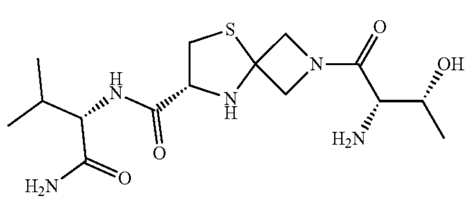 [SMILES: CC(C)[C@H](NC(=O)[C@@H]1CSC2(CN(C(=O)[C@@H](N)[C@@H](C)O)C2)N1)C(N)=O] | A-380 | 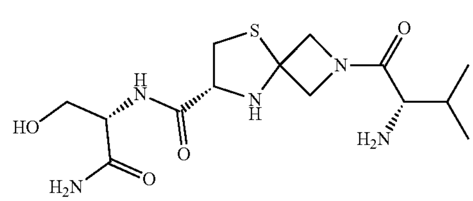 [SMILES: CC(C)[C@H](N)C(=O)N1CC2(C1)N[C@H](C(=O)N[C@@H](CO)C(N)=O)CS2] |

-continued
| Number | Structural formula | Number | Structural formula |
|---|---|---|---|
| A-381 | 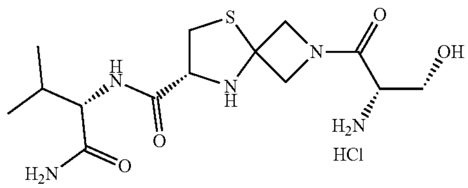 | A-382 | 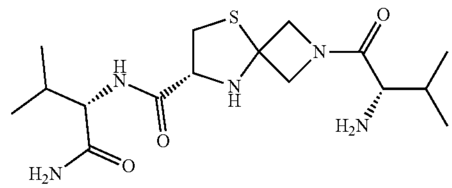 [SMILES: CC(C)[C@H](N)C(=O)N1CC2(C1)N[C@H](C(=O)N[C@H](C(N)=O)C(C)C)CS2] |
| A-383 | 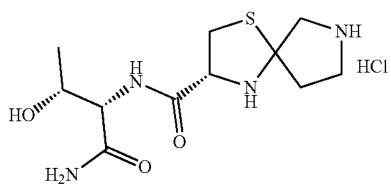 | A-384 | 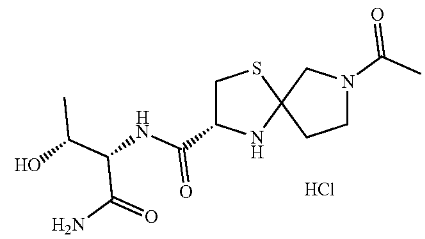 [SMILES: CC(=O)N1CCC2(C1)N[C@H](C(=O)N[C@H](C(N)=O)[C@@H](C)O)CS2 ; Cl] |
| A-385 | 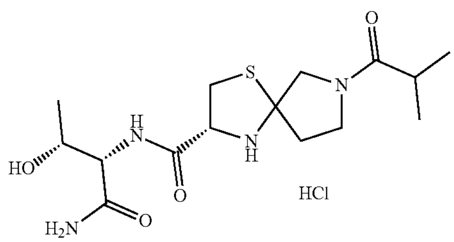 [SMILES: CC(C)C(=O)N1CCC2(C1)N[C@H](C(=O)N[C@H](C(N)=O)[C@@H](C)O)CS2 ; Cl] | A-386 | 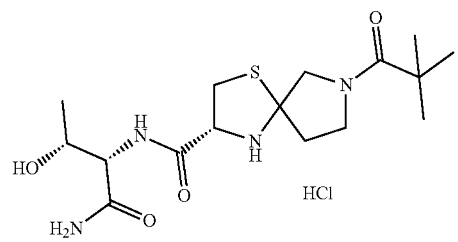 [SMILES: C[C@@H](O)[C@H](NC(=O)[C@@H]1CSC2(CCN(C(=O)C(C)(C)C)C2)N1)C(N)=O ; Cl] |
| A-387 | 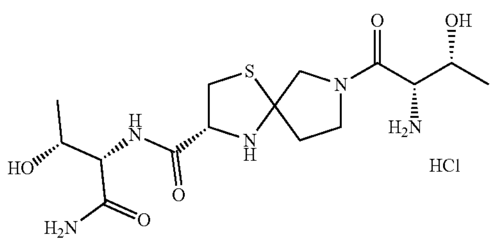 [SMILES: C[C@@H](O)[C@H](N)C(=O)N1CCC2(C1)N[C@H](C(=O)N[C@H](C(N)=O)[C@@H](C)O)CS2 ; Cl] | A-388 | 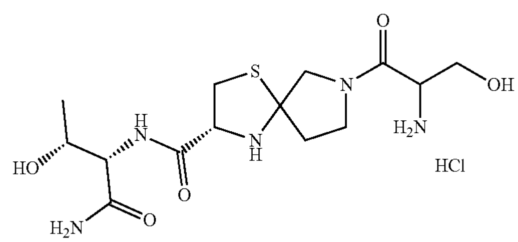 [SMILES: C[C@@H](O)[C@H](NC(=O)[C@@H]1CSC2(CCN(C(=O)C(N)CO)C2)N1)C(N)=O ; Cl] |
| A-389 | 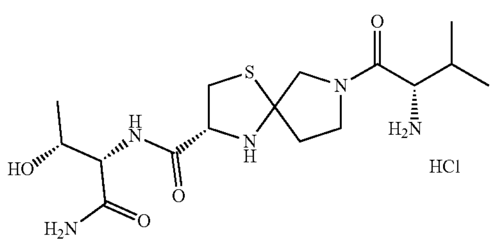 [SMILES: CC(C)[C@H](N)C(=O)N1CCC2(C1)N[C@H](C(=O)N[C@H](C(N)=O)[C@@H](C)O)CS2 ; Cl] | A-390 | 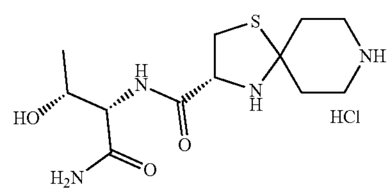 |
| A-391 | 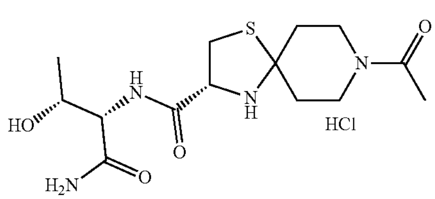 [SMILES: CC(=O)N1CCC2(CC1)N[C@H](C(=O)N[C@H](C(N)=O)[C@@H](C)O)CS2 ; Cl] | A-392 | 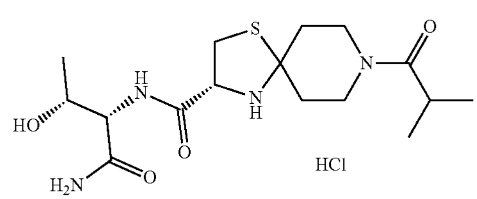 [SMILES: CC(C)C(=O)N1CCC2(CC1)N[C@H](C(=O)N[C@H](C(N)=O)[C@@H](C)O)CS2 ; Cl] |
| A-393 | 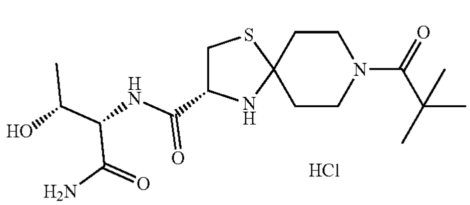 [SMILES: C[C@@H](O)[C@H](NC(=O)[C@@H]1CSC2(CCN(C(=O)C(C)(C)C)CC2)N1)C(N)=O ; Cl] | A-394 | 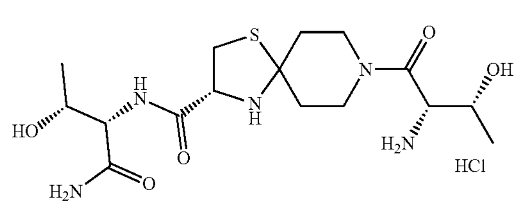 [SMILES: C[C@@H](O)[C@H](N)C(=O)N1CCC2(CC1)N[C@H](C(=O)N[C@H](C(N)=O)[C@@H](C)O)CS2 ; Cl] |

-continued
| Number | Structural formula | Number | Structural formula |
|---|---|---|---|
| A-395 | 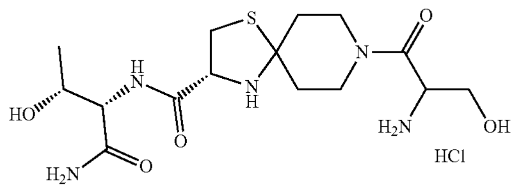 [SMILES: C[C@@H](O)[C@H](NC(=O)[C@@H]1CSC2(CCN(C(=O)C(N)CO)CC2)N1)C(N)=O ; Cl] | A-396 | 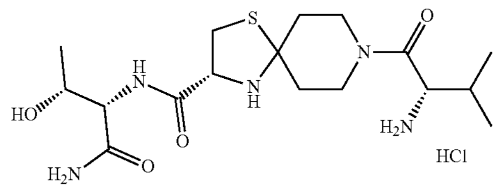 [SMILES: CC(C)[C@H](N)C(=O)N1CCC2(CC1)N[C@H](C(=O)N[C@H](C(N)=O)[C@@H](C)O)CS2 ; Cl] |
| A-397 | 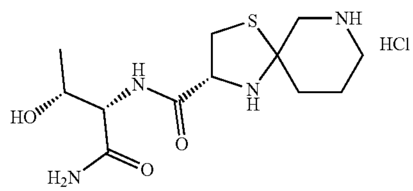 [SMILES: C[C@@H](O)[C@H](NC(=O)[C@@H]1CSC2(CCCNC2)N1)C(N)=O ; Cl] | A-398 | 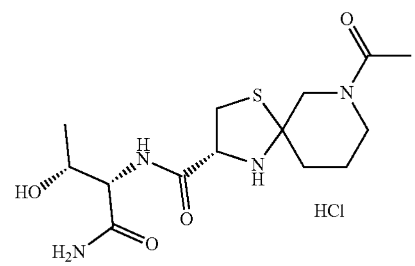 [SMILES: CC(=O)N1CCCC2(C1)N[C@H](C(=O)N[C@H](C(N)=O)[C@@H](C)O)CS2 ; Cl] |
| A-399 | 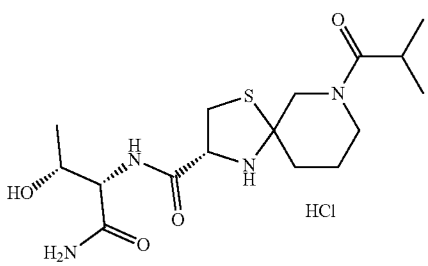 [SMILES: CC(C)C(=O)N1CCCC2(C1)N[C@H](C(=O)N[C@H](C(N)=O)[C@@H](C)O)CS2 ; Cl] | A-400 | 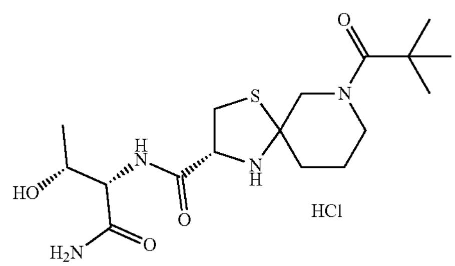 [SMILES: C[C@@H](O)[C@H](NC(=O)[C@@H]1CSC2(CCCN(C(=O)C(C)(C)C)C2)N1)C(N)=O ; Cl] |
| A-401 | 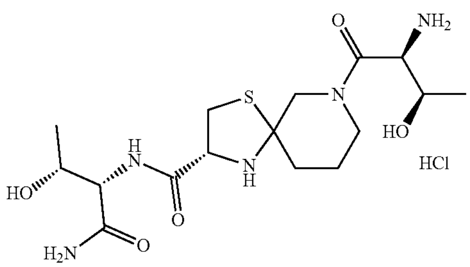 [SMILES: C[C@@H](O)[C@H](N)C(=O)N1CCCC2(C1)N[C@H](C(=O)N[C@H](C(N)=O)[C@@H](C)O)CS2 ; Cl] | A-402 | 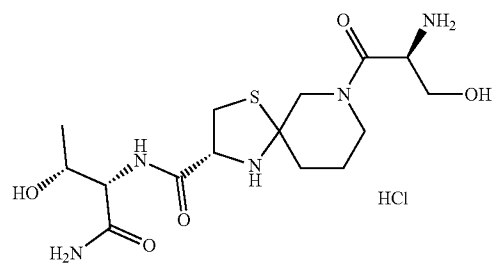 [SMILES: C[C@@H](O)[C@H](NC(=O)[C@@H]1CSC2(CCCN(C(=O)[C@@H](N)CO)C2)N1)C(N)=O ; Cl] |
| A-403 | 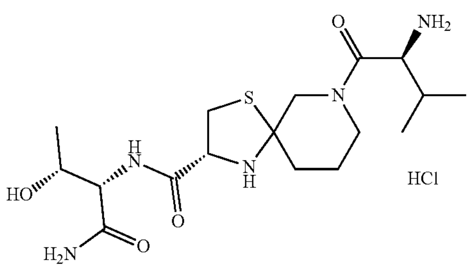 [SMILES: CC(C)[C@H](N)C(=O)N1CCCC2(C1)N[C@H](C(=O)N[C@H](C(N)=O)[C@@H](C)O)CS2 ; Cl] | A-404 | 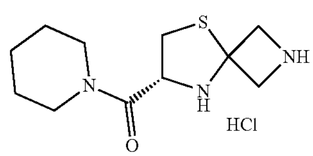 [SMILES: O=C([C@@H]1CSC2(CNC2)N1)N1CCCCC1 ; Cl] |
| A-405 | 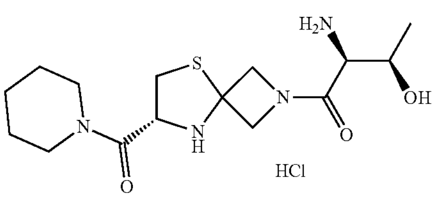 [SMILES: C[C@@H](O)[C@H](N)C(=O)N1CC2(C1)N[C@H](C(=O)N1CCCCC1)CS2 ; Cl] | A-406 | 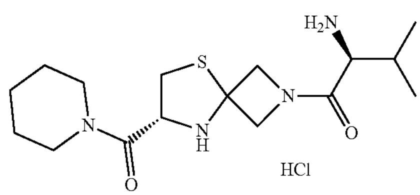 [SMILES: CC(C)[C@H](N)C(=O)N1CC2(C1)N[C@H](C(=O)N1CCCCC1)CS2 ; Cl] |

-continued
| Number | Structural formula | Number | Structural formula |
|---|---|---|---|
| A-407 | 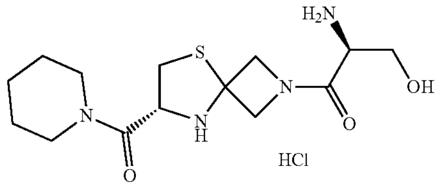 [SMILES: N[C@@H](CO)C(=O)N1CC2(C1)N[C@H](C(=O)N1CCCCC1)CS2 ; Cl] HCl | A-408 | 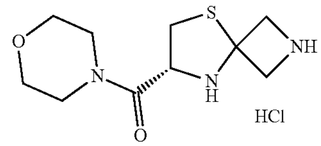 [SMILES: O=C([C@@H]1CSC2(CNC2)N1)N1CCOCC1 ; Cl] HCl |
| A-409 | 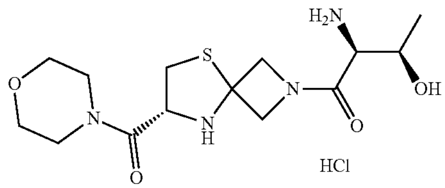 [SMILES: C[C@@H](O)[C@H](N)C(=O)N1CC2(C1)N[C@H](C(=O)N1CCOCC1)CS2 ; Cl] HCl | A-410 | 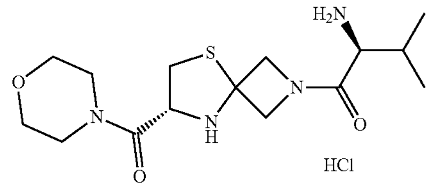 [SMILES: CC(C)[C@H](N)C(=O)N1CC2(C1)N[C@H](C(=O)N1CCOCC1)CS2 ; Cl] HCl |
| A-411 | 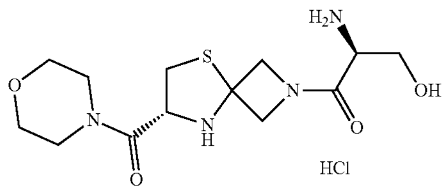 [SMILES: N[C@@H](CO)C(=O)N1CC2(C1)N[C@H](C(=O)N1CCOCC1)CS2 ; Cl] HCl | A-412 | 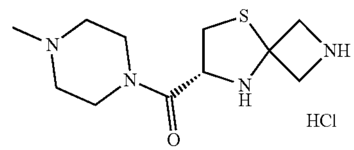 [SMILES: CN1CCN(C(=O)[C@@H]2CSC3(CNC3)N2)CC1 ; Cl] HCl |
| A-413 | 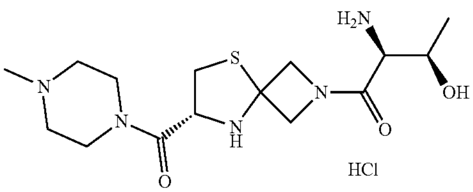 [SMILES: C[C@@H](O)[C@H](N)C(=O)N1CC2(C1)N[C@H](C(=O)N1CCN(C)CC1)CS2 ; Cl] HCl | A-414 | 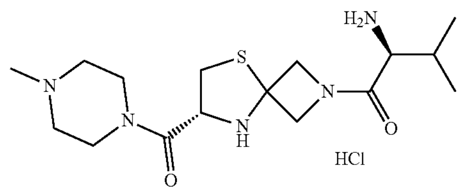 [SMILES: CC(C)[C@H](N)C(=O)N1CC2(C1)N[C@H](C(=O)N1CCN(C)CC1)CS2 ; Cl] HCl |
| A-415 | 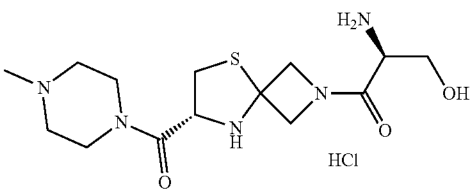 [SMILES: CN1CCN(C(=O)[C@@H]2CSC3(CN(C(=O)[C@@H](N)CO)C3)N2)CC1 ; Cl] HCl | A-416 | 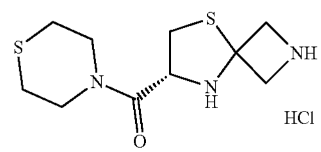 [SMILES: O=C([C@@H]1CSC2(CNC2)N1)N1CCSCC1 ; Cl] HCl |
| A-417 | 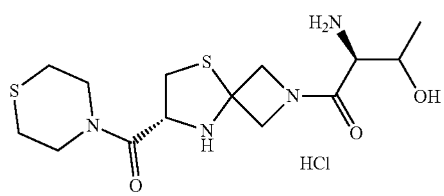 [SMILES: CC(O)[C@H](N)C(=O)N1CC2(C1)N[C@H](C(=O)N1CCSCC1)CS2 ; Cl] HCl | A-418 | 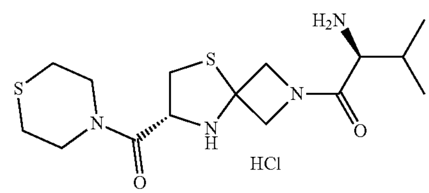 [SMILES: CC(C)[C@H](N)C(=O)N1CC2(C1)N[C@H](C(=O)N1CCSCC1)CS2 ; Cl] HCl |
| A-419 | 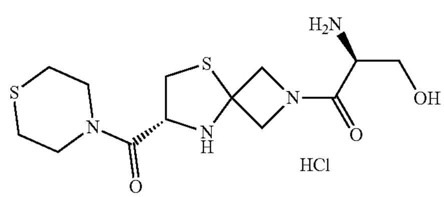 [SMILES: N[C@@H](CO)C(=O)N1CC2(C1)N[C@H](C(=O)N1CCSCC1)CS2 ; Cl] HCl | A-420 | 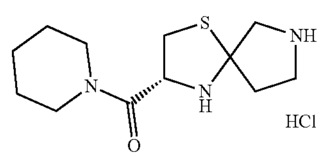 [SMILES: O=C([C@@H]1CSC2(CCNC2)N1)N1CCCCC1 ; Cl] HCl |
| A-421 | 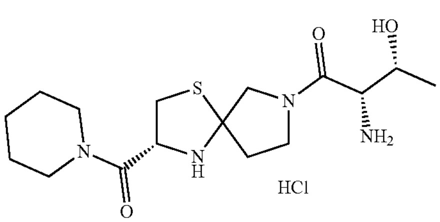 [SMILES: C[C@@H](O)[C@H](N)C(=O)N1CCC2(C1)N[C@H](C(=O)N1CCCCC1)CS2 ; Cl] HCl | A-422 | 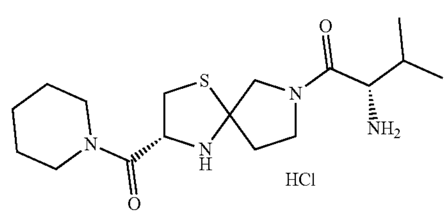 [SMILES: CC(C)[C@H](N)C(=O)N1CCC2(C1)N[C@H](C(=O)N1CCCCC1)CS2 ; Cl] HCl |

-continued
| Number | Structural formula | Number | Structural formula |
|---|---|---|---|
| A-423 | 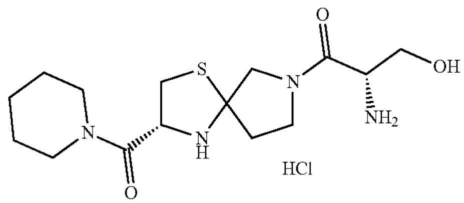 [SMILES: N[C@@H](CO)C(=O)N1CCC2(C1)N[C@H](C(=O)N1CCCCC1)CS2 ; Cl] | A-424 | 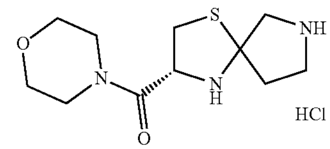 [SMILES: O=C([C@@H]1CSC2(CCNC2)N1)N1CCOCC1 ; Cl] |
| A-425 | 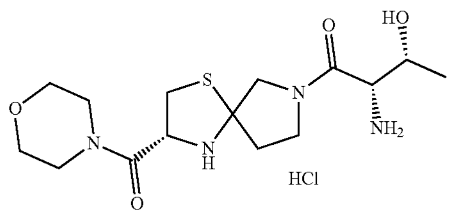 [SMILES: C[C@@H](O)[C@H](N)C(=O)N1CCC2(C1)N[C@H](C(=O)N1CCOCC1)CS2 ; Cl] | A-426 | 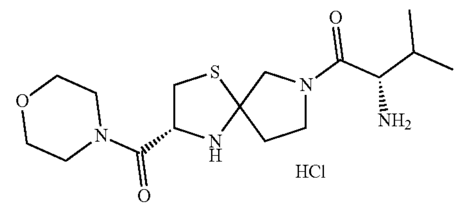 [SMILES: CC(C)[C@H](N)C(=O)N1CCC2(C1)N[C@H](C(=O)N1CCOCC1)CS2 ; Cl] |
| A-427 | 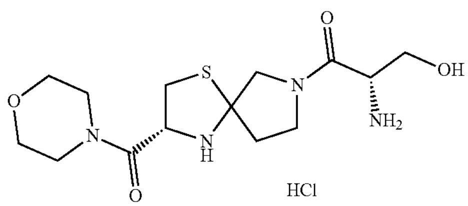 [SMILES: N[C@@H](CO)C(=O)N1CCC2(C1)N[C@H](C(=O)N1CCOCC1)CS2 ; Cl] | A-428 | 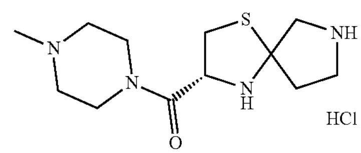 [SMILES: CN1CCN(C(=O)[C@@H]2CSC3(CCNC3)N2)CC1 ; Cl] |
| A-429 | 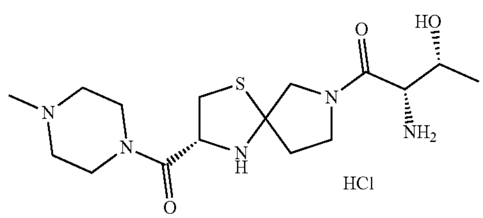 [SMILES: C[C@@H](O)[C@H](N)C(=O)N1CCC2(C1)N[C@H](C(=O)N1CCN(C)CC1)CS2 ; Cl] | A-430 | 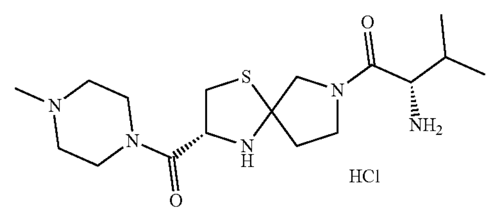 [SMILES: CC(C)[C@H](N)C(=O)N1CCC2(C1)N[C@H](C(=O)N1CCN(C)CC1)CS2 ; Cl] |
| A-431 | 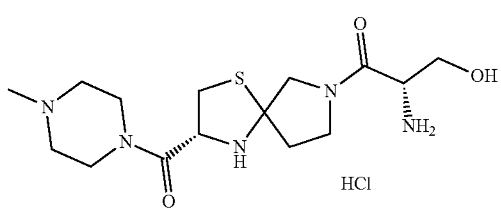 [SMILES: CN1CCN(C(=O)[C@@H]2CSC3(CCN(C(=O)[C@@H](N)CO)C3)N2)CC1 ; Cl] | A-432 | 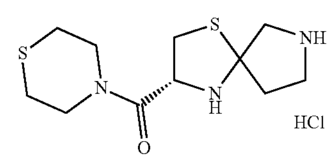 [SMILES: O=C([C@@H]1CSC2(CCNC2)N1)N1CCSCC1 ; Cl] |
| A-433 | 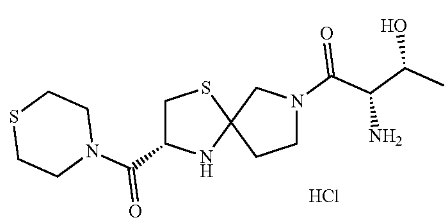 [SMILES: C[C@@H](O)[C@H](N)C(=O)N1CCC2(C1)N[C@H](C(=O)N1CCSCC1)CS2 ; Cl] | A-434 | 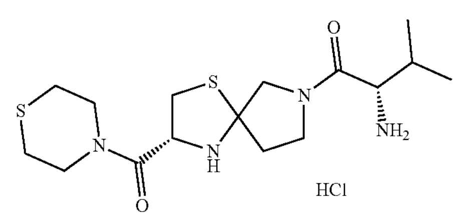 [SMILES: CC(C)[C@H](N)C(=O)N1CCC2(C1)N[C@H](C(=O)N1CCSCC1)CS2 ; Cl] |
| A-435 | 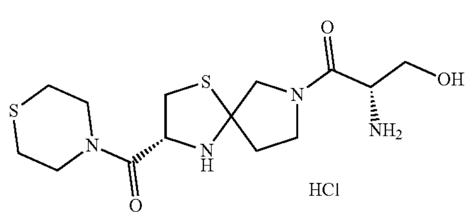 [SMILES: N[C@@H](CO)C(=O)N1CCC2(C1)N[C@H](C(=O)N1CCSCC1)CS2 ; Cl] | A-436 | 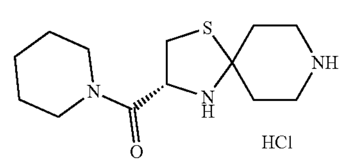 [SMILES: O=C([C@@H]1CSC2(CCNCC2)N1)N1CCCCC1 ; Cl] |

-continued
| Number | Structural formula | Number | Structural formula |
| --- | --- | --- | --- |
| A-437 | 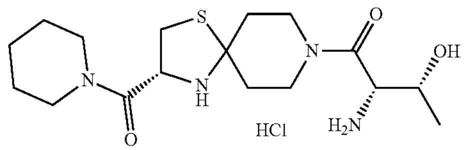 [SMILES: C[C@@H](O)[C@H](N)C(=O)N1CCC2(CC1)N[C@H](C(=O)N1CCCCC1)CS2 ; Cl] | A-438 | 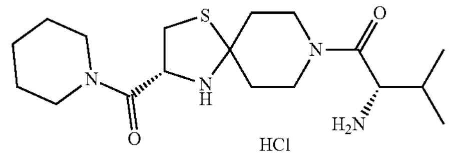 [SMILES: CC(C)[C@H](N)C(=O)N1CCC2(CC1)N[C@H](C(=O)N1CCCCC1)CS2 ; Cl] |
| A-439 | 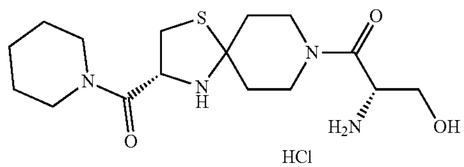 [SMILES: N[C@@H](CO)C(=O)N1CCC2(CC1)N[C@H](C(=O)N1CCCCC1)CS2 ; Cl] | A-440 | 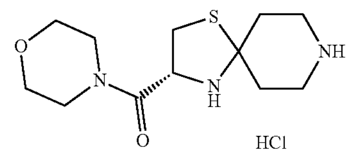 [SMILES: O=C([C@@H]1CSC2(CCNCC2)N1)N1CCOCC1 ; Cl] |
| A-441 | 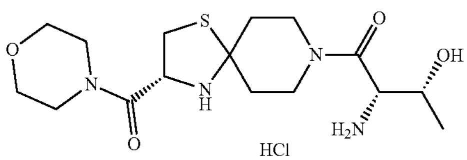 [SMILES: C[C@@H](O)[C@H](N)C(=O)N1CCC2(CC1)N[C@H](C(=O)N1CCOCC1)CS2 ; Cl] | A-442 | 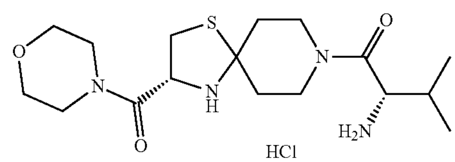 [SMILES: CC(C)[C@H](N)C(=O)N1CCC2(CC1)N[C@H](C(=O)N1CCOCC1)CS2 ; Cl] |
| A-443 | 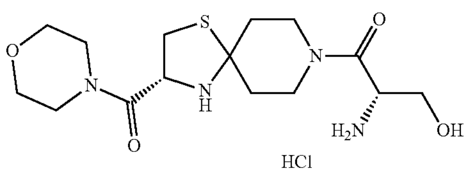 [SMILES: N[C@@H](CO)C(=O)N1CCC2(CC1)N[C@H](C(=O)N1CCOCC1)CS2 ; Cl] | A-444 | 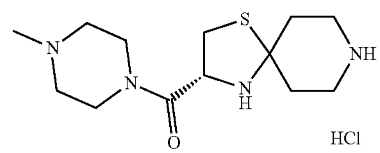 [SMILES: CN1CCN(C(=O)[C@@H]2CSC3(CCNCC3)N2)CC1 ; Cl] |
| A-445 | 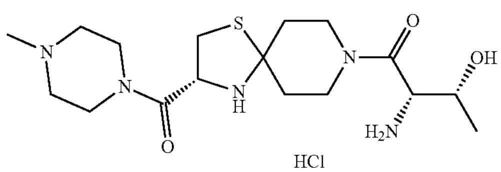 [SMILES: C[C@@H](O)[C@H](N)C(=O)N1CCC2(CC1)N[C@H](C(=O)N1CCN(C)CC1)CS2 ; Cl] | A-446 | 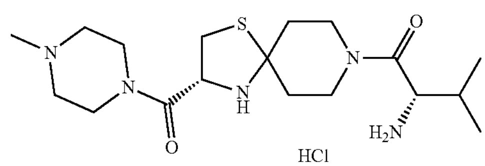 [SMILES: CC(C)[C@H](N)C(=O)N1CCC2(CC1)N[C@H](C(=O)N1CCN(C)CC1)CS2 ; Cl] |
| A-447 | 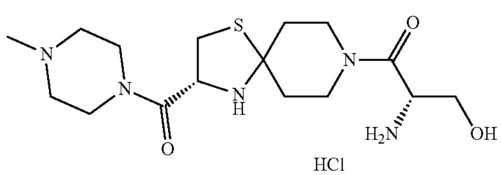 [SMILES: CN1CCN(C(=O)[C@@H]2CSC3(CCN(C(=O)[C@@H](N)CO)CC3)N2)CC1 ; Cl] | A-448 | 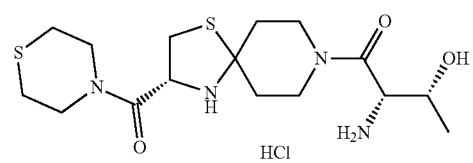 [SMILES: C[C@@H](O)[C@H](N)C(=O)N1CCC2(CC1)N[C@H](C(=O)N1CCSCC1)CS2 ; Cl] |
| A-449 | 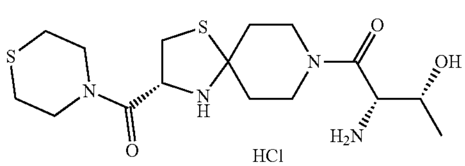 [SMILES: C[C@@H](O)[C@H](N)C(=O)N1CCC2(CC1)N[C@H](C(=O)N1CCSCC1)CS2 ; Cl] | A-450 | 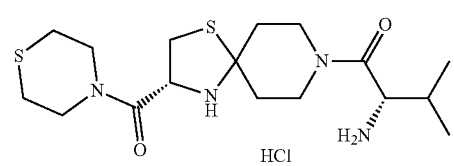 [SMILES: CC(C)[C@H](N)C(=O)N1CCC2(CC1)N[C@H](C(=O)N1CCSCC1)CS2 ; Cl] |
| A-451 | 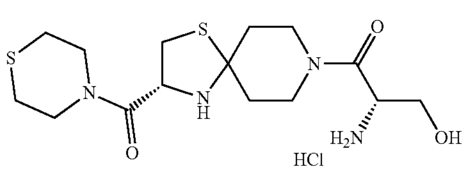 [SMILES: N[C@@H](CO)C(=O)N1CCC2(CC1)N[C@H](C(=O)N1CCSCC1)CS2 ; Cl] | A-452 | 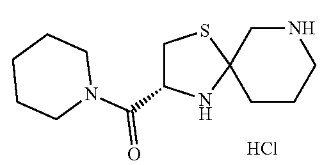 [SMILES: O=C([C@@H]1CSC2(CCCNC2)N1)N1CCCCC1 ; Cl] |

-continued
| Number | Structural formula | Number | Structural formula |
|---|---|---|---|
| A-453 | 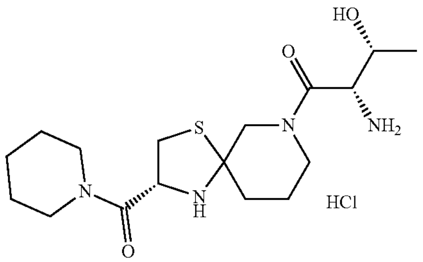 [SMILES: C[C@@H](O)[C@H](N)C(=O)N1CCCC2(C1)N[C@H](C(=O)N1CCCCC1)CS2 ; Cl] | A-454 | 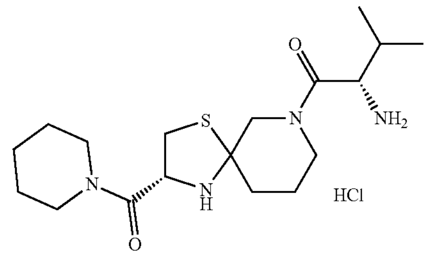 [SMILES: CC(C)[C@H](N)C(=O)N1CCCC2(C1)N[C@H](C(=O)N1CCCCC1)CS2 ; Cl] |
| A-455 | 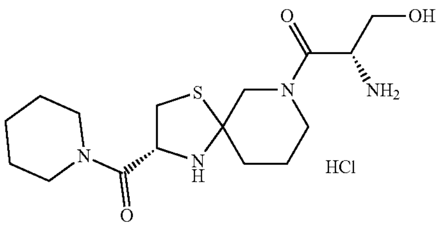 [SMILES: N[C@@H](CO)C(=O)N1CCCC2(C1)N[C@H](C(=O)N1CCCCC1)CS2 ; Cl] | A-456 | 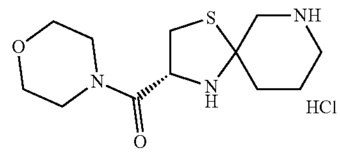 [SMILES: O=C([C@@H]1CSC2(CCCNC2)N1)N1CCOCC1 ; Cl] |
| A-457 | 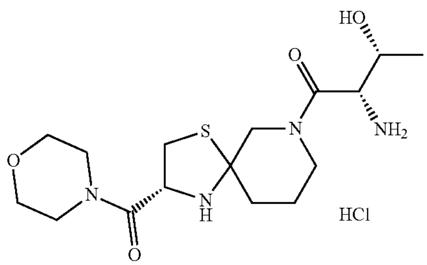 [SMILES: C[C@@H](O)[C@H](N)C(=O)N1CCCC2(C1)N[C@H](C(=O)N1CCOCC1)CS2 ; Cl] | A-458 | 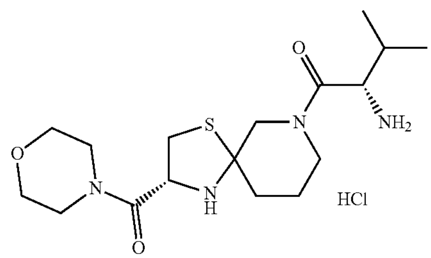 [SMILES: CC(C)[C@H](N)C(=O)N1CCCC2(C1)N[C@H](C(=O)N1CCOCC1)CS2 ; Cl] |
| A-459 | 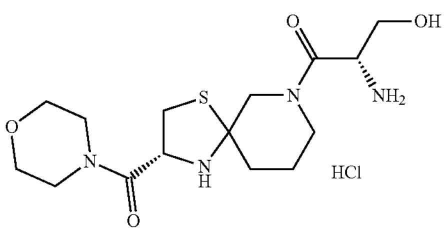 [SMILES: N[C@@H](CO)C(=O)N1CCCC2(C1)N[C@H](C(=O)N1CCOCC1)CS2 ; Cl] | A-460 | 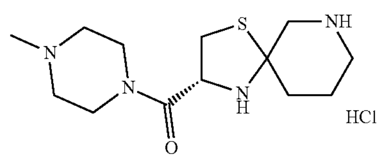 [SMILES: CN1CCN(C(=O)[C@@H]2CSC3(CCCNC3)N2)CC1 ; Cl] |
| A-461 | 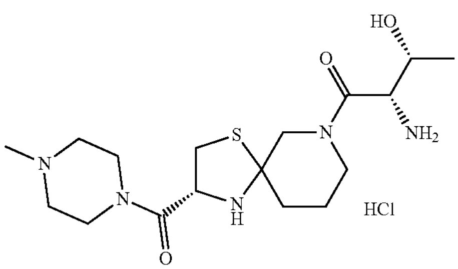 [SMILES: C[C@@H](O)[C@H](N)C(=O)N1CCCC2(C1)N[C@H](C(=O)N1CCN(C)CC1)CS2 ; Cl] | A-462 | 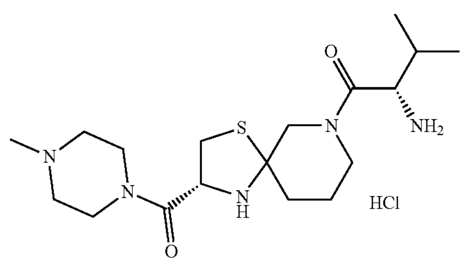 [SMILES: CC(C)[C@H](N)C(=O)N1CCCC2(C1)N[C@H](C(=O)N1CCN(C)CC1)CS2 ; Cl] |
| A-463 | 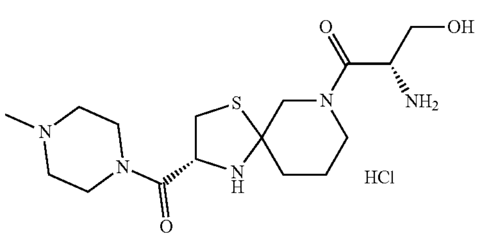 [SMILES: CN1CCN(C(=O)[C@@H]2CSC3(CCCN(C(=O)[C@@H](N)CO)C3)N2)CC1 ; Cl] | A-464 | 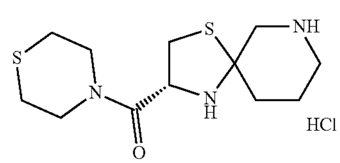 [SMILES: O=C([C@@H]1CSC2(CCCNC2)N1)N1CCSCC1 ; Cl] |

-continued
| Number | Structural formula | Number | Structural formula |
|---|---|---|---|
| A-465 | 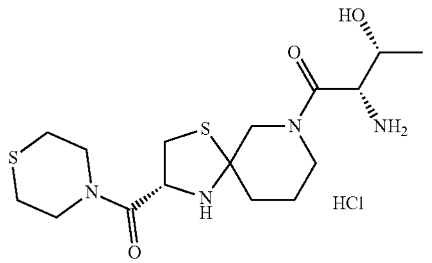 [SMILES: C[C@@H](O)[C@H](N)C(=O)N1CCCC2(C1)N[C@H](C(=O)N1CCSCC1)CS2 ; Cl] | A-466 | 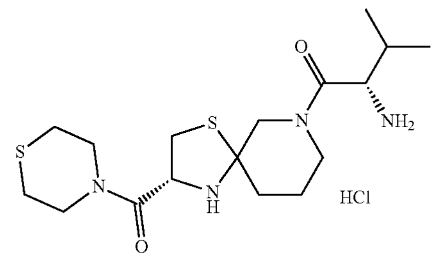 [SMILES: CC(C)[C@H](N)C(=O)N1CCCC2(C1)N[C@H](C(=O)N1CCSCC1)CS2 ; Cl] |
| A-467 | 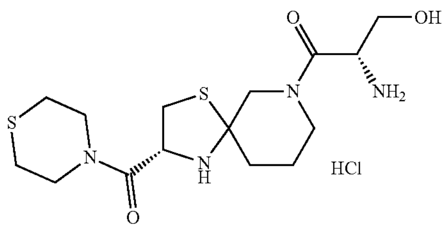 [SMILES: N[C@@H](CO)C(=O)N1CCCC2(C1)N[C@H](C(=O)N1CCSCC1)CS2 ; Cl] | A-468 | 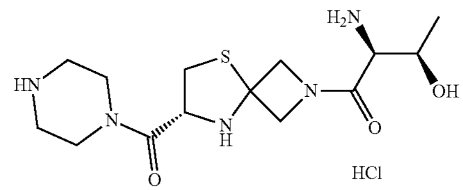 [SMILES: C[C@@H](O)[C@H](N)C(=O)N1CC2(C1)N[C@H](C(=O)N1CCNCC1)CS2 ; Cl] |
| A-469 | 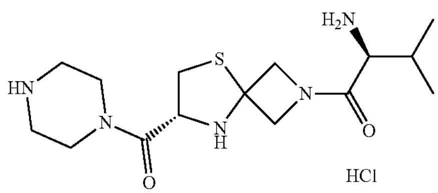 [SMILES: CC(C)[C@H](N)C(=O)N1CC2(C1)N[C@H](C(=O)N1CCNCC1)CS2 ; Cl] | A-470 | 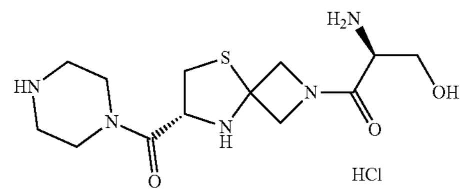 [SMILES: N[C@@H](CO)C(=O)N1CC2(C1)N[C@H](C(=O)N1CCNCC1)CS2 ; Cl] |
| A-471 | 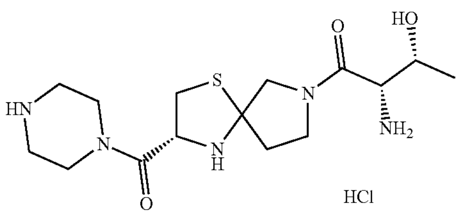 [SMILES: C[C@@H](O)[C@H](N)C(=O)N1CCC2(C1)N[C@H](C(=O)N1CCNCC1)CS2 ; Cl] | A-472 | 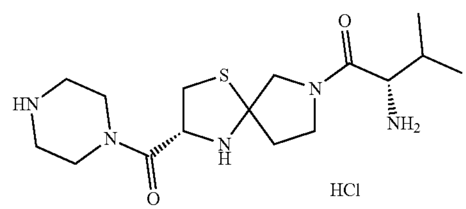 [SMILES: CC(C)[C@H](N)C(=O)N1CCC2(C1)N[C@H](C(=O)N1CCNCC1)CS2 ; Cl] |
| A-473 | 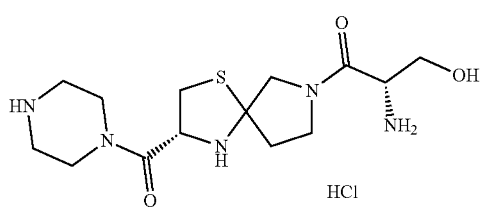 [SMILES: N[C@@H](CO)C(=O)N1CCC2(C1)N[C@H](C(=O)N1CCNCC1)CS2 ; Cl] | A-474 | 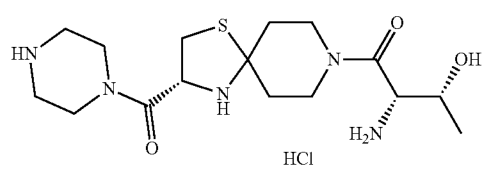 [SMILES: C[C@@H](O)[C@H](N)C(=O)N1CCC2(CC1)N[C@H](C(=O)N1CCNCC1)CS2 ; Cl] |
| A-475 | 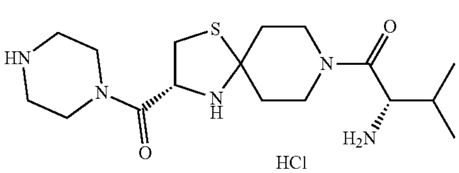 [SMILES: CC(C)[C@H](N)C(=O)N1CCC2(CC1)N[C@H](C(=O)N1CCNCC1)CS2 ; Cl] | A-476 | 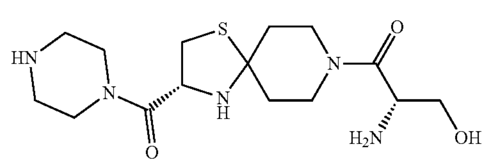 |
| A-477 | 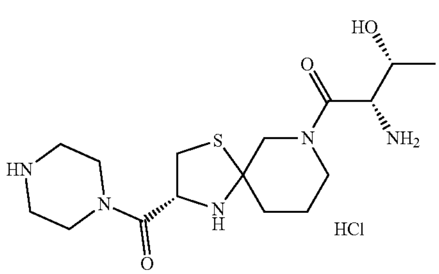 [SMILES: C[C@@H](O)[C@H](N)C(=O)N1CCCC2(C1)N[C@H](C(=O)N1CCNCC1)CS2 ; Cl] | A-478 | 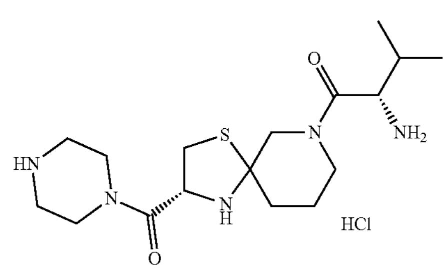 [SMILES: CC(C)[C@H](N)C(=O)N1CCCC2(C1)N[C@H](C(=O)N1CCNCC1)CS2 ; Cl] |

-continued

| Number | Structural formula | Number | Structural formula |
|---|---|---|---|
| A-479 | 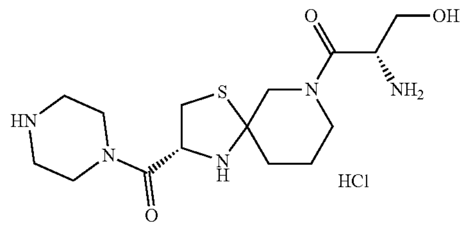 [SMILES: N[C@@H](CO)C(=O)N1CCCC2(C1)N[C@H](C(=O)N1CCNCC1)CS2 ; Cl] | | |

Preparation of Compound

The compound of the invention can be prepared by various methods known in the field.

In some embodiments, when $R_1$, $R_2$ and $R_3$ are H in the formula I, the compound of the formula I can be prepared by the following steps:

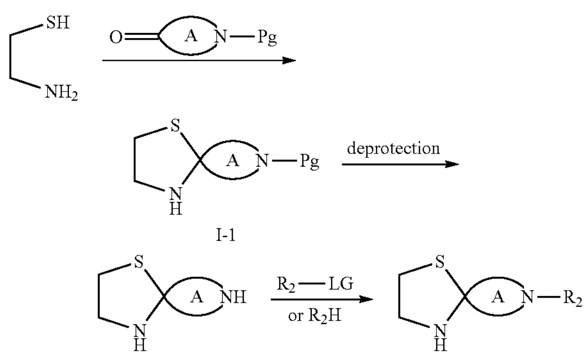

I-1

I-2

I-3

In some embodiments, the following series of the compounds of the formula I can be further obtained from the compound of the formula I-1:

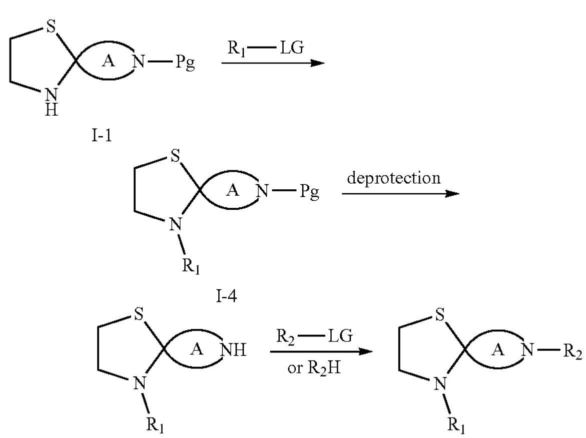

I-1

I-4

I-5

I-6

In some embodiments, the following series of the compounds of the formula I can be obtained from L-Cysteine Methyl Ester Hydrochloride as a starting material:

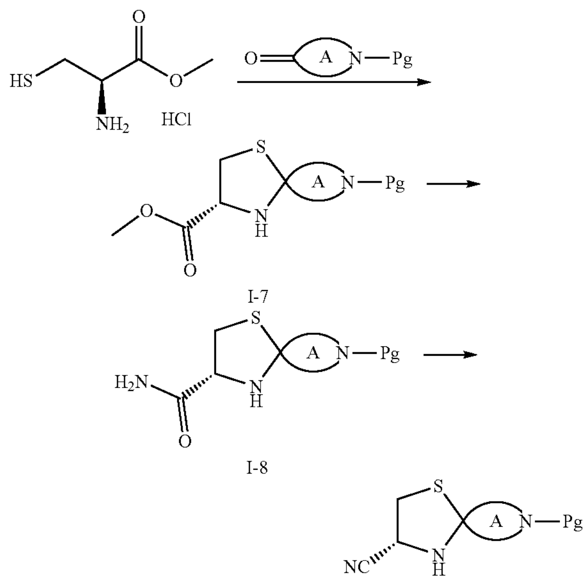

I-7

I-8

I-9

In some embodiments, the compounds of the formulas I-7, I-8, and I-9 can be respectively further deprotected, and reacted with $R_2$-LG or $R_3$H to obtain the corresponding compound of the formula I.

In the above scheme, LG represents a leaving group of a nucleophilic substitution reaction, e.g., halogen, etc.; Pg represents an amino protecting group, e.g., Boc, Fmoc, etc.

In some embodiments, the sequence of the above experimental steps can be adjusted according to a target product structure.

Treatment and Pharmaceutical Composition

In another respect, the invention provides a pharmaceutical composition, comprising a compound of the invention, a pharmaceutically acceptable salt or ester, stereoisomer or solvate thereof; optionally, the pharmaceutical composition further comprises one or more pharmaceutically acceptable excipients.

In some embodiments, the pharmaceutical composition of the invention comprises the compound of the invention, and its pharmaceutically acceptable excipients.

In some embodiments, the pharmaceutical composition of the present invention contains 0.1 to 90 weight % of the compound of the formula I and/or its physiologically acceptable salt.

The compound in the pharmaceutical composition of the present invention, a pharmaceutically acceptable salt or ester, stereoisomer or solvate thereof can be used for a subject for:

(a) Regulation (e.g., up- or down-regulation) of activity of an NMDA receptor;
(b) Enhancement of activity of an NMDA receptor;
(c) Prevention of depression;
(d) Treatment of depression;
(e) Prevention of anxiety;
(f) Treatment of anxiety;
(g) Prevention of stroke;
(h) Treatment of stroke;
(i) Prevention of Huntington's disease;
(j) Treatment of Huntington's disease;
(k) Prevention of Alzheimer's disease;
(l) Treatment of Alzheimer's disease;
(m) Prevention of neuralgia;
(n) Treatment of neuralgia;
(o) Prevention of schizophrenia;
(p) Treatment of schizophrenia;
(q) Any combination of (a)-(p).

In another respect, the present invention provides use of the compound, a pharmaceutically acceptable salt or ester, stereoisomer or solvate thereof in preparation of medicaments for:

(a) Regulation (e.g., up- or down-regulation) of activity of an NMDA receptor;
(b) Enhancement of activity of an NMDA receptor;
(c) Prevention of depression;
(d) Treatment of depression;
(e) Prevention of anxiety;
(f) Treatment of anxiety;
(g) Prevention of stroke;
(h) Treatment of stroke;
(i) Prevention of Huntington's disease;
(j) Treatment of Huntington's disease;
(k) Prevention of Alzheimer's disease;
(l) Treatment of Alzheimer's disease;
(m) Prevention of neuralgia;
(n) Treatment of neuralgia;
(o) Prevention of schizophrenia;
(p) Treatment of schizophrenia;
(q) Any combination of (a)-(p).

In another respect, the present invention provides a method for preventing and/or treating depression, anxiety, stroke, Huntington's disease, Alzheimer's disease, neuralgia or schizophrenia in subjects, the method includes administering an effective amount of the compound of the invention, pharmaceutically acceptable salt or ester, stereoisomer or solvate thereof or the pharmaceutical composition of the invention to the subjects in need.

In another respect, the present invention provides a method for regulating (e.g., up- or down-regulating) activity of NMDA receptor (e.g., a human NMDA receptor) in vivo or in vitro, including providing a subject, a mammalian cell or an NMDA receptor with an effective amount of the compound of the formula I of the invention, pharmaceutically acceptable salt or ester, stereoisomer or solvate thereof.

In another respect, the present invention provides the compound of the formula I, pharmaceutically acceptable salt or ester, stereoisomer or solvate thereof for use in treatment and/or prevention of depression, anxiety, stroke, Huntington's disease, Alzheimer's disease, neuralgia or schizophrenia.

In another respect, the present invention provides the compound of the formula I, pharmaceutically acceptable salt or ester, stereoisomer or solvate thereof for use in in-vivo or in-vitro regulation (e.g., up- or down-regulation) of the activity of an NMDA receptor (e.g., human NMDA receptor).

The compound of the present invention, a pharmaceutically acceptable salt or ester, stereoisomer or solvate thereof, or the pharmaceutical composition of the present invention can be prepared to any dosage form known in the medical field, such as tablets, pills, suspensions, emulsions, solutions, gels, capsules, powders, granules, elixir, lozenges, suppositories, injections (including injections, sterile powders for injection, and concentrated solutions for injection), inhalants, sprays, etc. A preferred dosage form depends on an intended administration mode and therapeutic use. The pharmaceutical composition of the invention should be sterile and stable under production and storage conditions. One preferred dosage form is an injection. The injection can be a sterile injectable solution. For example, the sterile injectable solution can be prepared by the following steps: doping a required dose of the compound of the present invention, a pharmaceutically acceptable salt or ester, stereoisomer or solvate thereof, in a suitable solvent, and optionally, doping other desired constituents (including, but not limited to, a pH modifying agent, a surfactant, an ionic strength enhancing agent, an isotonic agent, a preservative, a diluent, or any combination thereof) at the same time, and then the solution is subjected to filtration and sterilization. In addition, the sterile injectable solution can be prepared as a sterile lyophilized powder (e.g., by vacuum drying or freeze-drying) to facilitate storage and use. The sterile lyophilized powder can be dispersed in a suitable carrier before use, such as sterile pyrogen-free water.

In addition, the compound of the present invention, a pharmaceutically acceptable salt or ester, stereoisomer or solvate thereof may exist in the pharmaceutical composition in a unit dose form for application.

The compound of the present invention, a pharmaceutically acceptable salt or ester, stereoisomer or solvate thereof, and the pharmaceutical composition of the present invention can be applied by any suitable method known in the field including, but not limited to, oral administration, oral, sublingual, ocular, topical, parenteral, rectal, intrathecal, intracytoplasmic reticulum, inguinal, intravesical, topical (e.g., powder, ointments, or drops), or nasal routes. However, for many therapeutic uses, the preferred administration route/mode is parenteral administration (e.g., intravenous injection, subcutaneous injection, intraperitoneal injection, intramuscular injection). The technician should understand that an administration route and/or mode can be changed according to an intended purpose. In a preferred embodiment, the compound of the present invention, a pharmaceutically acceptable salt or ester, stereoisomers or solvate thereof, and a pharmaceutical composition are administered by intravenous infusion or injection.

The pharmaceutical composition of the present invention may include the compound of the invention, a pharmaceutically acceptable salt or ester, stereoisomers, or solvate thereof with a "therapeutically effective amount" or a "prophylactically effective amount". The term "prophylactically effective amount" refers to the amount sufficient to prevent, stop or delay the occurrence of diseases. The term "therapeutically effective amount" refers to the amount sufficient to treat or at least partially prevent a disease and its complications of a patient who already has the disease. The therapeutically effective amount of the compound, a pharmaceutically acceptable salt or ester, stereoisomer or solvate thereof may vary according to the following factors: severity of disease to be treated, an overall state of patient's own immune system, patient's general conditions such as age, weight and sex, an administration mode of medicine, and other concurrent treatment measures.

In the present invention, a dosage regimen can be adjusted to obtain the best target response (e.g., therapeutic or preventive response). For example, single administration can be applied, multiple administration over a period of time also can be applied, or a dose can be reduced or increased proportionally with the urgency of the treatment.

A typical non-limit range for prophylactically or therapeutically effective amount of the compound of the present invention, a pharmaceutically acceptable salt or ester, stereoisomer, or solvate thereof is 0.02 to 100 mg/kg, e.g., 0.1 to 100 mg/kg, 0.1 to 50 mg/kg, or 1 to 50 mg/kg. It should be noted that the dose can be changed according to the type and severity of symptoms of the disease to be treated. In addition, it is understood by technicians in the field that, for any particular patient, a particular dosage regimen should be adjusted over time in accordance with the patient's needs and the professional evaluation of a physician; and the dosage ranges given herein are for illustrative purposes only and do not limit the use or scope of the pharmaceutical composition of the present invention.

In the present invention, the subject can be a mammal such as a human.

In the present invention, unless otherwise stated, scientific and technical terms used herein have the meanings generally understood by the technicians in the field. Moreover, cell culture, biochemistry, nucleic acid chemistry, immunology laboratory and other operation steps used in this invention are all routine steps widely used in the corresponding fields. In the meantime, for a better understanding of the present invention, definitions and explanations of the relevant terms are provided below.

As used herein, the term "natural amino acids" mainly includes the following 20 kinds of common amino acids: alanine (Ala), arginine (Arg), aspartic acid (Asn), asparagine (Asp), cysteine (Cys), glutamine (Gln), glutamic acid (Glu), glycine (Gly), histidine (His), leucine (Leu), isoleucine (Ile), lysine (Lys), methionine (Met), phenylalanine (Phe), proline (Pro), serine (Ser), threonine (Thr), tryptophan (Trp), tyrosine (Tyr) and valine (Val). The amino acid molecules are known to contain two functional groups, an amino group and a carboxyl group. The "amino acid fragment" described in this invention refers to a remaining part of amino acid molecules after removing a hydrogen from the amino group or deleting a hydroxyl group from the carboxyl group. Therefore, the "carboxyl residue" refers to the structure remaining after one hydroxyl group is deleted from the carboxyl group in the amino acid molecule.

As used herein, the term "alkyl" is defined as a linear or branched saturated aliphatic hydrocarbon group. In some embodiments, the alkyl contains 1 to 6 (e.g., 1, 2, 3, 4, 5, or 6) carbon atoms. For example, as used herein, the term "C1-C6 alkyl" refers to straight or branched alkyl groups of 1 to 6 carbon atoms (e.g. methyl, ethyl, n-propyl, isopropyl, n-butyl, isobutyl, sec-butyl, tert-butyl, n-amyl, isoamyl, neoamyl or n-hexyl, etc.).

As used herein, the term "C1-C6 alkoxy" refers to the C1-C6 alkyl-O-group, wherein the C1-C6 alkyl is described previously. Unrestricted examples of suitable C1-C6 alkoxy include methoxy, ethoxy, and isopropoxy groups, and the like.

As used herein, the term "C2-C6 acyl" refers to a univalent group containing 2 to 6 (e.g. 2, 3, 4, 5, or 6) carbon atoms with a general formula R—C(O)—, wherein R can be an alkyl, enyl, etc. Unrestricted examples of suitable C2-C6 acyl include acetyl, propionyl, isopropionyl, n-butyryl, sec-butyryl, t-butyryl, n-pentanoyl, isovaleryl, and tervaloyl.

As used herein, the term "C1-C6 alkoxycarbonyl" refers to the C1-C6 alkyl-OC(O)-group, wherein the C1-C6 alkyl is described previously. Unrestricted examples of the suitable C1-C6 alkoxycarbonyl include methoxycarbonyl, ethoxycarbonyl, propoxycarbonyl, tert-butoxycarbonyl, etc.

As used herein, the term "aryl" refers to a monocyclic or condensed ring group with aromaticity. For example, phenyl, naphthyl, etc.

As used herein, the term "aliphatic heterocycle" refers to a cyclic aliphatic hydrocarbon that contains at least one ring heteroatom selected from N, O, and S. In some embodiments, the term "3- to 8-membered aliphatic heterocycle" refers to the above aliphatic heterocycle containing 3 to 8 ring members (e.g., 3, 4, 5, 6, 7, or 8), e.g., 3- to 8-membered N-containing aliphatic heterocycle, 4- to 6-membered N-containing aliphatic heterocycle. Specific examples include, but are not limited to:

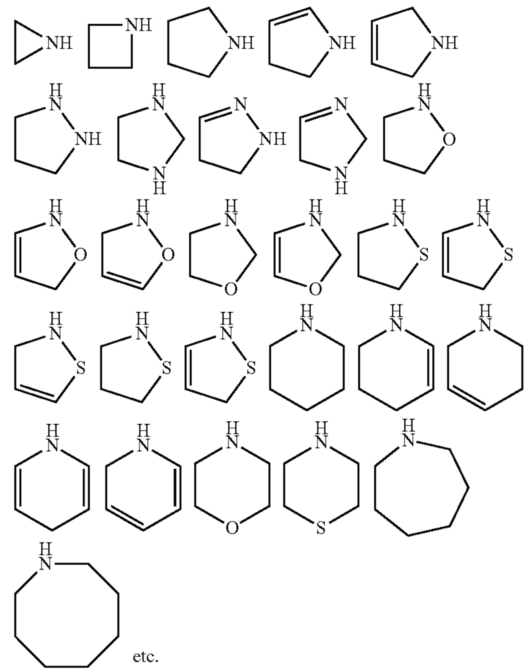

etc.

As used herein, the term "nitrogen-containing aliphatic heterocycle" refers to the aliphatic heterocycle containing at least one N atom, wherein the aliphatic heterocycle is defined as previously; the term of 3- to 8-membered nitrogen-containing aliphatic heterocycle refers to the nitrogen-containing aliphatic heterocycle described above that contains 3 to 8 ring members (e.g., 3, 4, 5, 6, 7, or 8).

As used herein, the term "3- to 8-membered nitrogen-containing aliphatic heterocycle-C1-C4 acyl" refers to a monovalent group of the 3- to 8-membered nitrogen-containing aliphatic heterocycle-R—C(O)-structure, wherein, the 3- to 8-membered nitrogen-containing aliphatic heterocycle is described previously, and R does not exist or is alkyl, enyl, etc. Examples include, but are not limited to:

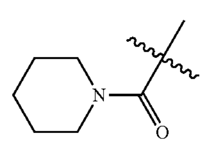,
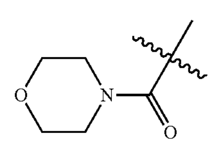,

-continued

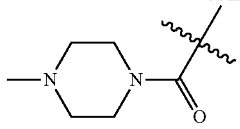,
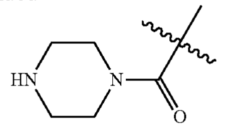
and
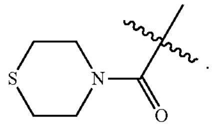.

As used herein, the terms "substitution" and "substituted" refer to selective substitution of one or more (e.g., one, two, three, or four) hydrogens connected to a specified atom by an indicated group, provided that the normal valence of the specified atom in the current situation is not exceeded and that the substitution results in a stable compound. The combination of substituents and/or variables are only allowed if such combination forms a stable compound.

If substituents are described as "independently selected from" a set of groups, each substituent is selected independently of the other. Therefore, each substituent may be the same or different from another (other) substituent.

As used herein, the term "one or more" means 1 or more under reasonable conditions, e.g. 2, 3, 4, 5 or 10.

Unless otherwise indicated, as used herein, a connection point of the substituent may come from any suitable position of the substituent.

As used herein, the term "stereoisomer" refers to an isomer that has a same atom connection order but has different spatial arrangement modes of atoms, e.g., enantiomers, geometric isomers, etc. The term "enantiomer" indicates an isomer formed due to at least one asymmetric center. In a compound with one or more (e.g., one, two, three, or four) asymmetric centers, enantiomers and diastereomers can be generated. When the molecule contains double bonds, such as C═C, C═N or N═N double bonds, the two atoms connected by the double bonds cannot rotate freely and can also exist in the form of geometric isomers (cis/trans).

As used herein, a solid line ( ), a solid wedge line ( ) or a dashed wedge line ( ) can be used to delineate the chemical bonds of the compound of the present invention. The solid line is used to describe bonding to asymmetric carbon atoms, which indicates that all possible stereoisomers formed by the side carbon atoms are included. The solid or dashed wedge line is used to describe bonding to the asymmetric carbon atoms, which indicates the existence of the indicated stereoisomers.

The compound of the present invention may exist in the form of a solvate (preferably a hydrate), wherein the compound of the present invention contains a polar solvent as a structural element of crystal lattice of the compound, in particular water, methanol or ethanol. The amount of the polar solvent, especially water, can be existed in stoichiometric or non-stoichiometric ratios. It should be understood that, although any solvate of the compound of the formula I used in the treatment of the disease or condition of this application may provide different properties (including pharmacokinetic properties), once the solvate is absorbed into a subject, the compound of the formula I is obtained, such that the use of the compound of the formula I covers the use of any solvate of the compound of the formula I respectively.

It should also be understood that some of the compounds of the present invention may exist in free-form for therapeutic use or, where applicable, in the form of their pharmaceutically acceptable derivatives. In the present invention, the pharmaceutically acceptable derivative includes, but is not limited to, the pharmaceutically acceptable salt or ester that are capable of providing, directly or indirectly, the compound of the present invention or metabolites or residues thereof after the pharmaceutically acceptable derivative is administered to a patient in need of it.

The pharmaceutically acceptable salts of the compound include an acid addition salt and an alkali addition salt.

An overview of suitable salts can be seen in Stahl and Wermuth's "Handbook of Pharmaceutical Salts: Properties, Selection, and Use" (Wiley-VCH, 2002), or S. M. Berge et al., "Pharmaceutical Salts", J. Pharm. Sci. 1977, 66, 1-19. A method for preparing the pharmaceutically acceptable salts of the compound of the present invention is known to technicians in the field.

The suitable acid addition salt is formed from acids that form the pharmaceutically acceptable salts. The suitable base addition salt is formed from bases that form pharmaceutically acceptable salts. In some embodiments, suitable inorganic acids are hydrochloric acid, hydrobromic acid, hydroiodic acid, sulfuric acid, phosphoric acid, or nitric acid, etc.; organic acids are formic acid, acetic acid, acetoacetic acid, pyruvic acid, trifluoroacetic acid, propionic acid, butyric acid, caproic acid, enanthic acid, undecanoic acid, lauric acid, benzoic acid, salicylic acid, 2-(4-hydroxybenzoyl)-benzoic acid, camphoric acid, cinnamic acid, cyclopentanepropionic acid, glucaric acid, 3-hydroxy-2-naphthoic acid, nicotinic acid, pamoic acid, pectinic acid, 3-phenylpropionic acid, picric acid, pivalic acid, 2-hydroxyethanesulfonic acid, ecanoic acid, aminosulfonic acid, trifluoromethanesulphonic acid, dodecyl sulfuric acid, ethanesulfonic acid, benzenesulfonic acid, p-toluenesulfonic acid, methanesulfonic acid, 2-naphthalic acid, naphthalene disulfonic acid, camphoric acid, citric acid, tartaric acid, stearic acid, lactic acid, oxalic acid, propandioic acid, succinic acid, malic acid, adipic acid, alginic acid, maleic acid, fumaric acid, D-glucosylic acid, mandelic acid, ascorbic acid, glucoheptonic acid, glycerophosphoric acid, aspartic acid, sulfosalicylic acid, etc. For example, HCl (or hydrochloric acid), HBr (or a hydrobromic acid solution), methanesulfonic acid, sulfuric acid, tartaric acid, or fumaric acid can be used to form pharmaceutically acceptable salts with the compound represented by the formula I.

As used herein, the term "pharmaceutically acceptable ester" means an ester derived from the compound of the present invention, which includes a physiologically hydrolyzable ester (the ester can be hydrolyzed under physiological conditions to release the compound of the present invention in form of free acid or alcohol). The compound of the invention can also be an ester.

As used herein, the term "metabolic stability" refers to the ability of a compound to enter and stably exist in the body as a prototype drug and not be metabolized to other structural forms.

As used herein, the term "subject" can refer to a patient or other animals that receive a composition of the present invention to treat, prevent, mitigate, and/or alleviate a disease or condition described in the present invention, and the animals particularly refers to mammals such as humans, dogs, monkeys, cattle, horses, etc.

As used herein, the term "excipients" refers to an excipient or a medium used to administer the compound, including, but not limited to, diluents, disintegrants, precipitation inhibitors, surfactants, flow aids, adhesives, lubricants, coating materials, etc. The examples of excipients include but are not limited to aluminum monostearate, aluminum stearate, carboxymethylcellulose, sodium carboxymethylcellulose, crospovidone, glyceryl isostearate, glyceryl monostearate, hydroxyethyl cellulose, hydroxymethylcellulose, octacosyl hydroxystearate, hydroxypropyl cellulose, lactose, a lactose monohydrate, magnesium stearate, mannitol, microcrystalline cellulose, etc.

Specific Models for Carrying Out the Present Invention

The embodiments of the present invention will be completely described below in conjunction with examples, but it is understood by the technicians in the field that the following examples are intended only to illustrate the invention and are not considered to limit the scope of the invention. If no specific condition is indicated in the examples, the general condition or the condition recommended by a manufacturer shall be followed. The reagents or apparatuses used without indication of the manufacturer are conventional products that can be obtained by market purchase.

Abbreviation Table

| Abbreviation | Term |
|---|---|
| NMDA | N-methyl-D-aspartic acid |
| DCM | dichloromethane |
| DMF | N,N-DiMethylforMaMide |
| MeOH | Methanol |
| EtOAc | ethyl acetate |
| PE | Petroleum ether |
| TEA | Triethylamine |
| TFAA | Trifluoroacetic anhydride |
| tBu | tert-butyl |
| HOBt | N-Hydroxybenzotrizole |
| EDCI | N-(3-Dimethylaminopyl)-N'-Ethylcarbodiimede Hydrochloride |
| Thr | Threonine |
| Ser | Serine |
| Val | Valine |
| Boc | Tert-butoxycarbonyl |
| Fmoc | Fluorene methoxycarbonyl |
| TBTU | 2-(1H-Benzotriazole-1-yl)-1,1,3,3-tetramethyluronium tetrafluoroborate |
| TLC | thin layer chromatography |

EXEMPLARY SYNTHETIC SCHEME

Examples of Synthesis of A-001 and A-002

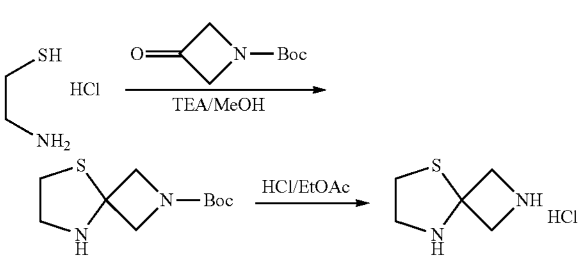

A-002 A-001

At −15° C., 1.14 g (10 mmol, 1.0eq) of a raw material mercaptoethylamine hydrochloride was dissolved in 100 ml of methanol, 1.75 ml (15 mmol, 1.5eq) of triethylamine was added and sufficiently dissociated, 1.8 g (10 mmol, 1.0eq) of 1-Boc-3-azetidinone was added, the materials were continuously reacted at a low temperature for 15 min and then transferred to room temperature; after the completion of the materials reaction was monitored by TLC, vacuum concentration was performed, a concentrate was dissolved with 100 ml of ethyl acetate, washed with a small amount of water for many times (15 ml×4), dried with anhydrous sodium sulfate, filtered, and then concentrated. A crude product was purified with a silica gel column (PE:EtOAc=2:1) to obtain a total of 2.25 g of a white solid A-002 with a yield of 92.6%. $^1$H-NMR (400 MHz, DMSO-$d_6$), δ ppm: 1.37 (s, 9H, —$CH_3$), 3.12 (t, 2H, J=8.2 Hz), 3.34 (t, 2H, J=6.1 Hz), 4.1-4.20 (d, 2H, J=9.2 Hz), 4.59-4.62 (d, 2H, J=9.5 Hz), 9.3 (s, 1H). M+1:231.11.

1 g (6 mmol) of an intermediate A-002 was dissolved in 10 mL of anhydrous ethyl acetate, and then 10 mL of 4 mol/L HCl/EtOAc was added and stirred overnight at room temperature, and a white solid was generated in the system; after the completion of the materials reaction was monitored by TLC, the reaction was terminated. Filtration and washing with anhydrous diethyl ether were performed, and then a total of 0.54 g of a white solid A-001 was obtained with a yield of 76%. $^1$H-NMR (400 MHz, DMSO-$d_6$), δ ppm: 3.10 (t, 2H, J=6.8 Hz), 3.37 (t, 2H, J=6.4 Hz), 4.1-4.15 (d, 2H, J=11.2 Hz), 4.55-4.6 (d, 2H, J=10.5 Hz), 9.5 (s, 1H), 9.8 (s, 1H). M+1:131.06.

According to the preparation method of A-002, the corresponding products A-016, A-030 and A-044 of five-membered ring or six-membered ring can be prepared. The methods were the same as that of A-002, except that the corresponding cycloketone was replaced; similarly, the corresponding products A-015, A-029 and A-043 of five-membered ring or six-membered ring were prepared according to the preparation method of A-001.

A-016: the raw material 1-Boc-3-azetidinone in the synthesis step of A-002 was replaced with N-Boc-3-pyrrolidone, and the rest operations were the same as those in the synthesis of A-002. M+1: 245.12.

A-030: the raw material 1-Boc-3-azetidinone in the synthesis step of A-002 was replaced with N-Boc-4-piperidone and the rest operations were the same as those in the synthesis of A-002. M+1: 259.14.

A-044: the raw material 1-Boc-3-azetidinone in the synthesis step of A-002 was replaced with N-Boc-3-piperidone, and the rest operations were the same as those in the synthesis of A-002. M+1: 259.14.

A-015: the intermediate A-002 in the synthesis step of A-001 was replaced with A-016, and the rest operations were the same as those in the synthesis of A-001. M+1: 145.07.

A-029: the intermediate A-002 in the synthesis step of A-001 was replaced with A-030, and the rest operations were the same as those in the synthesis of A-001. M+1: 159.09.

A-043: the intermediate A-002 in the synthesis step of A-001 was replaced with A-044, and the rest operations were the same as those in the synthesis of A-001. M+1: 159.09.

Example of A-003

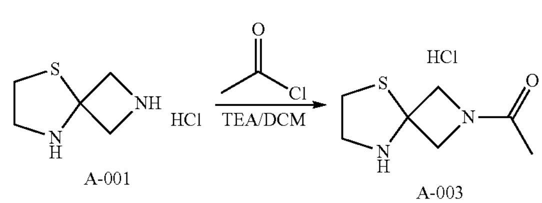

A-001 A-003

A total of 0.4 g (2.4 mmol) of the compound A-001 was dissolved in 20 ml of anhydrous DCM, and 665 μL (4.8 mmol) of TEA was added for dissociation; 155 μL (2.2 mmol) of acetyl chloride was added to 5 ml of DCM, and it was slowly dripped to the above reaction system with a dropper funnel under ice bath conditions, and the materials were continuously reacted at low temperature for half an hour and then moved to room temperature; the reaction was performed for 4 h at room temperature; when the completion of the materials reaction was monitored by TLC, the reaction was terminated. A small amount of water was used for washing (5 ml×3), an organic phase was taken, dried, filtered, concentrated, and separated through a silica gel column to obtain a brown oily substance, after stirring with hydrochloric acid to generate salt, a solid was generated, and a total of 0.31 g of a product A-003 was obtained with a yield of 61.9%. $^1$H-NMR (400 MHz, DMSO-$d_6$), δ ppm: 2.03 (s, 3H), 3.15 (t, 2H, J=6.8 Hz), 3.29 (t, 2H, J=7.4 Hz), 4.11-4.21 (d, 2H, J=7.1 Hz), 4.51-4.63 (d, 2H, J=8.1 Hz), 9.53 (s, 1H). M+1:173.07.

Examples of Preparation of A-004 and A-005

- A-004: acetyl chloride in the synthesis step of A-003 was replaced with isobutyryl chloride, and the rest operations were the same as those in the synthesis of A-003. M+1: 201.10.
- A-005: acetyl chloride in the synthesis step of A-003 was replaced with pivaloyl chloride, and the rest operations were the same as those in the synthesis of A-003. M+1: 215.11.

Examples of preparation of A-017 to A-019:

- A-017: A-001 in the synthesis step of A-003 was replaced with A-015, and the rest operations were the same as those in the synthesis of A-003. M+1: 187.08.
- A-018: A-001 in the synthesis step of A-003 was replaced with A-015 and acetyl chloride was replaced with isobutyryl chloride, and the rest operations were the same as those in the synthesis of A-003. M+1: 215.11.
- A-019: A-001 in the synthesis step of A-003 was replaced with A-015 and acetyl chloride was replaced with pivaloyl chloride, and the rest operations were the same as those in the synthesis of A-003. M+1: 229.13.

Examples of preparation of A-031 to A-033:

- A-031: A-001 in the synthesis step of A-003 was replaced with A-029, and the rest operations were the same as those in the synthesis of A-003. M+1: 201.10.
- A-032: A-001 in the synthesis step of A-003 was replaced with A-029 and acetyl chloride was replaced with isobutyryl chloride, and the rest operations were the same as those in the synthesis of A-003. M+1: 229.13.
- A-033: A-001 in the synthesis step of A-003 was replaced with A-029 and acetyl chloride was replaced with pivaloyl chloride, and the rest operations were the same as those in the synthesis of A-003. M+1: 243.15.

Examples of preparation of A-045 to A-047:

- A-045: A-001 in the synthesis step of A-003 was replaced with A-043, and the rest operations were the same as those in the synthesis of A-003. M+1: 201.10.
- A-046: A-001 in the synthesis step of A-003 was replaced with A-043 and acetyl chloride was replaced with isobutyryl chloride, and the rest operations were the same as those in the synthesis of A-003. M+1: 229.13.
- A-047: A-001 in the synthesis step of A-003 was replaced with A-043 and acetyl chloride was replaced with pivaloyl chloride, and the rest operations were the same as those in the synthesis of A-003. M+1: 243.15.

Example of A-006

The example illustrates a synthesis method of compound A-006.

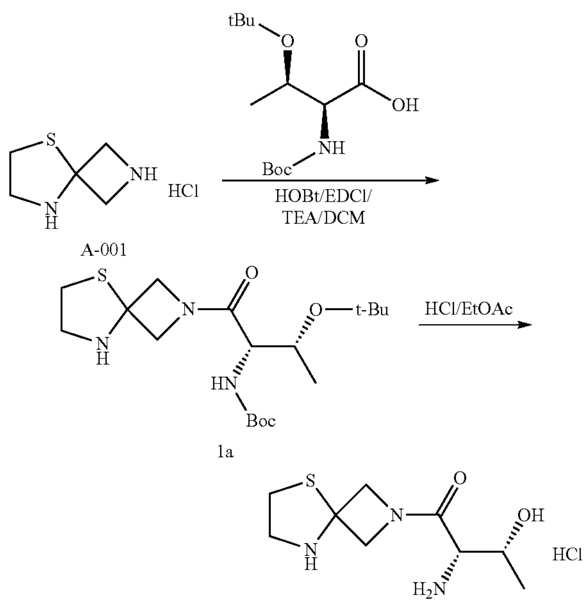

A-001

1a

A-006

A total of 0.4 g (2.4 mmol) of the intermediate A-001 was dissolved in 20 ml of anhydrous DCM, 665 μL (4.8 mmol) of TEA was added for dissociation, and after stirring for 5 min, 0.63 g (2.3 mmol) of Boc-tBu-Thr, 0.49 g (3.6 mmol) of HOBt, and 0.62 g (3.6 mmol) of EDCI were added and the raw materials were reacted overnight at room temperature. When the completion of the raw materials reaction was monitored by TLC, the reaction was terminated. A saturated citric acid aqueous solution was used for washing (10 mL×2), and an organic phase was taken, dried with anhydrous sodium sulfate, filtered, concentrated, and separated through a silica gel column to obtain a total of 0.61 g of a colorless oily substance of intermediate 1a with a yield of 68.8%. $^1$H-NMR (400 MHz, DMSO-$d_6$), δ ppm: 1.14-1.20 (m, 12H), 1.37 (s, 9H), 3.24 (t, 2H, J=7.2 Hz), 3.38-3.65 (m, 2H), 3.72-3.95 (m, 3H), 4.10-4.30 (m, 1H), 4.65-4.94 (m, 3H), 7.34 (s, 1H), 8.23 (s, 1H). M+1: 388.22.

A total of 0.5 g (1.3 mmol) of the intermediate 1a was dissolved in 5 ml of anhydrous ethyl acetate, and 10 mL of 4 mol/L HCl/EtOAc was added and the raw materials were reacted overnight at room temperature, and a white solid was generated in the system; when the completion of the materials reaction was monitored by TLC, the reaction was terminated. The product was filtered under reduced pressure and washed with anhydrous diethyl ether to obtain a total of 0.25 g of a white solid A-006 with a yield of 73%. $^1$H-NMR (400 MHz, DMSO-$d_6$), δ ppm: 1.21 (m, 3H), 3.21 (t, 2H, J=6.4 Hz), 3.36-3.65 (m, 2H), 3.7-3.97 (m, 3H), 4.10-4.30 (m, 1H), 4.60-4.71 (m, 2H), 4.86-5.01 (m, 1H), 5.65 (s, 1H), 8.23-8.28 (d, 2H, J=21 Hz). M+1: 232.10.

Examples of Preparation of A-007 to A-014

A-007:

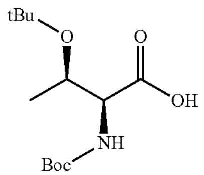 [SMILES: C[C@@H](OC(C)(C)C)[C@H](NC(=O)OC(C)(C)C)C(=O)O]

in the synthesis step of A-006 was replaced with

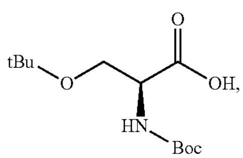 [SMILES: CC(C)(C)OC[C@H](NC(=O)OC(C)(C)C)C(=O)O]

and the rest operations were the same as those in A-006 synthesis. M+1: 218.09.

A-007-1:

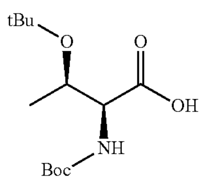 [SMILES: C[C@@H](OC(C)(C)C)[C@H](NC(=O)OC(C)(C)C)C(=O)O]

in the synthesis step of A-006 was replaced with

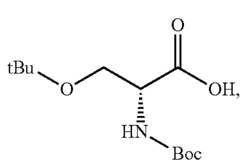 [SMILES: CC(C)(C)OC[C@@H](NC(=O)OC(C)(C)C)C(=O)O]

and the rest operations were the same as those in A-006 synthesis. M+1: 218.09.

A-008:

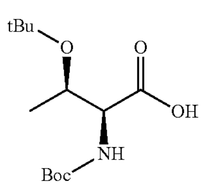 [SMILES: C[C@@H](OC(C)(C)C)[C@H](NC(=O)OC(C)(C)C)C(=O)O]

Boc in the synthesis step of A-006 was replaced with

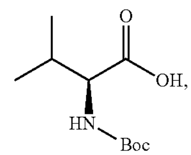

and the rest operations were the same as those in A-006 synthesis. M+1: 230.12.

A-008-1:

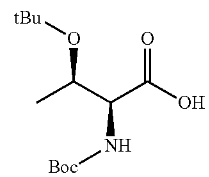 [SMILES: C[C@@H](OC(C)(C)C)[C@H](NC(=O)OC(C)(C)C)C(=O)O]

in the synthesis step of A-006 was replaced with

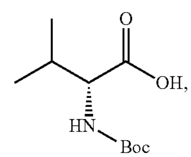

and the rest operations were the same as those in A-006 synthesis. M+1: 230.12.

A-009:

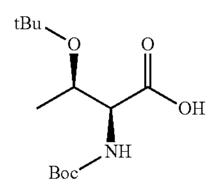 [SMILES: C[C@@H](OC(C)(C)C)[C@H](NC(=O)OC(C)(C)C)C(=O)O]

in the synthesis step of A-006 was replaced with

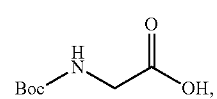

and the rest operations were the same as those in A-006 synthesis. M+1: 188.08.

A-010:

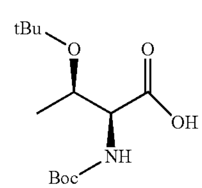 [SMILES: C[C@@H](OC(C)(C)C)[C@H](NC(=O)OC(C)(C)C)C(=O)O]

in the synthesis step of A-006 was replaced with

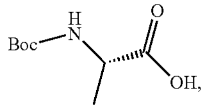

and the rest operations were the same as those in A-006 synthesis. M+1: 202.09.

A-011:

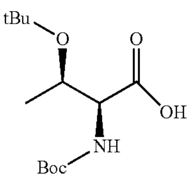 [SMILES: C[C@@H](OC(C)(C)C)[C@H](NC(=O)OC(C)(C)C)C(=O)O]

in the synthesis step of A-006 was replaced with

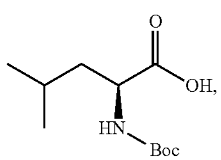 [SMILES: CC(C)C[C@H](NC(=O)OC(C)(C)C)C(=O)O]

and the rest operations were the same as those in A-006 synthesis. M+1: 244.14.

A-012:

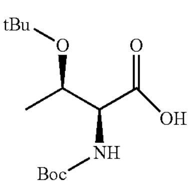 [SMILES: C[C@@H](OC(C)(C)C)[C@H](NC(=O)OC(C)(C)C)C(=O)O]

in the synthesis step of A-006 was replaced with

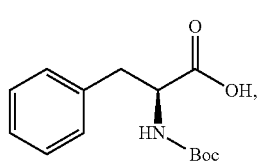

and the rest operations were the same as those in A-006 synthesis. M+1: 278.12.

A-013:

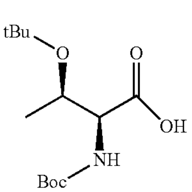 [SMILES: C[C@@H](OC(C)(C)C)[C@H](NC(=O)OC(C)(C)C)C(=O)O]

in the synthesis step of A-006 was replaced with

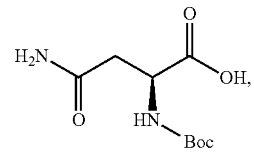 [SMILES: CC(C)(C)OC(=O)N[C@@H](CC(N)=O)C(=O)O]

and the rest operations were the same as those in A-006 synthesis. M+1: 245.10.

A-014:

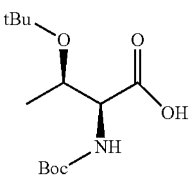 [SMILES: C[C@@H](OC(C)(C)C)[C@H](NC(=O)OC(C)(C)C)C(=O)O]

in the synthesis step of A-006 was replaced with

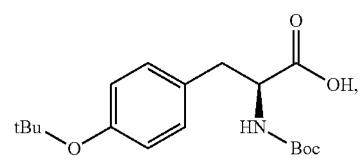 [SMILES: CC(C)(C)OC(=O)N[C@@H](Cc1ccc(OC(C)(C)C)cc1)C(=O)O]

and the rest operations were the same as those in A-006 synthesis. M+1: 294.12.

Examples of Preparation of A-020 to A-028

A-020: A-001 in the synthesis step of A-006 was replaced with A-015, and the rest operations were the same as those in A-006 synthesis. M+1: 246.12.

A-021: A-001 in the synthesis step of A-006 was replaced with A-015,

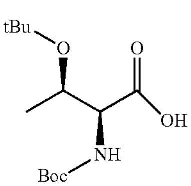 [SMILES: C[C@@H](OC(C)(C)C)[C@H](NC(=O)OC(C)(C)C)C(=O)O]

was replaced with

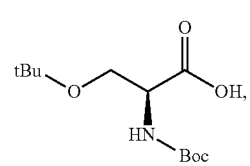 [SMILES: CC(C)(C)OC[C@H](NC(=O)OC(C)(C)C)C(=O)O]

and the rest operations were the same as those in A-006 synthesis. M+1: 232.10.

A-022: A-001 in the synthesis step of A-006 was replaced with A-015,

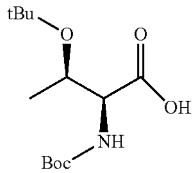 [SMILES: C[C@@H](OC(C)(C)C)[C@H](NC(=O)OC(C)(C)C)C(=O)O]

was replaced with

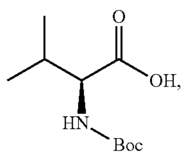

and the rest operations were the same as those in A-006 synthesis. M+1: 244.14.

A-023: A-001 in the synthesis step of A-006 was replaced with A-015,

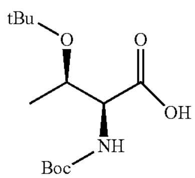 [SMILES: C[C@@H](OC(C)(C)C)[C@H](NC(=O)OC(C)(C)C)C(=O)O]

was replaced with

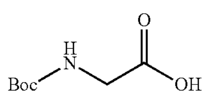

and the rest operations were the same as those in A-006 synthesis. M+1: 202.09.

A-024: A-001 in the synthesis step of A-006 was replaced with A-015,

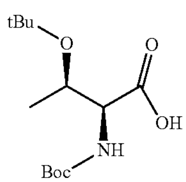

was replaced with

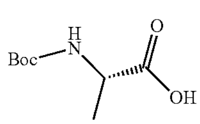

and the rest operations were the same as those in A-006 synthesis. M+1: 216.11.

A-025: A-001 in the synthesis step of A-006 was replaced with A-015,

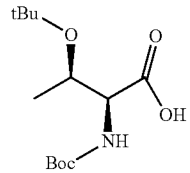 [SMILES: C[C@@H](OC(C)(C)C)[C@H](NC(=O)OC(C)(C)C)C(=O)O]

was replaced with

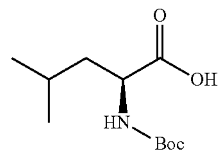 [SMILES: CC(C)C[C@H](NC(=O)OC(C)(C)C)C(=O)O]

and the rest operations were the same as those in A-006 synthesis. M+1: 258.16.

A-026: A-001 in the synthesis step of A-006 was replaced with A-015,

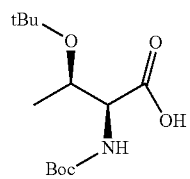 [SMILES: C[C@@H](OC(C)(C)C)[C@H](NC(=O)OC(C)(C)C)C(=O)O]

was replaced with

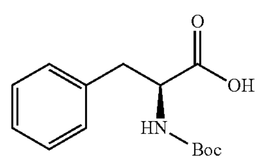 [SMILES: CC(C)(C)OC(=O)N[C@@H](Cc1ccccc1)C(=O)O]

and the rest operations were the same as those in A-006 synthesis. M+1: 292.14.

A-027: A-001 in the synthesis step of A-006 was replaced with A-015,

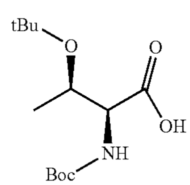 [SMILES: C[C@@H](OC(C)(C)C)[C@H](NC(=O)OC(C)(C)C)C(=O)O]

was replaced with

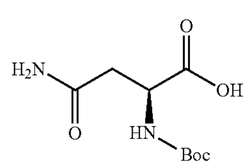 [SMILES: CC(C)(C)OC(=O)N[C@@H](CC(N)=O)C(=O)O]

and the rest operations were the same as those in A-006 synthesis. M+1: 259.12.

A-028: A-001 in the synthesis step of A-006 was replaced with A-015,

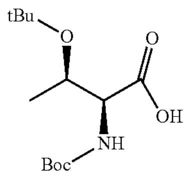

was replaced with

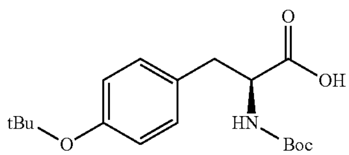 [SMILES: CC(C)(C)OC(=O)N[C@@H](Cc1ccc(OC(C)(C)C)cc1)C(=O)O]

and the rest operations were the same as those in A-006 synthesis. M+1: 308.14.

Examples of Preparation of A-034 to A-042

A-034: A-001 in the synthesis step of A-006 was replaced with A-029, and the rest operations were the same as those in A-006 synthesis. M+1: 260.14.

A-035: A-001 in the synthesis step of A-006 was replaced with A-029,

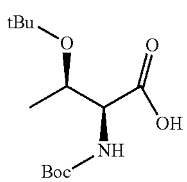

was replaced with

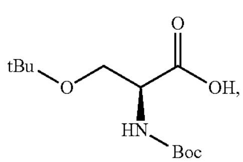 [SMILES: CC(C)(C)OC[C@H](NC(=O)OC(C)(C)C)C(=O)O]

and the rest operations were the same as those in A-006 synthesis. M+1: 246.12.

A-036: A-001 in the synthesis step of A-006 was replaced with A-029,

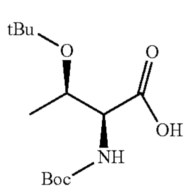

was replaced with

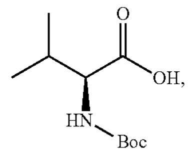

and the rest operations were the same as those in A-006 synthesis. M+1: 258.16.

A-037: A-001 in the synthesis step of A-006 was replaced with A-029,

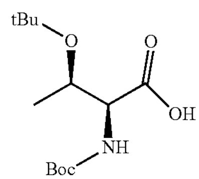 [SMILES: C[C@@H](OC(C)(C)C)[C@H](NC(=O)OC(C)(C)C)C(=O)O]

was replaced with

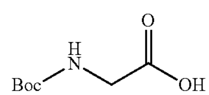 [SMILES: CC(C)(C)OC(=O)NCC(=O)O]

and the rest operations were the same as those in A-006 synthesis. M+1: 216.11.

A-038: A-001 in the synthesis step of A-006 was replaced with A-029,

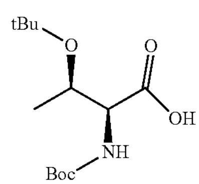 [SMILES: C[C@@H](OC(C)(C)C)[C@H](NC(=O)OC(C)(C)C)C(=O)O]

was replaced with

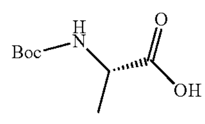

and the rest operations were the same as those in A-006 synthesis. M+1: 230.12.

A-039: A-001 in the synthesis step of A-006 was replaced with A-029,

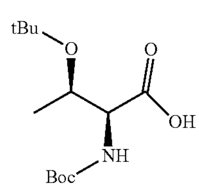 [SMILES: C[C@@H](OC(C)(C)C)[C@H](NC(=O)OC(C)(C)C)C(=O)O]

was replaced with

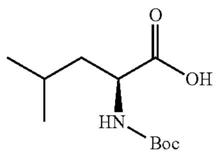 [SMILES: CC(C)C[C@H](NC(=O)OC(C)(C)C)C(=O)O]

and the rest operations were the same as those in A-006 synthesis. M+1: 272.17.

A-040: A-001 in the synthesis step of A-006 was replaced with A-029,

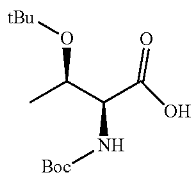 [SMILES: C[C@@H](OC(C)(C)C)[C@H](NC(=O)OC(C)(C)C)C(=O)O]

was replaced with

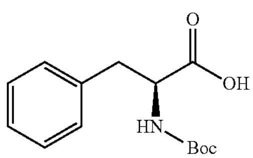 [SMILES: CC(C)(C)OC(=O)N[C@@H](Cc1ccccc1)C(=O)O]

and the rest operations were the same as those in A-006 synthesis. M+1: 306.16.

A-041: A-001 in the synthesis step of A-006 was replaced with A-029,

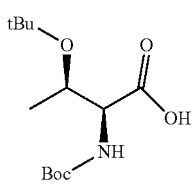 [SMILES: C[C@@H](OC(C)(C)C)[C@H](NC(=O)OC(C)(C)C)C(=O)O]

was replaced with

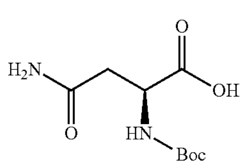

and the rest operations were the same as those in A-006 synthesis. M+1: 273.13.

A-042: A-001 in the synthesis step of A-006 was replaced with A-029,

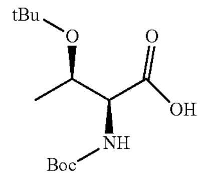 [SMILES: C[C@@H](OC(C)(C)C)[C@H](NC(=O)OC(C)(C)C)C(=O)O]

was replaced with

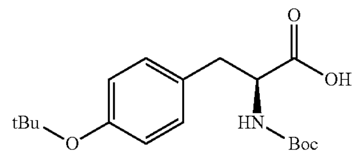 [SMILES: CC(C)(C)OC(=O)N[C@@H](Cc1ccc(OC(C)(C)C)cc1)C(=O)O]

and the rest operations were the same as those in A-006 synthesis. M+1: 322.15.

Examples of Preparation of A-048 to A-056

A-048: A-001 in the synthesis step of A-006 was replaced with A-043, and the rest operations were the same as those in A-006 synthesis. M+1: 260.14.

A-049: A-001 in the synthesis step of A-006 was replaced with A-043,

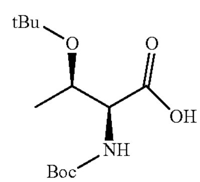 [SMILES: C[C@@H](OC(C)(C)C)[C@H](NC(=O)OC(C)(C)C)C(=O)O]

was replaced with

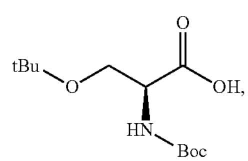 [SMILES: CC(C)(C)OC[C@H](NC(=O)OC(C)(C)C)C(=O)O]

and the rest operations were the same as those in A-006 synthesis. M+1: 246.12.

A-050: A-001 in the synthesis step of A-006 was replaced with A-043,

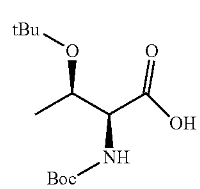 [SMILES: C[C@@H](OC(C)(C)C)[C@H](NC(=O)OC(C)(C)C)C(=O)O]

was replaced with

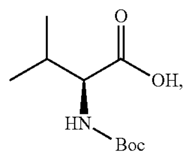

and the rest operations were the same as those in A-006 synthesis. M+1: 258.16.

A-051: A-001 in the synthesis step of A-006 was replaced with A-043,

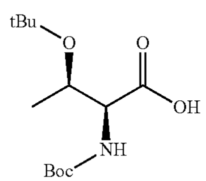 [SMILES: C[C@@H](OC(C)(C)C)[C@H](NC(=O)OC(C)(C)C)C(=O)O]

was replaced with

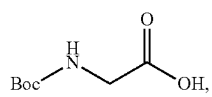

and the rest operations were the same as those in A-006 synthesis. M+1: 216.11.

A-052: A-001 in the synthesis step of A-006 was replaced with A-043,

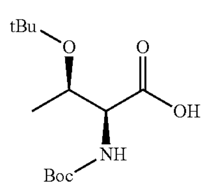 [SMILES: C[C@@H](OC(C)(C)C)[C@H](NC(=O)OC(C)(C)C)C(=O)O]

was replaced with

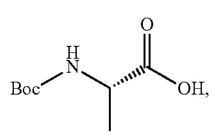

and the rest operations were the same as those in A-006 synthesis. M+1: 230.12.

A-053: A-001 in the synthesis step of A-006 was replaced with A-043,

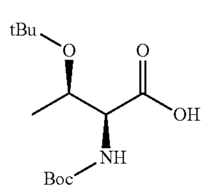 [SMILES: C[C@@H](OC(C)(C)C)[C@H](NC(=O)OC(C)(C)C)C(=O)O]

was replaced with

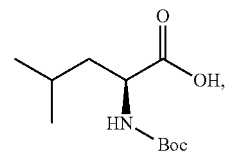 [SMILES: CC(C)C[C@H](NC(=O)OC(C)(C)C)C(=O)O]

and the rest operations were the same as those in A-006 synthesis. M+1: 272.17.

A-054: A-001 in the synthesis step of A-006 was replaced with A-043,

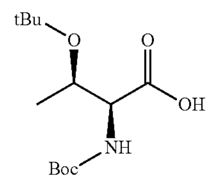 [SMILES: C[C@@H](OC(C)(C)C)[C@H](NC(=O)OC(C)(C)C)C(=O)O]

was replaced with

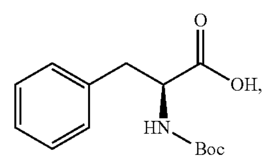 [SMILES: CC(C)(C)OC(=O)N[C@@H](Cc1ccccc1)C(=O)O]

and the rest operations were the same as those in A-006 synthesis. M+1: 306.16.

A-055: A-001 in the synthesis step of A-006 was replaced with A-043,

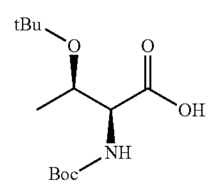 [SMILES: C[C@@H](OC(C)(C)C)[C@H](NC(=O)OC(C)(C)C)C(=O)O]

was replaced with

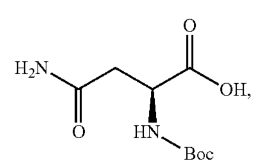 [SMILES: CC(C)(C)OC(=O)N[C@@H](CC(N)=O)C(=O)O]

and the rest operations were the same as those in A-006 synthesis. M+1: 273.13.

A-056: A-001 in the synthesis step of A-006 was replaced with A-043,

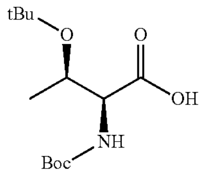 [SMILES: C[C@@H](OC(C)(C)C)[C@H](NC(=O)OC(C)(C)C)C(=O)O]

was replaced with

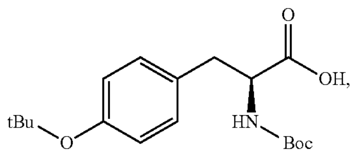 [SMILES: CC(C)(C)OC(=O)N[C@@H](Cc1ccc(OC(C)(C)C)cc1)C(=O)O]

and the rest operations were the same as those in A-006 synthesis. M+1: 322.15.

Example of A-059

The example illustrates a synthesis method of compound A-059.

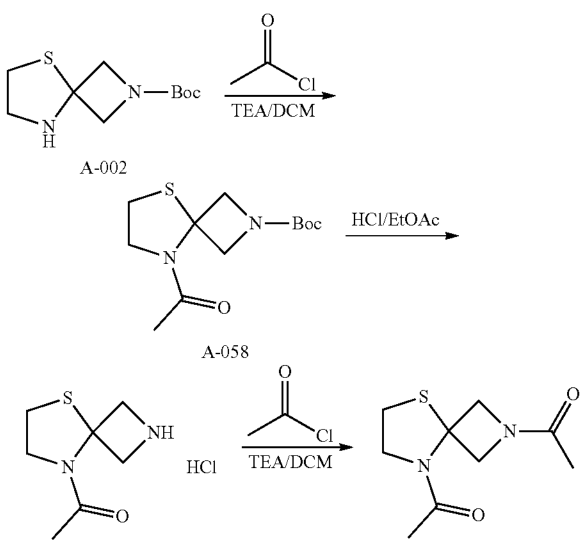

A-002

A-058

A-057

A-059

1. Synthesis of an Intermediate A-058

A total of 0.6 g (2.6 mmol) of the compound A-002 was dissolved in 20 ml of anhydrous DCM, and 1.4 mL (10 mmol) of TEA was added; 350 μL (5 mmol) of acetyl chloride was added to 5 mL of DCM, and it was slowly dripped to the above reaction system with a dropper funnel under ice bath conditions, and the materials were reacted at low temperature for half an hour and then moved to room temperature, the reaction was continually performed for 4 h at room temperature; when the completion of the materials reaction was monitored by TLC, the reaction was terminated. After washing with water (10 mL×3), an organic phase was taken, dried, filtered, concentrated, and separated through a silica gel column to obtain a total of 0.57 g of a brown oily substance A-058 with a yield of 81.4%. $^1$H-NMR (400 MHz, DMSO-$d_6$), δ ppm: 1.38 (s, 9H), 2.05 (s, 3H), 3.14 (t, 2H, J=7.8 Hz), 3.35 (t, 2H, J=5.8 Hz), 4.13-4.22 (d, 2H, J=8.7 Hz), 4.60-4.63 (d, 2H, J=10.2 Hz). M+1: 273.12.

2. Synthesis of an Intermediate A-057

A-057 was obtained by deprotecting A-058 and was synthesized in the same method as that of A-001. $^1$H-NMR (400 MHz, DMSO-$d_6$), δ ppm: 2.06 (s, 3H), 3.17 (t, 2H, J=6.3 Hz), 3.34 (t, 2H, J=5.8 Hz), 4.09-4.17 (d, 2H, J=6.9 Hz), 4.49-4.61 (d, 2H, J=7.9 Hz), 9.21 (s, 1H). M+1:173.07.

3. Synthesis of the End Product A-059

A synthesis method of the end product A-059 was the same as that of the A-058. $^1$H-NMR (400 MHz, DMSO-$d_6$), δ ppm: 1.73 (s, 3H), 2.06 (s, 3H), 3.01 (t, 2H, J=6 Hz), 3.74-3.82 (m, 3H), 4.05-4.07 (d, 1H, J=10 Hz), 4.64-4.66 (d, 1H, J=9.6 Hz), 4.90-4.92 (d, 1H, J=8.8 Hz). M+1: 215.08.

According to the synthesis method of A-058, the following products were prepared:

Examples of Preparation of A-070, A-078, A-086

A-070: A-002 was replaced with A-016, and the rest operations were the same as those in A-058 synthesis. M+1: 287.14.

A-078: A-002 was replaced with A-030, and the rest operations were the same as those in A-058 synthesis. M+1: 301.15.

A-086: A-002 was replaced with A-044, and the rest operations were the same as those in A-058 synthesis. M+1: 301.15.

Examples of Preparation of A-094, A-102, A-110, A-118

A-094: acetyl chloride was replaced with isobutyryl chloride, and the rest operations were the same as those in A-058 synthesis. M+1: 301.15.

A-102: A-002 was replaced with A-016, acetyl chloride was replaced with isobutyryl chloride, and the rest operations were the same as those in A-058 synthesis. M+1: 315.17.

A-110: A-002 was replaced with A-030, acetyl chloride was replaced with isobutyryl chloride, and the rest operations were the same as those in A-058 synthesis. M+1: 329.18.

A-118: A-002 was replaced with A-044, acetyl chloride was replaced with isobutyryl chloride, and the rest operations were the same as those in A-058 synthesis. M+1: 329.18.

Examples of Preparation of A-126, A-134, A-142, A-150

A-126: acetyl chloride was replaced with pivaloyl chloride, and the rest operations were the same as those in A-058 synthesis. M+1: 315.17.

A-134: A-002 was replaced with A-016, acetyl chloride was replaced with pivaloyl chloride, and the rest operations were the same as those in A-058 synthesis. M+1: 329.18.

A-142: A-002 was replaced with A-030, acetyl chloride was replaced with pivaloyl chloride, and the rest operations were the same as those in A-058 synthesis. M+1: 343.20.

A-150: A-002 was replaced with A-044, acetyl chloride was replaced with pivaloyl chloride, and the rest operations were the same as those in A-058 synthesis. M+1: 343.20.

Examples of Preparation of A-158, A-166, A-174, A-182

A-158: The solvent was replaced with DMF, acetyl chloride was replaced with isobutyl iodide, TEA was replaced with potassium carbonate, and the rest operations were the same as those in A-058 synthesis. M+1: 287.17.

A-166: A-002 was replaced with A-016, the solvent was replaced with DMF, acetyl chloride was replaced with isobutyl iodide, TEA was replaced with potassium carbonate, and the rest operations were the same as those in A-058 synthesis. M+1: 301.19.

A-174: A-002 was replaced with A-030, the solvent was replaced with DMF, acetyl chloride was replaced with isobutyl iodide, TEA was replaced with potassium carbonate, and the rest operations were the same as those in A-058 synthesis. M+1: 315.20.

A-182: A-002 was replaced with A-044, the solvent was replaced with DMF, acetyl chloride was replaced with isobutyl iodide, TEA was replaced with potassium carbonate, and the rest operations were the same as those in A-058 synthesis. M+1: 315.20.

Examples of Preparation of A-190, A-198, A-206, A-214

A-190: isobutyl iodide was replaced with benzyl bromide, and the rest operations were the same as those in A-158 synthesis. M+1: 321.16.

A-198: isobutyl iodide was replaced with benzyl bromide, and the rest operations were the same as those in A-158 synthesis. M+1: 335.17.

A-206: isobutyl iodide was replaced with benzyl bromide, and the rest operations were the same as those in A-158 synthesis. M+1: 349.19.

A-214: isobutyl iodide was replaced with benzyl bromide, and the rest operations were the same as those in A-158 synthesis. M+1: 349.19.

Examples of Preparation of A-222, A-230, A-238, A-246

A-222: the solvent was replaced with DMF, acetyl chloride was replaced with iodomethane, TEA was replaced with potassium carbonate, and the rest operations were the same as those in A-058 synthesis. M+1: 245.12.

A-230: A-002 was replaced with A-016, the solvent was replaced with DMF, acetyl chloride was replaced with iodomethane, TEA was replaced with potassium carbonate, and the rest operations were the same as those in A-058 synthesis. M+1: 259.14.

A-238: A-002 was replaced with A-030, the solvent was replaced with DMF, acetyl chloride was replaced with iodomethane, TEA was replaced with potassium carbonate, and the rest operations were the same as those in A-058 synthesis. M+1: 273.16.

A-246: A-002 was replaced with A-044, the solvent was replaced with DMF, acetyl chloride was replaced with iodomethane, TEA was replaced with potassium carbonate, and the rest operations were the same as those in A-058 synthesis. M+1: 273.16.

According to the synthesis method of A-057, the following products were prepared:

Examples of Preparation of A-069, A-077 and A-085

A-069: A-058 was replaced with A-070, and the rest operations were the same as those in A-057 synthesis. M+1: 187.08.

A-077: A-058 was replaced with A-078, and the rest operations were the same as those in A-057 synthesis. M+1: 201.10.

A-085: A-058 was replaced with A-086, and the rest operations were the same as those in A-057 synthesis. M+1: 201.10.

Examples of Preparation of A-093, A-101, A-109 and A-117

A-093: A-058 was replaced with A-094, and the rest operations were the same as those in A-057 synthesis. M+1: 201.10.

A-101: A-058 was replaced with A-102, and the rest operations were the same as those in A-057 synthesis. M+1: 215.11.

A-109: A-058 was replaced with A-110, and the rest operations were the same as those in A-057 synthesis. M+1: 229.13.

A-117: A-058 was replaced with A-118, and the rest operations were the same as those in A-057 synthesis. M+1: 229.13.

Examples of Preparation of A-125, A-133, A-141 and A-149

A-125: A-058 was replaced with A-126, and the rest operations were the same as those in A-057 synthesis. M+1: 215.11.

A-133: A-058 was replaced with A-134, and the rest operations were the same as those in A-057 synthesis. M+1: 229.13.

A-141: A-058 was replaced with A-142, and the rest operations were the same as those in A-057 synthesis. M+1: 243.15.

A-149: A-058 was replaced with A-150, and the rest operations were the same as those in A-057 synthesis. M+1: 243.15.

Examples of Preparation of A-157, A-165, A-173 and A-181

A-157: A-058 was replaced with A-158, and the rest operations were the same as those in A-057 synthesis. M+1: 187.12.

A-165: A-058 was replaced with A-166, and the rest operations were the same as those in A-057 synthesis. M+1: 201.13.

A-173: A-058 was replaced with A-174, and the rest operations were the same as those in A-057 synthesis. M+1: 215.15.

A-181: A-058 was replaced with A-182, and the rest operations were the same as those in A-057 synthesis. M+1: 215.15.

Examples of Preparation of A-189, A-197, A-205 and A-213

A-189: A-058 was replaced with A-190, and the rest operations were the same as those in A-057 synthesis. M+1: 221.10.

A-197: A-058 was replaced with A-198, and the rest operations were the same as those in A-057 synthesis. M+1: 235.12.

A-205: A-058 was replaced with A-206, and the rest operations were the same as those in A-057 synthesis. M+1: 249.13.

A-213: A-058 was replaced with A-214, and the rest operations were the same as those in A-057 synthesis. M+1: 249.13.

Examples of Preparation of A-221, A-229, A-237 and A-245

A-221: A-058 was replaced with A-222, and the rest operations were the same as those in A-057 synthesis. M+1: 145.07.

A-229: A-058 was replaced with A-230, and the rest operations were the same as those in A-057 synthesis. M+1: 159.09.

A-237: A-058 was replaced with A-238, and the rest operations were the same as those in A-057 synthesis. M+1: 173.10.

A-245: A-058 was replaced with A-246, and the rest operations were the same as those in A-057 synthesis. M+1: 173.10.

According to the synthesis method of A-059, the following products were prepared:

Examples of Preparation of A-060, A-061

A-060: A-057 was used as a raw material, acetyl chloride was replaced with isobutyryl chloride, and the rest operations were the same as those in A-059 synthesis. M+1: 243.11.

A-061: A-057 was used as a raw material, acetyl chloride was replaced with pivaloyl chloride, and the rest operations were the same as those in A-059 synthesis. M+1: 257.12.

Examples of Preparation of A-062 to A-064

A-062: A-057 was used as a raw material, the solvent was replaced with DMF, acetyl chloride was replaced with iodomethane, TEA was replaced with potassium carbonate, and the rest operations were the same as those in A-059 synthesis. M+1: 187.08.

A-063: A-057 was used as a raw material, the solvent was replaced with DMF, acetyl chloride was replaced with iodoethane, TEA was replaced with potassium carbonate, and the rest operations were the same as those in A-062 synthesis. M+1: 201.10.

A-064: A-057 was used as a raw material, the solvent was replaced with DMF, acetyl chloride was replaced with

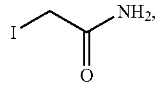

TEA was replaced with potassium carbonate, and the rest operations were the same as those in A-062 synthesis. M+1: 230.09.

Examples of Preparation of A-071 to A-073

A-071: A-069 was used as a raw material, and the rest operations were the same as those in A-059. M+1: 229.09.

A-072: A-069 was used as a raw material, acetyl chloride was replaced with isobutyryl chloride, and the rest operations were the same as those in A-059 synthesis. M+1: 257.12.

A-073: A-069 was used as a raw material, acetyl chloride was replaced with pivaloyl chloride, and the rest operations were the same as those in A-059 synthesis. M+1: 271.14.

Examples of Preparation of A-079 to A-081

A-079: A-077 was used as a raw material, and the rest operations were the same as those in A-059 synthesis. M+1: 243.11.

A-080: A-077 was used as a raw material, acetyl chloride was replaced with isobutyryl chloride, and the rest operations were the same as those in A-059 synthesis. M+1: 271.14.

A-081: A-077 was used as a raw material, acetyl chloride was replaced with pivaloyl chloride, and the rest operations were the same as those in A-059 synthesis. M+1: 285.16.

Examples of Preparation of A-087 to A-089

A-087: A-085 was used as a raw material, and the rest operations were the same as those in A-059 synthesis. M+1: 243.11.

A-088: A-085 was used as a raw material, acetyl chloride was replaced with isobutyryl chloride, and the rest operations were the same as those in A-059 synthesis. M+1: 271.14.

A-089: A-085 was used as a raw material, acetyl chloride was replaced with pivaloyl chloride, and the rest operations were the same as those in A-059 synthesis. M+1: 285.16.

Examples of Preparation of A-095 to A-097

A-095: A-093 was used as a raw material, acetyl chloride was replaced with

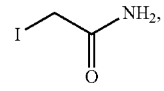

and the rest operations were the same as those in A-059 synthesis. M+1: 258.12.

A-096: A-093 was used as a raw material, acetyl chloride was replaced with isobutyryl chloride, and the rest operations were the same as those in A-059 synthesis. M+1: 271.14.

A-097: A-093 was used as a raw material, acetyl chloride was replaced with pivaloyl chloride, and the rest operations were the same as those in A-059 synthesis. M+1: 285.16.

Examples of Preparation of A-103 to A-105

A-103: A-101 was used as a raw material, and the rest operations were the same as those in A-059 synthesis. M+1: 257.12.

A-104: A-101 was used as a raw material, acetyl chloride was replaced with isobutyryl chloride, and the rest operations were the same as those in A-059 synthesis. M+1: 285.16.

A-105: A-101 was used as a raw material, acetyl chloride was replaced with pivaloyl chloride, and the rest operations were the same as those in A-059 synthesis. M+1: 299.17.

Examples of Preparation of A-111 to A-113

A-111: A-109 was used as a raw material, and the rest operations were the same as those in A-059 synthesis;

A-112: A-109 was used as a raw material, acetyl chloride was replaced with isobutyryl chloride, and the rest operations were the same as those in A-059 synthesis. M+1: 299.17.

A-113: A-109 was used as a raw material, acetyl chloride was replaced with pivaloyl chloride, and the rest operations were the same as those in A-059 synthesis. M+1: 313.19.

Examples of Preparation of A-119 to A-121

A-119: A-117 was used as a raw material, and the rest operations were the same as those in A-059 synthesis. M+1: 271.14.

A-120: A-117 was used as a raw material, acetyl chloride was replaced with isobutyryl chloride, and the rest operations were the same as those in A-059 synthesis. M+1: 299.17.

A-121: A-117 was used as a raw material, acetyl chloride was replaced with pivaloyl chloride, and the rest operations were the same as those in A-059 synthesis. M+1: 313.19.

Examples of Preparation of A-127 to A-129

A-127: A-125 was used as a raw material, and the rest operations were the same as those in A-059. M+1: 257.12.

A-128: A-125 was used as a raw material, acetyl chloride was replaced with isobutyryl chloride, and the rest operations were the same as those in A-059 synthesis. M+1: 285.16.

A-129: A-125 was used as a raw material, acetyl chloride was replaced with pivaloyl chloride, and the rest operations were the same as those in A-059 synthesis. M+1: 299.17.

Examples of Preparation of A-135 to A-137

A-135: A-133 was used as a raw material, and the rest operations were the same as those in A-059 synthesis. M+1: 271.14.

A-136: A-133 was used as a raw material, acetyl chloride was replaced with isobutyryl chloride, and the rest operations were the same as those in A-059 synthesis. M+1: 299.17.

A-137: A-133 was used as a raw material, acetyl chloride was replaced with pivaloyl chloride, and the rest operations were the same as those in A-059 synthesis. M+1: 313.19.

Examples of Preparation of A-143 to A-145

A-143: A-141 was used as a raw material, and the rest operations were the same as those in A-059 synthesis. M+1: 285.16.

A-144: A-141 was used as a raw material, acetyl chloride was replaced with isobutyryl chloride, and the rest operations were the same as those in A-059 synthesis. M+1: 313.19.

A-145: A-141 was used as a raw material, acetyl chloride was replaced with pivaloyl chloride, and the rest operations were the same as those in A-059 synthesis. M+1: 327.20.

Examples of Preparation of A-151 to A-153

A-151: A-149 was used as a raw material, and the rest operations were the same as those in A-059 synthesis. M+1: 285.16.

A-152: A-149 was used as a raw material, acetyl chloride was replaced with isobutyryl chloride, and the rest operations were the same as those in A-059 synthesis. M+1: 313.19.

A-153: A-149 was used as a raw material, acetyl chloride was replaced with pivaloyl chloride, and the rest operations were the same as those in A-059 synthesis. M+1: 327.20.

Examples of Preparation of A-159 to A-161

A-159: A-157 was used as a raw material, and the rest operations were the same as those in A-059 synthesis. M+1: 229.13.

A-160: A-157 was used as a raw material, acetyl chloride was replaced with isobutyryl chloride, and the rest operations were the same as those in A-059 synthesis. M+1: 257.16.

A-161: A-157 was used as a raw material, acetyl chloride was replaced with pivaloyl chloride, and the rest operations were the same as those in A-059 synthesis. M+1: 271.18.

Examples of Preparation of A-167 to A-169

A-167: A-165 was used as a raw material, and the rest operations were the same as those in A-059 synthesis. M+1: 243.15.

A-168: A-165 was used as a raw material, acetyl chloride was replaced with isobutyryl chloride, and the rest operations were the same as those in A-059 synthesis. M+1: 271.18.

A-169: A-165 was used as a raw material, acetyl chloride was replaced with pivaloyl chloride, and the rest operations were the same as those in A-059 synthesis. M+1: 285.19.

Examples of Preparation of A-175 to A-177

A-175: A-173 was used as a raw material, and the rest operations were the same as those in A-059 synthesis. M+1: 257.16.

A-176: A-173 was used as a raw material, acetyl chloride was replaced with isobutyryl chloride, and the rest operations were the same as those in A-059 synthesis. M+1: 285.19.

A-177: A-173 was used as a raw material, acetyl chloride was replaced with pivaloyl chloride, and the rest operations were the same as those in A-059 synthesis. M+1: 299.21.

Examples of Preparation of A-183 to A-185

A-183: A-181 was used as a raw material, and the rest operations were the same as those in A-059 synthesis. M+1: 257.16.

A-184: A-181 was used as a raw material, acetyl chloride was replaced with isobutyryl chloride, and the rest operations were the same as those in A-059 synthesis. M+1: 285.19.

A-185: A-181 was used as a raw material, acetyl chloride was replaced with pivaloyl chloride, and the rest operations were the same as those in A-059 synthesis. M+1: 299.21.

Examples of Preparation of A-191 to A-193

A-191: A-189 was used as a raw material, and the rest operations were the same as those in A-059 synthesis. M+1: 263.11.

A-192: A-189 was used as a raw material, acetyl chloride was replaced with isobutyryl chloride, and the rest operations were the same as those in A-059 synthesis. M+1: 291.15.

A-193: A-189 was used as a raw material, acetyl chloride was replaced with pivaloyl chloride, and the rest operations were the same as those in A-059 synthesis. M+1: 305.16.

Examples of Preparation of A-199 to A-201

A-199: A-197 was used as a raw material, and the rest operations were the same as those in A-059 synthesis. M+1: 277.13.

A-200: A-197 was used as a raw material, acetyl chloride was replaced with isobutyryl chloride, and the rest operations were the same as those in A-059 synthesis. M+1: 305.16.

A-201: A-197 was used as a raw material, acetyl chloride was replaced with pivaloyl chloride, and the rest operations were the same as those in A-059 synthesis. M+1: 319.18.

Examples of Preparation of A-207 to A-209

A-207: A-205 was used as a raw material, and the rest operations were the same as those in A-059 synthesis. M+1: 291.15.

A-208: A-205 was used as a raw material, acetyl chloride was replaced with isobutyryl chloride, and the rest operations were the same as those in A-059 synthesis. M+1: 319.18.

A-209: A-205 was used as a raw material, acetyl chloride was replaced with pivaloyl chloride, and the rest operations were the same as those in A-059 synthesis. M+1: 333.19.

Examples of Preparation of A-215 to A-217

A-215: A-213 was used as a raw material, and the rest operations were the same as those in A-059 synthesis. M+1: 291.15.

A-216: A-213 was used as a raw material, acetyl chloride was replaced with isobutyryl chloride, and the rest operations were the same as those in A-059 synthesis. M+1: 319.18.

A-217: A-213 was used as a raw material, acetyl chloride was replaced with pivaloyl chloride, and the rest operations were the same as those in A-059 synthesis. M+1: 333.19.

Examples of Preparation of A-223 to A-225

A-223: A-221 was used as a raw material, and the rest operations were the same as those in A-059 synthesis. M+1: 187.08.

A-224: A-221 was used as a raw material, acetyl chloride was replaced with isobutyryl chloride, and the rest operations were the same as those in A-059 synthesis. M+1: 215.11.

A-225: A-221 was used as a raw material, acetyl chloride was replaced with pivaloyl chloride, and the rest operations were the same as those in A-059 synthesis. M+1: 229.13.

Examples of Preparation of A-231 to A-233

A-231: A-229 was used as a raw material, and the rest operations were the same as those in A-059 synthesis. M+1: 201.10.

A-232: A-229 was used as a raw material, acetyl chloride was replaced with isobutyryl chloride, and the rest operations were the same as those in A-059 synthesis. M+1: 229.13.

A-233: A-229 was used as a raw material, acetyl chloride was replaced with pivaloyl chloride and the rest operations were the same as those in A-059 synthesis. M+1: 243.15.

Examples of Preparation of A-239 to A-241

A-239: A-237 was used as a raw material, and the rest operations were the same as those in A-059 synthesis. M+1: 215.11.

A-240: A-237 was used as a raw material, acetyl chloride was replaced with isobutyryl chloride, and the rest operations were the same as those in A-059 synthesis. M+1: 243.15.

A-241: A-237 was used as a raw material, acetyl chloride was replaced with pivaloyl chloride and the rest operations were the same as those in A-059 synthesis. M+1: 257.16.

Examples of Preparation of A-247 to A-249

A-247: A-245 was used as a raw material, and the rest operations were the same as those in A-059. M+1: 215.11.

A-248: A-245 was used as a raw material, acetyl chloride was replaced with isobutyryl chloride, and the rest operations were the same as those in A-059 synthesis. M+1: 243.15.

A-249: A-245 was used as a raw material, acetyl chloride was replaced with pivaloyl chloride, and the rest operations were the same as those in A-059 synthesis. M+1: 257.16.

Example of A-066

The example illustrates a synthesis method of compound A-066.

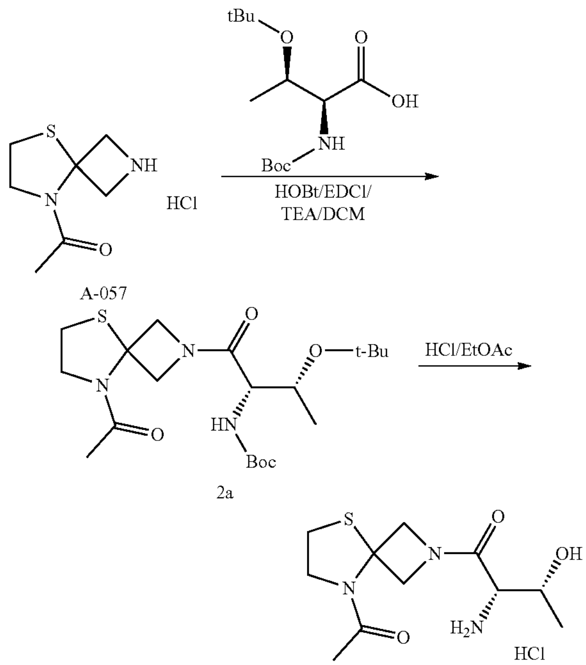

A-057

2a

A-006

1. Synthesis Method of an Intermediate 2a

Under ice bath conditions, a total of 0.3 g (1.74 mmol) of the compound A-057 was dissolved in 20 ml of anhydrous DCM, and 490 μL (3.5 mmol) of TEA was added and stirred for dissociation for 5 min, 0.49 g (1.74 mmol) of Boc-tBu-Thr, 0.35 g (2.6 mmol) of HOBt and 0.5 g (2.6 mmol) of EDCI were added, the raw materials were gradually returned to room temperature, the reaction was performed for 6 h at room temperature; when the completion of the raw materials reaction was monitored by TLC, the reaction was terminated. A saturated citric acid aqueous solution was used for washing (10 mL×3), and an organic phase was taken, dried with anhydrous sodium sulfate, filtered, concentrated, and separated through a silica gel column to obtain a total of 0.59 g of a colorless oily substance of an intermediate 2a with a yield of 78%. $^1$H-NMR (400 MHz, DMSO-$d_6$), δ ppm: 1.13-1.22 (m, 12H), 1.37 (s, 9H), 2.34 (s, 3H), 3.25 (t, 2H, J=5.9 Hz), 3.37-3.98 (m, 4H), 4.09-4.28 (m, 1H), 4.58-4.89 (m, 3H), 7.89 (s, 1H). M+1: 430.23.

2. Synthesis Method of the End Product A-066

A total of 0.5 g (1.17 mmol) of the intermediate 2a was dissolved in 5 mL of anhydrous ethyl acetate, 10 mL of 4 mol/L HCl/EtOAc was added, and the materials were reacted overnight at room temperature, and a white solid was generated in the system; when the completion of the materials reaction was monitored by TLC, the reaction was terminated.

The product was filtered under reduced pressure and washed with anhydrous diethyl ether to obtain a total of 0.26 g of a white solid A-066 with a yield of 72.6%. $^1$H-NMR (400 MHz, DMSO-$d_6$), δ ppm: 1.17-1.22 (m, 3H), 2.36 (s, 3H), 3.23 (t, 2H, J=6.7 Hz), 3.35-3.95 (m, 4H), 4.12-4.32 (m, 1H), 4.58-4.92 (m, 3H), 5.65 (s, 1H), 8.21-8.29 (d, 2H, J=19 Hz). M+1: 274.11.

Examples of Preparation of A-065, A-067 and A-068

A-065: the raw material

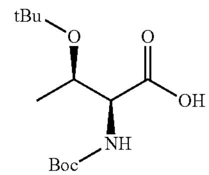 [SMILES: C[C@@H](OC(C)(C)C)[C@H](NC(=O)OC(C)(C)C)C(=O)O]

was replaced with

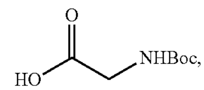

and the rest operations were the same as those in A-066 synthesis. M+1: 230.09.

A-067: the raw material

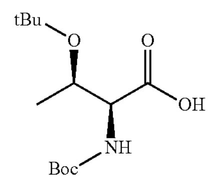 [SMILES: C[C@@H](OC(C)(C)C)[C@H](NC(=O)OC(C)(C)C)C(=O)O]

was replaced with

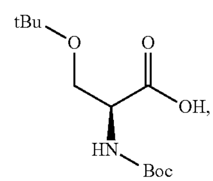 [SMILES: CC(C)(C)OC[C@H](NC(=O)OC(C)(C)C)C(=O)O]

and the rest operations were the same as those in A-066 synthesis. M+1: 260.10.

A-068: the raw material

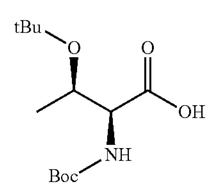 [SMILES: C[C@@H](OC(C)(C)C)[C@H](NC(=O)OC(C)(C)C)C(=O)O]

was replaced with

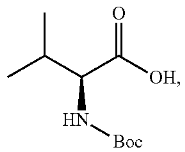

and the rest operations were the same as those in A-066 synthesis. M+1: 272.14.

Examples of Preparation of A-074 to A-076

A-074: A-057 was replaced with A-069, and the rest operations were the same as those in A-066 synthesis. M+1:288.13.

A-075: A-057 was replaced with A-069, the raw material

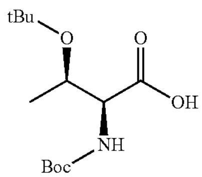 [SMILES: C[C@@H](OC(C)(C)C)[C@H](NC(=O)OC(C)(C)C)C(=O)O]

was replaced with

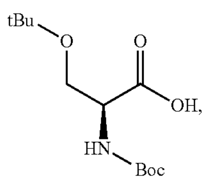 [SMILES: CC(C)(C)OC[C@H](NC(=O)OC(C)(C)C)C(=O)O]

and the rest operations were the same as those in A-066. M+1: 274.11.

A-076: A-057 was replaced with A-069, the raw material

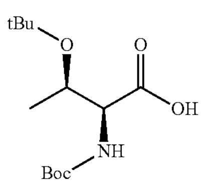 [SMILES: C[C@@H](OC(C)(C)C)[C@H](NC(=O)OC(C)(C)C)C(=O)O]

was replaced with

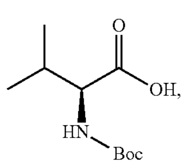

and the rest operations were the same as those in A-066. M+1: 286.15.

Examples of Preparation of A-082 to A-084

A-082: A-057 was replaced with A-077, and the rest operations were the same as those in A-066 synthesis.

A-083: A-057 was replaced with A-077, the raw material

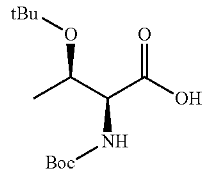 [SMILES: C[C@@H](OC(C)(C)C)[C@H](NC(=O)OC(C)(C)C)C(=O)O]

was replaced with

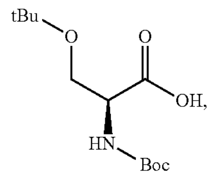 [SMILES: CC(C)(C)OC[C@H](NC(=O)OC(C)(C)C)C(=O)O]

and the rest operations were the same as those in A-066 synthesis. M+1: 288.13.

A-084: A-057 was replaced with A-077, the raw material

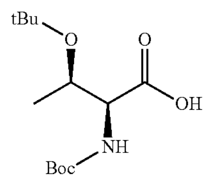 [SMILES: C[C@@H](OC(C)(C)C)[C@H](NC(=O)OC(C)(C)C)C(=O)O]

was replaced with

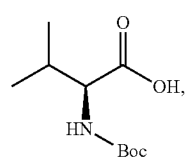

and the rest operations were the same as those in A-066 synthesis. M+1: 300.17.

Examples of Preparation of A-090 to A-092

A-090: A-057 was replaced with A-085, and the rest operations were the same as those in A-066 synthesis. M+1: 302.15.

A-091: A-057 was replaced with A-085, the raw material

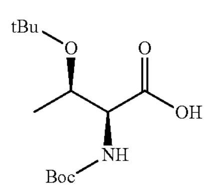 [SMILES: C[C@@H](OC(C)(C)C)[C@H](NC(=O)OC(C)(C)C)C(=O)O]

was replaced with

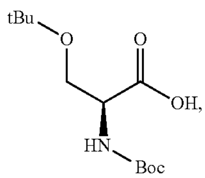 [SMILES: CC(C)(C)OC[C@H](NC(=O)OC(C)(C)C)C(=O)O]

and the rest operations were the same as those in A-066 synthesis. M+1: 288.13.

A-092: A-057 was replaced with A-085, the raw material

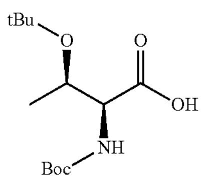 [SMILES: C[C@@H](OC(C)(C)C)[C@H](NC(=O)OC(C)(C)C)C(=O)O]

was replaced with

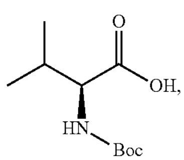

and the rest operations were the same as those in A-066 synthesis. M+1: 300.17.

Examples of Preparation of A-098 to A-100

A-098: A-057 was replaced with A-093, and the rest operations were the same as those in A-066 synthesis. M+1: 302.15.

A-099: A-057 was replaced with A-093, the raw material

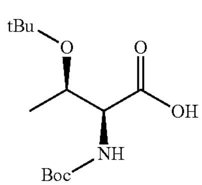 [SMILES: C[C@@H](OC(C)(C)C)[C@H](NC(=O)OC(C)(C)C)C(=O)O]

was replaced with

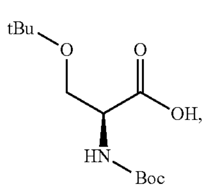 [SMILES: CC(C)(C)OC[C@H](NC(=O)OC(C)(C)C)C(=O)O]

and the rest operations were the same as those in A-066. M+1: 288.13.

A-100: A-057 was replaced with A-093, the raw material

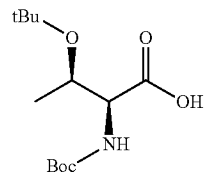 [SMILES: C[C@@H](OC(C)(C)C)[C@H](NC(=O)OC(C)(C)C)C(=O)O]

was replaced with

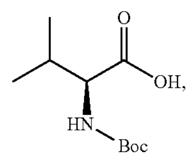

and the rest operations were the same as those in A-066 synthesis. M+1: 300.17.

Examples of Preparation of A-106 to A-108

A-106: A-057 was replaced with A-101, and the rest operations were the same as those in A-066 synthesis. M+1: 316.16.

A-107: A-057 was replaced with A-101, the raw material

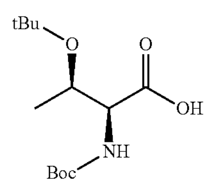 [SMILES: C[C@@H](OC(C)(C)C)[C@H](NC(=O)OC(C)(C)C)C(=O)O]

was replaced with

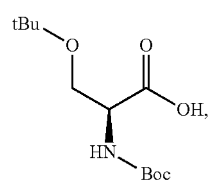 [SMILES: CC(C)(C)OC[C@H](NC(=O)OC(C)(C)C)C(=O)O]

and the rest operations were the same as those in A-066 synthesis. M+1: 302.15.

A-108: A-057 was replaced with A-101, the raw material

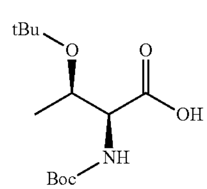 [SMILES: C[C@@H](OC(C)(C)C)[C@H](NC(=O)OC(C)(C)C)C(=O)O]

was replaced with

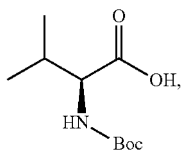

and the rest operations were the same as those in A-066 synthesis. M+1: 314.18.

Examples of Preparation of A-114 to A-116

A-114: A-057 was replaced with A-109, and the rest operations were the same as those in A-066 synthesis. M+1: 330.18.

A-115: A-057 was replaced with A-109, the raw material

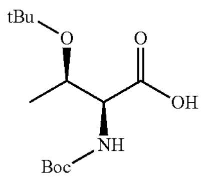 [SMILES: C[C@@H](OC(C)(C)C)[C@H](NC(=O)OC(C)(C)C)C(=O)O]

was replaced with

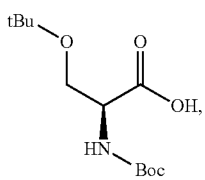 [SMILES: CC(C)(C)OC[C@H](NC(=O)OC(C)(C)C)C(=O)O]

and the rest operations were the same as those in A-066 synthesis. M+1: 316.16.

A-116: A-057 was replaced with A-109, the raw material

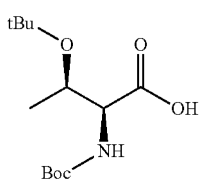 [SMILES: C[C@@H](OC(C)(C)C)[C@H](NC(=O)OC(C)(C)C)C(=O)O]

was replaced with

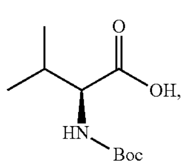

and the rest operations were the same as those in A-066 synthesis. M+1: 328.20.

Examples of Preparation of A-122 to A-124

A-122: A-057 was replaced with A-117, and the rest operations were the same as those in A-066 synthesis. M+1: 330.18.

A-123: A-057 was replaced with A-117, the raw material

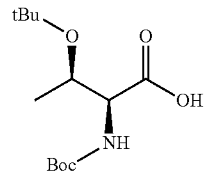 [SMILES: C[C@@H](OC(C)(C)C)[C@H](NC(=O)OC(C)(C)C)C(=O)O]

was replaced with

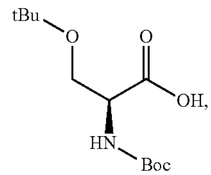 [SMILES: CC(C)(C)OC[C@H](NC(=O)OC(C)(C)C)C(=O)O]

and the rest operations were the same as those in A-066 synthesis. M+1: 316.16.

A-124: A-057 was replaced with A-117, the raw material

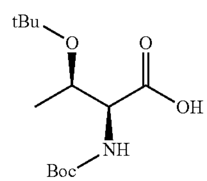 [SMILES: C[C@@H](OC(C)(C)C)[C@H](NC(=O)OC(C)(C)C)C(=O)O]

was replaced with

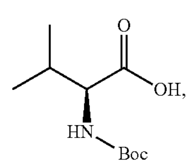

and the rest operations were the same as those in A-066 synthesis. M+1: 328.20.

Examples of Preparation of A-130 to A-132

A-130: A-057 was replaced with A-125, and the rest operations were the same as those in A-066 synthesis. M+1: 316.16.

A-131: A-057 was replaced with A-125, the raw material

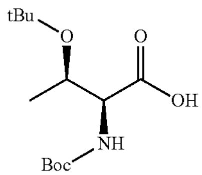 [SMILES: C[C@@H](OC(C)(C)C)[C@H](NC(=O)OC(C)(C)C)C(=O)O]

was replaced with

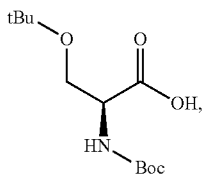 [SMILES: CC(C)(C)OC[C@H](NC(=O)OC(C)(C)C)C(=O)O]

and the rest operations were the same as those in A-066 synthesis. M+1: 302.15.

A-132: A-057 was replaced with A-125, the raw material

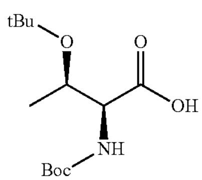 [SMILES: C[C@@H](OC(C)(C)C)[C@H](NC(=O)OC(C)(C)C)C(=O)O]

was replaced with

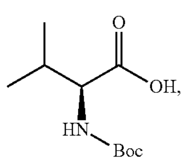

and the rest operations were the same as those in A-066 synthesis. M+1: 314.18.

Examples of Preparation of A-138 to A-140

A-138: A-057 was replaced with A-133, and the rest operations were the same as those in A-066 synthesis. M+1: 330.18.

A-139: A-057 was replaced with A-133, the raw material

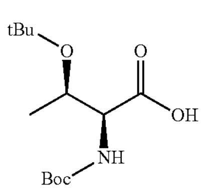 [SMILES: C[C@@H](OC(C)(C)C)[C@H](NC(=O)OC(C)(C)C)C(=O)O]

was replaced with

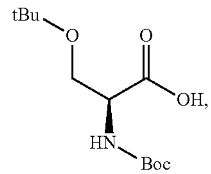 [SMILES: CC(C)(C)OC[C@H](NC(=O)OC(C)(C)C)C(=O)O]

and the rest operations were the same as those in A-066 synthesis. M+1: 316.16.

A-140: A-057 was replaced with A-133, the raw material

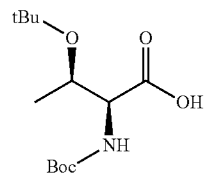 [SMILES: C[C@@H](OC(C)(C)C)[C@H](NC(=O)OC(C)(C)C)C(=O)O]

was replaced with

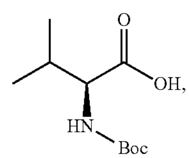

and the rest operations were the same as those in A-066 synthesis. M+1: 328.20.

Examples of Preparation of A-146 to A-148

A-146: A-057 was replaced with A-141, and the rest operations were the same as those in A-066 synthesis. M+1: 344.19.

A-147: A-057 was replaced with A-141, the raw material

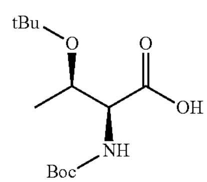 [SMILES: C[C@@H](OC(C)(C)C)[C@H](NC(=O)OC(C)(C)C)C(=O)O]

was replaced with

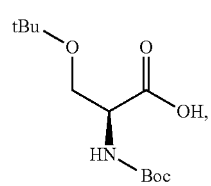 [SMILES: CC(C)(C)OC[C@H](NC(=O)OC(C)(C)C)C(=O)O]

and the rest operations were the same as those in A-066 synthesis. M+1: 330.18.

A-148: A-057 was replaced with A-141, the raw material

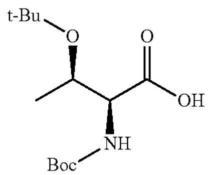 [SMILES: C[C@@H](OC(C)(C)C)[C@H](NC(=O)OC(C)(C)C)C(=O)O]

was replaced with

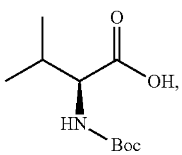

and the rest operations were the same as those in A-066 synthesis. M+1: 342.21.

Examples of Preparation of A-154 to A-156

A-154: A-057 was replaced with A-149, and the rest operations were the same as those in A-066 synthesis. M+1: 344.19.

A-155: A-057 was replaced with A-149, the raw material

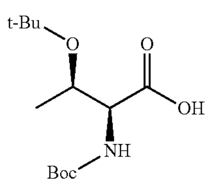 [SMILES: C[C@@H](OC(C)(C)C)[C@H](NC(=O)OC(C)(C)C)C(=O)O]

was replaced with

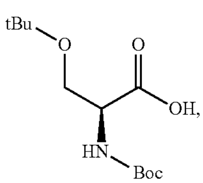 [SMILES: CC(C)(C)OC[C@H](NC(=O)OC(C)(C)C)C(=O)O]

and the rest operations were the same as those in A-066 synthesis. M+1: 330.18.

A-156: A-057 was replaced with A-149, the raw material

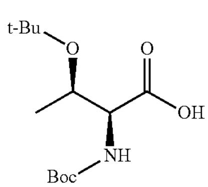 [SMILES: C[C@@H](OC(C)(C)C)[C@H](NC(=O)OC(C)(C)C)C(=O)O]

was replaced with

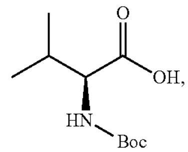

and the rest operations were the same as those in A-066 synthesis. M+1: 342.21.

Examples of Preparation of A-162 to A-164

A-162: A-057 was replaced with A-157, and the rest operations were the same as those in A-066 synthesis. M+1: 288.17.

A-163: A-057 was replaced with A-157, the raw material

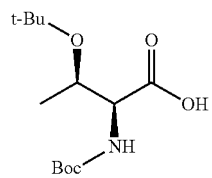 [SMILES: C[C@@H](OC(C)(C)C)[C@H](NC(=O)OC(C)(C)C)C(=O)O]

was replaced with

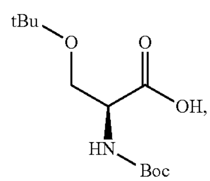 [SMILES: CC(C)(C)OC[C@H](NC(=O)OC(C)(C)C)C(=O)O]

and the rest operations were the same as those in A-066 synthesis. M+1: 274.15.

A-164: A-057 was replaced with A-157, the raw material

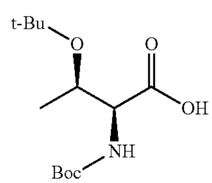 [SMILES: C[C@@H](OC(C)(C)C)[C@H](NC(=O)OC(C)(C)C)C(=O)O]

was replaced with

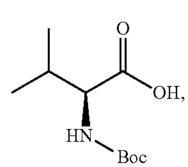

and the rest operations were the same as those in A-066 synthesis. M+1: 286.19.

Examples of Preparation of A-170 to A-172

A-170: A-057 was replaced with A-165, and the rest operations were the same as those in A-066 synthesis. M+1: 302.18.

A-171: A-057 was replaced with A-165, the raw material

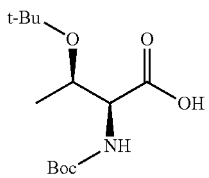 [SMILES: C[C@@H](OC(C)(C)C)[C@H](NC(=O)OC(C)(C)C)C(=O)O]

was replaced with

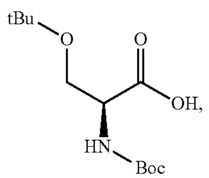 [SMILES: CC(C)(C)OC[C@H](NC(=O)OC(C)(C)C)C(=O)O]

and the rest operations were the same as those in A-066 synthesis. M+1: 288.17.

A-172: A-057 was replaced with A-165, the raw material

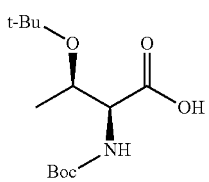 [SMILES: C[C@@H](OC(C)(C)C)[C@H](NC(=O)OC(C)(C)C)C(=O)O]

was replaced with

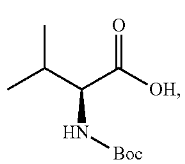

and the rest operations were the same as those in A-066 synthesis. M+1: 300.20.

Examples of Preparation of A-178 to A-180

A-178: A-057 was replaced with A-173, and the rest operations were the same as those in A-066 synthesis. M+1: 316.20.

A-179: A-057 was replaced with A-173, the raw material

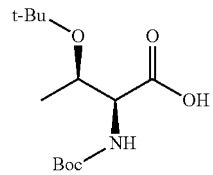 [SMILES: C[C@@H](OC(C)(C)C)[C@H](NC(=O)OC(C)(C)C)C(=O)O]

was replaced with

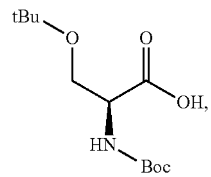 [SMILES: CC(C)(C)OC[C@H](NC(=O)OC(C)(C)C)C(=O)O]

and the rest operations were the same as those in A-066 synthesis. M+1: 302.18.

A-180: A-057 was replaced with A-173, the raw material

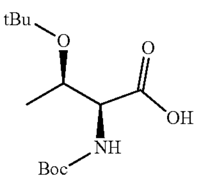 [SMILES: C[C@@H](OC(C)(C)C)[C@H](NC(=O)OC(C)(C)C)C(=O)O]

was replaced with

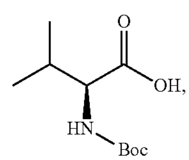

and the rest operations were the same as those in A-066 synthesis. M+1: 314.22.

Examples of Preparation of A-186 to A-188

A-186: A-057 was replaced with A-181, and the rest operations were the same as those in A-066 synthesis. M+1: 315.20.

A-187: A-057 was replaced with A-181, the raw material

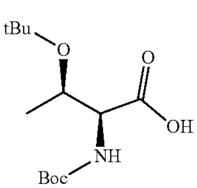 [SMILES: C[C@@H](OC(C)(C)C)[C@H](NC(=O)OC(C)(C)C)C(=O)O]

was replaced with

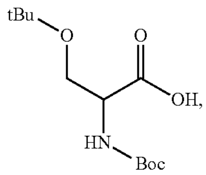 [SMILES: CC(C)(C)OCC(NC(=O)OC(C)(C)C)C(=O)O]

and the rest operations were the same as those in A-066 synthesis. M+1: 302.18.

A-188: A-057 was replaced with A-181, the raw material

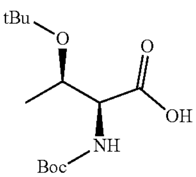 [SMILES: C[C@@H](OC(C)(C)C)[C@H](NC(=O)OC(C)(C)C)C(=O)O]

was replaced with

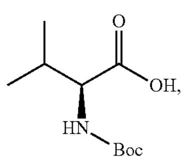

and the rest operations were the same as those in A-066 synthesis. M+1: 314.22.

Examples of Preparation of A-194 to A-196

A-194: A-057 was replaced with A-189, and the rest operations were the same as those in A-066 synthesis. M+1: 322.15.

A-195: A-057 was replaced with A-189, the raw material

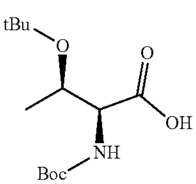 [SMILES: C[C@@H](OC(C)(C)C)[C@H](NC(=O)OC(C)(C)C)C(=O)O]

was replaced with

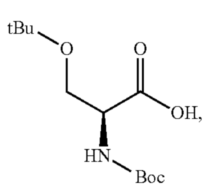 [SMILES: CC(C)(C)OC[C@H](NC(=O)OC(C)(C)C)C(=O)O]

and the rest operations were the same as those in A-066 synthesis. M+1: 308.14.

A-196: A-057 was replaced with A-189, the raw material

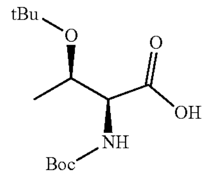 [SMILES: C[C@@H](OC(C)(C)C)[C@H](NC(=O)OC(C)(C)C)C(=O)O]

was replaced with

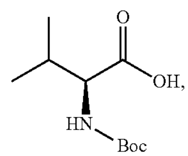

and the rest operations were the same as those in A-066 synthesis. M+1: 320.17.

Examples of Preparation of A-202 to A-204

A-202: A-057 was replaced with A-197, and the rest operations were the same as those in A-066 synthesis. M+1: 336.17.

A-203: A-057 was replaced with A-197, the raw material

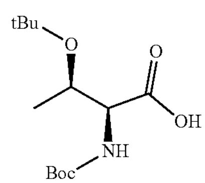 [SMILES: C[C@@H](OC(C)(C)C)[C@H](NC(=O)OC(C)(C)C)C(=O)O]

was replaced with

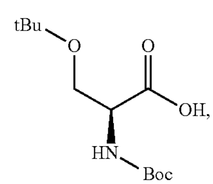 [SMILES: CC(C)(C)OC[C@H](NC(=O)OC(C)(C)C)C(=O)O]

and the rest operations were the same as those in A-066 synthesis. M+1: 322.15.

A-204: A-057 was replaced with A-197, the raw material

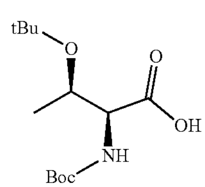 [SMILES: C[C@@H](OC(C)(C)C)[C@H](NC(=O)OC(C)(C)C)C(=O)O]

was replaced with

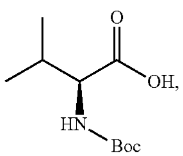

and the rest operations were the same as those in A-066 synthesis. M+1: 334.19.

Examples of Preparation of A-210 to A-212

A-210: A-057 was replaced with A-205, and the rest operations were the same as those in A-066 synthesis. M+1: 350.18.

A-211: A-057 was replaced with A-205, the raw material

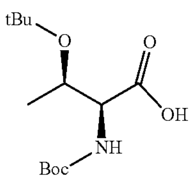 [SMILES: C[C@@H](OC(C)(C)C)[C@H](NC(=O)OC(C)(C)C)C(=O)O]

was replaced with

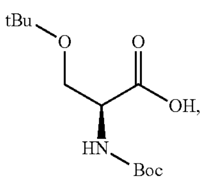 [SMILES: CC(C)(C)OC[C@H](NC(=O)OC(C)(C)C)C(=O)O]

and the rest operations were the same as those in A-066 synthesis. M+1: 336.17.

A-212: A-057 was replaced with A-205, the raw material

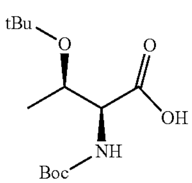

was replaced with

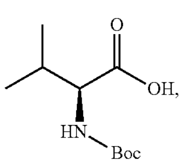

and the rest operations were the same as those in A-066 synthesis. M+1: 348.20.

Examples of Preparation of A-218 to A-220

A-218: A-057 was replaced with A-213, and the rest operations were the same as those in A-066 synthesis. M+1: 350.18.

A-219: A-057 was replaced with A-213, the raw material

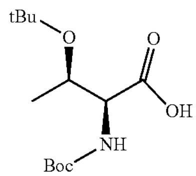 [SMILES: C[C@@H](OC(C)(C)C)[C@H](NC(=O)OC(C)(C)C)C(=O)O]

was replaced with

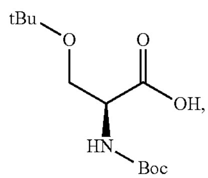 [SMILES: CC(C)(C)OC[C@H](NC(=O)OC(C)(C)C)C(=O)O]

and the rest operations were the same as those in A-066 synthesis. M+1: 336.17.

A-220: A-057 was replaced with A-213, the raw material

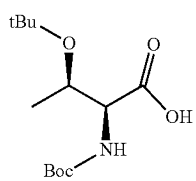 [SMILES: C[C@@H](OC(C)(C)C)[C@H](NC(=O)OC(C)(C)C)C(=O)O]

was replaced with

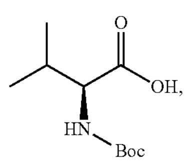

and the rest operations were the same as those in A-066 synthesis. M+1: 348.20.

Examples of Preparation of A-226 to A-228

A-226: A-057 was replaced with A-221, and the rest operations were the same as those in A-066 synthesis. M+1: 246.12.

A-227: A-057 was replaced with A-221, the raw material

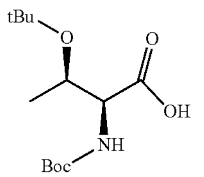

was replaced with

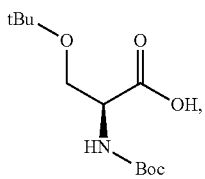 [SMILES: CC(C)(C)OC[C@H](NC(=O)OC(C)(C)C)C(=O)O]

and the rest operations were the same as those in A-066 synthesis. M+1: 232.10.

A-228: A-057 was replaced with A-221, the raw material

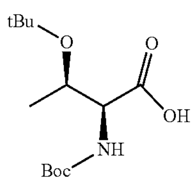

was replaced with

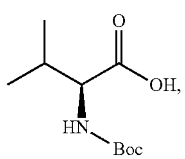

and the rest operations were the same as those in A-066 synthesis. M+1: 244.14.

Examples of Preparation of A-234 to A-236

A-234: A-057 was replaced with A-229, and the rest operations were the same as those in A-066 synthesis. M+1: 260.14.

A-235: A-057 was replaced with A-229, the raw material

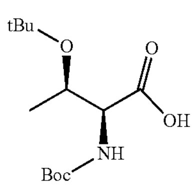 [SMILES: C[C@@H](OC(C)(C)C)[C@H](NC(=O)OC(C)(C)C)C(=O)O]

was replaced with

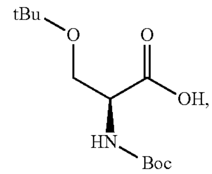 [SMILES: CC(C)(C)OC[C@H](NC(=O)OC(C)(C)C)C(=O)O]

and the rest operations were the same as those in A-066 synthesis. M+1: 246.12.

A-236: A-057 was replaced with A-229, the raw material

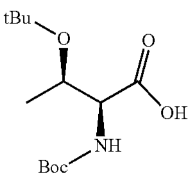 [SMILES: C[C@@H](OC(C)(C)C)[C@H](NC(=O)OC(C)(C)C)C(=O)O]

was replaced with

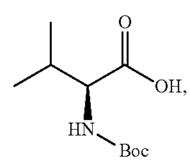

and the rest operations were the same as those in A-066 synthesis. M+1: 258.16.

Examples of Preparation of A-242 to A-244

A-242: A-057 was replaced with A-237, and the rest operations were the same as those in A-066 synthesis. M+1: 274.15.

A-243: A-057 was replaced with A-237, the raw material

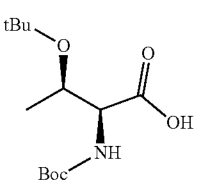 [SMILES: C[C@@H](OC(C)(C)C)[C@H](NC(=O)OC(C)(C)C)C(=O)O]

was replaced with

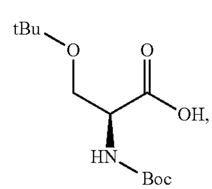 [SMILES: CC(C)(C)OC[C@H](NC(=O)OC(C)(C)C)C(=O)O]

and the rest operations were the same as those in A-066 synthesis. M+1: 260.14.

A-244: A-057 was replaced with A-237, the raw material

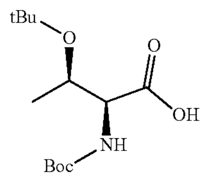 [SMILES: C[C@@H](OC(C)(C)C)[C@H](NC(=O)OC(C)(C)C)C(=O)O]

was replaced with

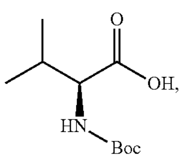

and the rest operations were the same as those in A-066 synthesis. M+1: 272.17.

Examples of Preparation of A-250 to A-252

A-250: A-057 was replaced with A-245, and the rest operations were the same as those in A-066 synthesis. M+1: 274.15.

A-251: A-057 was replaced with A-245, the raw material

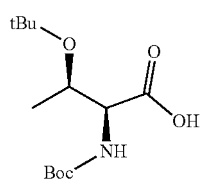 [SMILES: C[C@@H](OC(C)(C)C)[C@H](NC(=O)OC(C)(C)C)C(=O)O]

was replaced with

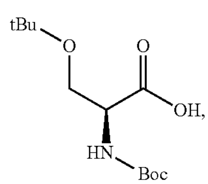 [SMILES: CC(C)(C)OC[C@H](NC(=O)OC(C)(C)C)C(=O)O]

and the rest operations were the same as those in A-066 synthesis. M+1: 260.14.

A-252: A-057 was replaced with A-245, the raw material

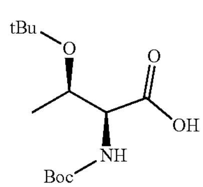 [SMILES: C[C@@H](OC(C)(C)C)[C@H](NC(=O)OC(C)(C)C)C(=O)O]

was replaced with

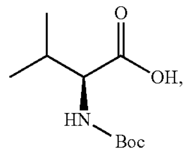

and the rest operations were the same as those in A-066 synthesis. M+1: 272.17.

Example A-253

The example illustrates a synthesis method of compound A-253.

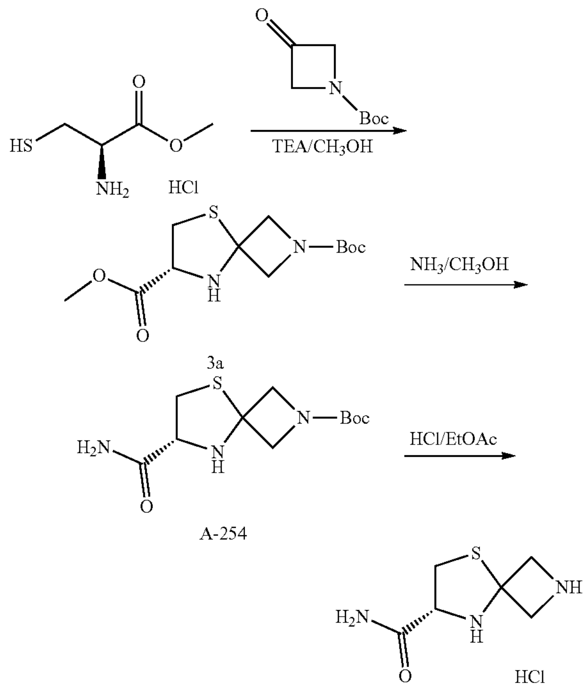

HCl

3a

A-254

HCl

A-253

1. Synthesis Method of an Intermediate 3a

Under −15° C., 1.8 g (10 mmol) of a raw material L-cysteine methyl ester hydrochloride was dissolved in 100 mL of methanol, fully stirred to be dissolved, 1.75 mL (15 mmol) of TEA was added, after the raw material was fully dissociated, 1.8 g (10 mmol, 1.0 eq) of a raw material 1-Boc-3-azetidinone was added, then continued to be subjected to a low-temperature reaction for 15 min, and transferred to room temperature. After reaction at room temperature for 4 h, when the completion of the materials reaction was monitored by TLC, a reaction solution was subjected to rotary evaporation, a concentrate was dissolved with 100 mL of ethyl acetate, washed with a small amount of water for multiple times (15 ml×4), dried with anhydrous sodium sulfate, filtered, and then subjected to rotary evaporation. A crude product was purified with a silica column (PE:EtOAc=2:1) to obtain a total of 2.4 g of a yellow transparent oily intermediate 3a with a yield of 83%. $^1$H-NMR (400 MHz, DMSO-$d_6$), δ ppm: 1.37 (s, 9H), 3.06-3.55 (m, 6H), 3.91-4.19 (m, 4H), 8.69 (s, 1H). M+1: 289.11.

2. Synthesis Method of an Intermediate A-254

A total of 0.8 g (2.8 mmol) of the intermediate 3a was dissolved in 5 mL of anhydrous methanol, 5 mL of 7 mol/L $NH_3/CH_3OH$ solution was added, stirred overnight at room temperature; when the completion of the materials reaction was monitored by TLC, the reaction was terminated. After vacuum concentration, a white solid was obtained, the traits were improved by stirring with petroleum ether, and the material was filtered to obtain 0.68 g of a white solid, namely A-254, with a yield of 90.7%. $^1H$-NMR (400 MHz, DMSO-$d_6$), δ ppm: 1.37 (s, 9H), 3.02-3.27 (m, 2H), 3.36-3.45 (m, 1H), 3.94-4.23 (m, 4H), 8.14 (s, 2H), 8.78 (s, 1H). M+1: 274.11.

3. Synthesis Method of Product A-253

0.4 g of A-254 was dissolved in 3 mL of anhydrous ethyl acetate, a total of 5 mL of 4 mol/L HCl/EtOAc was added, and stirred at room temperature for 4 h; when the completion of the materials reaction was monitored by TLC, a white solid was obtained in the system, then filtered and washed with the anhydrous ether to obtain 0.21 g of the end product A-253 with a yield of 70%. $^1H$-NMR (400 MHz, DMSO-$d_6$), δ ppm: 3.04-3.28 (m, 2H), 3.37-3.42 (m, 1H), 3.91-4.22 (m, 4H), 8.15 (s, 2H), 8.54 (s, 1H). M+1: 174.06.

Similarly, in the synthesis of the intermediate 3a, the raw material 1-Boc-3-azetidinone was replaced with N-Boc-3-pyrrolidone, N-Boc-4-piperidone, and N-Boc-3-piperidone, and the other operations were the same as those of the synthesis of the intermediate 3a, and an intermediate 3b, an intermediate 3c, and an intermediate 3d were prepared respectively.

3b

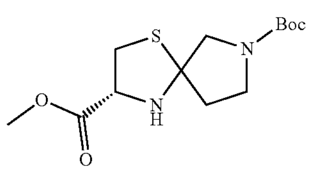

3c

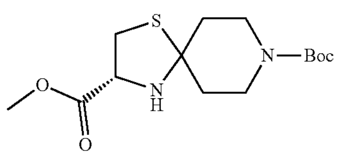

3d

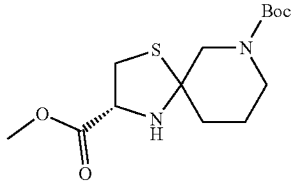

Examples of Preparation of A-262, A-270, A-278

A-262: the intermediate 3a was replaced with the intermediate 3b, and the rest operations were the same as those in A-254 synthesis. M+1: 288.13.

A-270: the intermediate 3a was replaced with the intermediate 3c, and the rest operations were the same as those in A-254 synthesis. M+1: 302.15.

A-278: the intermediate 3a was replaced with the intermediate 3d, and the rest operations were the same as those in A-254 synthesis. M+1: 302.15.

Examples of Preparation of A-261, A-269 and A-277

A-261: A-254 was replaced with A-262, and the rest operations were the same as those in A-253 synthesis. M+1: 188.08.

A-269: A-254 was replaced with A-270, and the rest operations were the same as those in A-253 synthesis. M+1: 202.09.

A-277: A-254 was replaced with A-278, and the rest operations were the same as those in A-253 synthesis. M+1: 202.09.

Example A-255

The example illustrates a synthesis method of compound A-255.

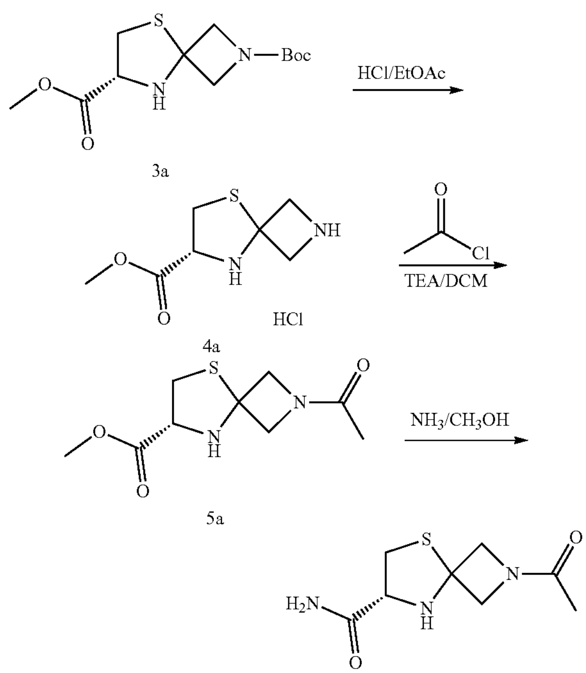

3a

4a

5a

A-255

1. Synthesis Method of an Intermediate 4a

A total of 2.4 g (8.3 mmol) of the intermediate 3a was dissolved in 10 mL of anhydrous ethyl acetate, and 20 mL of 4 mol/L hydrochloric acid/ethyl acetate solution was added under ice bath, the raw materials were reacted overnight, an off-white solid was precipitated; when the completion of the raw materials reaction was monitored by TLC, 1.8 g of an intermediate 4a was obtained after filtration, washed with anhydrous ether, and dried. $^1H$-NMR (400 MHz, DMSO-$d_6$), δ ppm: 3.05-3.55 (m, 6H), 3.91-4.19 (m, 4H), 8.26 (s, 1H), 8.69 (s, 1H). M+1: 189.06.

2. Synthesis Method of an Intermediate 5a 1.6 g (7.15 mmol) of the intermediate 4a was dissolved in 20 mL DCM under ice bath, and after being added 4 mL (28 mmol) of TEA for dissociation, 1 mL (14 mmol) of acetyl chloride was slowly added dropwise, the raw materials were gradually returned to room temperature and reacted overnight; when the completion of the raw materials reaction was monitored by TLC, the reaction was terminated; a saturated citric acid aqueous solution was used for washing (10 mL×3), an organic phase was taken, dried with anhydrous sodium sulfate, filtered, concentrated, and separated through a silica gel column to obtain 1.53 g of a yellowish oily substance, namely an intermediate 5a, with a yield of 76.5%. $^1$H-NMR (400 MHz, DMSO-$d_6$), δ ppm: 2.05 (s, 3H), 3.07-3.53 (m, 6H), 3.95-4.21 (m, 4H), 8.48 (s, 1H). M+1: 231.07.

3. Synthesis Method of a Product A-255

The intermediate 5a was ammonolyzed, and the synthesis method of this step was the same as that of A-254. $^1$H-NMR (400 MHz, DMSO-$d_6$), δ ppm: 2.04 (s, 3H), 3.02-3.25 (m, 2H), 3.38-3.47 (m, 1H), 3.97-4.22 (m, 4H), 8.23 (s, 2H), 9.01 (s, 1H). M+1: 216.07.

In the synthesis of the intermediate 4a, the raw material intermediate 3a was replaced with the intermediate 3b, the intermediate 3c and the intermediate 3d respectively, and the other operations were the same as those in the synthesis of the intermediate 4a, and an intermediate 4b, an intermediate 4c and an intermediate 4d were prepared respectively;

- similarly, in the synthesis process of the intermediate 5a, the raw material intermediate 4a was replaced with the intermediate 4b, the intermediate 4c and the intermediate 4d respectively, and the other operations were the same as those in the synthesis of the intermediate 5a, and an intermediate 5b, an intermediate 5c and an intermediate 5d were prepared respectively;
- similarly, in the synthesis of the intermediate 5a, acetyl chloride was replaced with isobutyryl chloride and pivaloyl chloride respectively, and an intermediate 6a, an intermediate 6b, an intermediate 6c, and an intermediate 6d, and an intermediate 7a, an intermediate 7b, an intermediate 7c, and an intermediate 7d were prepared respectively.

4b

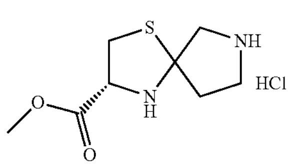

4c

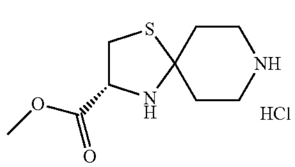

4d

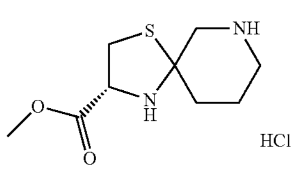

-continued

5b

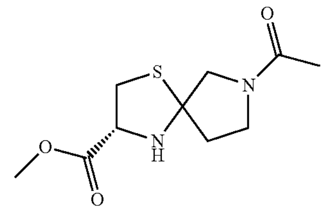

5c

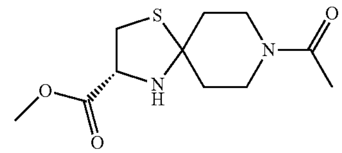

5d

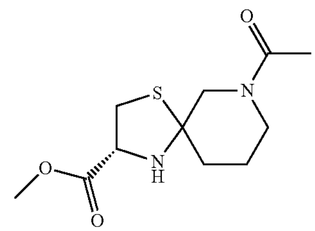

6a

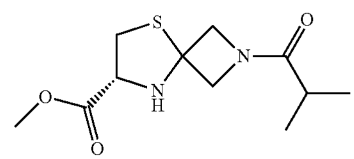

6b

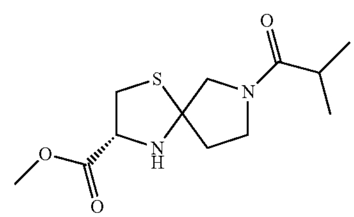

6c

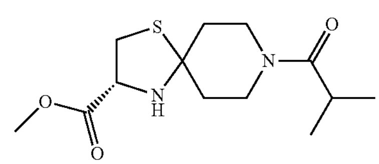

6d

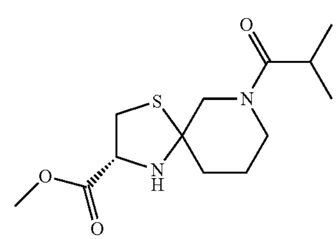

7a

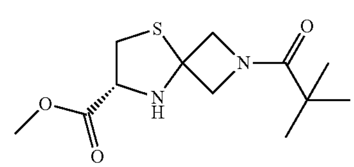

-continued

7b

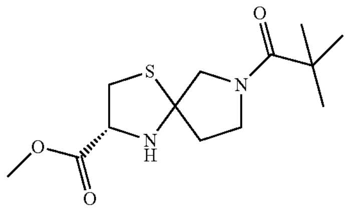

7c

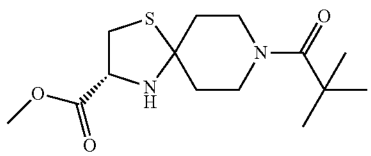

7d

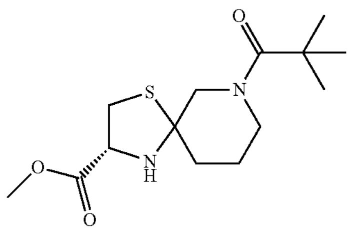

Preparation of A-256 and A-257

A-256: the intermediate 5a was replaced with the intermediate 6a, and other operations were the same as those in A-255 synthesis. M+1: 244.10.

A-257: the intermediate 5a was replaced with the intermediate 7a, and other operations were the same as those in A-255 synthesis. M+1: 258.12.

Preparation of A-263 and A-265

A-263: the intermediate 5a was replaced with the intermediate 5b, and other operations were same as those in A-255 synthesis. M+1: 230.09.

A-264: the intermediate 5a was replaced with the intermediate 6b, and other operations were same as those in A-255 synthesis. M+1: 258.12.

A-265: the intermediate 5a was replaced with the intermediate 7b, and other operations were same as those in A-255 synthesis. M+1: 272.14.

Preparation of A-271 and A-273

A-271: the intermediate 5a was replaced with the intermediate 5c, and other operations were same as those in A-255 synthesis. M+1: 244.10.

A-272: the intermediate 5a was replaced with the intermediate 6c, and other operations were same as those in A-255 synthesis. M+1: 272.14.

A-273: the intermediate 5a was replaced with the intermediate 7c, and other operations were same as those in A-255 synthesis. M+1: 286.15.

Preparation of A-279 and A-281

A-279: the intermediate 5a was replaced with the intermediate 5d, and other operations were same as those in A-255 synthesis. M+1: 244.10.

A-280: the intermediate 5a was replaced with the intermediate 6d, and other operations were same as those in A-255 synthesis. M+1: 272.14.

A-281: the intermediate 5a was replaced with the intermediate 7d, and other operations were same as those in A-255 synthesis. M+1: 286.15.

Example of A-258

The example illustrates a synthesis method of compound A-258.

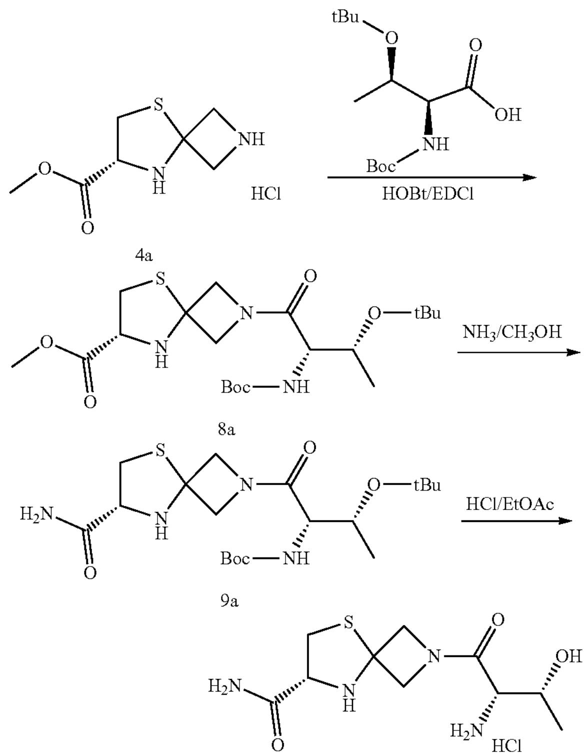

4a

8a

9a

A-258

1. Synthesis Method of an Intermediate 8a

A total of 1.8 g (8 mmol) of the intermediate 4a was dissolved in 50 mL of dichloromethane, 0.89 g (8.8 mmol) of triethylamine was added under ice bath, and the materials were fully dissociated, then 2.2 g (8 mmol) of Boc-tBu-Thr, 1.18 g (8.8 mmol) of HOBt and 1.68 g (8.8 mmol) of EDCI were added, and the raw materials were naturally returned to room temperature for a reaction; after the completion of the raw materials reaction was monitored by TLC, a citric acid aqueous solution, a saturated sodium bicarbonate solution and a saturated sodium chloride solution were used for washing in order, and the material was dried with anhydrous sodium sulfate, filtered and concentrated. A concentrate was purified with a silica gel column, wherein the ratio of petroleum ether to ethyl acetate was 1:1, and a total of 1.9 g of an intermediate 8a was obtained with a yield of 53%. $^1$H-NMR (400 MHz, DMSO-$d_6$), δ ppm: 1.12-1.20 (m, 12H), 1.37 (s, 9H), 3.14-3.41 (m, 2H), 3.59-3.87 (m, 5H), 4.04-4.84 (m, 5H), 7.84 (s, 1H), 8.52 (s, 1H). M+1: 446.22.

2. Synthesis Method of an Intermediate 9a

A total of 1.5 g (3.37 mmol) of the intermediate 8a was dissolved in a small amount of methanol, and 10 mL of 7 mol/L $NH_3/CH_3OH$ solution was added under ice bath, and the raw materials were reacted overnight; after the completion of the raw materials reaction was monitored by TLC, a reaction solution was subjected to rotary evaporation to obtain a total of 1.45 g of an off-white solid intermediate 9a with a yield of 99.4%. $^1$H-NMR (400 MHz, DMSO-$d_6$), δ ppm: 1.12-1.22 (m, 12H), 1.37 (s, 9H), 3.15-3.43 (m, 2H), 3.59-3.89 (m, 2H), 4.07- 4.81 (m, 5H), 7.84 (s, 1H), 8.24 (s, 2H), 8.57 (s, 1H). M+1: 431.22

3. Synthesis Method of a Product A-258

A total of 1.3 g (3 mmol) of the intermediate 9a was dissolved in 10 mL of anhydrous ethyl acetate, and 10 mL of 4 mol/L HCl/EtOAc solution was added under ice bath, and the materials were gradually returned to room temperature and reacted for 6 h; when the completion of the raw materials reaction was monitored by TLC, a white solid was precipitated in the system, filtered, and washed with anhydrous diethyl ether to obtain a total of 0.81 g of the end product A-258 with a yield of 86.1%. $^1$H-NMR (400 MHz, DMSO-$d_6$), δ ppm: 1.12-1.17 (m, 3H), 3.05-3.17 (m, 1H), 3.39-3.43 (m, 1H), 3.72-3.92 (m, 2H), 4.06-4.81 (m, 5H), 5.65 (s, 1H), 7.55 (s, 1H), 7.93 (s, 2H), 8.24 (s, 2H). M+1: 275.11.

The intermediate 4a was respectively replaced with the intermediate 4b, the intermediate 4c and the intermediate 4d, and an intermediate 8b, an intermediate 8c and an intermediate 8d were respectively prepared; and an intermediate 9b, an intermediate 9c and an intermediate 9d were prepared accordingly.

The intermediate 4a was respectively replaced with the intermediate 4b, the intermediate 4c and the intermediate 4d, the raw material

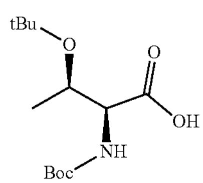 [SMILES: C[C@@H](OC(C)(C)C)[C@H](NC(=O)OC(C)(C)C)C(=O)O]

was replaced with

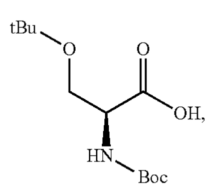 [SMILES: CC(C)(C)OC[C@H](NC(=O)OC(C)(C)C)C(=O)O]

and an intermediate 10a, an intermediate 10b, an intermediate 10c and an intermediate 10d were prepared respectively; and an intermediate 11a, an intermediate 11b, an intermediate 11c and an intermediate 11d were prepared accordingly.

The intermediate 4a was respectively replaced with the intermediate 4b, the intermediate 4c and the intermediate 4d, the raw material

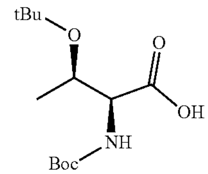 [SMILES: C[C@@H](OC(C)(C)C)[C@H](NC(=O)OC(C)(C)C)C(=O)O]

was replaced with

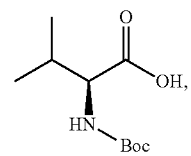

and an intermediate 12a, an intermediate 12b, an intermediate 12c and an intermediate 12d were prepared respectively; and an intermediate 13a, an intermediate 13b, an intermediate 13c and an intermediate 13d were prepared accordingly.

8a

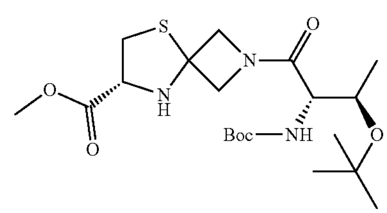

8b

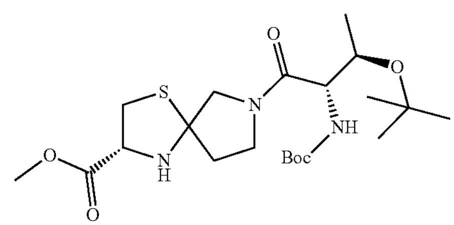

8c

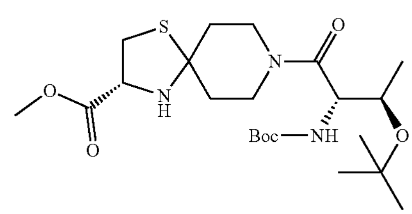

8d

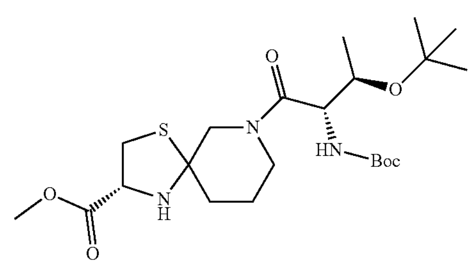

-continued
9a
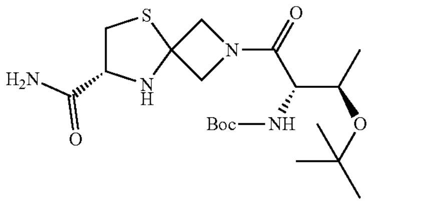
9b
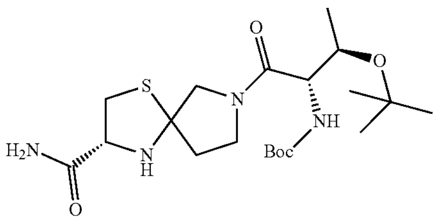
9c
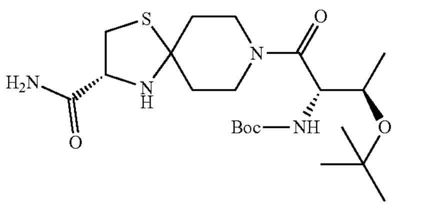
9d
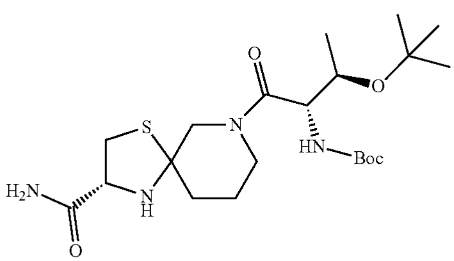
10a
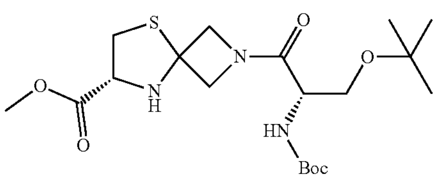
10b
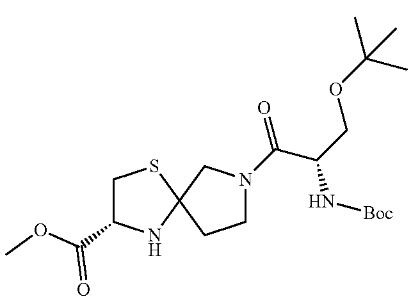
10c
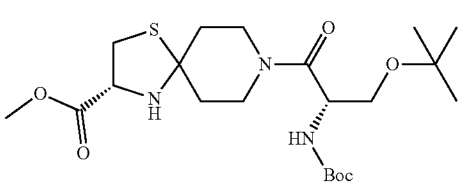
-continued
10d
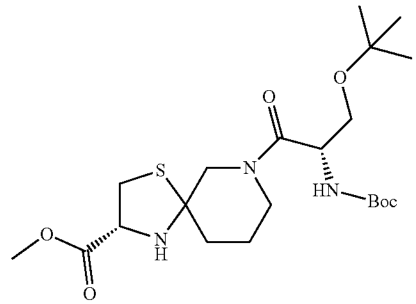
11a
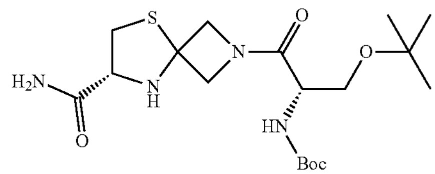
11b
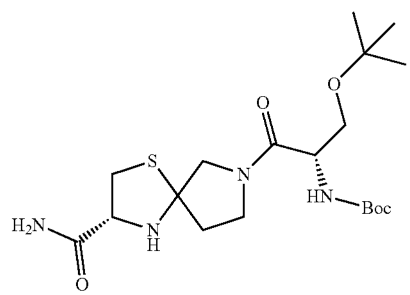
11c
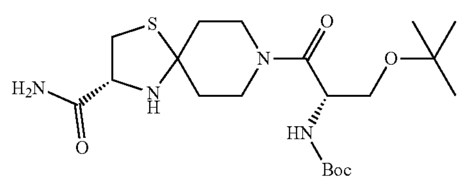
11d
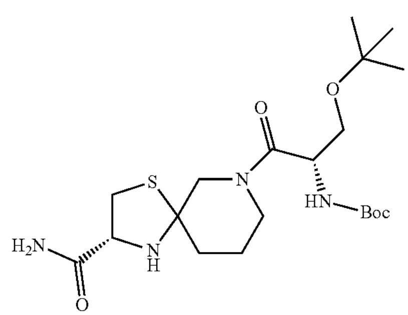
12a
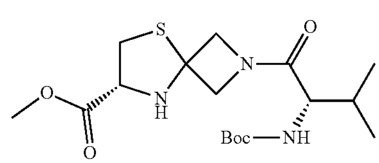

-continued

12b

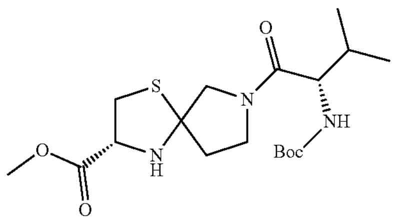

12c

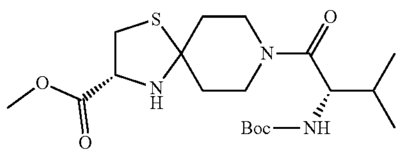

12d

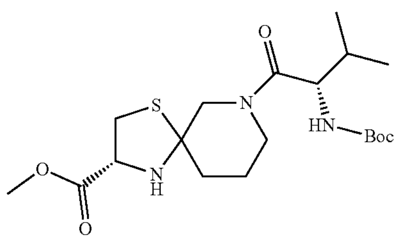

13a

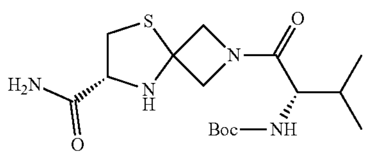

13b

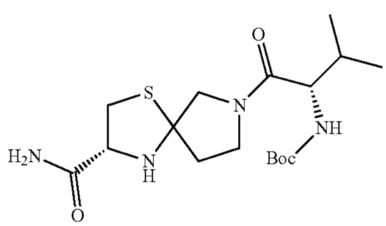

13c

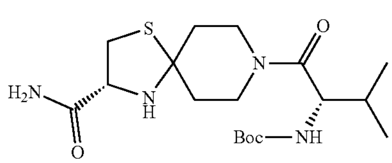

13d

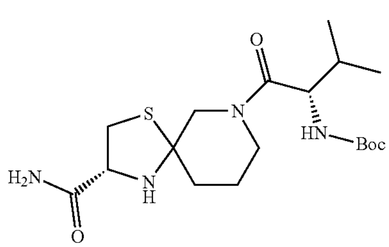

Examples of Preparation of A-259 to A-260

A-259: the raw material

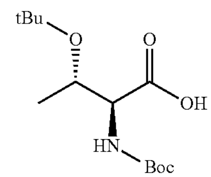 [SMILES: C[C@H](OC(C)(C)C)[C@H](NC(=O)OC(C)(C)C)C(=O)O]

was replaced with

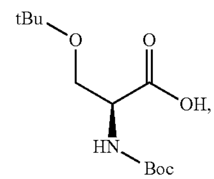 [SMILES: CC(C)(C)OC[C@H](NC(=O)OC(C)(C)C)C(=O)O]

and the rest operations were the same as those in A-258 synthesis. M+1: 261.09.

A-260: the raw material

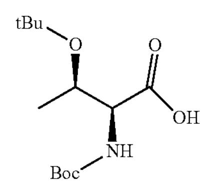 [SMILES: C[C@@H](OC(C)(C)C)[C@H](NC(=O)OC(C)(C)C)C(=O)O]

was replaced with

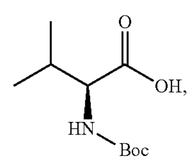

and the rest operations were the same as those in A-258 synthesis. M+1: 273.13.

Examples of Preparation of A-266 to A-268

A-266: the raw material intermediate 4a was replaced with the intermediate 4b, and the rest operations were the same as those in A-258 synthesis. M+1: 289.13.

A-267: the raw material intermediate 4a was replaced with the intermediate 4b, the raw material

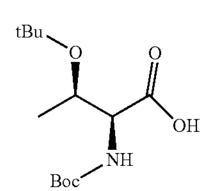 [SMILES: C[C@@H](OC(C)(C)C)[C@H](NC(=O)OC(C)(C)C)C(=O)O]

was replaced with

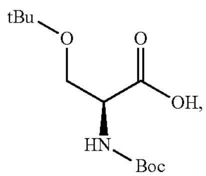 [SMILES: CC(C)(C)OC[C@H](NC(=O)OC(C)(C)C)C(=O)O]

and the rest operations were the same as those in A-258 synthesis. M+1: 275.11.

A-268: the raw material intermediate 4a was replaced with the intermediate 4b, the raw material

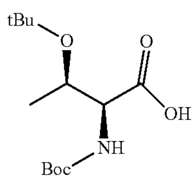 [SMILES: C[C@@H](OC(C)(C)C)[C@H](NC(=O)OC(C)(C)C)C(=O)O]

was replaced with

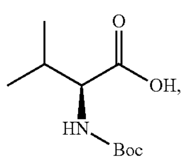

and the rest operations were the same as those in A-258 synthesis. M+1: 287.15.

Examples of Preparation of A-274 to A-276

A-274: the raw material intermediate 4a was replaced with the intermediate 4c, and the rest operations were the same as those in A-258 synthesis. M+1: 303.14.

A-275: the raw material intermediate 4a was replaced with the intermediate 4c, the raw material

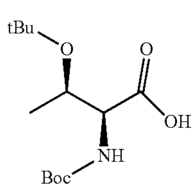 [SMILES: C[C@@H](OC(C)(C)C)[C@H](NC(=O)OC(C)(C)C)C(=O)O]

was replaced with

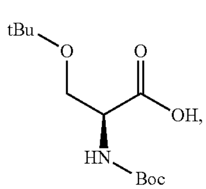 [SMILES: CC(C)(C)OC[C@H](NC(=O)OC(C)(C)C)C(=O)O]

and the rest operations were the same as those in A-258 synthesis. M+1: 289.13.

A-276: the raw material intermediate 4a was replaced with the intermediate 4c, the raw material

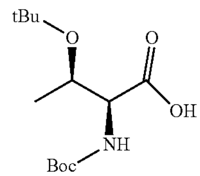 [SMILES: C[C@@H](OC(C)(C)C)[C@H](NC(=O)OC(C)(C)C)C(=O)O]

was replaced with

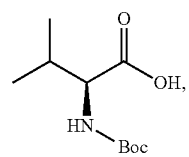

and the rest operations were the same as those in A-258 synthesis. M+1: 301.16.

Examples of Preparation of A-282 to A-284

A-282: the raw material intermediate 4a was replaced with the intermediate 4d, and the rest operations were the same as those in A-258 synthesis. M+1: 303.14.

A-283: the raw material intermediate 4a was replaced with the intermediate 4d, the raw material

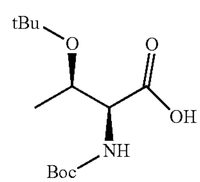 [SMILES: C[C@@H](OC(C)(C)C)[C@H](NC(=O)OC(C)(C)C)C(=O)O]

was replaced with

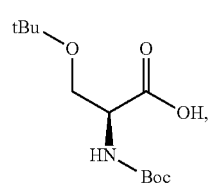 [SMILES: CC(C)(C)OC[C@H](NC(=O)OC(C)(C)C)C(=O)O]

and the rest operations were the same as those in A-258 synthesis. M+1: 289.13.

A-284: the raw material intermediate 4a was replaced with the intermediate 4d, the raw material

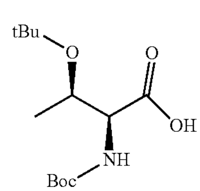 [SMILES: C[C@@H](OC(C)(C)C)[C@H](NC(=O)OC(C)(C)C)C(=O)O]

was replaced with

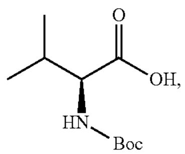

and the the rest operations were the same as those in A-258 synthesis. M+1: 301.16.

Example of A-285

The example illustrates a synthesis method of compound A-285.

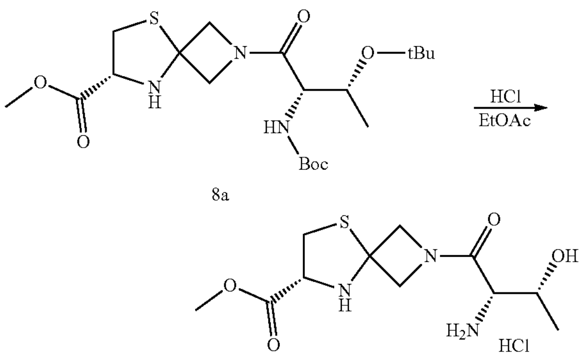

8a

A-285

Under ice bath conditions, 0.8 g (1.74 mmol) of the intermediate 8a was dissolved in 10 mL of anhydrous ethyl acetate, and a total of 5 mL of 4 mol/L HCl/EtOAc was added, and the raw materials were gradually returned to room temperature and reacted for 4 hours; when the completion of the raw materials reaction was monitored by TLC, a white solid was generated in the system. The reaction was terminated, after vacuum filtration a filter cake was taken, continuously stirred for 10 min in 15 mL of anhydrous ethyl acetate, and then filtered to obtain a total of 0.51 g of white solid A-285 with a yield of 90.1%. $^1$H-NMR (400 MHz, DMSO-$d_6$), δ ppm: 1.12-1.17 (m, 3H), 3.07-3.19 (m, 1H), 3.38-3.42 (m, 1H), 3.68-3.91 (m, 5H), 4.07-4.83 (m, 5H), 5.63 (s, 1H), 7.53 (s, 1H), 7.88 (s, 2H). M+1: 290.11.

Examples of Preparation of A-286 and A-287

A-286: the intermediate 8a was replaced with the intermediate 10a, and the rest operations were the same as those in A-285 synthesis. M+1: 276.09.

A-287: the intermediate 8a was replaced with the intermediate 12a, and the rest operations were the same as those in A-285 synthesis. M+1: 288.13.

Examples of Preparation of A-288 and A-290

A-288: the intermediate 8a was replaced with the intermediate 8b, and the rest operations were the same as those in A-285 synthesis. M+1: 304.13.

A-289: the intermediate 8a was replaced with the intermediate 10b, and the rest operations were the same as those in A-285 synthesis. M+1: 290.11.

A-290: the intermediate 8a was replaced with the intermediate 12b, and the rest operations were the same as those in A-285 synthesis. M+1: 302.15.

Examples of Preparation of A-291 and A-293

A-291: the intermediate 8a was replaced with the intermediate 8c, and the rest operations were the same as those in A-285 synthesis. M+1: 318.14.

A-292: the intermediate 8a was replaced with the intermediate 10c, and the rest operations were the same as those in A-285 synthesis. M+1: 304.13.

A-293: the intermediate 8a was replaced with the intermediate 12c, and the rest operations were the same as those in A-285 synthesis. M+1: 316.16.

Examples of Preparation of A-294 and A-296

A-294: the intermediate 8a was replaced with the intermediate 8d, and the rest operations were the same as those in A-285 synthesis. M+1: 318.14.

A-295: the intermediate 8a was replaced with the intermediate 10d, and the rest operations were the same as those in A-285 synthesis. M+1: 304.13.

A-296: the intermediate 8a was replaced with the intermediate 12d, and the rest operations were the same as those in A-285 synthesis. M+1: 316.16.

Example of A-302

The example illustrates a synthesis method of compound A-302.

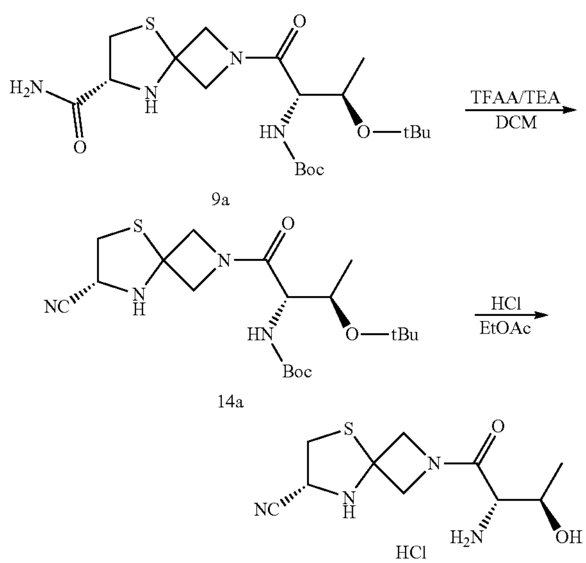

9a

14a

A-302

1. Synthesis Method of an Intermediate 14a 0.7 g (1.6 mmol) of the intermediate 9a was dissolved in 10 mL of anhydrous DCM, 832 μL (6 mmol) of TEA was added, 0.7 g of trifluoroacetic anhydride (TFAA, 3.2 mmol) was added under ice bath conditions, and the materials were gradually returned to room temperature, and stirred at the room temperature for 12 h; when the completion of the raw materials reaction was monitored by TLC, the reaction was terminated; an organic phase was washed with 10 mL of water and 10 mL of saturated aqueous sodium chloride respectively, dried with anhydrous sodium sulfate, filtrated, concentrated, and separated through a silica gel column (PE:EtOAc=2:1) to obtain a total of 0.62 g of an end-product intermediate 14a with a yield of 92%. $^1$H-NMR (400 MHz, DMSO-$d_6$), δ ppm: 1.13-1.21 (m, 12H), 1.37 (s, 9H), 3.03-3.14 (m, 1H), 3.39-3.42 (m, 1H), 3.69-3.86 (m, 2H), 4.03-4.75 (m, 5H), 7.81 (s, 1H), 8.34 (s, 1H). M+1: 413.21.

2. Preparation of A-302

0.5 g of the intermediate 14a was dissolved in 10 mL of anhydrous ethyl acetate under ice bath conditions, fully stirred and dissolved, a total of 5 mL of 4 mol/L HCl/EtOAc was added, the raw material was gradually returned to room temperature and reacted at room temperature for 5 hours, and a yellow solid was generated in the system; when the completion of the raw materials reaction was monitored by TLC, the reaction was terminated. After filtration, a filter cake was taken and stirred with anhydrous ethyl acetate for 15 min and then filtered to obtain a total of 0.26 g of A-302 with a yield of 83%. $^1$H-NMR (400 MHz, DMSO-$d_6$), δ ppm: 1.13-1.18 (m, 3H), 3.06-3.18 (m, 1H), 3.39-3.42 (m, 1H), 3.74-3.91 (m, 2H), 4.05-4.79 (m, 5H), 5.68 (s, 1H), 8.29 (s, 2H), 8.52 (s, 1H). M+1: 257.10.

Examples of Preparation of A-297 to A-301, A-303 and A-304

A-297: the intermediate 9a was replaced with A-254, and the rest operations were the same as those of A-302. M+1: 156.05.

A-298: the intermediate 9a was replaced with A-254, and the rest operations were the same as those of the intermediate 14a. M+1: 256.10.

A-299: the intermediate 9a was replaced with A-255, and the rest operations were the same as those of the intermediate 14a. M+1: 198.06.

A-300: the intermediate 9a was replaced with A-256, and the rest operations were the same as those of the intermediate 14a. M+1: 226.09.

A-301: the intermediate 9a was replaced with A-257, and the rest operations were the same as those of the intermediate 14a. M+1: 240.11.

A-303: the intermediate 9a was replaced with the intermediate 11a, and the rest operations were the same as those of A-302. M+1: 243.08.

A-304: the intermediate 9a was replaced with the intermediate 13a, and the rest operations were the same as those of A-302. M+1: 255.12.

Examples of Preparation of A-305 to A-312

A-305: the intermediate 9a was replaced with A-262, and the rest operations were the same as those of A-302. M+1: 170.07.

A-306: the intermediate 9a was replaced with A-262, and the rest operations were the same as those of the intermediate 14a. M+1: 270.12.

A-307: the intermediate 9a was replaced with A-263, and the rest operations were the same as those of the intermediate 14a. M+1: 212.08.

A-308: the intermediate 9a was replaced with A-264, and the rest operations were the same as those of the intermediate 14a. M+1: 240.11.

A-309: the intermediate 9a was replaced with A-265, and the rest operations were the same as those of the intermediate 14a. M+1: 254.12.

A-310: the intermediate 9a was replaced with the intermediate 9b, and the rest operations were the same as those of A-302. M+1: 271.12.

A-311: the intermediate 9a was replaced with the intermediate 11b, and the rest operations were the same as those of A-302. M+1: 257.10.

A-312: the intermediate 9a was replaced with the intermediate 13b, and the rest operations were the same as those of A-302. M+1: 269.14.

Examples of Preparation of A-313 to A-320

A-313: the intermediate 9a was replaced with A-270, and the rest operations were the same as those of A-302. M+1: 184.08

A-314: the intermediate 9a was replaced with A-270, and the rest operations were the same as those of the intermediate 14a. M+1: 284.14.

A-315: the intermediate 9a was replaced with A-271, and the rest operations were the same as those of the intermediate 14a. M+1: 226.09.

A-316: the intermediate 9a was replaced with A-272, and the rest operations were the same as those of the intermediate 14a. M+1: 254.12.

A-317: the intermediate 9a was replaced with A-273, and the rest operations were the same as those of the intermediate 14a. M+1: 268.14.

A-318: the intermediate 9a was replaced with the intermediate 9c, and the rest operations were the same as those of A-302. M+1: 285.13.

A-319: the intermediate 9a was replaced with the intermediate 11c, and the rest operations were the same as those of A-302. M+1: 271.12.

A-320: the intermediate 9a was replaced with the intermediate 13c, and the rest operations were the same as those of A-302. M+1: 283.15.

Examples of Preparation of A-321 to A-328

A-321: the intermediate 9a was replaced with A-278, and the rest operations were the same as those of A-302. M+1: 184.08.

A-322: the intermediate 9a was replaced with A-278, and the rest operations were the same as those of the intermediate 14a. M+1: 284.14.

A-323: the intermediate 9a was replaced with A-279, and the rest operations were the same as those of the intermediate 14a. M+1: 226.09.

A-324: the intermediate 9a was replaced with A-280, and the rest operations were the same as those of the intermediate 14a. M+1: 254.12.

A-325: the intermediate 9a was replaced with A-281, and the rest operations were the same as those of the intermediate 14a. M+1: 268.14.

A-326: the intermediate 9a was replaced with the intermediate 9d, and the rest operations were the same as those of A-302. M+1: 285.13.

A-327: the intermediate 9a was replaced with the intermediate 11d, and the rest operations were the same as those of A-302. M+1: 271.12.

A-328: the intermediate 9a was replaced with the intermediate 13d, and the rest operations were the same as those of A-302. M+1: 283.15.

Example of Synthesis of A-329

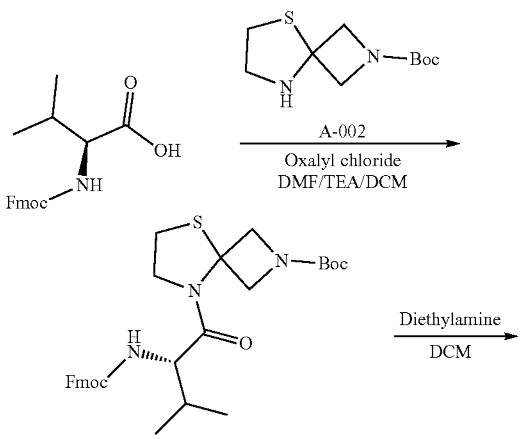

15a

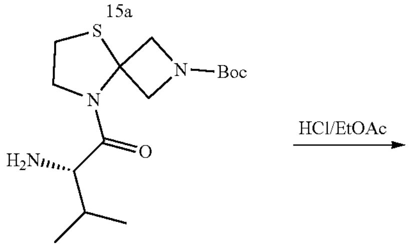

16a

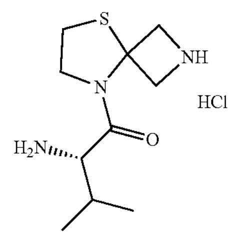

A-329

1. Synthesis of Intermediate 15a

Under ice bath, 0.5 g (1.5 mmol) of Fmoc-Val was dissolved in 10 mL of anhydrous DCM, 2 drops of DMF were added for catalysis, then 230 μL (1.65 mmol) of TEA was added, 133 μL (1.58 mmol) of oxalyl chloride was added drop by drop, and the raw materials were returned to room temperature, and reacted overnight; when the completion of the raw materials reaction was monitored by TLC, 0.35 g (1.5 mmol) of compound A-002 was added to the reaction system, and the reaction system was continuously stirred at the room temperature for 4 h; when the completion of the raw materials reaction was monitored by TLC, the reaction was terminated; saturated citric acid was used for washing twice, saturated sodium chloride solution was used for washing once, and an organic phase was taken, dried with anhydrous sodium sulfate, filtered, concentrated, and separated through a silica gel column (PE:EtOAC=3:1) to obtain a total of 0.69 g of colorless oily substance with a yield of 83.3%. $^{1}$H-NMR (400 MHz, DMSO-$d_6$), δ ppm: 1.12-1.23 (m, 6H), 1.37 (9H), 2.15-2.25 (m, 1H), 3.16-3.73 (m, 5H), 4.16-4.79 (m, 8H), 7.21-8.29 (m, 9H). M+1: 552.25.

2. Synthesis of Intermediate 16a 0.48 g of the intermediate 15a was dissolved in 5 mL of anhydrous acetonitrile, 5 mL of diethylamine was added, and the raw materials were reacted at 50° C. for 4 h; when the completion of the raw materials reaction was monitored by TLC, the reaction was terminated; the reaction product was subjected to rotary evaporation under reduced pressure, 10 ml of DCM was added, and the product was continuously subjected to rotary evaporation, then the above steps were repeated twice; and then 0.25 g of an oily substance with a yield of 87.2% was obtained by separating through a silica gel column. $^{1}$H-NMR (400 MHz, DMSO-$d_6$), δ ppm: 1.12-1.20 (m, 6H), 1.37 (s, 9H), 2.14-2.27 (m, 1H), 3.13-3.77 (m, 5H), 4.13-4.57 (m, 4H), 8.23 (s, 2H). M+1: 330.18.

3. Synthesis of A-329

0.25 g of the intermediate 16 was dissolved in 4 mL of ethyl acetate, 3 mL of 4 mol/L HCl/EtOAc was added, and the raw materials were stirred at room temperature for 3 h; when the completion of the raw materials reaction was monitored by TLC, a white solid was generated in the system, filtered, and dried to obtain 0.16 g of the white solid with a yield of 79%. $^{1}$H-NMR (400 MHz, DMSO-$d_6$), δ ppm: 1.12-1.19 (m, 6H), 2.14-2.25 (m, 1H), 3.13-3.75 (m, 5H), 4.16-4.61 (m, 4H), 8.29 (s, 2H), 9.01 (s, 1H). M+1: 230.12.

Example of Synthesis of A-330

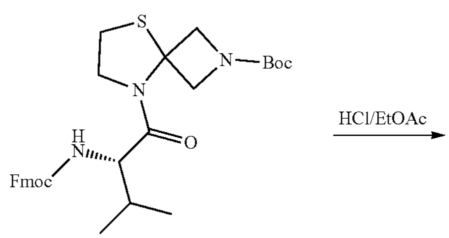

15a

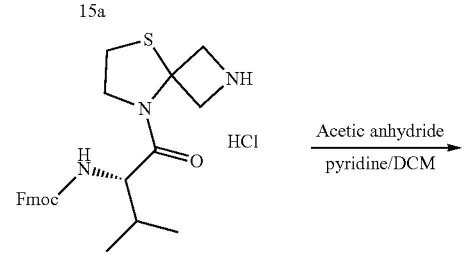

17a

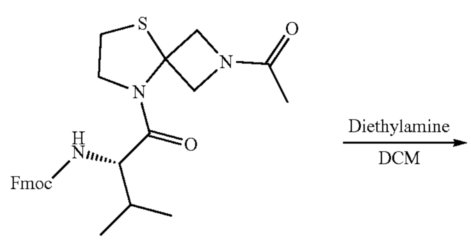

18a

-continued

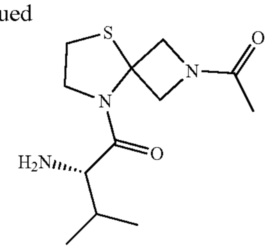

A-330

Synthesis of Intermediate 17a

The synthesis method was similar to that of A-329, and a total of 0.65 g of a yellowish solid was obtained with a yield of 89.3%. $^1$H-NMR (400 MHz, DMSO-$d_6$), δ ppm: 1.14-1.27 (m, 6H), 2.15-2.25 (m, 1H), 3.16-3.73 (m, 5H), 4.16-4.79 (m, 8H), 7.21-8.29 (m, 9H). M+1: 452.19.

Synthesis of Intermediate 18a

Under ice bath conditions, a total of 0.62 g of the intermediate 17 was dissolved in 10 mL of anhydrous DCM, 300 μL of TEA was added for dissociation, 185 μL of acetic anhydride was slowly added dropwise, and the raw materials were gradually returned to room temperature and continuously reacted for 6 h; when the completion of the raw materials reaction was monitored by TLC, the reaction was terminated; the mixture was washed with a saturated citric acid aqueous solution and then with a saturated sodium chloride solution, dried with anhydrous sodium sulfate, filtered, concentrated, and separated through a silica gel column to obtain 0.52 g of an oily substance with a yield of 83%. $^1$H-NMR (400 MHz, DMSO-$d_6$), δ ppm: 1.13-1.27 (m, 6H), 2.05-2.27 (m, 4H), 3.15-3.70 (m, 5H), 4.12-4.75 (m, 8H), 7.21-8.28 (m, 9H). M+1: 494.2.

Example of Synthesis of A-330

The synthesis method was similar to that of the intermediate 16a, and a total of 0.38 g of an oily substance was obtained, HCl/EtOAc was added and the mixture was stirred, then a white solid was generated in the system, filtered, and dried to obtain 0.34 g of a product A-330. $^1$H-NMR (400 MHz, DMSO-$d_6$), δ ppm: 1.12-1.18 (m, 6H), 2.05-2.24 (m, 4H), 3.11-3.78 (m, 5H), 4.12-4.65 (m, 4H), 8.60 (s, 2H). M+1: 272.14.

Example of Synthesis of A-331

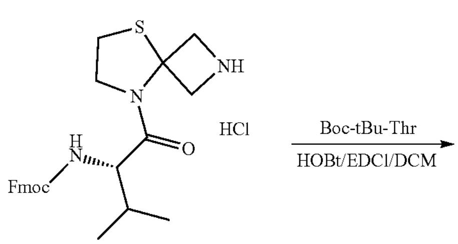

17a

-continued

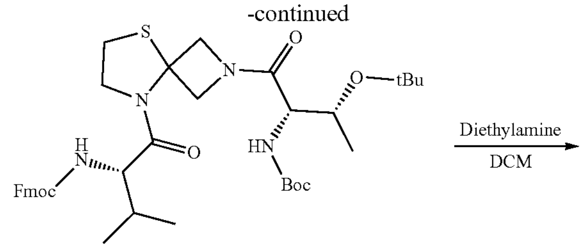

19a

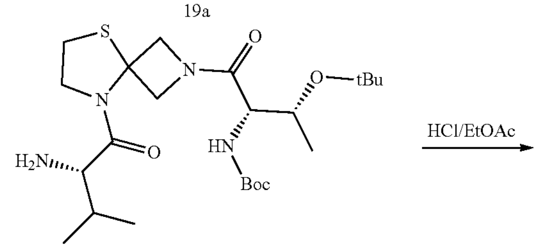

20a

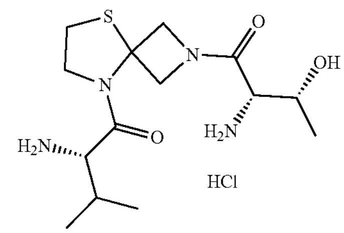

A-331

Synthesis of intermediate 19a

The synthesis method was similar to that of the intermediate 8a, and a total of 1.52 g of a colorless oily substance was obtained with a yield of 81.3%. $^1$H-NMR (400 MHz, DMSO-$d_6$), δ ppm: 1.03-1.37 (m, 27H), 2.32-2.38 (m, 1H), 3.02-3.73 (m, 4H), 4.14-4.68 (m, 10H), 7.12-8.32 (m, 10H). M+1: 709.36.

Synthesis of Intermediate 20a

The synthesis method was similar to that of the intermediate 16a, and 0.84 g of an oily substance was obtained with a yield of 86.9%. $^1$H-NMR (400 MHz, DMSO-$d_6$), δ ppm: 1.01-1.38 (m, 27H), 2.32-2.38 (m, 1H), 3.05-3.77 (m, 4H), 4.12-4.71 (m, 7H), 7.76 (s, 1H), 8.35 (s, 2H). M+1: 487.29.

Example of Synthesis of A-331

The synthesis method was similar to that of A-329, and 0.49 g of a white solid was obtained with a yield of 87.5%. $^1$H-NMR (400 MHz, DMSO-$d_6$), δ ppm: 1.07-1.22 (m, 9H), 2.18-2.27 (m, 1H), 3.07-3.78 (m, 7H), 4.14-4.59 (m, 4H), 5.72 (s, 1H), 8.21-8.32 (m, 4H). M+1: 331.17.

Example of Synthesis of A-347 and A-348

A-347:

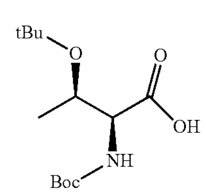 [SMILES: C[C@@H](OC(C)(C)C)[C@H](NC(=O)OC(C)(C)C)C(=O)O]

in the synthesis steps of A-331 was replaced with

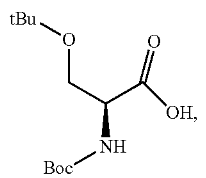 [SMILES: CC(C)(C)OC[C@H](NC(=O)OC(C)(C)C)C(=O)O]

and the rest operation was the same as that in the A-331 synthesis. M+1: 317.16.

A-348:

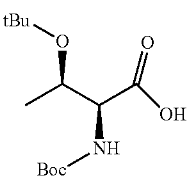 [SMILES: C[C@@H](OC(C)(C)C)[C@H](NC(=O)OC(C)(C)C)C(=O)O]

in the synthesis steps of A-331 was replaced with

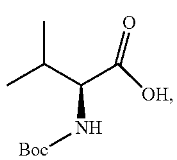

and the rest operations were the same as those in A-331 synthesis. M+1: 329.20.

Example of Synthesis of A-332

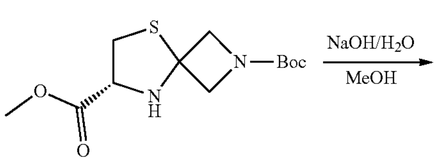

3a

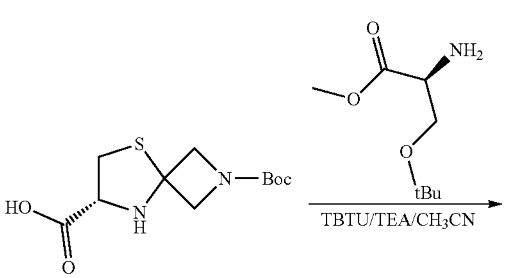

21a

-continued

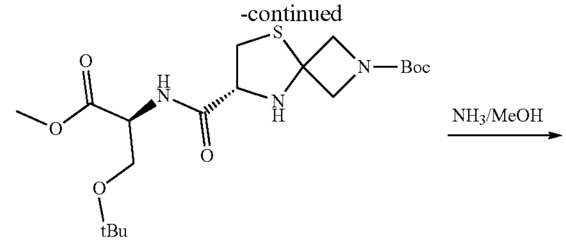

22a

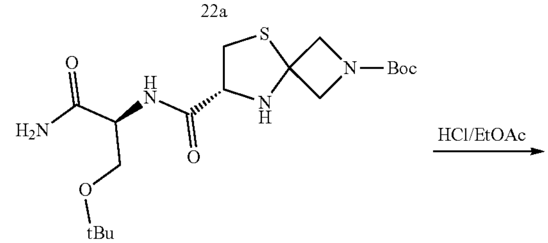

23a

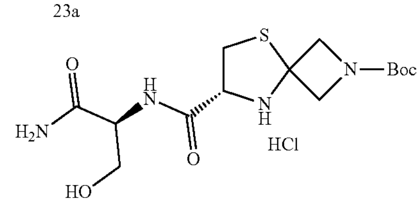

A-332

Synthesis of Intermediate 21a 5.2 g (18 mmol) of the intermediate 3a was dissolved in 20 mL of methanol, 3.6 g (90 mmol) of NaOH was taken and dissolved in 10 mL of water to obtain an aqueous NaOH solution, the aqueous NaOH solution was slowly added to the system of the intermediate 3a under ice bath conditions and the color of the reaction solution became darker, and the raw materials were gradually returned to room temperature and reacted for 3 hours; when the completion of the raw materials reaction was monitored by TLC, the reaction was terminated; the mixture was concentrated under reduced pressure to remove methanol in the system, pH value of the concentrate was adjusted to slightly acidic with dilute hydrochloric acid, a white solid was precipitated from the system, filtered, and dried by infrared lamp, and 4.3 g of the white solid was obtained with a yield of 86.9%. $^1$H-NMR (400 MHz, DMSO-$d_6$), δ ppm: 1.37 (s, 9H), 3.06-3.56 (m, 3H), 3.94-4.23 (m, 4H), 8.54 (s, 1H). M−1: 273.1.

Synthesis of Intermediate 22a

Under ice bath conditions, a total of 0.8 g (2.9 mmol) of the intermediate 21a was dissolved in 20 mL of acetonitrile, 0.8 mL (5.8 mmol) of TEA and 1.1 g (3.5 mmol) of TBTU were added, then 0.53 g (3.1 mmol) of O-tert-butyl-L-serine methyl ester hydrochloride was added, and the raw materials were gradually returned to the room temperature and reacted for 4 hours; when the completion of the raw materials reaction was monitored by TLC, the reaction was terminated. The mixture was washed with saturated citric acid and then washed with saturated sodium chloride, dried with anhydrous sodium sulfate, filtered, concentrated, and separated through a silica gel column to obtain 0.86 g of an oily substance with a yield of 76.1%. $^1$H-NMR (400 MHz, DMSO-$d_6$), δ ppm: 1.13 (s, 9H), 1.42 (s, 9H), 2.67-4.38 (m, 13H), 7.43 (s, 1H), 8.21 (s, 1H). M+1: 432.21.

Synthesis of Intermediate 23a

The synthesis method was similar to that of the intermediate 9a, and a total of 0.76 g of an oily substance was obtained with a yield of 93.5%. $^1$H-NMR (400 MHz, DMSO-$d_6$), δ ppm: 1.13 (s, 9H), 1.42 (s, 9H), 2.67-4.38 (m, 10H), 7.06-7.21 (m, 3H), 8.21 (s, 1H). M+1: 417.21.

Example of Synthesis of A-332

The synthesis method was similar to that of A-329, and a total of 0.53 g of a white solid was obtained with a yield of 81.3%. $^1$H-NMR (400 MHz, DMSO-$d_6$), δ ppm: 2.67-4.54 (m, 10H), 4.94 (s, 1H), 7.21-8.11 (m, 5H). M+1: 261.10.

Example of Synthesis of A-370

A-370: the synthesis method was similar to that of A-332,

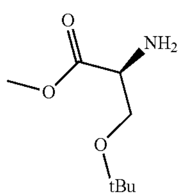

in A-332 synthesis was replaced with

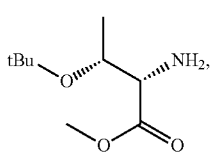

and the rest operations were the same as those of A-332. M+1: 275.11.

Examples of Synthesis of A-383, A-390 and A-397

A-383: the intermediate 5a in A-332 synthesis was replaced with the intermediate 5b,

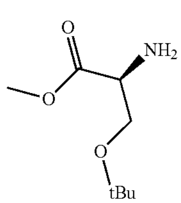

was replaced with

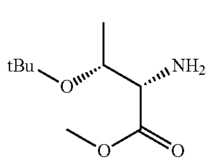

and the rest operations were the same as those in the A-332 synthesis. M+1: 289.13.

A-390: the intermediate 5a in A-332 synthesis was replaced with the intermediate 5c,

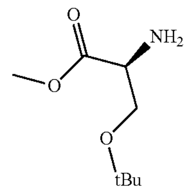

was replaced with

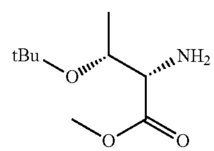

and the rest operations were the same as those in the A-332 synthesis. M+1: 303.14.

A-397: the intermediate 5a in A-332 synthesis was replaced with the intermediate 5d,

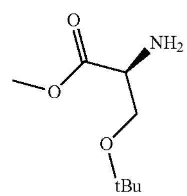

was replaced with

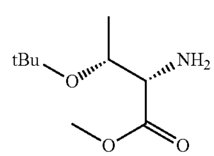

and the rest operations were the same as those in the A-332 synthesis. M+1: 303.14.

Example of Synthesis of A-371

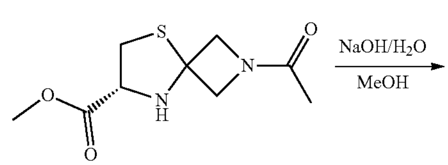

5a

-continued

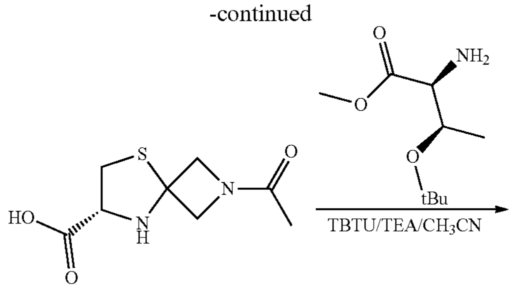

24a

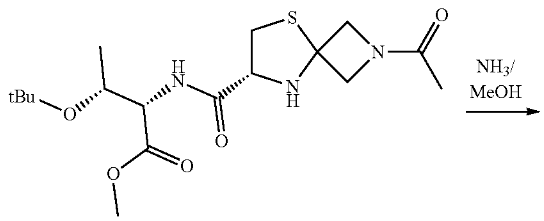

25a

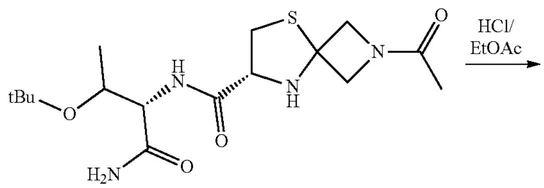

26a

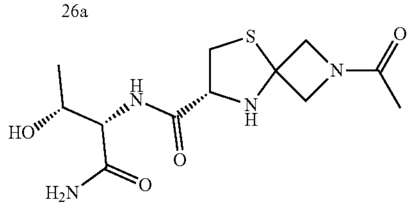

A-371

Synthesis of Intermediate 24a

The synthesis method was similar to that of the intermediate 21a, and a total of 0.68 g of an oily substance was obtained with a yield of 76.7%. $^1$H-NMR (400 MHz, DMSO-$d_6$), δ ppm: 2.10 (s, 3H), 2.67-2.92 (m, 2H), 3.67 (m, 1H), 4.12-4.38 (m, 4H), 7.06 (s, 1H), 12.39 (s, 1H). M+1: 217.06.

Synthesis of Intermediate 25a

The synthesis method was similar to that of the intermediate 22a, and a total of 0.93 g of an oily substance was obtained with a yield of 79.1%. $^1$H-NMR (400 MHz, DMSO-$d_6$), δ ppm: 1.13 (s, 12H), 2.10 (s, 3H), 2.67-2.92 (m, 2H), 3.67 (s, 3H), 3.69-4.38 (m, 7H), 7.06 (s, 1H), 8.32 (s, 1H). M+1: 374.17.

Synthesis of Intermediate 26a

The synthesis method was similar to that of the intermediate 23a, and a total of 0.67 g of a substance was obtained with a yield of 75.2%. $^1$H-NMR (400 MHz, DMSO-$d_6$), δ ppm: 1.13 (s, 12H), 2.10 (s, 3H), 2.67-2.92 (m, 2H), 3.33-4.38 (m, 7H), 7.06 (s, 1H), 7.21 (s, 2H), 8.32 (s, 1H). M+1: 359.17.

Synthesis of A-371

The synthesis method was similar to that of A-332, and a total of 0.48 g of a colorless oily substance was obtained, and then evacuated by an oil pump to obtain a white solid with a yield of 85.7%. $^1$H-NMR (400 MHz, DMSO-$d_6$), δ ppm: 2.10 (s, 6H), 2.33-2.85 (m, 2H), 4.12-4.54 (m, 7H), 4.94 (s, 1H), 7.21 (s, 2H), 8.26 (s, 2H). M+1: 303.11.

Example of Synthesis of A-333

A-333:

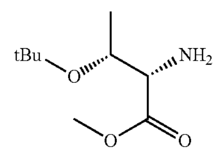

in the synthesis steps of A-371 was replaced with

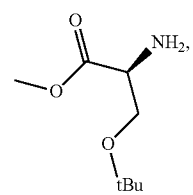

and the rest operations were the same as those of A-371. M+1: 317.12.

Examples of A-372 and A-373

A-372: 5a in the synthesis steps of A-371 was replaced with 6a, and the rest operations were the same as those of A-371. M+1: 345.16.

A-373: 5a in the synthesis steps of A-371 was replaced with 7a, and the rest operations were the same as those of A-371. M+1: 359.17.

Examples of Synthesis of A-384, A-391 and A-398

A-384: the intermediate 5a in the synthesis steps of A-371 was replaced with the intermediate 5b, and the rest operations were the same as those of A-371. M+1: 331.14.

A-391: the intermediate 5a in the synthesis steps of A-371 was replaced with the intermediate 5c, and the rest operations were the same as those of A-371. M+1: 345.16.

A-398: the intermediate 5a in the synthesis steps of A-371 was replaced with the intermediate 5d, and the rest operations were the same as those of A-371. M+1: 345.16.

Examples of Synthesis of A-385 and A-386

A-385: the intermediate 5a in the synthesis steps of A-371 was replaced with the intermediate 6b, and the rest operations were the same as those of A-371. M+1: 359.17.

A-386: the intermediate 5a in the synthesis steps of A-371 was replaced with the intermediate 7b, and the rest operations were the same as those of A-371. M+1: 373.19.

Examples of Synthesis of A-392 and A-393

A-392: the intermediate 5a in the synthesis steps of A-371 was replaced with the intermediate 6c, and the rest operations were the same as those of A-371. M+1: 373.18.

A-393: the intermediate 5a in the synthesis steps of A-371 was replaced with the intermediate 7c, and the rest operations were the same as those of A-371. M+1: 387.2.

Examples of Synthesis of A-399 and A-400

A-399: the intermediate 5a in the synthesis steps of A-371 was replaced with the intermediate 6d, and the rest operations were the same as those of A-371. M+1: 373.19.

A-400: the intermediate 5a in the synthesis steps of A-371 was replaced with the intermediate 7d, and the rest operations were the same as those of A-371. M+1: 387.21.

Example of Synthesis of A-334

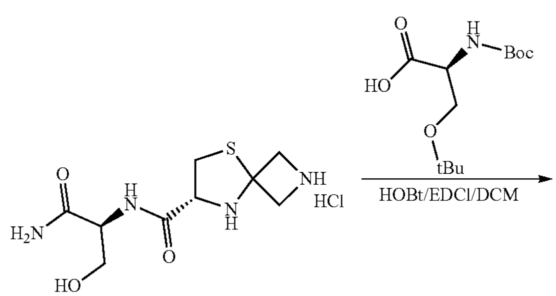

A-332

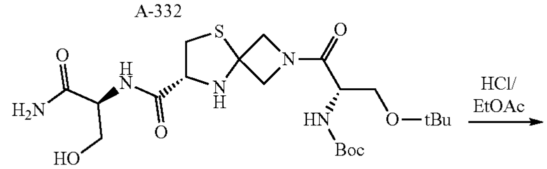

27a

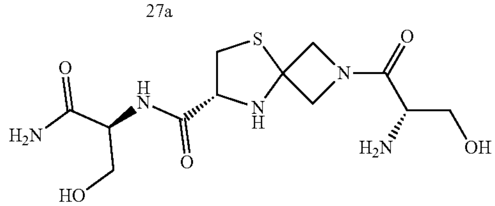

A-334

Synthesis of Intermediate 27a

The synthesis method was similar to that of the intermediate 19a, and a total of 0.56 g of a colorless oily substance was obtained with a yield of 75.4%. $^1$H-NMR (400 MHz, DMSO-$d_6$), δ ppm: 1.19 (s, 9H), 1.42 (s, 9H), 2.32-2.67 (m, 2H), 3.33-4.54 (m, 11H), 4.94 (s, 1H), 7.06 (s, 1H), 7.21 (s, 2H), 7.31 (s, 1H), 8.06 (s, 1H). M+1: 504.24.

Synthesis of A-334

The synthesis method was similar to that of A-371, and a total of 0.31 g of a white solid was obtained with a yield of 87.9%. $^1$H-NMR (400 MHz, DMSO-$d_6$), δ ppm: 2.67-2.92 (m, 2H), 3.54-4.52 (m, 11H), 5.08 (s, 2H), 7.06-7.21 (m, 3H), 8.32 (s, 1H), 8.92 (s, 2H). M+1: 348.13.

Example of Synthesis of A-335

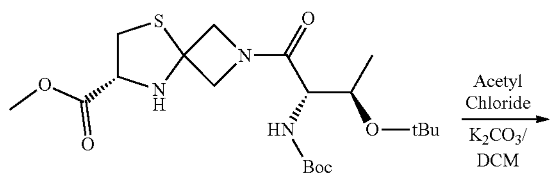

8a

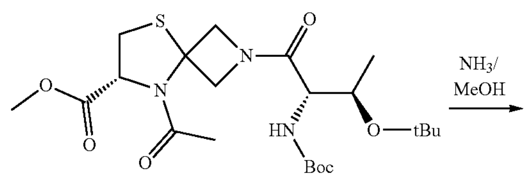

28a

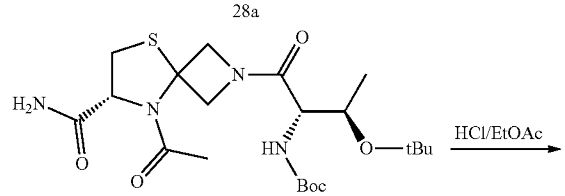

29a

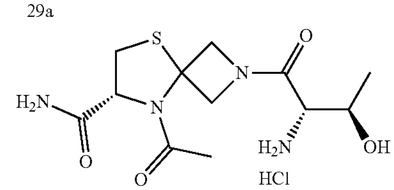

A-335

Synthesis of Intermediate 28a

Under ice bath conditions, a total of 0.7 g of the intermediate 8a was dissolved in 20 mL of DCM, 0.4 g of $K_2CO_3$ was added, 170 μL of acetyl chloride was dissolved in 5 mL of DCM to obtain a solution, and the solution was dripped to the reaction system and the raw materials were gradually returned to room temperature and reacted for 4 hours; when the completion of the raw materials reaction was monitored by TLC, the reaction was terminated; the mixture was washed with a saturated citric acid solution and then washed with a saturated sodium chloride solution, dried with anhydrous sodium sulfate, filtered, concentrated, and separated by a silica gel column to obtain a total of 0.53 g of a colorless oily substance intermediate 27a with a yield of 69%. $^1$H-NMR (400 MHz, DMSO-$d_6$), δ ppm: 1.13-1.23 (m, 12H), 1.37 (s, 9H), 2.05 (s, 3H), 3.15-3.43 (m, 2H), 3.61-3.87 (m, 5H), 4.05-4.87 (m, 5H), 7.84 (s, 1H). M+1: 488.24.

Synthesis of Intermediate 29a

The synthesis method was similar to that of the intermediate 23a, and a total of 0.46 g of an oily substance was obtained with a yield of 92.6%. $^{1}$H-NMR (400 MHz, DMSO-$d_6$), δ ppm: 1.13-1.25 (m, 12H), 1.37 (s, 9H), 2.04 (s, 3H), 3.16-3.44 (m, 2H), 3.62-3.87 (m, 2H), 4.06-4.85 (m, 5H), 7.84 (s, 1H), 8.35 (s, 2H). M+1: 473.24.

Synthesis of A-335

The synthesis method was similar to that of A-329, and a total of 0.25 g of a white solid was obtained with a yield of 87.5%. $^{1}$H-NMR (400 MHz, DMSO-$d_6$), δ ppm: 1.13-1.17 (m, 3H), 2.03 (s, 3H), 3.07-3.18 (m, 1H), 3.39-3.43 (m, 1H), 3.73-3.92 (m, 2H), 4.07-4.83 (m, 5H), 5.63 (s, 1H), 7.57 (s, 1H), 7.95 (s, 1H), 8.25 (s, 2H). M+1: 317.12.

Example of Synthesis of A-336

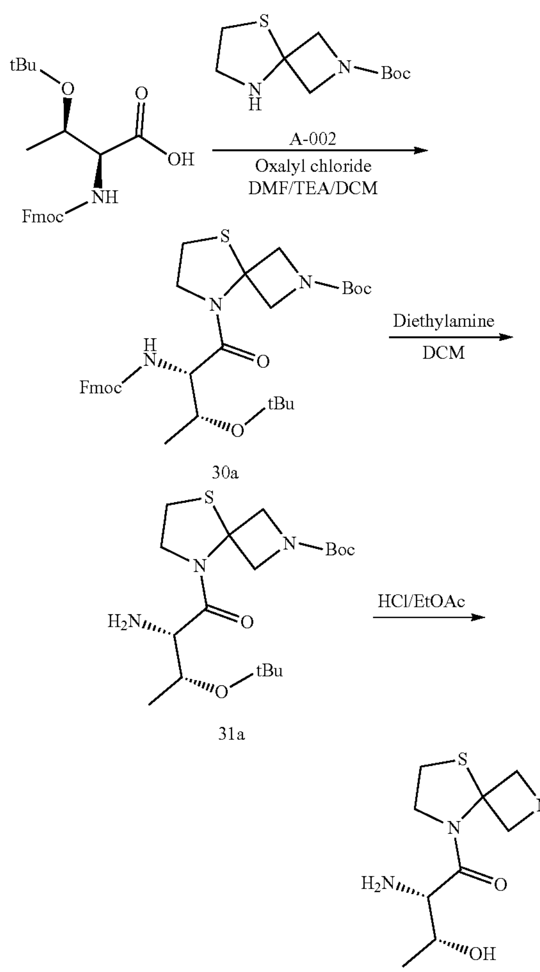

A-336

Synthesis of Intermediate 30a

The synthesis method was similar to that of the intermediate 15a, and a total of 0.89 g of a yellow powdered solid was obtained with a yield of 78.6%. $^{1}$H-NMR (400 MHz, DMSO-$d_6$), δ ppm: 1.13-1.42 (m, 21H), 2.7-3.57 (m, 4H), 4.26-4.51 (m, 9H), 7.28-7.91 (m, 9H). M+1: 610.29.

Synthesis of Intermediate 31a

The synthesis method was similar to that of the intermediate 16a, and a total of 0.45 g of a yellow solid was obtained with a yield of 80.3%. $^{1}$H-NMR (400 MHz, DMSO-$d_6$), δ ppm: 1.13-1.42 (m, 21H), 2.7-3.57 (m, 4H), 4.26-4.51 (m, 9H), 8.96 (s, 1H). M+1: 388.22.

Synthesis of A-336

The synthesis method was similar to that of A-329, and a total of 0.22 g of white powder was obtained with a yield of 70.9%. $^{1}$H-NMR (400 MHz, DMSO-$d_6$), δ ppm: 1.16 (d, 3H), 2.70 (t, 2H), 3.47-4.21 (m, 8H), 5.37 (s, 1H), 8.96 (s, 3H). M+1: 232.11.

Examples of Synthesis of A-349, A-356 and A-363

A-349: A-002 in the synthesis steps of A-336 was replaced with A-016, and the rest operations were the same as those in A-336 synthesis. M+1: 246.12.

A-356: A-002 in the synthesis steps of A-336 was replaced with A-030, and the rest operations were the same as those in A-336 synthesis. M+1: 260.14.

A-363: A-002 in the synthesis steps of A-336 was replaced with A-044, and the rest operations were the same as those in A-336 synthesis. M+1: 260.11.

Example of Synthesis of A-337

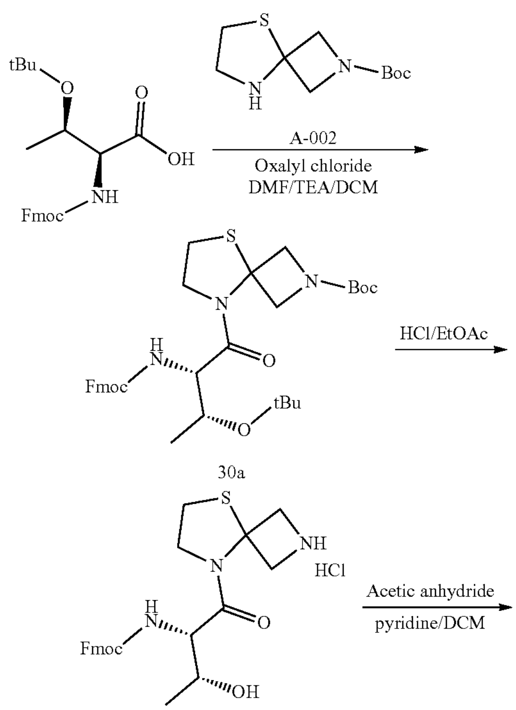

32a

-continued

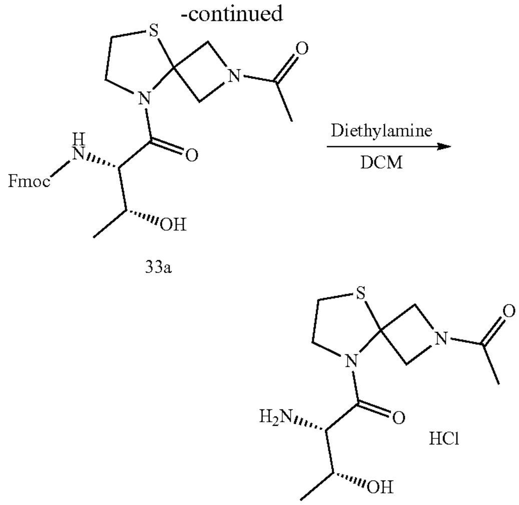

33a

A-337

Synthesis of Intermediate 32a

The synthesis method was similar to that of the intermediate 17a, and a total of 0.42 g of white powder was obtained with a yield of 102.4%. $^1$H-NMR (400 MHz, DMSO-$d_6$), δ ppm: 1.43 (s, 3H), 2.7-3.57 (m, 4H), 4.26-4.51 (m, 9H), 5.44 (s, 1H), 7.28-7.91 (m, 10H). M+1: 454.18.

Synthesis of Intermediate 33a

The synthesis method was similar to that of 18a, and a total of 0.33 g of a solid was obtained with a yield of 77.6%. $^1$H-NMR (400 MHz, DMSO-$d_6$), δ ppm: 1.43 (s, 3H), 2.10 (s, 3H), 2.7-3.57 (m, 4H), 4.26-4.51 (m, 9H), 5.44 (s, 1H), 7.28-7.91 (m, 9H). M+1: 496.19.

Synthesis of A-337

The synthesis method was similar to that of A-330, and a total of 0.14 g was obtained with a yield of 70%. $^1$H-NMR (400 MHz, DMSO-$d_6$), δ ppm: 1.43 (s, 3H), 2.10 (s, 3H), 2.7-3.57 (m, 4H), 4.26-4.51 (m, 9H), 5.44 (s, 1H), 7.8 (s, 2H). M+1: 274.12.

In the synthesis process of the intermediate 30a, the intermediate A-002 was replaced with the intermediate A-016, the intermediate A-030 and the intermediate A-044 respectively, and the other operations were the same as those of the synthesis of the intermediate 30a, and an intermediate 30b, an intermediate 30c and an intermediate 30d were prepared respectively;

similarly, in the synthesis of the intermediate 32a, the intermediate 30a was replaced with the intermediate 30b, the intermediate 30c and the intermediate 30d respectively, and the other operations were the same as those of the synthesis of the intermediate 32a, and the intermediate 32b, intermediate 32c and intermediate 32d were prepared respectively.

similarly, in the synthesis process of the intermediate 33a, the intermediate 30a was replaced with the intermediate 30b, the intermediate 30c and the intermediate 30d respectively, and the other operations were the same as those in the synthesis of the intermediate 33a, and an intermediate 33b, an intermediate 33c and an intermediate 33d were prepared respectively;

similarly, in the synthesis of the intermediate 33a, acetyl chloride was replaced with isobutyryl chloride and pivaloyl chloride respectively, and an intermediate 34a, an intermediate 34b, an intermediate 34c, and an intermediate 34d, and an intermediate 35a, an intermediate 35b, an intermediate 35c, and an intermediate 35d were prepared respectively.

30b

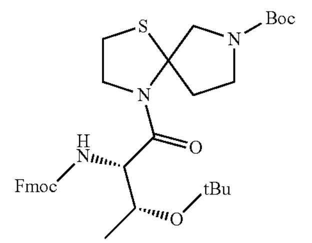

30c

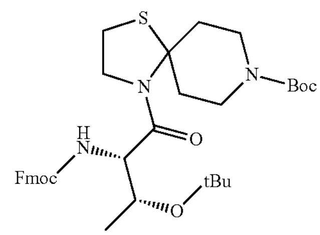

30d

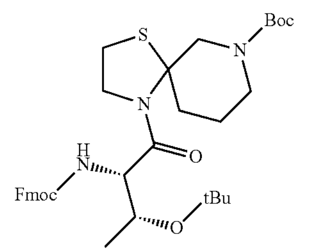

32b

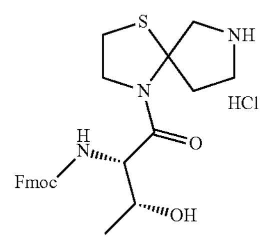

32c

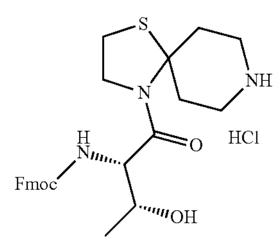

32d

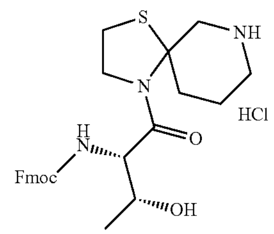

-continued
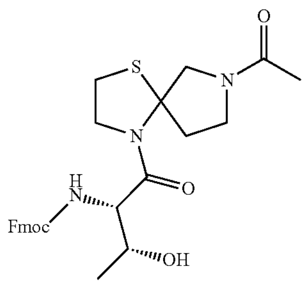
33b
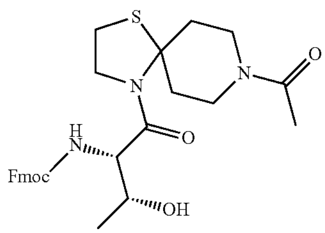
33c
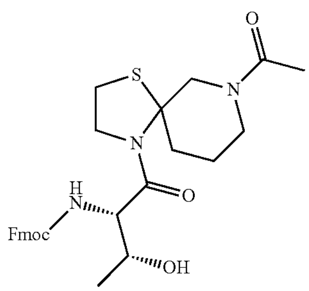
33d
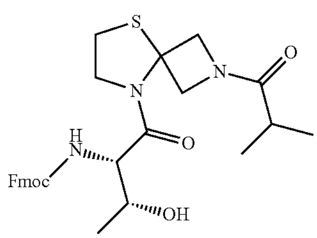
34a
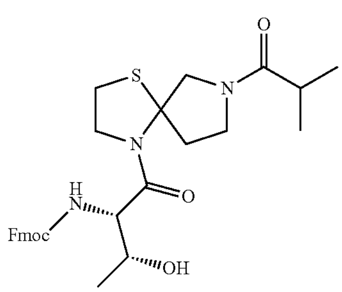
34b
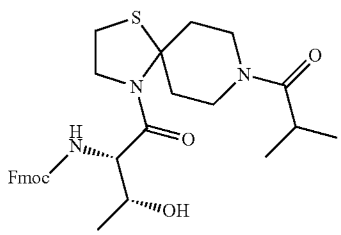
34c
-continued
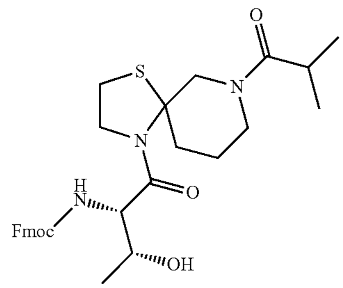
34d
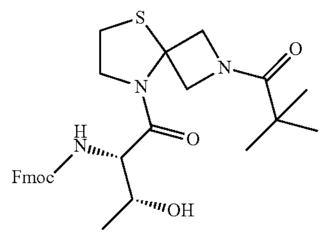
35a
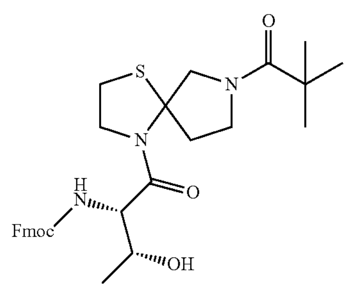
35b
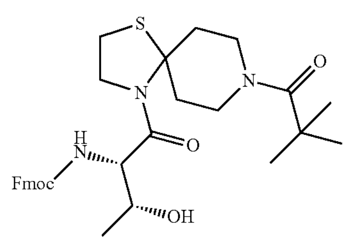
35c
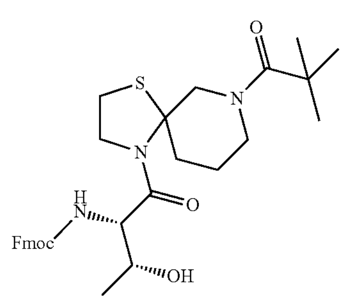
35d Examples of Synthesis of A-338 to A-343

A-338:

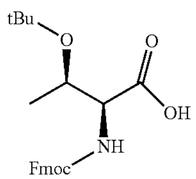

in A-337 synthesis was replaced with

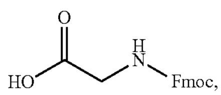

and the rest operations were the same as those in A-337 synthesis. M+1: 230.09.

A-339:

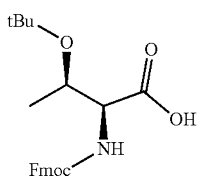

in A-337 synthesis was replaced with

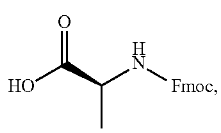

and the rest operations were the same as those in A-337 synthesis. M+1: 244.11.

A-340:

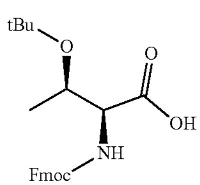

in A-337 synthesis was replaced with

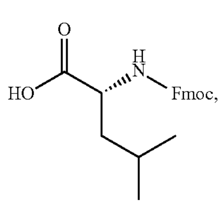

and the rest operations were the same as those in A-337 synthesis. M+1: 286.15.

A-341:

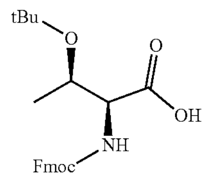

in A-337 synthesis was replaced with

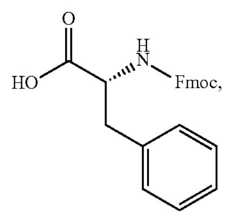

and the rest operations were the same as those in A-337 synthesis. M+1: 320.14.

A-342:

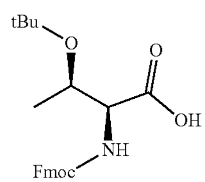

in A-337 synthesis was replaced with

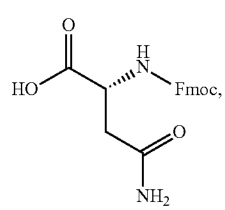

and the rest operations were the same as those of A-337. M+1: 287.11.

A-343:

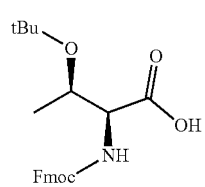

in A-337 synthesis was replaced with

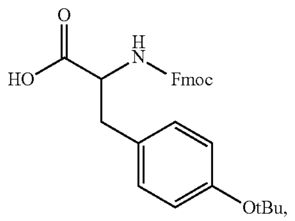

and the rest operations were the same as those in A-337 synthesis. M+1: 336.13.

Examples of Synthesis of A-344 and A-345

A-344: 33a in A-337 synthesis was replaced with 34a, and the rest operations were the same as those of A-337. M+1: 302.15.

A-345: 33a in A-337 synthesis was replaced with 35a, and the rest operations were the same as those of A-337. M+1: 316.17.

Examples of Synthesis of A-350, A-357 and A-364

A-350: 33a in A-337 synthesis was replaced with 33b, and the rest operations were the same as those of A-337. M+1: 288.13.

A-357: 33a in A-337 synthesis was replaced with 33c, and the rest operations were the same as those of A-337. M+1: 302.15.

A-364: 33a in A-337 synthesis was replaced with 33d, and the rest operations were the same as those of A-337. M+1: 302.1.

Examples of Synthesis of A-351, A-352, A-358, A-359, A-365 and A-366

A-351: 33a in A-337 synthesis was replaced with 34b, and the rest operations were the same as those of A-337. M+1: 316.17.

A-352: 33a in A-337 synthesis was replaced with 35b, and the rest operations were the same as those of A-337. M+1: 330.18.

A-358: 33a in A-337 synthesis was replaced with 34c, and the rest operations were the same as those of A-337. M+1: 330.18.

A-359: 33a in A-337 synthesis was replaced with 35c, and the rest operations were the same as those of A-337. M+1: 344.20.

A-365: 33a in the A-337 synthesis was replaced with 34d, and the rest operations were the same as those of A-337. M+1: 330.16.

A-366: 33a in A-337 synthesis was replaced with 35d, and the rest operations were the same as those of A-337. M+1: 344.15.

Example of Synthesis of A-346

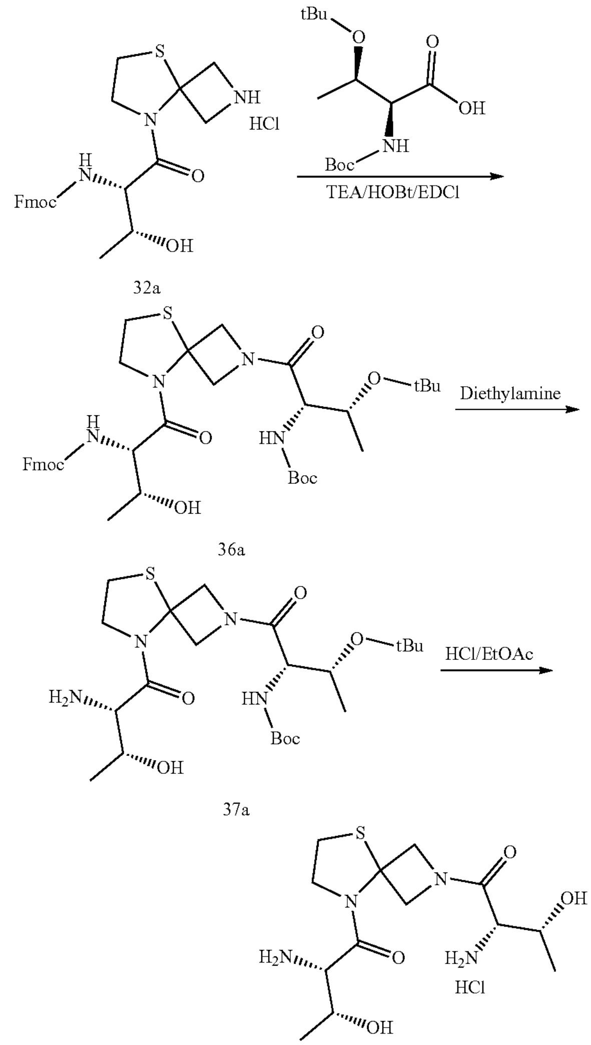

32a

36a

37a

A-346

Synthesis of Intermediate 36a

The synthesis method was similar to that of 1a, and a total of 0.22 g of yellow powder was obtained with a yield of 37%. $^1$H-NMR (400 MHz, DMSO-$d_6$), δ ppm: 1.13-1.42 (m, 24H), 2.7-3.57 (m, 4H), 4.26-4.70 (m, 11H), 5.37 (s, 1H), 7.28-7.90 (m, 10H). M+1: 711.34.

Synthesis of Intermediate 37a

The synthesis method was similar to that of the intermediate 16a, and 0.13 g of a solid was obtained with a yield of 41%. $^1$H-NMR (400 MHz, DMSO-$d_6$), δ ppm: 1.13-1.42 (m, 24H), 2.7 (t, 2H), 3.47-4.64 (m, 10H), 5.37 (s, 1H), 7.28-7.90 (m, 3H). M+1: 489.27.

Synthesis of A-346

The synthesis method was similar to that of A-331, 59 mg of a substance was obtained with a yield of 22.3%. $^1$H-NMR (400 MHz, DMSO-$d_6$), δ ppm: 1.16 (s, 6H), 2.7 (t, 2H), 3.47-4.64 (m, 10H), 5.37 (s, 2H), 8.95 (s, 4H). M+1: 333.16.

In the synthesis of an intermediate 36a, the intermediate 32a was replaced with 32b, 32c and 32d respectively, and the other operations were the same as those of the synthesis of the intermediate 36a, and an intermediate 36b-1, an intermediate 36c-1 and an intermediate 36d-1 were prepared respectively;

similarly, in the synthesis of the intermediate 36a, the raw material intermediate was respectively replaced with 32b, 32c and 32d,

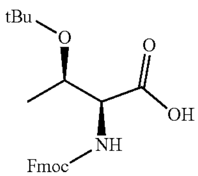

was respectively replaced with

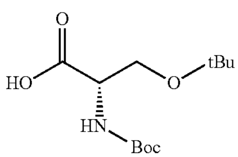

and

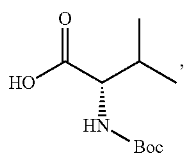

, so that 36b-2, 36b-3, 36c-2, 36c-3, 36d-2 and 36d-3 were obtained respectively.

36b-1

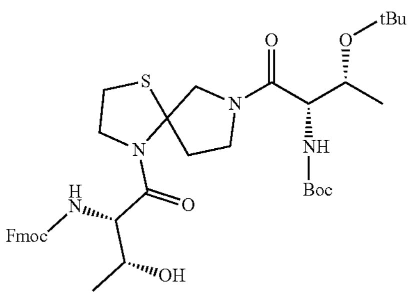

36c-1

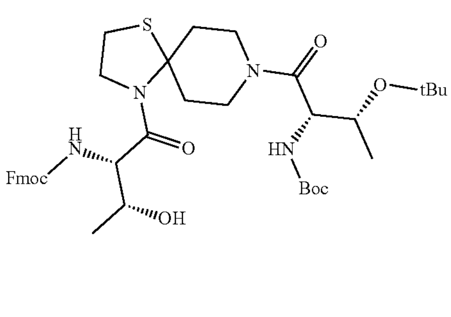

-continued 36d-1

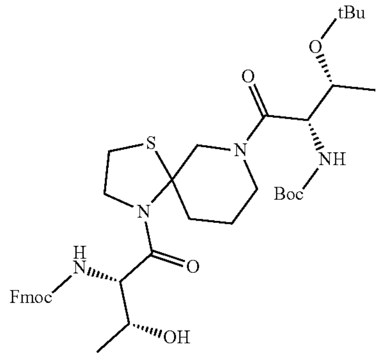

36b-2

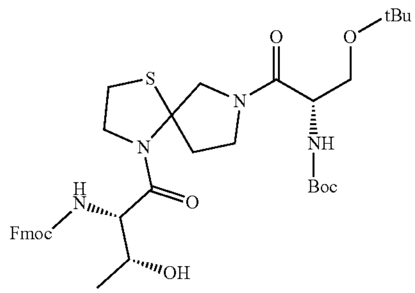

36c-2

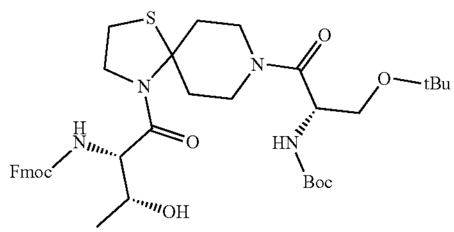

36d-2

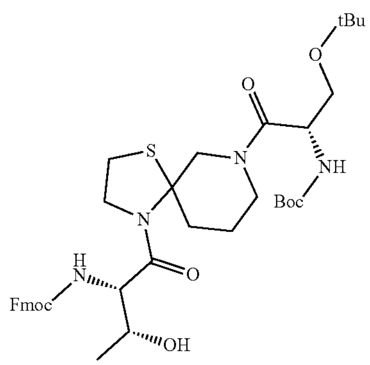

36b-3

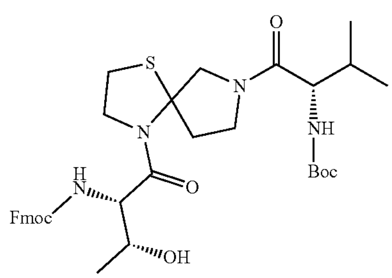

-continued 36c-3

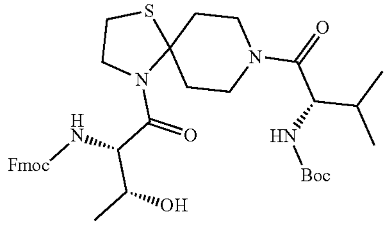

36d-3

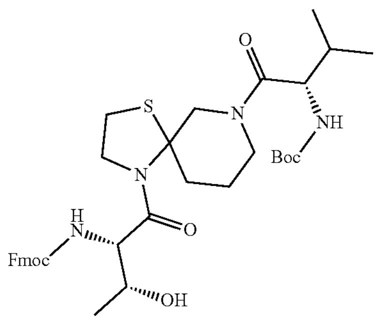

Examples of Synthesis of A-353, A-360 and A-367

A-353: 36a in A-346 synthesis was replaced with 36b-1, and the rest operations were the same as those of A-346. M+1: 347.17.

A-360: 36a in A-346 synthesis was replaced with 36c-1, and the rest operations were the same as those of A-346. M+1: 361.19.

A-367: 36a in A-346 synthesis was replaced with 36d-1, and the rest operations were the same as those of A-346. M+1: 361.2.

Examples of Synthesis of A-354, A-355, A-361, A-362, A-368 and A-369

A-354: 36a in A-346 synthesis was replaced with 36b-2, and the rest operations were the same as those of A-346. M+1: 333.16.

A-355: 36a in A-346 synthesis was replaced with 36b-3, and the rest operations were the same as those of A-346. M+1: 345.19.

A-361: 36a in A-346 synthesis was replaced with 36c-2, and the rest operations were the same as those of A-346. M+1: 347.17.

A-362: 36a in A-346 synthesis was replaced with 36c-3, and the rest operations were the same as those of A-346. M+1: 359.21.

A-368: 36a in the synthesis of A-346 was replaced with 36d-2, and the rest operations were the same as those of A-346. M+1: 347.3.

A-369: 36a in A-346 synthesis was replaced with 36d-3, and the rest operations were the same as those of A-346. M+1: 359.25.

Example of Synthesis of A-374

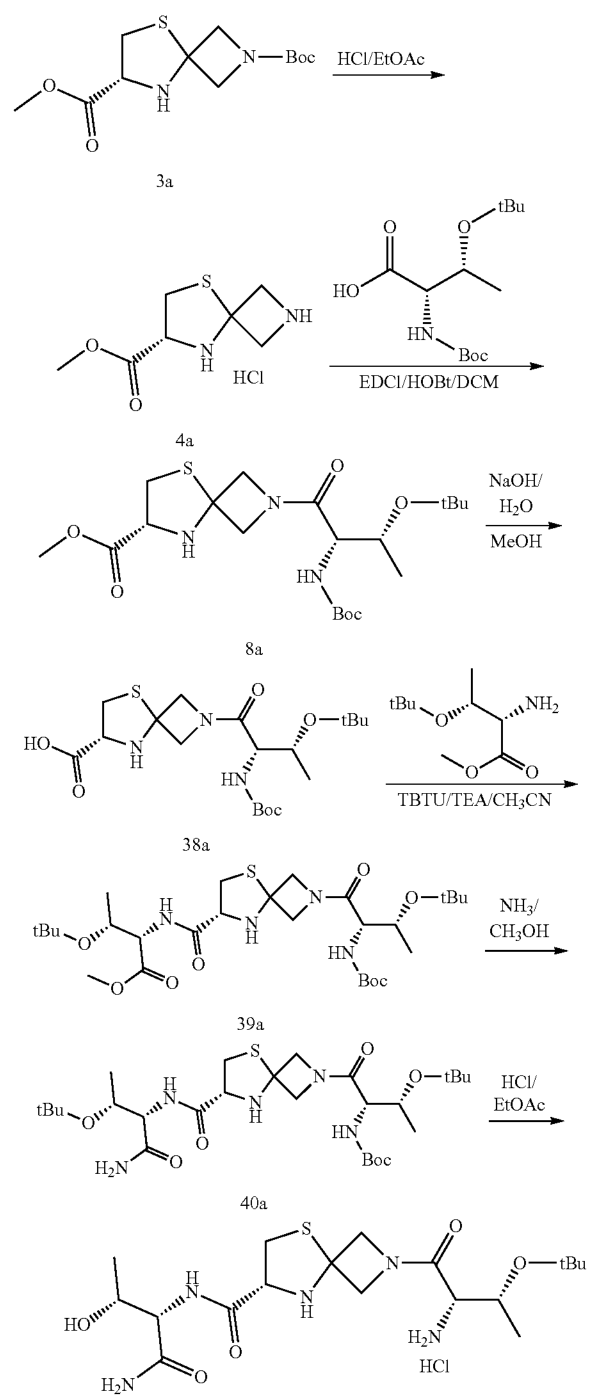

A-374

Synthesis of Intermediate 38a 8.0 g (18 mmol) of the intermediate 8a was dissolved in 30 mL of methanol, 3.6 g (90 mmol) of NaOH was taken and dissolved in 10 mL of water to obtain an aqueous NaOH solution, the aqueous NaOH solution was slowly added to the reaction system of the intermediate 8a under ice bath conditions, the color of the reaction solution became darker, and the raw materials were gradually returned to room temperature and reacted for 3 hours; when the completion of the raw materials reaction was monitored by TLC, the reaction was terminated; the mixture was concentrated under reduced pressure to remove methanol in the system, pH value of the system was adjusted to slightly acidic by dilute hydrochloric acid, a white solid was precipitated from the system, filtered, and dried by infrared lamp, and 4.3 g of the white solid was obtained with a yield of 58.1%. $^1$H-NMR (400 MHz, DMSO-$d_6$), δ ppm: 1.13 (s, 12H), 1.37 (s, 9H), 2.67-3.77 (m, 3H), 4.12-4.64 (m, 6H), 7.39-7.06 (m, 2H), 12.01 (s, 1H). M−1: 432.1.

Synthesis of Intermediate 39a

Under ice bath conditions, a total of 4.3 g (10 mmol) of the intermediate 38a was dissolved in 20 mL of acetonitrile, 2.7 mL (20 mmol) of TEA and 3.78 g (12 mmol) of TBTU were added, then 1.83 g (10.7 mmol) of O-tert-butyl-L-serine methyl ester hydrochloride was added, and the raw materials were gradually returned to room temperature and reacted for 4 hours; when the completion of the raw materials reaction was monitored by TLC, the reaction was terminated. The mixture was washed with saturated citric acid and then washed with saturated sodium chloride, dried with anhydrous sodium sulfate, filtered, concentrated, and separated by a silica gel column to obtain 4.58 g of an oily substance with a yield of 76.1%. $^1$H-NMR (400 MHz, DMSO-$d_6$), δ ppm: 1.13 (s, 24H), 1.37 (s, 9H), 2.67-3.84 (m, 3H), 3.67 (s, 3H), 4.12-4.64 (m, 8H), 7.39-8.06 (m, 3H). M+1: 603.34.

Synthesis of Intermediate 40a

A total of 4.58 g (7.60 mmol) of the intermediate 39a was dissolved in a small amount of methanol, and 10 mL of 7 mol/L $NH_3/CH_3OH$ solution was added under ice bath, and the raw materials were reacted overnight; after the completion of the raw materials reaction was monitored by TLC, a reaction solution was subjected to rotary evaporation to obtain a total of 4.04 g of an off-white solid intermediate 40a with a yield of 90.4%. $^1$H-NMR (400 MHz, DMSO-$d_6$), δ ppm: 1.13 (s, 24H), 1.37 (s, 9H), 2.67-3.84 (m, 3H), 4.12-4.64 (m, 8H), 7.39- 8.06 (m, 5H). M+1: 588.34.

Synthesis of A-374

1 g of the intermediate 40a was dissolved in 4 mL of ethyl acetate, 3 mL of 4 mol/L HCl/EtOAc was added, and the raw materials were stirred at room temperature for 3 h; when the completion of the raw materials reaction was monitored by TLC, a white solid was generated in the system, then filtered, and dried to obtain 0.51 g of a white solid with a yield of 79%. $^1$H-NMR (400 MHz, DMSO-$d_6$), δ ppm: 1.16 (m, 6H), 2.67-4.62 (m, 11H), 5.32 (s, 2H), 7.3 (s, 2H), 8.96 (s, 4H). M+1: 376.16.

In the synthesis of the intermediate 38a, the raw material

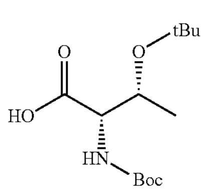

was replaced with

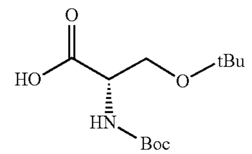

and

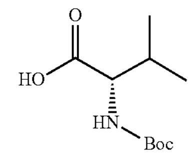

respectively, and the other operations were the same as those of the synthesis of the intermediate 38a, so that an intermediate 38b and an intermediate 38c were prepared respectively;

38b

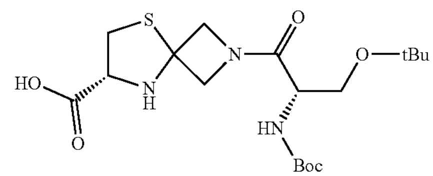

38c

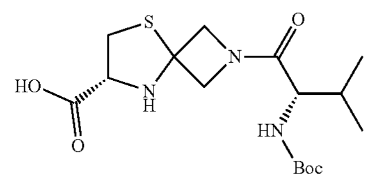

similarly, in the synthesis of the intermediate 39a, the raw material

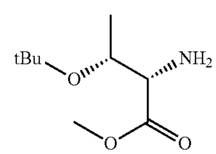

was respectively replaced with

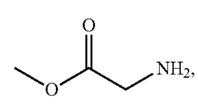

,

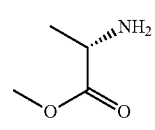

and

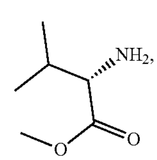

, and 39b, 39c and 39d were obtained respectively;

39b

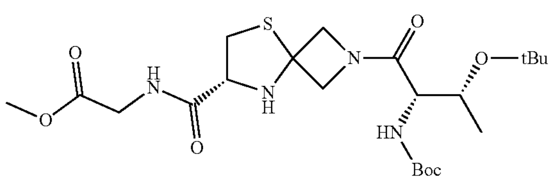

39c

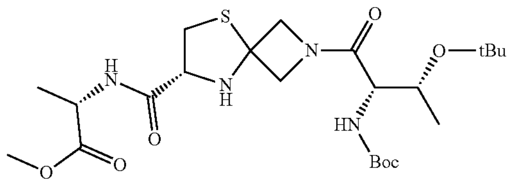

39d

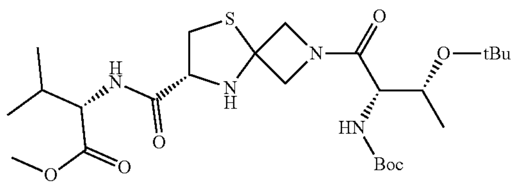

Examples of Synthesis of A-375 and A-376

A-375: the intermediate 38a in A-374 synthesis was replaced with 38b, and the rest operations were the same as those of A-374. M+1: 362.15.

A-376: the intermediate 38a in the A-374 synthesis was replaced with 38c, and the rest operations were the same as those of A-374. M+1: 374.18.

Examples of Synthesis of A-377, A-378, A-379, A-380, A-381 and A-382

A-377: the intermediate 39a in A-374 synthesis was replaced with 39b, and the rest operations were the same as those of A-374. M+1: 332.13.

A-378: 39a in the synthesis step of the intermediate 39a was replaced with 39c, and the rest operations were the same as those of A-374. M+1: 346.15.

A-379: the intermediate 39a in A-374 synthesis was replaced with 39d, and the rest operations were the same as those of A-374. M+1: 388.20.

A-380: the intermediate 38a in A-374 synthesis was replaced with 38c,

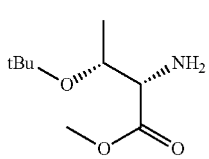

in the synthesis step of the intermediate 39a was replaced with

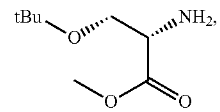, and the rest operations were the same as those of A-374. M+1: 422.18.

A-381: the intermediate 38a in A-374 synthesis was replaced with 38b,

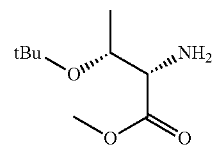

in the synthesis step of the intermediate 39a was replaced with

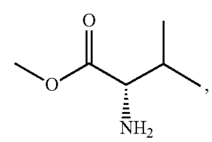, and the rest operations were the same as those of A-374. M+1: 389.16.

A-382: The intermediate 38a in A-374 synthesis was replaced with 38c,

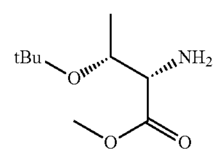

in the synthesis step of the intermediate 39a was replaced with

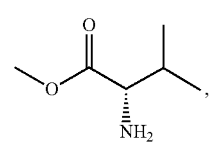, and the rest operations were the same as those of A-374. M+1: 438.18.

Examples of Synthesis of A-387, A-388 and A-389

A-387: the intermediate 3a in A-374 synthesis was replaced with 3b, and the rest operations were the same as those of A-374. M+1: 390.18.

A-388: the intermediate 3a in A-374 synthesis was replaced with 3b,

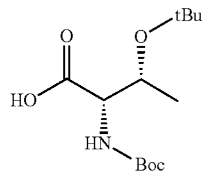 [SMILES: C[C@@H](OC(C)(C)C)[C@H](NC(=O)OC(C)(C)C)C(=O)O]

in the synthesis step of the intermediate 38a was replaced with

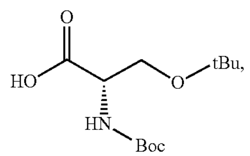 [SMILES: CC(C)(C)OC[C@H](NC(=O)OC(C)(C)C)C(=O)O]

and the rest operations were the same as those of A-374. M+1: 376.16.

A-389: the intermediate 3a in A-374 synthesis was replaced with 3b,

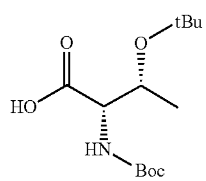 [SMILES: C[C@@H](OC(C)(C)C)[C@H](NC(=O)OC(C)(C)C)C(=O)O]

in the synthesis step of the intermediate 38a was replaced with

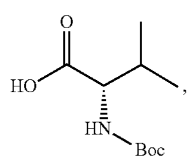

Boc, and the rest operations were the same as those of A-374. M+1: 388.2.

Examples of Synthesis of A-394, A-395 and A-396

A-394: the intermediate 3a in A-374 synthesis was replaced with 3c, and the rest operations were the same as those of A-374. M+1: 404.19.

A-395: the intermediate 3a in A-374 synthesis was replaced with 3c,

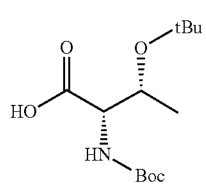 [SMILES: C[C@@H](OC(C)(C)C)[C@H](NC(=O)OC(C)(C)C)C(=O)O]

the synthesis step of the intermediate 38a was replaced with

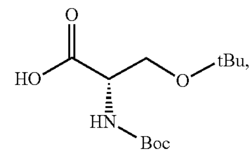 [SMILES: CC(C)(C)OC[C@H](NC(=O)OC(C)(C)C)C(=O)O]

and the rest operations were the same as those of A-374. M+1: 390.18.

A-396: the intermediate 3a in A-374 synthesis was replaced with 3c,

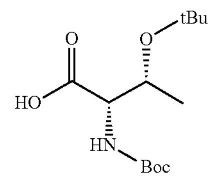 [SMILES: C[C@@H](OC(C)(C)C)[C@H](NC(=O)OC(C)(C)C)C(=O)O]

in the synthesis step of the intermediate 38a was replaced with

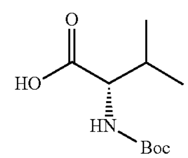

and the rest operations were the same as those of A-374. M+1: 402.21.

Examples of Synthesis of A-401, A-402 and A-403

A-401: the intermediate 3a in A-374 synthesis was replaced with 3d, and the rest operations were the same as those of A-374. M+1: 404.19.

A-402: the intermediate 3a in A-374 synthesis was replaced with 3d,

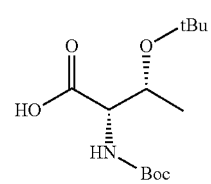 [SMILES: C[C@@H](OC(C)(C)C)[C@H](NC(=O)OC(C)(C)C)C(=O)O]

in the synthesis step of the intermediate 38a was replaced with

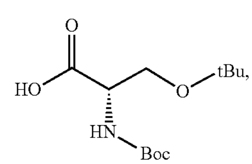 [SMILES: CC(C)(C)OC[C@H](NC(=O)OC(C)(C)C)C(=O)O]

and the rest operations were the same as those of A-374. M+1: 390.18.

A-403: the intermediate 3a in A-374 synthesis was replaced with 3d,

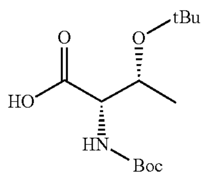 [SMILES: C[C@@H](OC(C)(C)C)[C@H](NC(=O)OC(C)(C)C)C(=O)O]

in the synthesis step of the intermediate 38a was replaced with

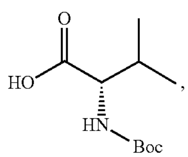

and the rest operations were the same as those of A-374. M+1: 402.21.

Example of Synthesis of A-405

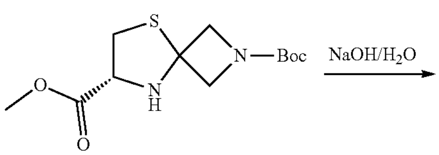

3a

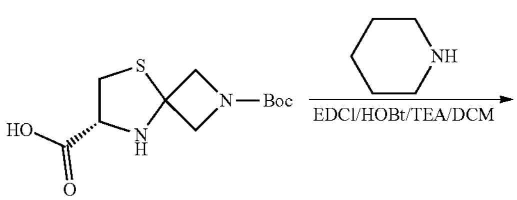

21a

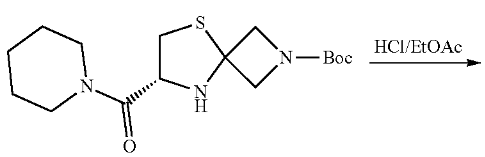

41a

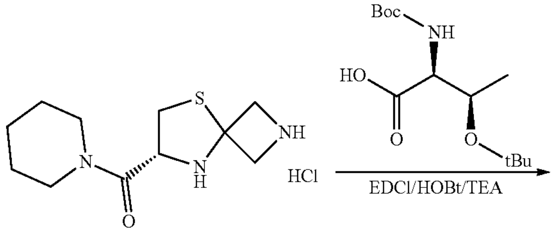

A-404

-continued

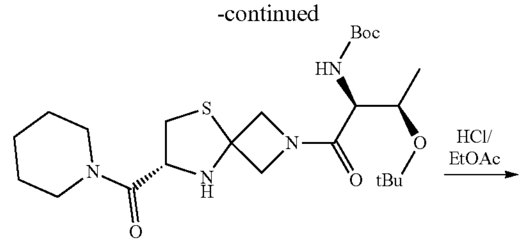

42a

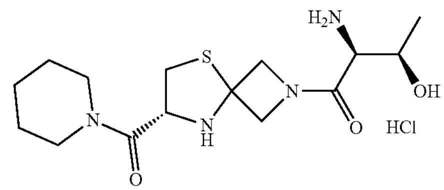

A-405

Synthesis of Intermediate 41a 21a (4.32 g, 15.7 mmol) was added to 100 ml of DCM (insoluble) under ice bath conditions, a solid in the solution was gradually dissolved after adding 2.5 eq of TEA, 1.1 eq of piperidine, 1.2 eq of HOBt and 1.2 eq of EDCI were added, and the raw materials were subjected to a thermal reaction for 10 min and then reacted overnight at room temperature; after the completion of the raw materials reaction was monitored by TLC (PE:EA=1:1), the mixture was washed sequentially with water, saturated citric acid solution and saturated saline, dried with anhydrous sodium sulfate and filtered, and a filtrate was concentrated and separated by column chromatography to obtain 4.9 g of a substance with a yield of 90%. 1H-NMR (400 MHz, DMSO-d6), δ ppm: 1.42 (s, 9H), 1.55-2.92 (m, 8H), 3.54-4.38 (m, 9H), 7.28 (s, 1H). M+1: 342.18.

Synthesis of A-404

The intermediate 41a (4.9 g, 14.4 mmol) was added to ethyl acetate for complete dissolution, then 28 ml of HCl-EtOAc solution was added, the raw materials were stirred at room temperature for 6 h; when the completion of the raw materials reaction was monitored by TLC (PE:EA=1:2), the mixture was filtered, and a filter cake was washed with ethyl acetate, and dried to obtain 4.69 g of a white solid with a yield of 93%. $^1$H-NMR (400 MHz, DMSO-d6), δ ppm: 1.55-2.92 (m, 8H), 3.54-4.38 (m, 9H), 7.28 (s, 2H). M+1: 242.13.

Synthesis of Intermediate 42a

Under ice bath conditions, A-404 (0.5 g, 1.8 mmol) was added to 20 ml of DCM, a solid was insoluble, and the solid was gradually dissolved after adding 2.5 eq of TEA, 1.1 eq of Boc-tBu-Thr, 1.2 eq of HOBt and 1.2 eq of EDCI were added, and the raw materials were subjected to a thermal reaction for 10 min and reacted at room temperature for 5 h; after the completion of the raw materials reaction was monitored by TLC (DCM:MeOH=10:1), the mixture was sequentially washed with water, saturated citric acid solution and saturated saline, then dried with anhydrous sodium sulfate and filtered, and a filtrate was concentrated and separated by column chromatography to obtain 0.85 g substance with a yield of 94%. $^1$H-NMR (400 MHz, DMSO-$d_6$), δ ppm: 1.16 (s, 21H), 1.55-2.92 (m, 8H), 3.54-4.64 (m, 11H), 7.28 (s, 2H). M+1: 499.29.

Synthesis of A-405

The intermediate 42a was added to 8 ml ethyl acetate for complete dissolution, 8 ml of HCl-EtOAc solution was added, the raw materials were stirred at room temperature for 6 h; after the completion of the raw materials reaction was monitored by TLC (PE:EA=1:2), the mixture was filtered, and a filter cake was washed with ethyl acetate, and then dried to obtain 0.45 g of a white solid with a yield of 69.6%. $^1$H-NMR (400 MHz, DMSO-$d_6$), δ ppm: 1.16 (s, 3H), 1.55-2.92 (m, 8H), 3.54-4.38 (m, 11H), 5.37 (s, 1H), 7.28 (s, 1H), 8.93 (s, 2H). M+1: 343.18.

Examples of Synthesis of A-408, A-412 and A-416

A-408:

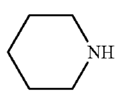

in A-404 synthesis was replaced with

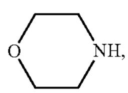

and the rest operations were the same as those in A-404 synthesis. M+1: 244.11.

A-412:

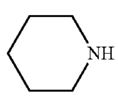

in A-404 synthesis was replaced with

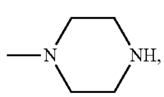

and the rest operations were the same as those in A-404 synthesis. M+1: 257.14.

A-416:

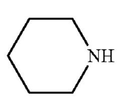

in A-404 synthesis was replaced with

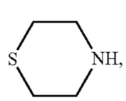

and the rest operations were the same as those in A-404 synthesis. M+1: 260.08.

Examples of Synthesis of A-406 and A-407

A-406:

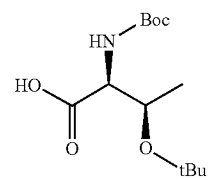 [SMILES: C[C@@H](OC(C)(C)C)[C@H](NC(=O)OC(C)(C)C)C(=O)O]

in A-405 synthesis was replaced with

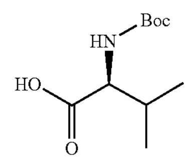

and the rest operations were the same as those in A-405 synthesis. M+1: 341.20.

A-407:

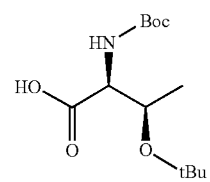 [SMILES: C[C@@H](OC(C)(C)C)[C@H](NC(=O)OC(C)(C)C)C(=O)O]

in A-405 synthesis was replaced with

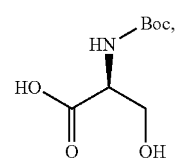

and the rest operations were the same as those in A-405 synthesis. M+1: 329.16.

Examples of Synthesis of A-409, A-410 and A-411

A-409: A-404 in A-405 synthesis was replaced with A-408, and the rest operations were the same as those in A-405 synthesis. M+1: 345.16.

A-410: A-404 in A-405 synthesis was replaced with A-408,

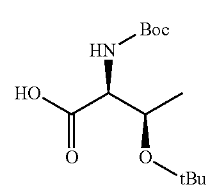 [SMILES: C[C@@H](OC(C)(C)C)[C@H](NC(=O)OC(C)(C)C)C(=O)O]

was replaced with

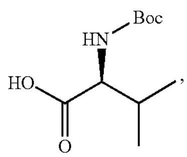

and the rest operations were the same as those of A-405. M+1: 343.18.

A-411: A-404 in A-405 synthesis was replaced with A-408,

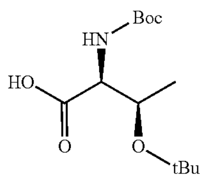

was replaced with

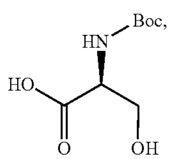

and the rest operations were the same as those of A-405. M+1: 331.14.

Examples of Synthesis of A-413, A-414 and A-415

A-413: A-404 in A-405 synthesis was replaced with A-412, and the rest operations were the same as those in A-405 synthesis. M+1: 358.19.

A-414: A-404 in A-405 synthesis was replaced with A-412,

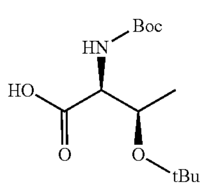

was replaced with

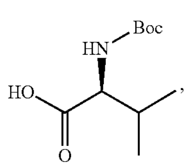

and the rest operations were the same as those in A-405 synthesis. M+1: 356.21.

A-415: A-404 in A-405 synthesis was replaced with A-412,

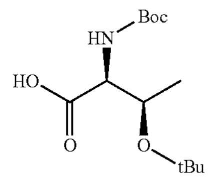 [SMILES: C[C@@H](OC(C)(C)C)[C@H](NC(=O)OC(C)(C)C)C(=O)O]

was replaced with

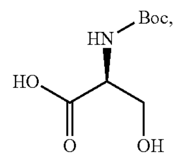

and the rest operations were the same as those of A-405. M+1: 344.17.

Examples of Synthesis of A-417, A-418 and A-419

A-417: A-404 in A-405 synthesis was replaced with A-416, and the rest operations were the same as those in A-405 synthesis. M+1: 361.13.

A-418: A-404 in A-405 synthesis was replaced with A-416,

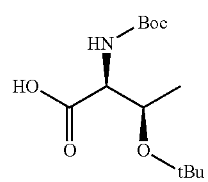 [SMILES: C[C@@H](OC(C)(C)C)[C@H](NC(=O)OC(C)(C)C)C(=O)O]

was replaced with

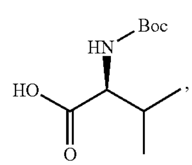

and the rest operations were the same as those of A-405. M+1: 359.15.

A-419: A-404 in A-405 synthesis was replaced with A-416,

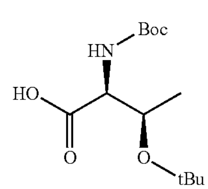 [SMILES: C[C@@H](OC(C)(C)C)[C@H](NC(=O)OC(C)(C)C)C(=O)O]

was replaced with

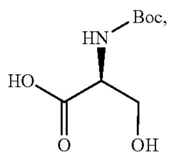

and the rest operations were the same as those of A-405. M+1: 347.12.

Examples of Synthesis of A-420, A-436 and A-452

A-420: the intermediate 3a in A-404 synthesis was replaced with 3b, and the rest operations were the same as those of A-404. M+1: 256.14.

A-436: the intermediate 3a in A-404 synthesis was replaced with 3c, and the rest operations were the same as those of A-404. M+1: 270.16.

A-452: the intermediate 3a in A-404 synthesis was replaced with 3d, and the rest operations were the same as those of A-404. M+1: 270.16.

Examples of Synthesis of A-421, A-422 and A-423

A-421: A-404 in A-405 synthesis was replaced with A-420, and the rest operations were the same as those in A-405 synthesis. M+1: 357.19.

A-422: A-404 in A-405 synthesis was replaced with A-420,

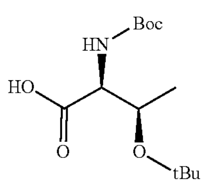 [SMILES: C[C@@H](OC(C)(C)C)[C@H](NC(=O)OC(C)(C)C)C(=O)O]

was replaced with

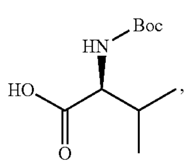

and the rest operations were the same as those in A-405 synthesis. M+1: 355.21.

A-423: A-404 in A-405 synthesis was replaced with A-420,

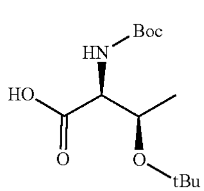 [SMILES: C[C@@H](OC(C)(C)C)[C@H](NC(=O)OC(C)(C)C)C(=O)O]

was replaced with

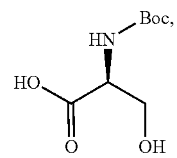

and the rest operations were the same as those in A-405 synthesis. M+1: 343.18.

Examples of Synthesis of A-424, A-428 and A-432

A-424: 3a in A-404 synthesis was replaced with 3b,

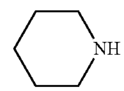

was replaced with

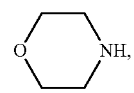

and the rest operations were the same as those of A-404. M+1: 258.12.

A-428: 3a in A-404 synthesis was replaced with 3b,

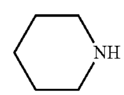

was replaced with

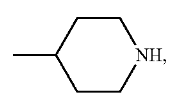

and the rest operations were the same as those of A-404. M+1: 271.15.

A-432: 3a in A-404 synthesis was replaced with 3b,

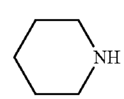

was replaced with

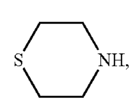

and the rest operations were the same as those of A-404. M+1: 274.10.

Examples of Synthesis of A-425, A-426 and A-427

A-425: A-404 in A-405 synthesis was replaced with A-424, and the rest operations were the same as those in A-405 synthesis. M+1: 359.17.

A-426: A-404 in A-405 synthesis was replaced with A-424,

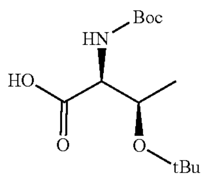 [SMILES: C[C@@H](OC(C)(C)C)[C@H](NC(=O)OC(C)(C)C)C(=O)O]

was replaced with

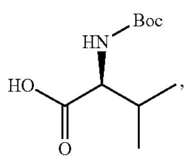, and the rest operations were the same as those of A-405. M+1: 357.19.

A-427: A-404 in A-405 synthesis was replaced with A-424,

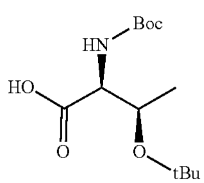 [SMILES: C[C@@H](OC(C)(C)C)[C@H](NC(=O)OC(C)(C)C)C(=O)O]

was replaced with

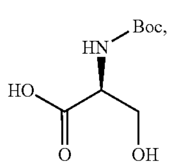, and the rest operations were the same as those in A-405 synthesis. M+1: 345.16.

Examples of Synthesis of A-429, A-430 and A-431

A-429: A-404 in A-405 synthesis was replaced with A-428, and the rest operations were the same as those in A-405 synthesis. M+1: 372.20.

A-430: A-404 in A-405 synthesis was replaced with A-428,

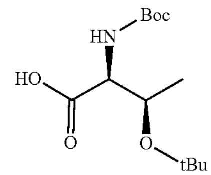 [SMILES: C[C@@H](OC(C)(C)C)[C@H](NC(=O)OC(C)(C)C)C(=O)O]

was replaced with

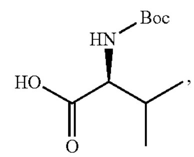, and the rest operations were the same as those of A-405. M+1: 370.22.

A-431: A-404 in A-405 synthesis was replaced with A-428,

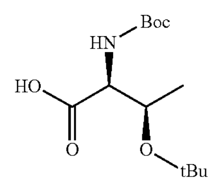 [SMILES: C[C@@H](OC(C)(C)C)[C@H](NC(=O)OC(C)(C)C)C(=O)O]

was replaced with

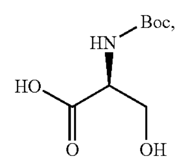 [SMILES: CC(C)(C)OC(=O)N[C@@H](CO)C(=O)O], and the rest operations were the same as those in A-405 synthesis. M+1: 358.19.

Examples of Synthesis of A-433, A-434 and A-435

A-433: A-404 in A-405 synthesis was replaced with A-432, and the rest operations were the same as those in A-405 synthesis. M+1: 375.15.

A-434: A-404 in A-405 synthesis was replaced with A-432,

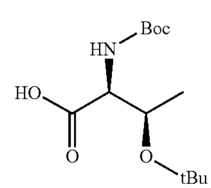 [SMILES: C[C@@H](OC(C)(C)C)[C@H](NC(=O)OC(C)(C)C)C(=O)O]

was replaced with

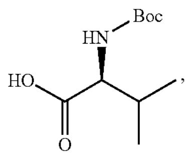

and the rest operations were the same as those in A-405 synthesis. M+1: 373.17.

A-435: A-404 in A-405 synthesis was replaced with A-432,

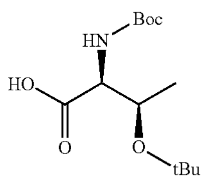 [SMILES: C[C@@H](OC(C)(C)C)[C@H](NC(=O)OC(C)(C)C)C(=O)O]

was replaced with

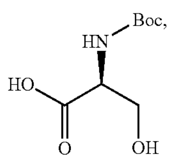

and the rest operations were the same as those in A-405 synthesis. M+1: 361.13.

Examples of Synthesis of A-437, A-438 and A-439

A-437: A-404 in A-405 synthesis was replaced with A-436, and the rest operations were the same as those in A-405 synthesis. M+1: 371.21.

A-438: A-404 in A-405 synthesis was replaced with A-436,

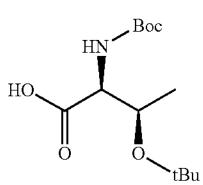 [SMILES: C[C@@H](OC(C)(C)C)[C@H](NC(=O)OC(C)(C)C)C(=O)O]

replaced with

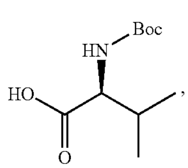

and the rest operations were the same as those in A-405 synthesis. M+1: 369.23.

A-439: A-404 in A-405 synthesis was replaced with A-436,

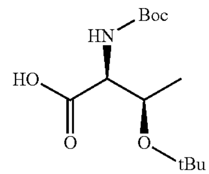 [SMILES: C[C@@H](OC(C)(C)C)[C@H](NC(=O)OC(C)(C)C)C(=O)O]

was replaced with

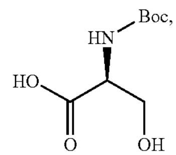 [SMILES: CC(C)(C)OC(=O)N[C@@H](CO)C(=O)O]

and the rest operations were the same as those in A-405 synthesis. M+1: 357.19.

Examples of Synthesis of A-440, A-444 and A-448

A-440: 3a in A-404 synthesis was replaced with 3c,

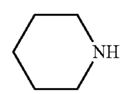

was replaced with

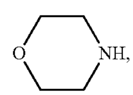

and the rest operations were the same as those of A-404, M+1: 272.14.

A-444: 3a in A-404 synthesis was replaced with 3c,

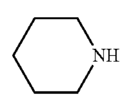

was replaced with

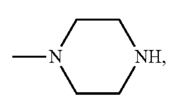

and the rest operations were the same as those of A-404. M+1: 285.17.

A-448: 3a in A-404 synthesis was replaced with 3c,

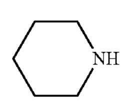

was replaced with

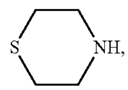

and the rest operations were the same as those of A-404. M+1: 288.12.

Examples of Synthesis of A-441, A-442 and A-443

A-441: A-404 in A-405 synthesis was replaced with A-440, and the rest operations were the same as those in A-405 synthesis. M+1: 373.19.

A-442: A-404 in A-405 synthesis was replaced with A-440,

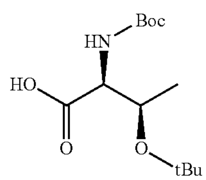 [SMILES: C[C@@H](OC(C)(C)C)[C@H](NC(=O)OC(C)(C)C)C(=O)O]

was replaced with

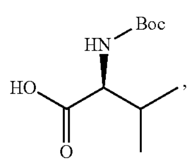

and the rest operations were the same as those in A-405 synthesis. M+1: 371.21.

A-443: A-404 in A-405 synthesis was replaced with A-440,

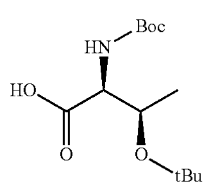

was replaced with

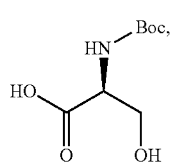

and the rest operations were the same as those in A-405 synthesis. M+1: 359.17.

Examples of Synthesis of A-445, A-446 and A-447

A-445: A-404 in A-405 synthesis was replaced with A-444, and the rest operations were the same as those in A-405 synthesis. M+1: 386.22.

A-446: A-404 in A-405 synthesis was replaced with A-444,

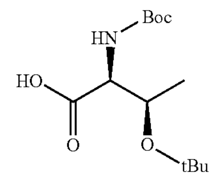 [SMILES: C[C@@H](OC(C)(C)C)[C@H](NC(=O)OC(C)(C)C)C(=O)O]

was replaced with

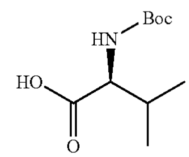

and the rest operations were the same as those in A-405 synthesis. M+1: 384.24.

A-447: A-404 in A-405 synthesis was replaced with A-444,

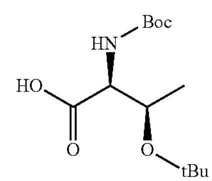 [SMILES: C[C@@H](OC(C)(C)C)[C@H](NC(=O)OC(C)(C)C)C(=O)O]

was replaced with

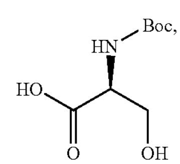

and the rest operations were the same as those in A-405 synthesis. M+1: 372.20.

Examples of Synthesis of A-449, A-450 and A-451

A-449: A-404 in A-405 synthesis was replaced with A-448, and the rest operations were the same as those in A-405 synthesis. M+1: 389.16.

A-450: A-404 in A-405 synthesis was replaced with A-448,

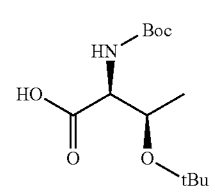 [SMILES: C[C@@H](OC(C)(C)C)[C@H](NC(=O)OC(C)(C)C)C(=O)O]

was replaced with

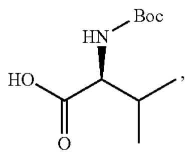

and the rest operations were the same as those in A-405 synthesis. M+1: 387.18.

A-451: A-404 in A-405 synthesis was replaced with A-448,

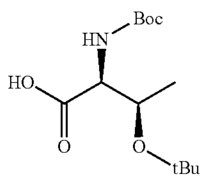 [SMILES: C[C@@H](OC(C)(C)C)[C@H](NC(=O)OC(C)(C)C)C(=O)O]

was replaced with

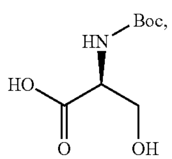

and the rest operations were the same as those in A-405 synthesis. M+1: 375.15.

Examples of Synthesis of A-456, A-460 and A-464

A-456: 3a in A-404 synthesis was replaced with 3d,

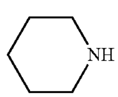

was replaced with

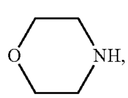

and the rest operations were the same as those of A-404. M+1: 272.14.

A-460: 3a in A-404 synthesis was replaced with 3d,

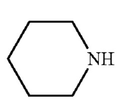

was replaced with

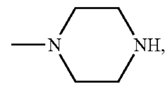

and the rest operations were the same as those of A-404. M+1: 285.17.

A-464: 3a in A-404 synthesis was replaced with 3d,

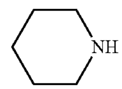

was replaced with

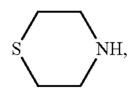

and the rest operations were the same as those of A-404. M+1: 288.12.

Examples of Synthesis of A-453, A-454 and A-455

A-453: A-404 in A-405 synthesis was replaced with A-452, and the rest operations were the same as those in A-405 synthesis. M+1: 371.21.

A-454: A-404 in A-405 synthesis was replaced with A-452,

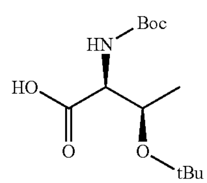 [SMILES: C[C@@H](OC(C)(C)C)[C@H](NC(=O)OC(C)(C)C)C(=O)O]

was replaced with

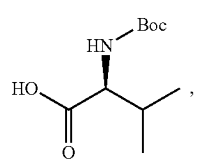

and the rest operations were the same as those in A-405 synthesis. M+1: 369.23.

A-455: A-404 in A-405 synthesis was replaced with A-452,

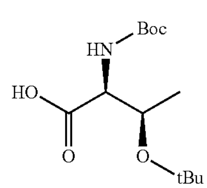 [SMILES: C[C@@H](OC(C)(C)C)[C@H](NC(=O)OC(C)(C)C)C(=O)O]

was replaced with

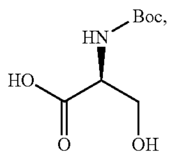

and the rest operations were the same as those in A-405 synthesis. M+1: 357.19.

Examples of Synthesis of A-457, A-458 and A-459

A-457: A-404 in A-405 synthesis was replaced with A-456, and the rest operations were the same as those in A-405 synthesis. M+1: 373.19.

A-458: A-404 in A-405 synthesis was replaced with A-456,

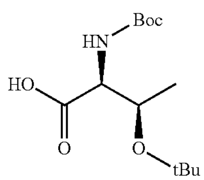

was replaced with

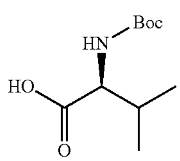
, and the rest operations were the same as those in A-405 synthesis. M+1: 371.21.

A-459: A-404 in A-405 synthesis was replaced with A-456,

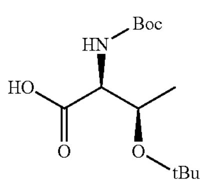 [SMILES: C[C@@H](OC(C)(C)C)[C@H](NC(=O)OC(C)(C)C)C(=O)O]

replaced with

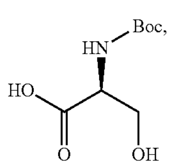

and the rest operations were the same as those in A-405 synthesis. M+1: 359.17.

Examples of Synthesis of A-461, A-462 and A-463

A-461: A-404 in A-405 synthesis was replaced with A-460, and the rest operations were the same as those in A-405 synthesis. M+1: 386.22.

A-462: A-404 in A-405 synthesis was replaced with A-460,

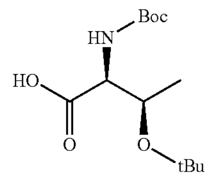 [SMILES: C[C@@H](OC(C)(C)C)[C@H](NC(=O)OC(C)(C)C)C(=O)O]

was replaced with

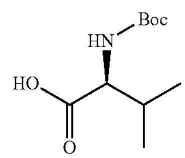
, and the rest operations were the same as those in A-405 synthesis. M+1: 384.24.

A-463: A-404 in A-405 synthesis was replaced with A-460,

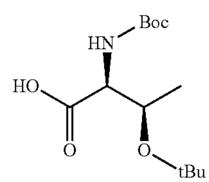 [SMILES: C[C@@H](OC(C)(C)C)[C@H](NC(=O)OC(C)(C)C)C(=O)O]

was replaced with

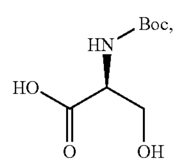

and the rest operations were the same as those in A-405 synthesis. M+1: 372.20.

Examples of Synthesis of A-465, A-466 and A-467

A-465: A-404 in A-405 synthesis was replaced with A-464, and the rest operations were the same as those in A-405 synthesis. M+1: 389.16.

A-466: A-404 in A-405 synthesis was replaced with A-464,

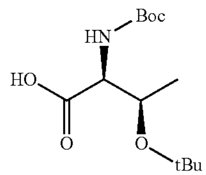 [SMILES: C[C@@H](OC(C)(C)C)[C@H](NC(=O)OC(C)(C)C)C(=O)O]

was replaced with

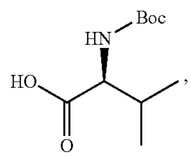

and the rest operations were the same as those in A-405 synthesis. M+1: 387.18.

A-467: A-404 in A-405 synthesis was replaced with A-464,

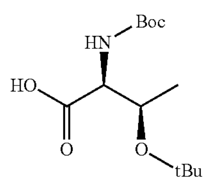 [SMILES: C[C@@H](OC(C)(C)C)[C@H](NC(=O)OC(C)(C)C)C(=O)O]

replaced with

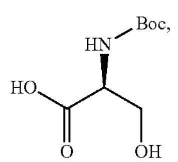

and the rest operations were the same as those in A-405 synthesis. M+1: 375.15.

Example of Synthesis of 468

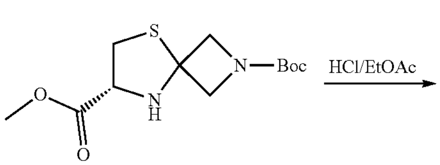

3a

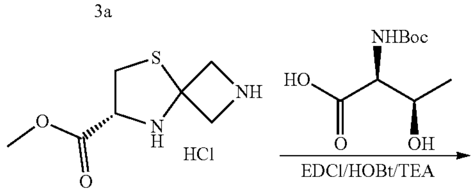

4a

-continued

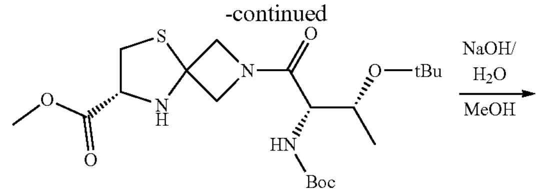

8a

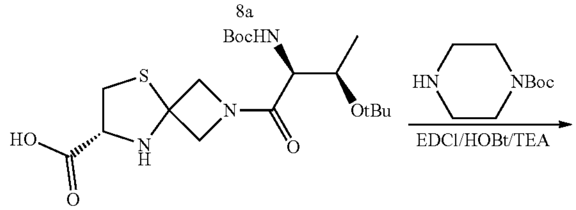

38a

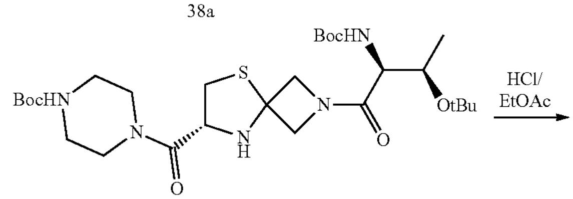

43a

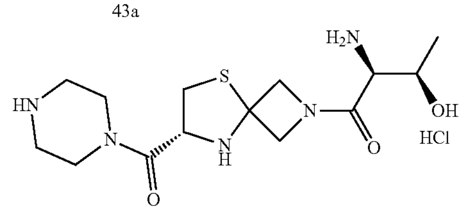

A-468

Synthesis of Intermediate 43a

Under ice bath conditions, the intermediate 38a (1.1 g, 2.55 mmol) was added into 50 ml of DCM, a solid was insoluble, and the solid was gradually dissolved after 2.5eq of TEA was added, then 1.1eq of N-Boc piperazine, 1.2eq of HOBt and 1.2eq of EDCI were added, and the raw materials were subjected to thermal reaction for 10 min and then reacted at room temperature overnight; after the completion of the raw materials reaction was monitored by TLC (DCM: MeOH=5:1), a mixture was washed sequentially with water, saturated citric acid solution and saturated saline, dried with anhydrous sodium sulfate, and filtered, and then a filtrate was concentrated and separated by column chromatography to obtain 0.87 g of substance with a yield of 57.2%. $^1$H-NMR (400 MHz, DMSO-$d_6$), δ ppm: 1.16 (s, 12H), 1.42 (s, 18H), 2.67-4.64 (m, 17H), 7.38 (s, 2H). M+1: 600.34.

Synthesis of A-468

The intermediate 43a (0.87 g, 1.45 mmol) was added to 10 ml of ethyl acetate, 10 ml of HCl-EtOAc solution was added, and the raw materials were stirred at room temperature for 6 h; when the completion of the raw materials reaction was monitored by TLC (PE:EA=1:2), a mixture was filtered, and a filter cake was washed with ethyl acetate, and dried to obtain 0.74 mg of a white solid with a yield of 95%. $^1$H-NMR (400 MHz, DMSO-$d_6$), δ ppm: 1.16 (s, 3H), 2.81-4.38 (m, 17H), 5.37 (s, 1H), 7.28 (s, 4H). M+1: 344.17.

Examples of Synthesis of A-469 and A-470

A-469:

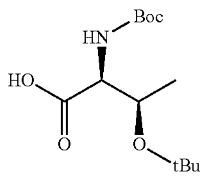 [SMILES: C[C@@H](OC(C)(C)C)[C@H](NC(=O)OC(C)(C)C)C(=O)O]

in A-468 synthesis was replaced with

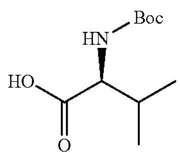, and the rest operations were the same as those of A-468. M+1: 342.19.

A-470:

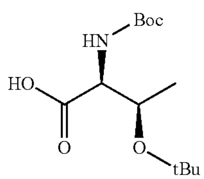 [SMILES: C[C@@H](OC(C)(C)C)[C@H](NC(=O)OC(C)(C)C)C(=O)O]

in A-468 synthesis was replaced with

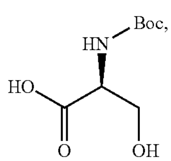

and the rest operations were the same as those in A-468 synthesis. M+1: 330.16.

Examples of Synthesis of A-471, A-472 and A-473

A-471: the intermediate 3a in A-468 synthesis was replaced with 3b, and the rest operations were the same as those of A-468. M+1: 358.19.

A-472: the intermediate 3a in A-468 synthesis was replaced with 3b,

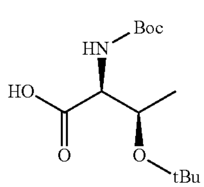 [SMILES: C[C@@H](OC(C)(C)C)[C@H](NC(=O)OC(C)(C)C)C(=O)O]

was replaced with

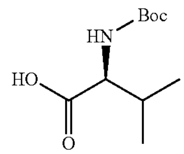, and the rest operations were the same as those of A-468. M+1: 356.21.

A-473: the intermediate 3a in A-468 synthesis was replaced with 3b,

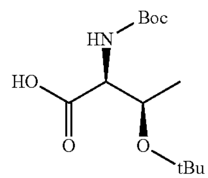 [SMILES: C[C@@H](OC(C)(C)C)[C@H](NC(=O)OC(C)(C)C)C(=O)O]

was replaced with

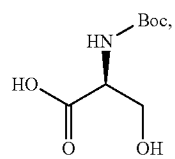

and the rest operations were the same as those of A-468. M+1: 344.17.

Examples of Synthesis of A-474, A-475 and A-476

A-474: the intermediate 3a in A-468 synthesis was replaced with 3c, and the rest operations were the same as those of A-468. M+1: 372.20.

A-475: the intermediate 3a in A-468 synthesis was replaced with 3c,

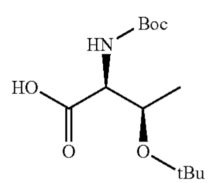 [SMILES: C[C@@H](OC(C)(C)C)[C@H](NC(=O)OC(C)(C)C)C(=O)O]

was replaced with

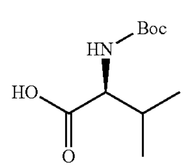, and the rest operations were the same as those of A-468. M+1: 370.22.

A-476: the intermediate 3a in A-468 synthesis was replaced with 3c,

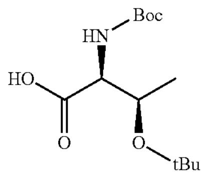 [SMILES: C[C@@H](OC(C)(C)C)[C@H](NC(=O)OC(C)(C)C)C(=O)O]

was replaced with

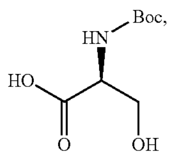

and the rest operations were the same as those of A-468. M+1: 358.19.

Examples of Synthesis of A-477, A-478 and A-479

A-477: the intermediate 3a in A-468 synthesis was replaced with 3c, and the rest operations were the same as those of A-468. M+1: 372.1.

A-478: the intermediate 3a in A-468 synthesis was replaced with 3c,

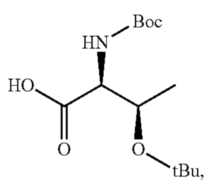 [SMILES: C[C@@H](OC(C)(C)C)[C@H](NC(=O)OC(C)(C)C)C(=O)O]

was replaced with

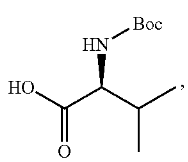

and the rest operations were the same as those of A-468. M+1: 370.2.

A-479: the intermediate 3a in A-468 synthesis was replaced with 3c,

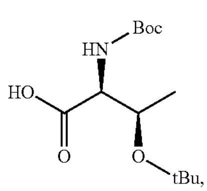 [SMILES: C[C@@H](OC(C)(C)C)[C@H](NC(=O)OC(C)(C)C)C(=O)O]

was replaced with

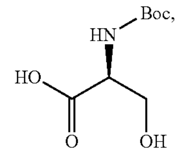

and the rest operations were the same as those of A-468. M+1: 358.19.

Test Example 1: In-Vitro Receptor Binding Assay

1. Experimental Purpose

The affinity of the tested compounds on NMDA receptor was researched by receptor ligand binding assays.

2. Experimental Method

Ten SD male rats of SPF grade were ordered and acclimated for 7 days for future use.

(1) Preparation of Crude Synaptosomes in Prefrontal Cortex and Hippocampus

After the rats were decapitated, the prefrontal cortex and hippocampus were rapidly separated on ice and weighed, 10 volumes of 50 mM Tris-HCl buffer (50 mM Tris-HCl, 5 mM $MgCl_2 \cdot 6H_2O$, 1 mM EDTA, 0.5% (W/V) BSA, 1 mM PMSF, 0.32 M sucrose, pH 7.4) was added, and the mixture was homogenized for five times at 1500 revolutions/min with 30 s each time. A homogenate was centrifuged for 10 min at 1000×g, and a supernatant was taken and centrifuged for 10 min at 40,000×g, the precipitates were collected, re-suspended with volumes of Tris-HCl buffer, incubated at 37° C. for 10 min, and centrifuged for 10 min at 40,000×g, finally the precipitates were re-suspended with the above buffer, aliquoted and stored at −80° C. for later use.

(2) Detection of Inhibitory Function of Tested Medicines on Binding of Crude Synaptosomes in Rats to $[^3H]$-MK-801

50 μg of rat crude synaptosomal proteins was added to all tubes respectively. A volume of 50 μl of MK-801 (dizocilpine) was added to a non-specific binding tube to achieve a final concentration of 100 μM, and the materials were reacted for 15 min in advance. 20 μL of control drug at corresponding concentration was added to the test tube for reaction for 15 min. A volume of 30 μl of labeled ligand $[^3H]$-MK-801 was successively added to all tubes to achieve a final concentration of 10 nM. All reaction tubes were supplemented to a volume of 200 μl with 50 mM Tris-HCl buffer (50 mM Tris-HCl, 5 mM $MgCl_2 \cdot 6H_2O$, 1 mM EDTA, 0.5% (WN) BSA, 0.1% $NaN_3$, pH 7.4). A reaction was carried out at 37° C. for 10 min. A type-49 glass fiber filter membrane was prepared and a sample was applied at the same time. The filter membrane was placed in a multi-head cell collector, and a reaction system was subjected to suction filtration under negative pressure and washed with an ice-cold 50 mM Tris-HCl buffer, 10 ml each time, for a total of 5 times. After suction drying, 1 ml of scintillation liquid was added to the filter membrane, the filter membrane was placed on a shaker for shaking for 1.5 h and then placed in a liquid scintillation counter on the next day to determine the radioactive intensity.

(3) Detection of Influence of Tested Medicines on NMDA Receptor Agonistic Properties in Rat Crude Synaptosomal Proteins 100 μg of rat crude synaptosomal proteins was added to all tubes respectively. 50 μl of 5,7-dichlorokynurenic acid was added to a non-specific binding tube to achieve a final concentration of 10 μM. All tubes were preloaded with 50 μM of glutamic acid, and the materials were reacted for 15 min in advance. 20 μL of control drug at corresponding concentration was added to the test tube, and then reacted for 15 min. 1 mM glycine was added to the maximum reaction tube. A volume of 30 μl of labeled ligand [$^3$H]-MK-801 was successively added to all tubes to achieve a final concentration of 10 nM, and reacted for 15 min. All reaction tubes were supplemented to a volume of 500 μl with 50 mM Tris-HCl buffer (50 mM Tris-HCl, 5 mM $MgCl_2 \cdot 6H_2O$, 1 mM EDTA, 0.5% (WN) BSA, 0.1% $NaN_3$, pH 7.4). A reaction was carried out at 37° C. for 15 min. A type-49 glass fiber filter membrane was prepared and a sample was applied at the same time. The filter membrane was placed in a multi-head cell collector, and the reaction system was subjected to suction filtration under negative pressure and washed with an ice-cold 50 mM Tris-HCl buffer, 10 ml each time, for a total of 5 times. After suction drying, 1 ml of scintillation liquid was added to the filter membrane, the filter membrane was placed on the shaker for shaking for 1.5 h and then placed in the liquid scintillation counter on the next day to determine the radioactive intensity.

(4) Data Processing and Statistical Analysis

GraphPad5.0 software was used to analyze the data, and the percentage of competitive inhibition was calculated through nonlinear fitting, wherein:

Percentage of competitive inhibition %=((total binding tube cpm−compound cpm)/(total binding tube cpm−non-specific binding tube cpm))×100%;

Specific binding amount=total binding amount−non-specific binding amount, wherein each binding site was determined by double compound tubes.

In an agonistic experiment, maximum [$^3$H]-MK-801 binding %=((tested compounds cpm−5,7 dichlorokynurenic acid cpm)/(1 mM glycine cpm−5,7 dichlorokynurenic acid cpm))×100%.

TABLE 2

Affinity and maximum agonistic efficacy of compounds of examples on NMDA

| Number | $IC_{50}$(nM) | Maximum agonistic efficacy (%) | Number | $IC_{50}$(nM) | Maximum agonistic efficacy (%) |
|---|---|---|---|---|---|
| A-002 | 0.33 | 45 | A-006 | 0.44 | 32 |
| A-007 | 0.89 | 56 | A-008 | 0.89 | 35 |
| A-016 | 0.35 | 56 | A-020 | 0.25 | 42 |
| A-030 | 0.35 | 39 | A-031 | 0.35 | 52 |
| A-034 | 0.89 | 25 | A-035 | 0.88 | 19 |
| A-036 | 0.89 | 28 | A-044 | 0.66 | 28 |
| A-048 | 0.55 | 38 | A-059 | 0.75 | 33 |
| A-066 | 0.35 | 29 | A-068 | 1.30 | 48 |
| A-074 | 0.89 | 38 | A-078 | 1.59 | 56 |
| A-079 | 1.25 | 41 | A-082 | 0.89 | 45 |
| A-090 | 0.45 | 36 | A-093 | 0.48 | 65 |
| A-098 | 0.98 | 28 | A-111 | 1.58 | 38 |
| A-114 | 0.89 | 35 | A-119 | 1.89 | 35 |
| A-122 | 1.65 | 38 | A-130 | 0.48 | 43 |
| A-162 | 0.45 | 38 | A-195 | 0.43 | 46 |
| A-226 | 0.33 | 45 | A-234 | 1.58 | 75 |
| A-256 | 0.89 | 28 | A-258 | 0.33 | 21 |
| A-260 | 0.26 | 26 | A-266 | 3.2 | 45 |
| A-272 | 0.54 | 19 | A-274 | 0.28 | 55 |
| A-275 | 0.35 | 12 | A-276 | 0.25 | 28 |
| A-282 | 0.32 | 35 | A-291 | 0.88 | 13 |
| A-303 | 0.24 | 35 | A-329 | 0.73 | 26 |
| A-331 | 0.59 | 31 | A-333 | 0.41 | 19 |
| A-334 | 0.38 | 34 | A-335 | 0.48 | 42 |

TABLE 2-continued

Affinity and maximum agonistic efficacy of compounds of examples on NMDA

| Number | $IC_{50}$(nM) | Maximum agonistic efficacy (%) | Number | $IC_{50}$(nM) | Maximum agonistic efficacy (%) |
|---|---|---|---|---|---|
| A-342 | 0.56 | 32 | A-353 | 0.48 | 53 |
| A-358 | 0.86 | 78 | A-367 | 0.29 | 39 |
| A-370 | 0.36 | 46 | A-378 | 1.66 | 49 |
| A-384 | 0.42 | 39 | A-390 | 0.39 | 55 |
| A-394 | 0.79 | 63 | A-401 | 0.44 | 75 |
| A-409 | 0.56 | 36 | A-421 | 0.38 | 45 |
| A-429 | 0.66 | 57 | A-437 | 0.33 | 42 |
| A-449 | 0.47 | 38 | A-463 | 0.52 | 59 |
| A-470 | 0.35 | 33 | A-476 | 0.96 | 56 |

The experimental results show that all the compounds of examples have NMDA receptor agonistic activity, and the maximum agonistic efficacy is between 12% and 78%, and the compounds belong to NMDA receptor partial agonists.

Test Example 2: In-Vivo Metabolism Study in Rats

The pharmacokinetic parameters such as exposure of plasma concentrations of the compounds of examples were evaluated by oral/tail intravenous injection model tests in rats in order to evaluate the in-vivo metabolic stability in rats.

The male SD rats weighing 200±20 g and being SPF grade were used in this experiment and purchased from SPF.

Preparation of intravenous solution: 1 mg of each tested medicine was weighed accurately, and a volume was metered to 5 mL with 0.9% sodium chloride solution to prepare 0.2 mg/mL. A dose volume was 1 mL for per 200 g of weight, and the dose was 1 mg for per 1 kg of weight based on the concentration conversion.

Preparation of intragastric solution: 10 mg of each tested medicine was accurately weighed, and a volume was metered to 10 mL with 0.9% sodium chloride solution to prepare 1 mg/mL of the solution. A dose volume was 2 mL for per 200 g of weight, and the dose was 10 mg for per 1 kg of weight based on the concentration conversion.

Rats were randomly divided into 8 groups, 6 rats were in each group, oral gavage administration and tail intravenous administration were performed according to the above doses. About 0.2 mL of orbital blood was collected before administration and at 2 min, 5 min, 15 min, 30 min, 1 h, 2 h, 3 h, 4 h and 6 h after administration, respectively, and centrifuged at 3000 rpm for 10 min at 4° C., and a supernatant was taken for LC/MS/MS determination. A DAS pharmacokinetics program was used to analyze the measured data and calculate the main pharmacokinetic parameters. The experimental results are shown in the following table.

TABLE 3

Pharmacokinetic parameters of compounds of examples

| Example | Mode of administration | $C_{max}$ (ng/mL) | $AUC_{(0\rightarrow t)}$ (ng/mL*h) | F (%) |
|---|---|---|---|---|
| A-006 | Oral | 18360 | 34957 | 21.2 |
| | Intravenous injection | 11633 | 16470 | |
| A-066 | Oral | 2083 | 7556 | 54.5 |
| | Intravenous injection | 1692 | 1385 | |
| A-082 | Oral | 5580 | 13431 | 19.6 |
| | Intravenous injection | 18267 | 6852 | |

TABLE 3-continued

| Pharmacokinetic parameters of compounds of examples | | | | |
|---|---|---|---|---|
| Example | Mode of administration | $C_{max}$ (ng/mL) | $AUC_{(0 \rightarrow t)}$ (ng/mL*h) | F (%) |
| A-098 | Oral | 767 | 1822 | 19.1 |
| | Intravenous injection | 1094 | 952 | |
| A-258 | Oral | 4907 | 11400 | 27.3 |
| | Intravenous injection | 3630 | 4178 | |
| A-260 | Oral | 6212 | 10849 | 74.6 |
| | Intravenous injection | 2240 | 1454 | |
| A-274 | Oral | 1883 | 3354 | 62.7 |
| | Intravenous injection | 2477 | 1628 | |

The results shows that the compounds of examples have good pharmacokinetic properties after oral/injection in rats.

Test Example 3: Animal Pharmacodynamic Test

Pharmacodynamic evaluation was performed by the forced swimming tests in rats. The experimental animals were male SD rats weighing 150 g-180 g and being SPF grade, and acclimated for one week after purchase, and then subjected to forced swimming tests, the rats need be fasted for 12 hours before the tests. The compounds of examples were dissolved with normal saline, and blank control group (normal saline) and example compound administration group were established. 8-10 rats were provided for each group.

On the day before the tests, the rats were placed in a glass cylinder with a height of 40 cm, an inner diameter of 18 cm, and a water depth of 23 cm for pre-swimming for 15 min, and a water temperature was 28° C. After the pre-swimming the rats were removed, wiped with a dry cloth, and dried with an electrical heater, then returned to a rearing cage, and administered. A formal forced swimming test was performed on the next day for a total of 5 min. The accumulated immobility time within 5 min was recorded, and a second forced swimming test was performed on the seventh day; the criteria for determining immobility were that the rats stopped struggling in the water, were in a floating state, and had only slight limb movements to keep the head floating on the water surface. The results are shown in Table 4, and the experimental data were statistically analyzed by GraphPad Prism 5.0 software.

TABLE 4

| Forced swimming test results of compounds of examples in rats | | | | |
|---|---|---|---|---|
| | Mode of | Dose | Reduction percentage (%) of floating time | |
| Group | administration | (mg/kg) | Day 2 | Day 7 |
| A-006 | Po | 0.1 | 36.4%* | 22.2% |
| A-007 | Po | 0.1 | 35.1%* | 32.4% |
| A-008 | Po | 0.1 | 54.9%** | 57.3%* |
| A-020 | Po | 0.1 | 51.8%* | 59.3%* |
| A-034 | Po | 0.1 | 71.9%** | 60.1* |
| A-066 | Po | 0.1 | 68%** | 55.3%* |
| A-098 | Po | 0.1 | 64.5%** | 13.9% |
| A-258 | Po | 0.1 | 74.8%** | 56.4%* |
| A-260 | Po | 0.1 | 31.6%* | 15.5% |

Note:
n = 8-10,
*P < 0.05
**P < 0.01
***P < 0.001 compared with the control group The experimental results show that intragastric administration with the compounds of examples is effective and the efficacy can be maintained after 2 to 7 days.

Although the embodiments of the invention have been described in detail, the technicians in the field will understand that various modifications and replacements may be made to those details according to all the instructions already disclosed, and these changes are within the scope of protection of the present invention. The full scope of the invention is given by the appended claims and any equivalents thereto.

The invention claimed is:

1. A compound represented by formula I:

I

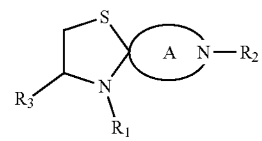

or a pharmaceutically acceptable salt, ester, or stereoisomer thereof wherein,

Ring A is selected from

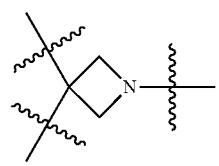,
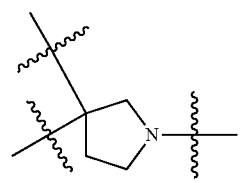,
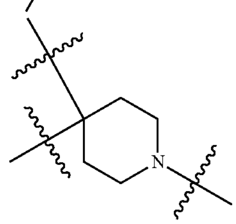,
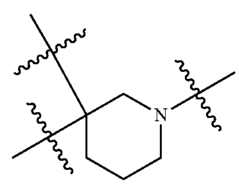,
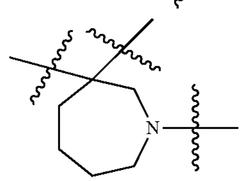 and
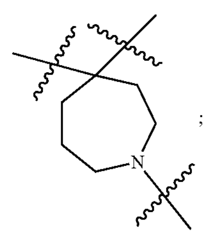;

$R_1$ is selected from H, C1-C6 alkyl, aryl-C1-C4 alkyl, C2-C6 acyl, —CONRR', and natural amino acid fragments;

when Ring A is

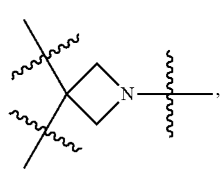 [SMILES: *N1CC(*)(*)C1], $R_2$ is selected from H, C1-C6 alkyl, C1-C6 alkoxycarbonyl, C2-C6 acyl, —CONRR', and natural amino acid fragments;

when Ring A is

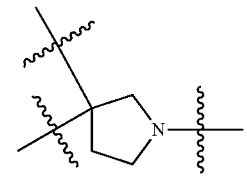,
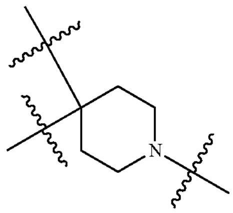,
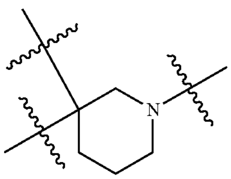,
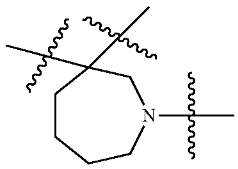
and
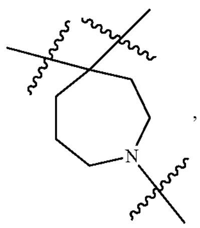, $R_2$ is selected from C1-C6 alkoxycarbonyl, C2-C6 acyl, —CONRR', and natural amino acid fragments;

$R_3$ is selected from H, cyano, 3- to 8-membered nitrogen-containing aliphatic heterocycle-C1-C4 acyl, C1-C6 alkoxycarbonyl, and —$CONHR_4$;

R and R' are each independently selected from H and C1-C6 alkyl;

$R_4$ is selected from H, natural amino acid fragments and carboxylic acid derivatives of the said natural amino acid fragments;

optionally, the C1-C6 alkyl, aryl-C1-C4 alkyl, C2-C6 acyl, C1-C6 alkoxycarbonyl, —CONRR', —$CONHR_4$, and natural amino acid fragments are each independently substituted by one or more substituents selected from: halogen, amino, hydroxyl, cyano, carboxyl, nitro, C1-C6 alkyl, and C1-C6 alkoxy; 3- to 8-membered nitrogen-containing aliphatic heterocycle-C1-C4 acyl is substituted by one or more substituents selected from: halogen, amino, hydroxyl, carboxyl, nitro, C1-C6 alkyl, and C1-C6 alkoxy;

wherein the natural amino acid fragments are selected from the carboxyl or amino residues of the following amino acids: Thr, Ser, Val, Gly, Ala, Ile, Leu, Phe, Tyr, Asp, and Gln; and, $R_1$, $R_2$ and $R_3$ satisfy:

(1) $R_1$, $R_2$ and $R_3$ are not H at the same time;

(2) when $R_1$ and $R_3$ are H, $R_2$ is not Boc;

(3) when formula I is

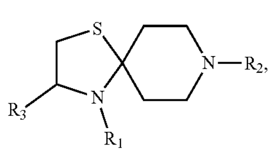

$R_1$ is

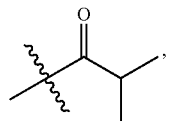 [SMILES: *C(=O)C(C)C], and $R_3$ is H, $R_2$ is not

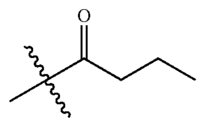,
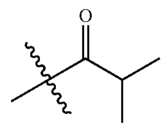,
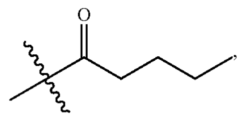,
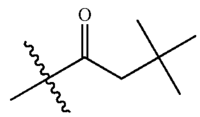,
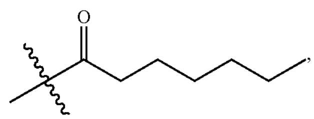,
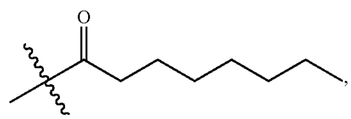,
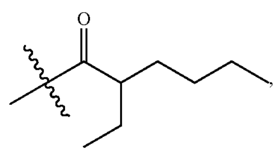,
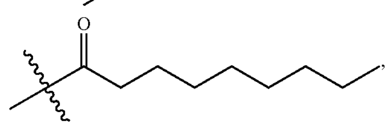,
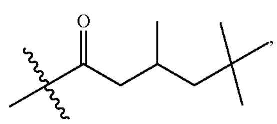,
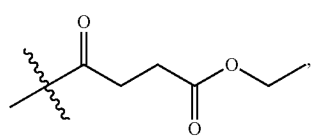,
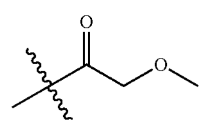,
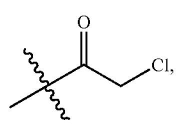
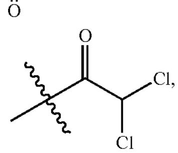
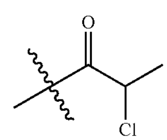,
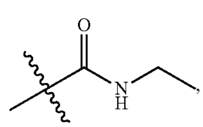,
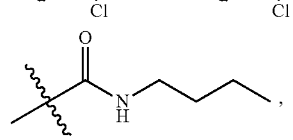,
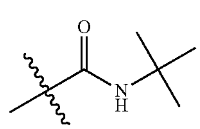
or
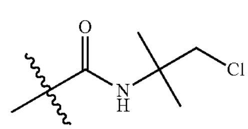;

(4) when formula I is

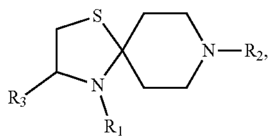

$R_1$ is

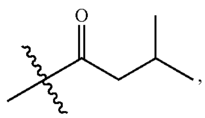 [SMILES: *C(=O)CC(C)C]

and $R_3$ is H, $R_2$ is not C2-C6 acyl or —CONRR';

(5) when formula I is

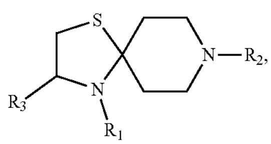

$R_1$ and $R_3$ are H, $R_2$ is not acetyl,

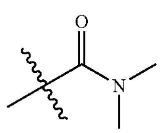 or 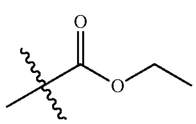 ;

(6) the compound of formula I is not

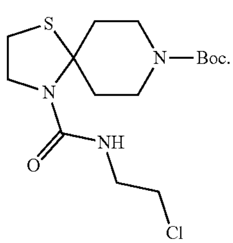 [SMILES: CC(C)(C)OC(=O)N1CCC2(CC1)SCCN2C(=O)NCCCl]

2. The compound according to claim 1, or a pharmaceutically acceptable salt, ester, or stereoisomer thereof, wherein Ring A is selected from

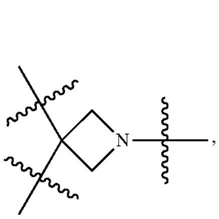 , 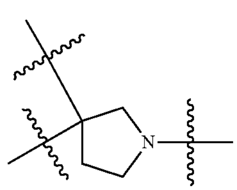 ,

-continued

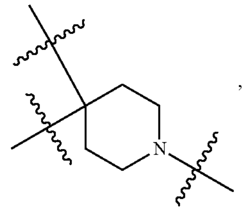 , 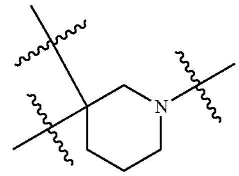 , and

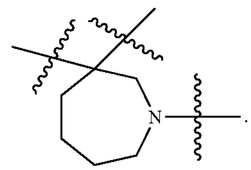 .

3. The compound according to claim 1, or a pharmaceutically acceptable salt, ester, or stereoisomer thereof, wherein, $R_1$ is selected from H, C1-C6 alkyl, phenyl-C1-C4 alkyl, C2-C6 acyl, and natural amino acid fragments.

4. The compound according to claim 1, or a pharmaceutically acceptable salt, stereoisomer thereof, wherein, when Ring A is

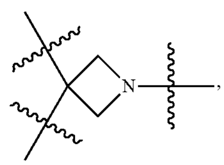 [SMILES: *N1CC(*)(*)C1] , $R_2$ is selected from H, C1-C6 alkyl, C1-C6 alkoxycarbonyl, C2-C6 acyl, and natural amino acid fragments;

when Ring A is

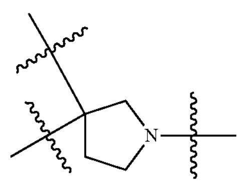 , 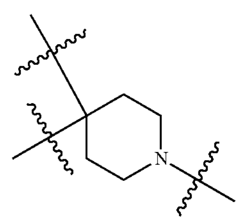 ,

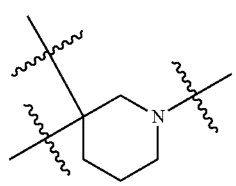 , 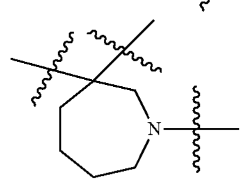 and

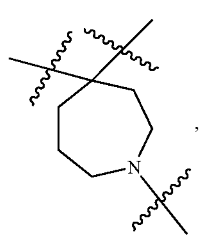 , $R_2$ is selected from C1-C6 alkoxycarbonyl C2-C6 acyl, and natural amino acid fragments;

optionally, the C1-C6 alkyl, aryl-C1-C4 alkyl, C2-C6 acyl, and natural amino acid fragments are each independently substituted by one or more substituents selected from: halogen, amino, hydroxyl, cyano, carboxyl, nitro, C1-C6 alkyl, and C1-C6 alkoxy.

5. The compound according to claim 1, or a pharmaceutically acceptable salt, ester, or stereoisomer thereof, wherein, $R_3$ is selected from H, cyano, 5- to 7-membered nitrogen-containing aliphatic heterocycle-C1-C3 acyl, C1-C4 alkoxycarbonyl and —$CONHR_4$; $R_4$ is selected from H, natural amino acid fragments, amide derivatives of the said natural amino acid fragments and cyano derivatives of the said natural amino acid fragments.

6. The compound according to claim 1, or a pharmaceutically acceptable salt, ester, or stereoisomer thereof, wherein the natural amino acid fragments are selected from the carboxyl or amino residues of the following amino acids: Thr, Ser, Val, Gly, Ala, Ile, Phe, Gln and Tyr.

7. The compound according to claim 1, or a pharmaceutically acceptable salt, ester, or stereoisomer thereof, wherein the compound is selected from:

A-003

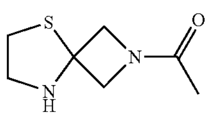

A-004

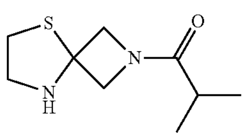

A-005

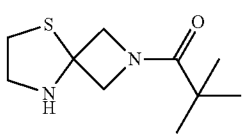

A-006

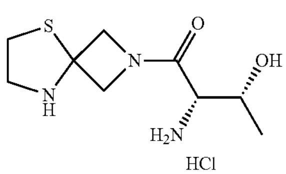

A-007

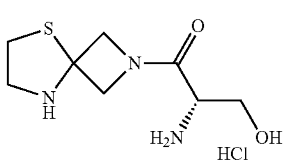

A-007-1

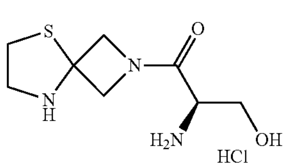

A-008

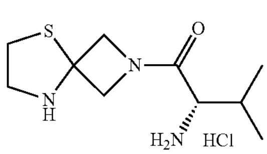

-continued

A-008-1

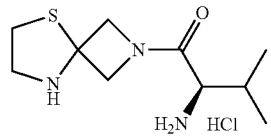

A-009

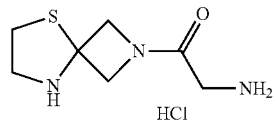

A-010

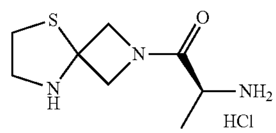

A-011

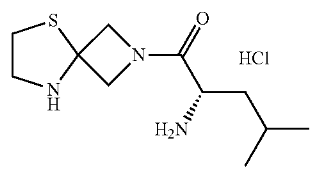

A-012

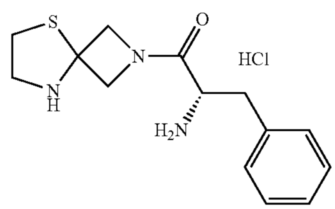

A-013

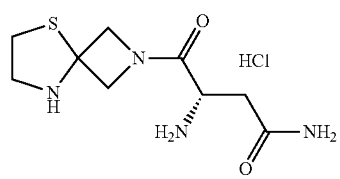

A-014

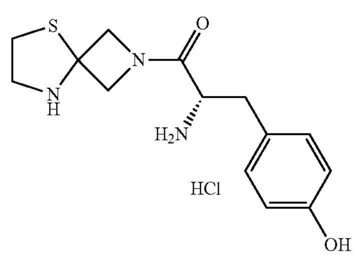

A-017

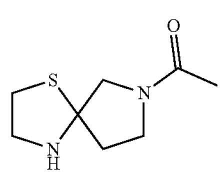

A-018

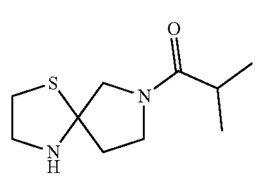

-continued
A-019
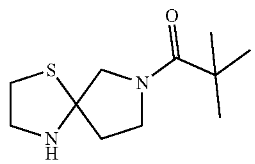
A-020
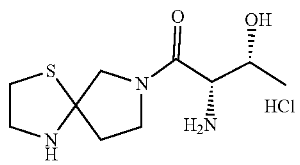
A-021
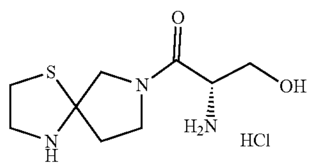
A-022
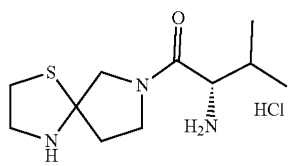
A-023
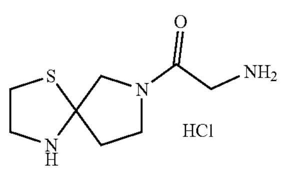
A-024
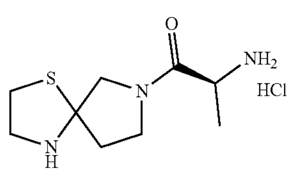
A-025
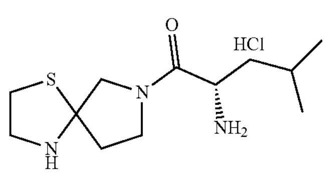
A-026
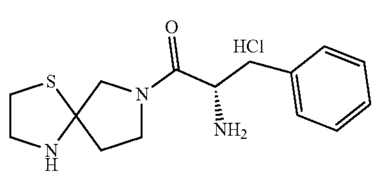
A-027
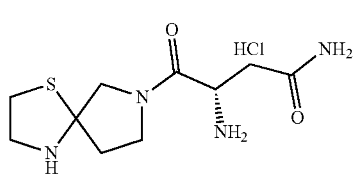
-continued
A-028
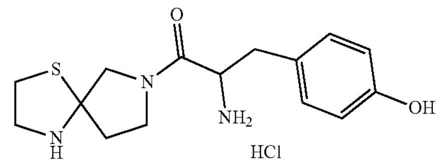
A-032
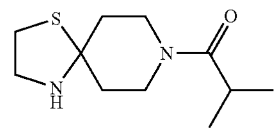
A-033
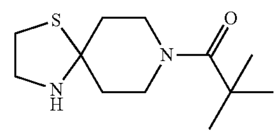
A-034
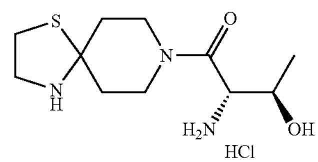
A-035
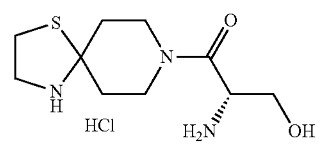
A-036
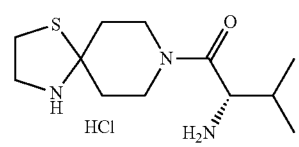
A-037
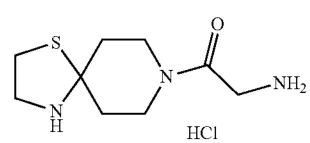
A-038
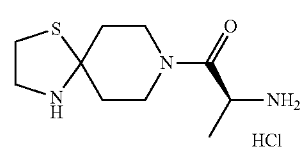
A-039
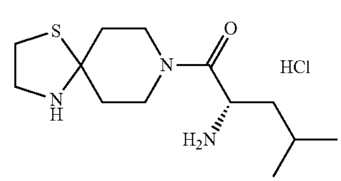
A-040
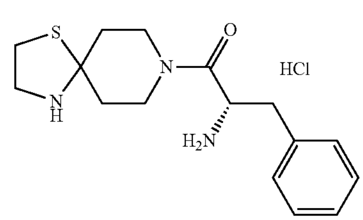

-continued
A-041
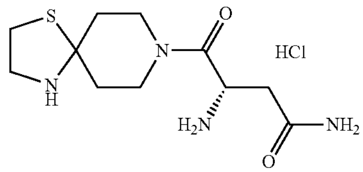
A-042
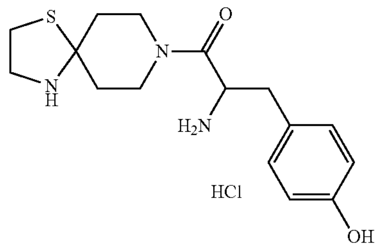
A-045
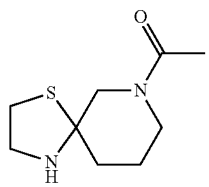
A-046
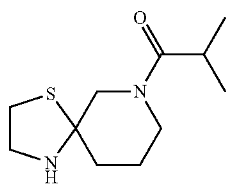
A-047
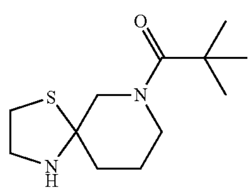
A-048
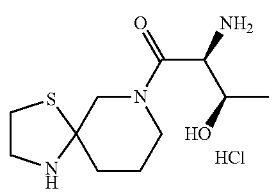
A-049
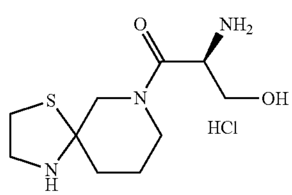
A-050
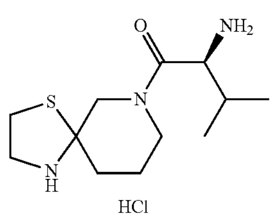
-continued
A-051
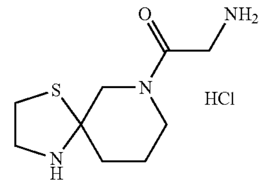
A-052
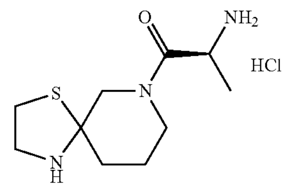
A-053
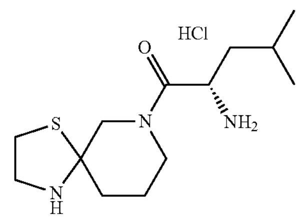
A-054
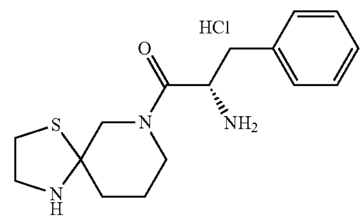
A-055
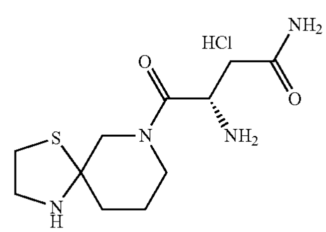
A-056
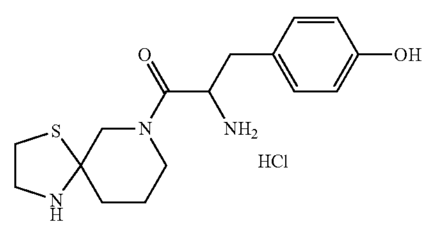
A-057
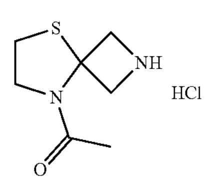
A-058
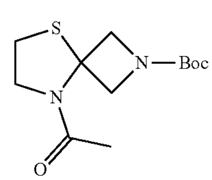

-continued
A-059
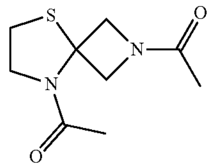
A-060
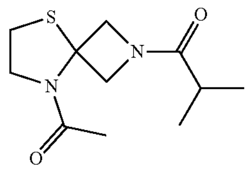
A-061
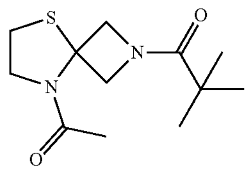
A-062
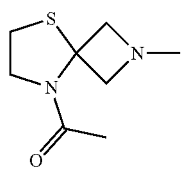
A-063
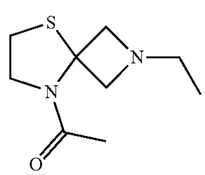
A-064
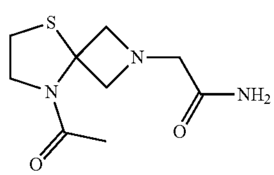
A-065
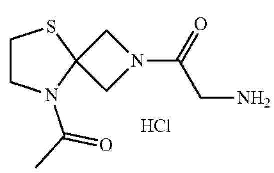
A-066
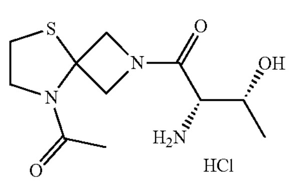
A-067
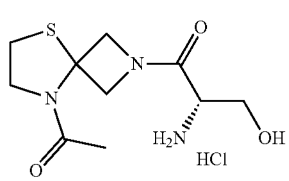
-continued
A-068
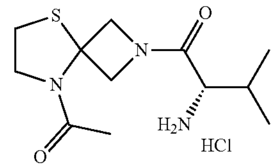
A-070
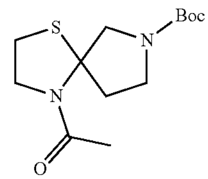
A-071
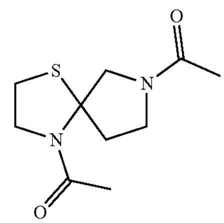
A-072
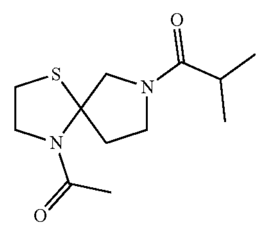
A-073
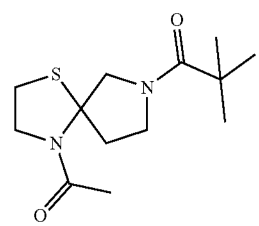
A-074
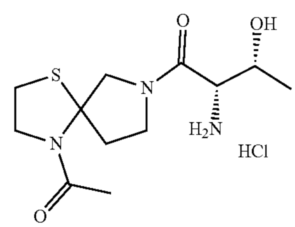
A-075
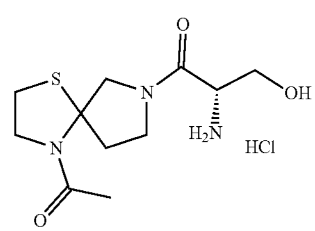

-continued
A-076
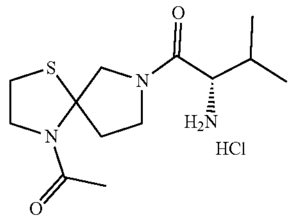
A-078
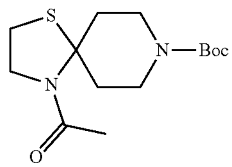
A-079
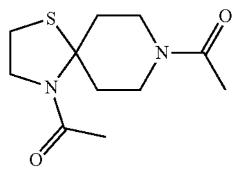
A-080
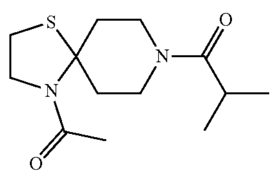
A-081
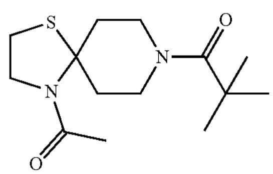
A-082
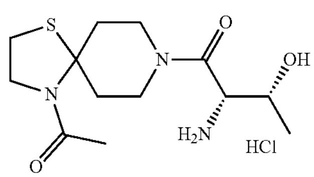
A-083
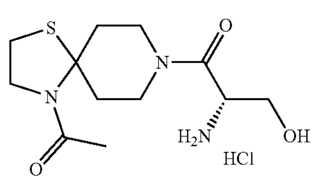
A-084
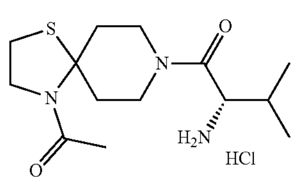
-continued
A-086
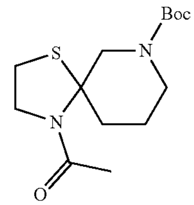
A-087
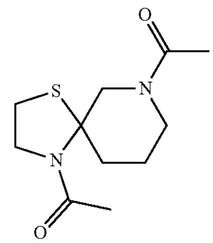
A-088
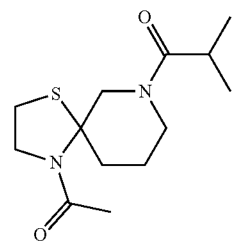
A-089
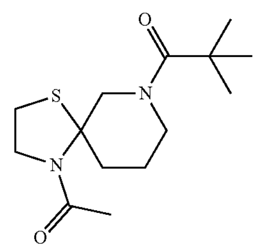
A-090
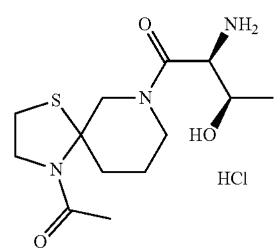
A-091
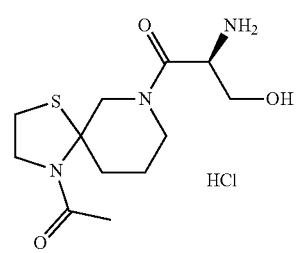

-continued
A-092
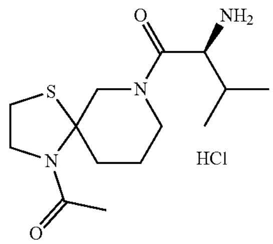
A-093
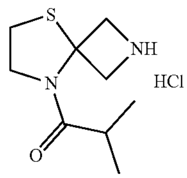
A-094
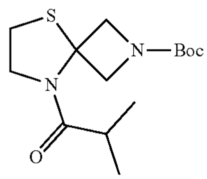
A-095
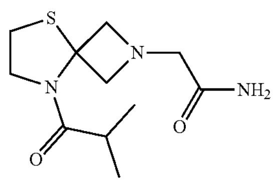
A-096
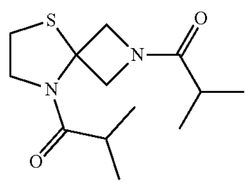
A-097
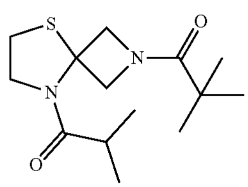
A-098
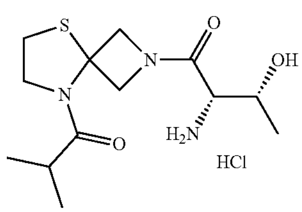
A-099
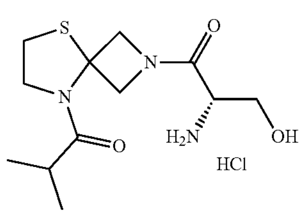
-continued
A-100
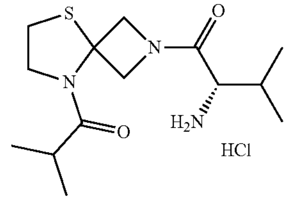
A-102
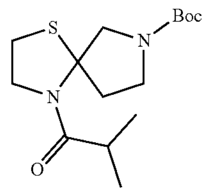
A-103
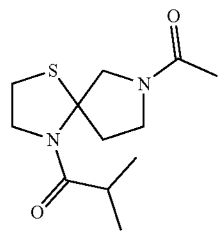
A-104
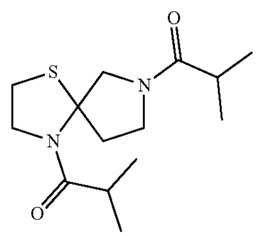
A-105
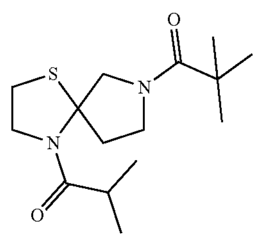
A-106
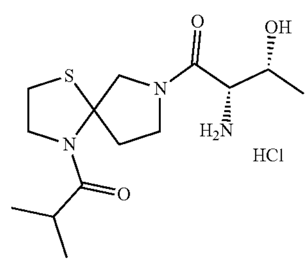
A-107
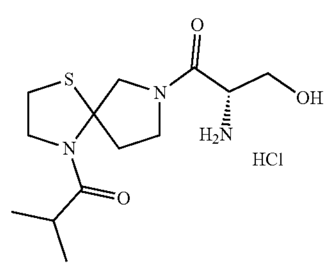

-continued
A-108
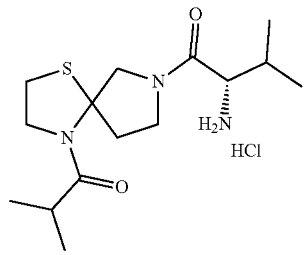
A-110
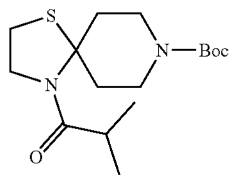
A-111
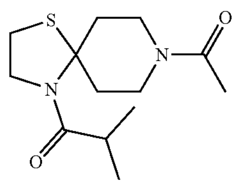
A-113
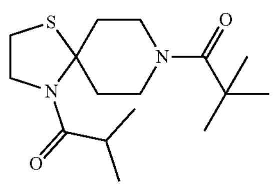
A-114
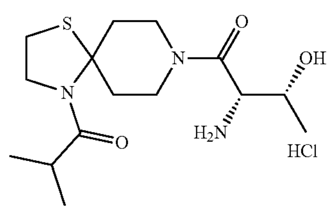
A-115
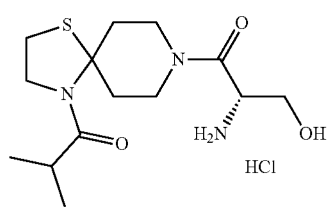
A-116
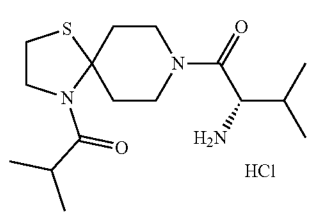
-continued
A-118
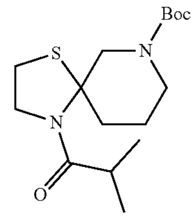
A-119
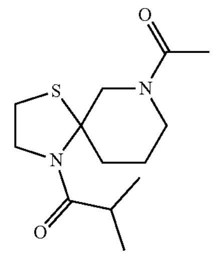
A-120
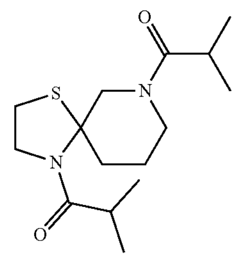
A-121
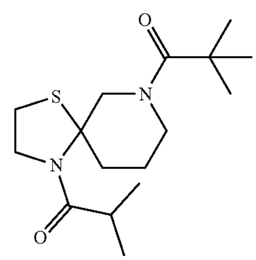
A-122
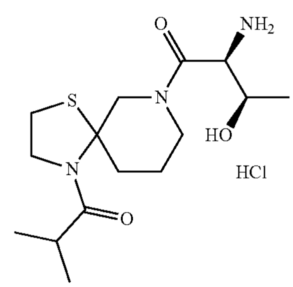
A-123
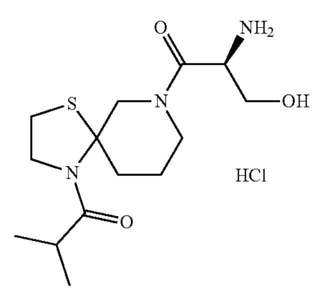

-continued
A-124
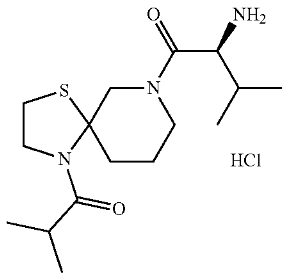
A-125
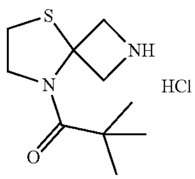
A-126
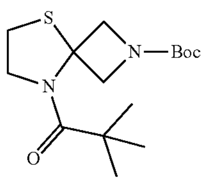
A-127
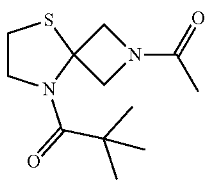
A-128
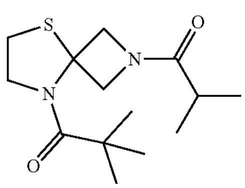
A-129
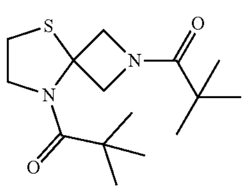
A-130
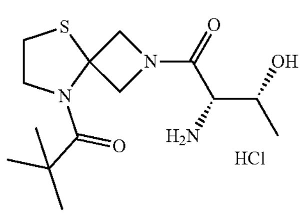
A-131
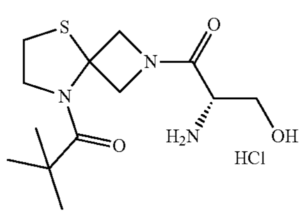
-continued
A-132
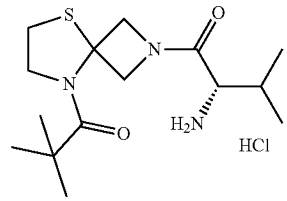
A-134
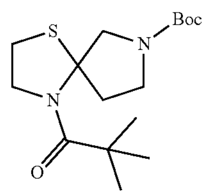
A-135
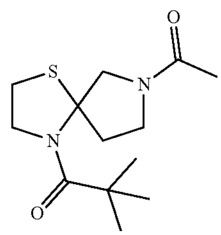
A-136
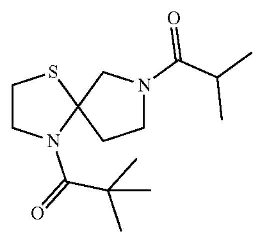
A-137
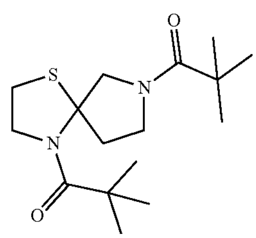
A-138
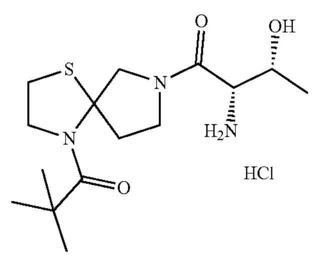
A-139
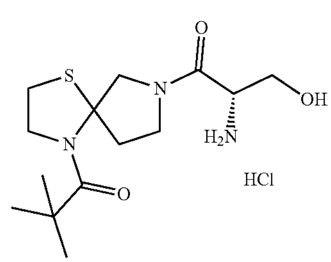

-continued
A-140
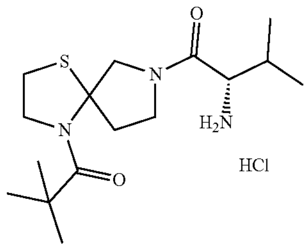
A-142
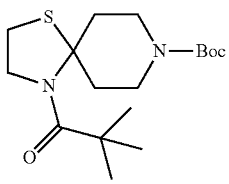
A-143
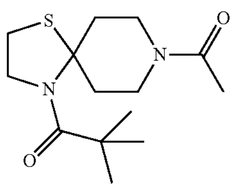
A-144
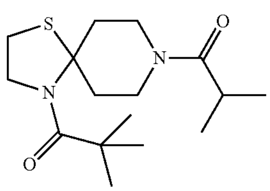
A-145
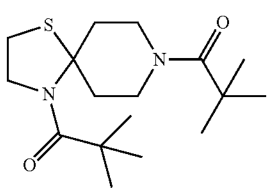
A-146
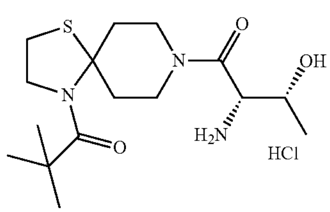
A-147
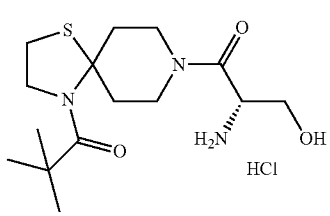
A-148
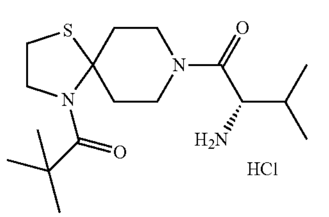
-continued
A-150
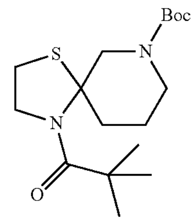
A-151
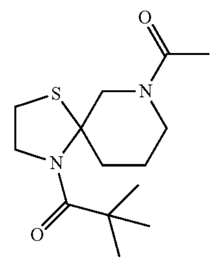
A-152
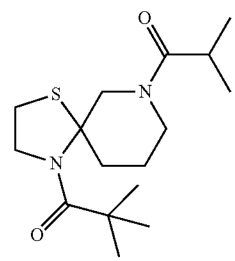
A-153
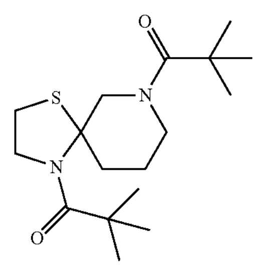
A-154
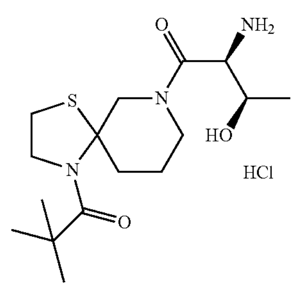
A-155
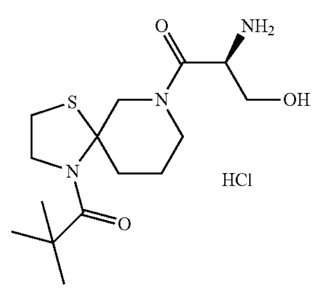

-continued
A-156
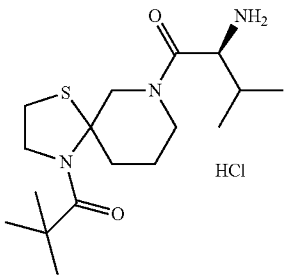
A-157
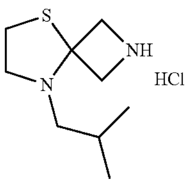
A-158
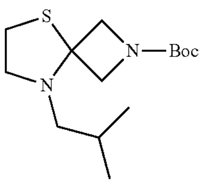
A-159
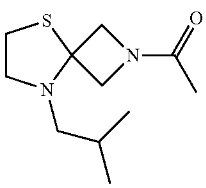
A-160
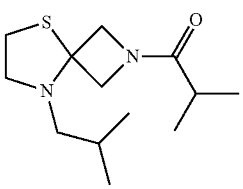
A-161
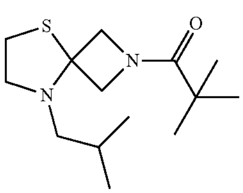
A-162
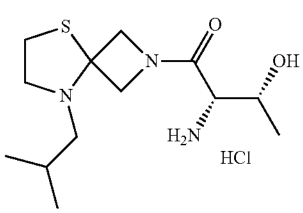
-continued
A-163
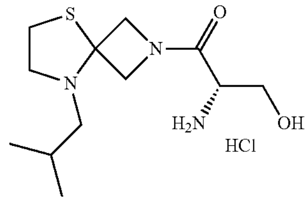
A-164
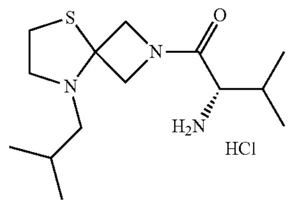
A-166
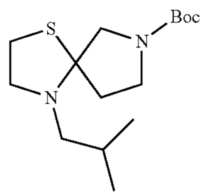
A-167
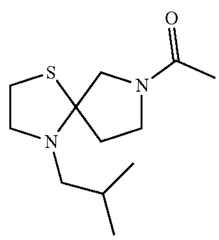
A-168
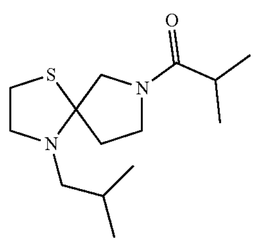
A-169
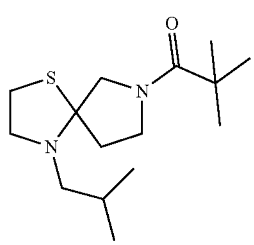
A-170
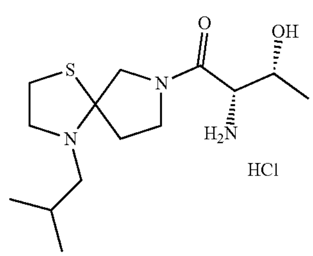

-continued
A-171
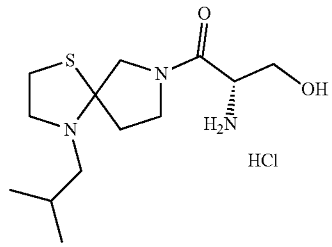
A-172
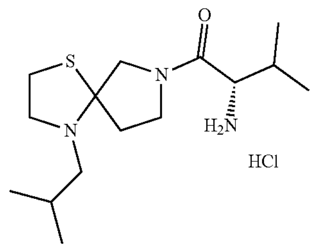
A-174
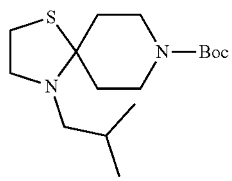
A-175
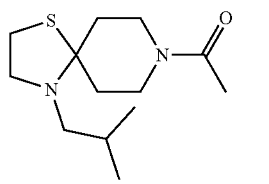
A-176
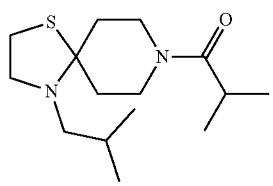
A-177
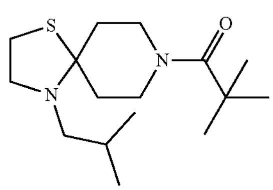
A-178
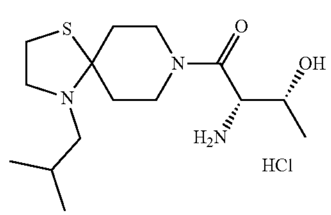
-continued
A-179
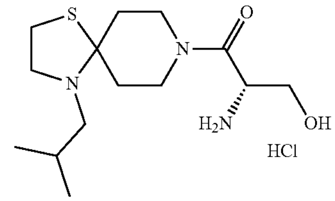
A-180
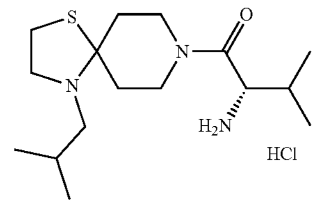
A-182
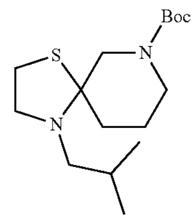
A-183
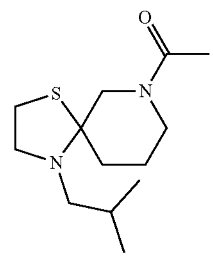
A-184
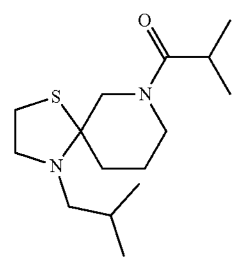
A-185
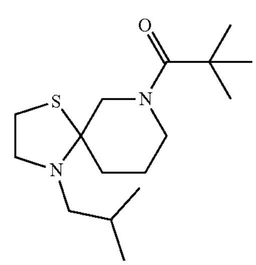

-continued
A-186
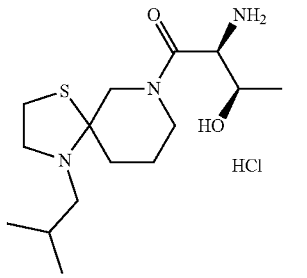
A-187
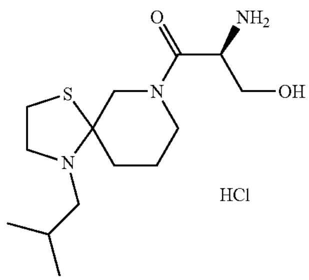
A-188
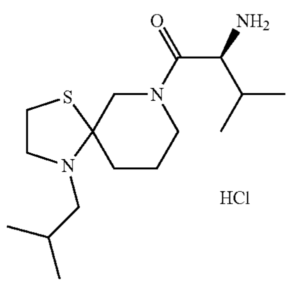
A-189
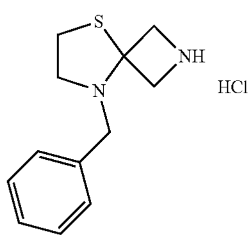
A-190
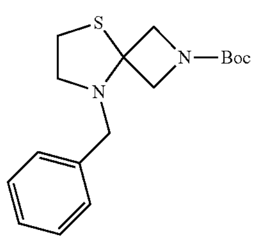
A-191
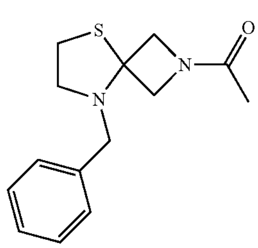
-continued
A-192
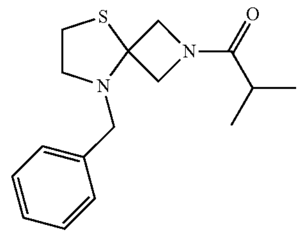
A-193
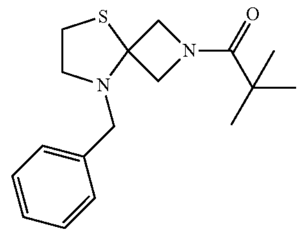
A-194
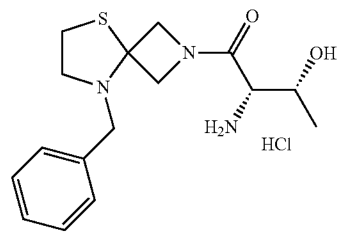
A-195
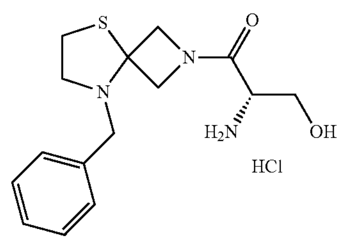
A-196
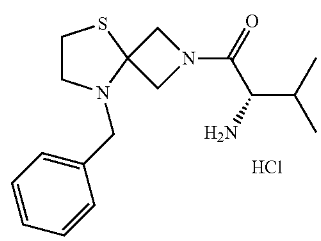
A-198
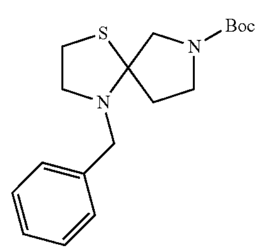

-continued
A-199
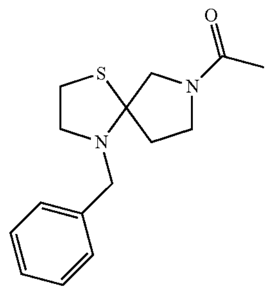
A-200
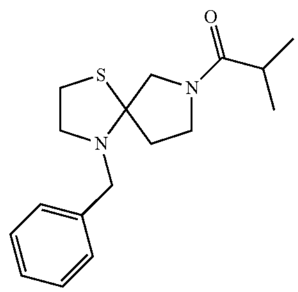
A-201
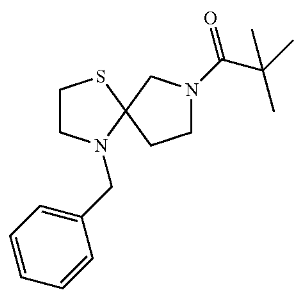
A-202
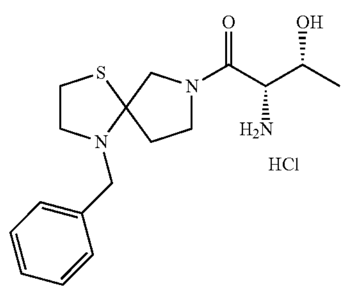
A-203
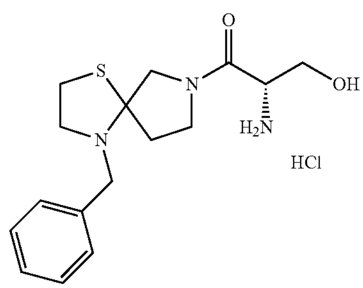
-continued
A-204
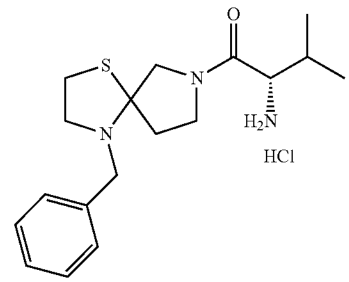
A-206
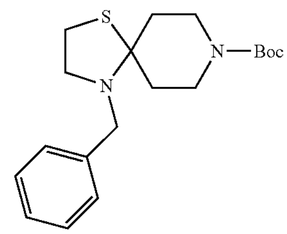
A-207
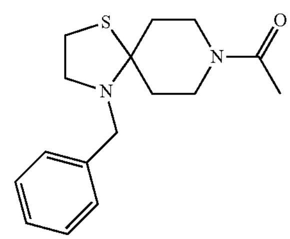
A-208
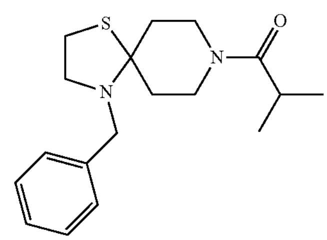
A-209
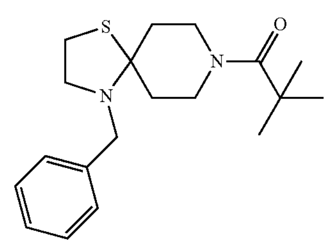
A-210
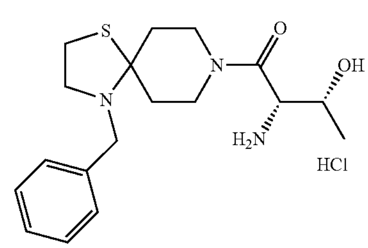

A-211
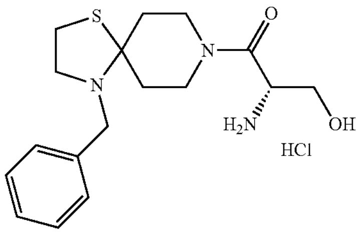
A-212
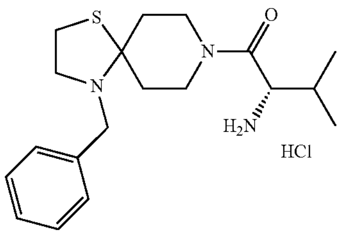
A-214
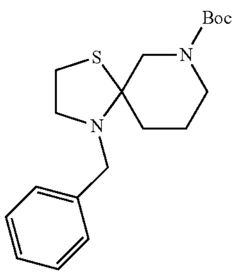
A-215
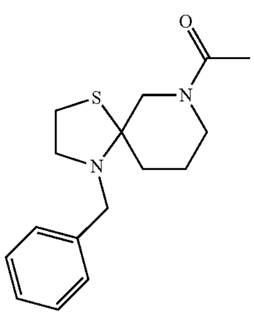
A-216
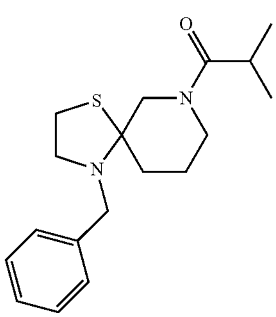
A-217
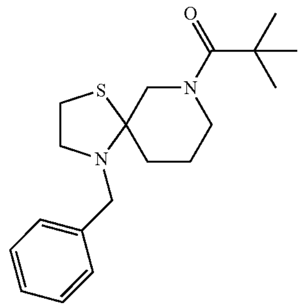
A-218
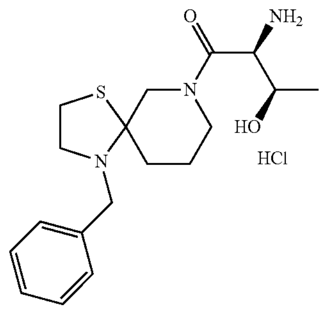
A-219
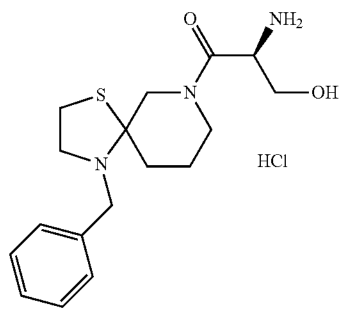
A-220
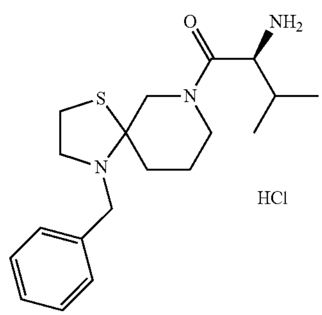
A-221
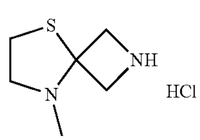
A-222
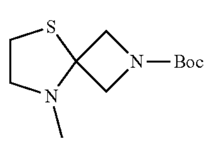

-continued
A-223
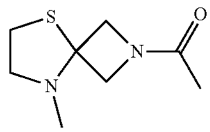
A-224
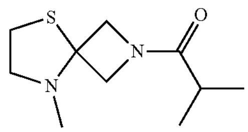
A-225
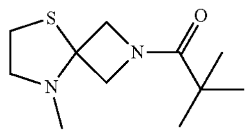
A-226
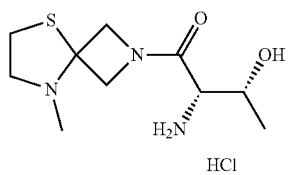
A-227
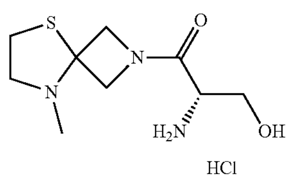
A-227
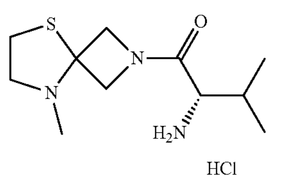
A-230
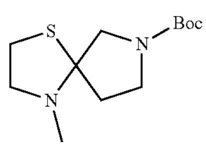
A-231
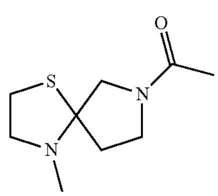
A-232
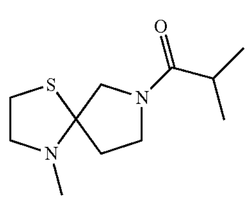
-continued
A-233
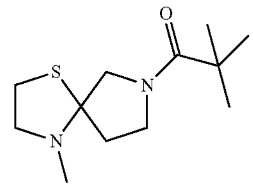
A-234
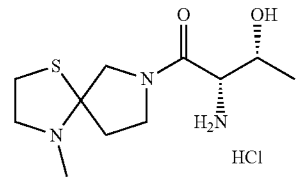
A-235
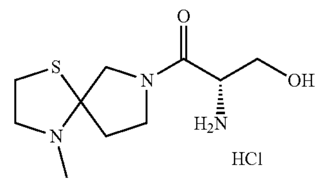
A-236
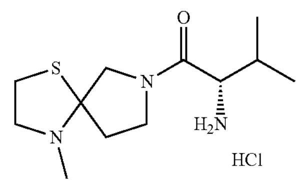
A-238
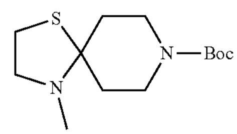
A-239
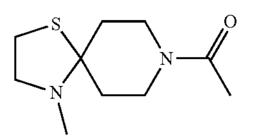
A-240
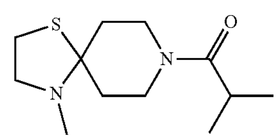
A-241
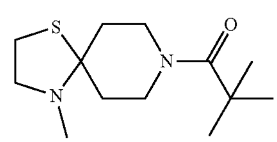
A-242
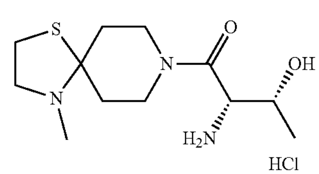

-continued
A-243
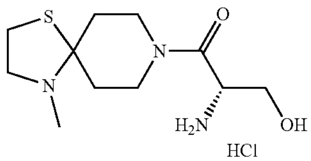
A-244
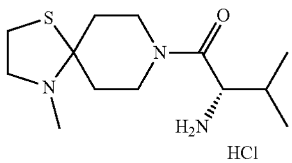
A-246
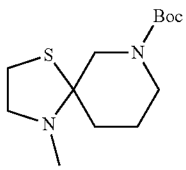
A-247
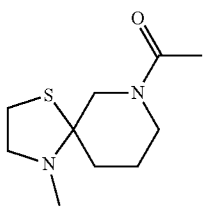
A-248
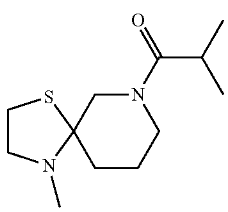
A-249
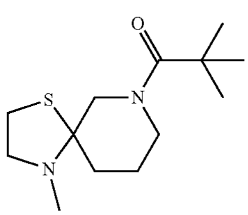
A-250
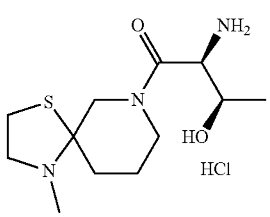
A-251
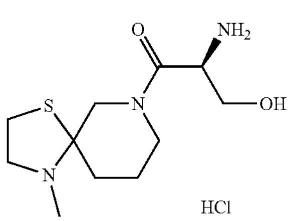
-continued
A-252
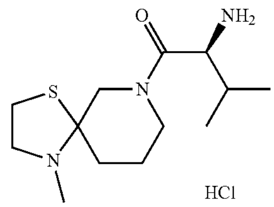
A-253
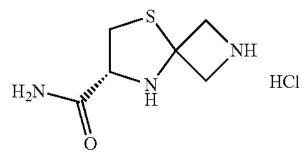
A-254
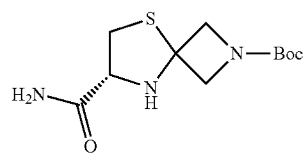
A-255
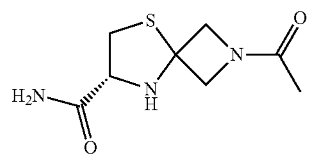
A-256
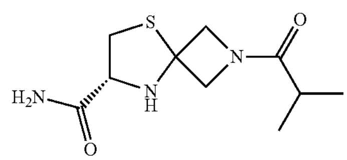
A-257
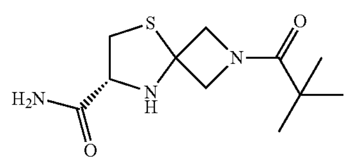
A-258
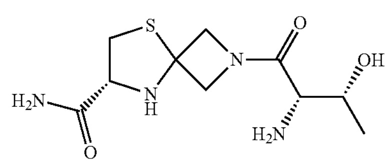
A-259
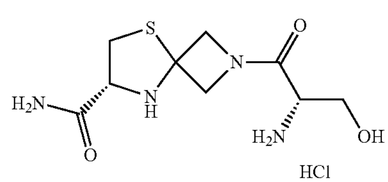
A-260
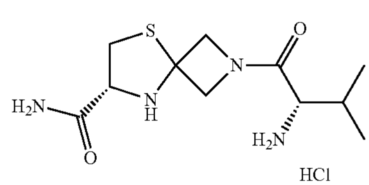

-continued
A-262
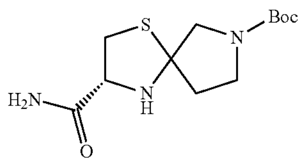
A-263
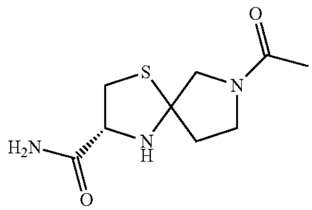
A-264
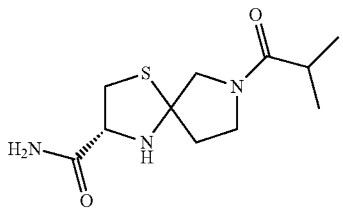
A-265
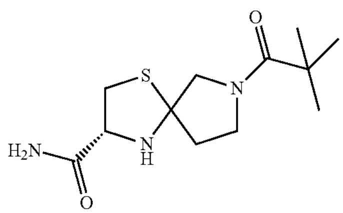
A-266
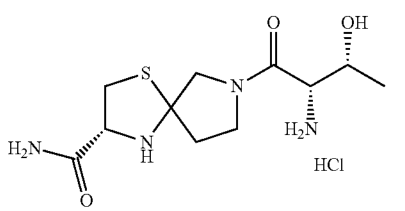
A-267
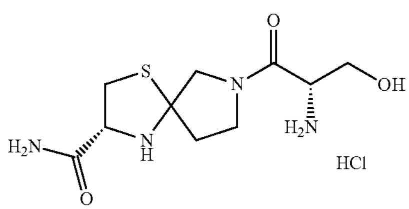
A-268
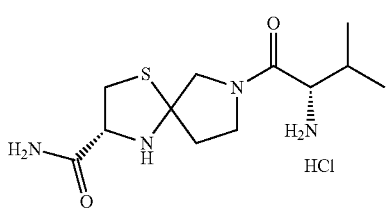
A-270
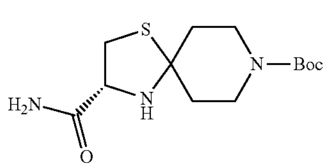
-continued
A-271
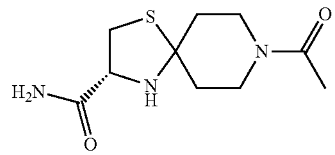
A-272
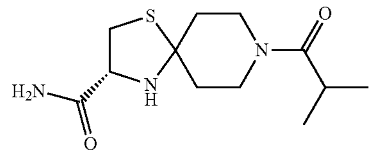
A-273
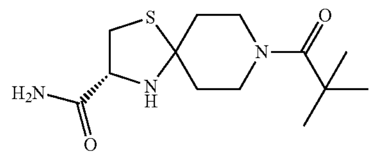
A-274
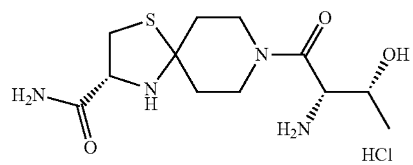
A-275
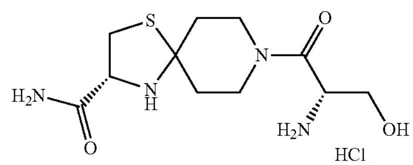
A-276
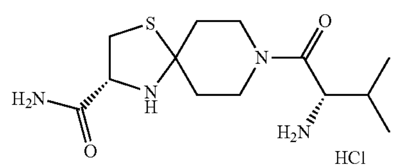
A-278
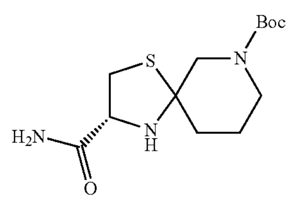
A-279
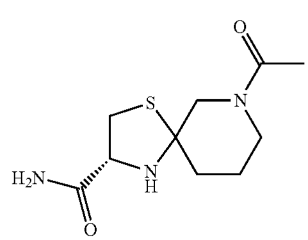

-continued
A-280
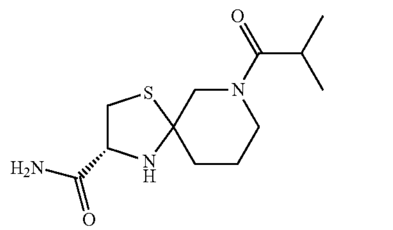
A-281
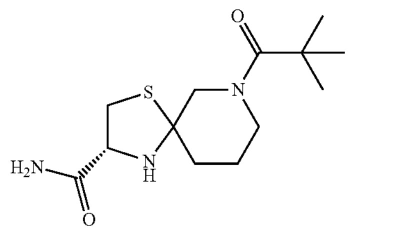
A-282
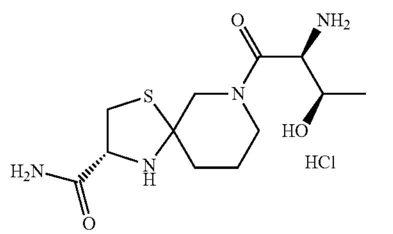
A-283
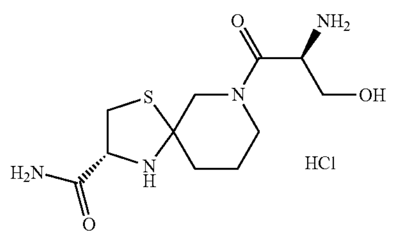
A-284
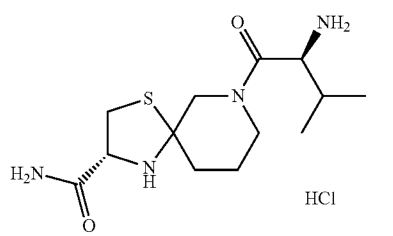
A-285
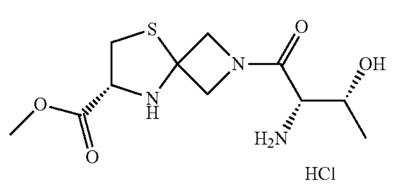
A-286
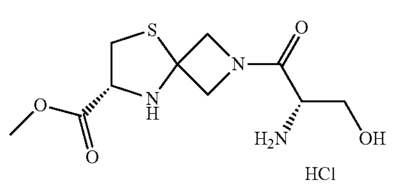
-continued
A-287
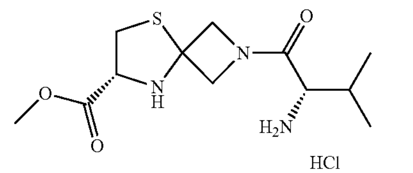
A-288
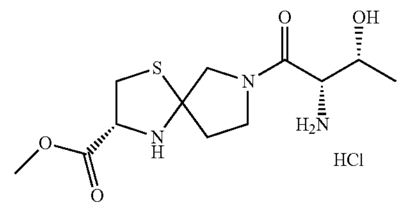
A-289
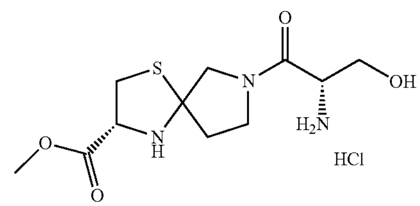
A-290
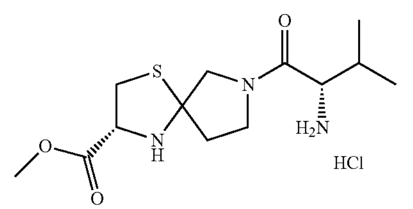
A-291
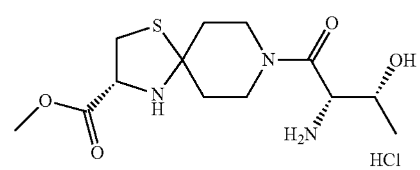
A-292
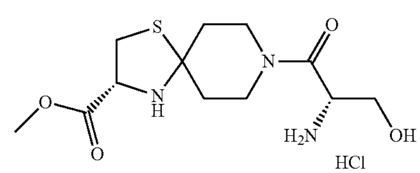
A-293
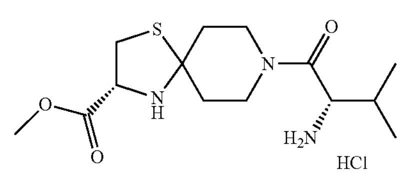
A-294
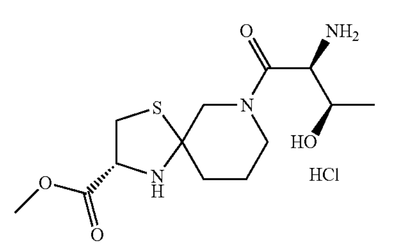

-continued
A-295
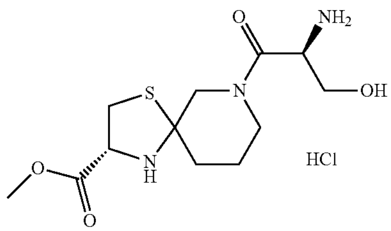
A-296
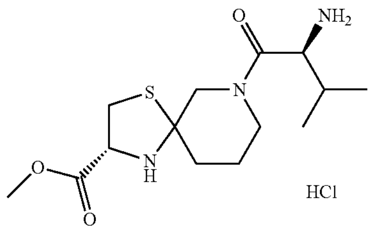
A-297
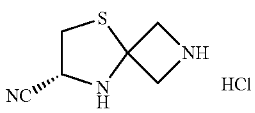
A-298
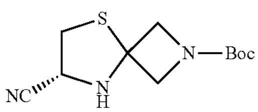
A-299
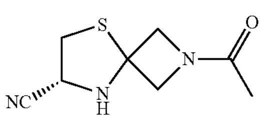
A-300
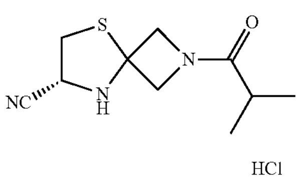
A-301
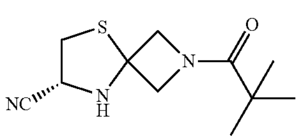
A-302
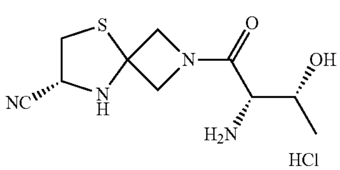
A-303
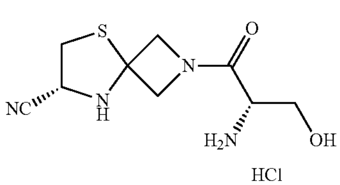
-continued
A-304
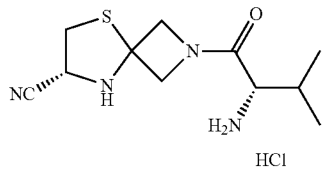
A-306
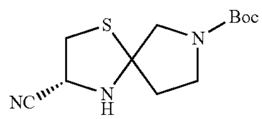
A-307
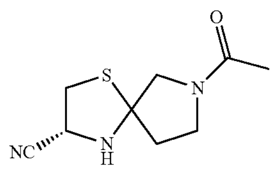
A-308
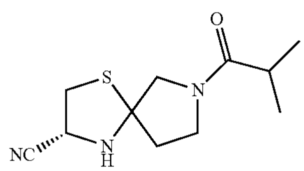
A-309
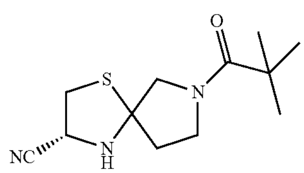
A-310
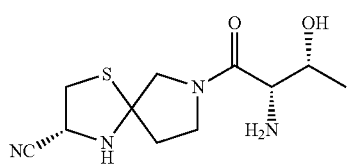
A-311
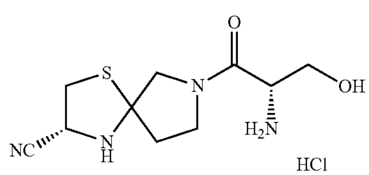
A-312
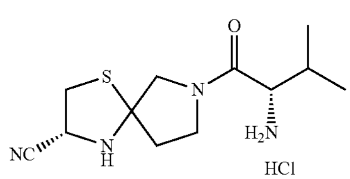
A-314
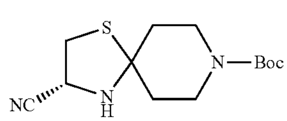
A-315
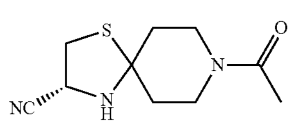

-continued
A-316
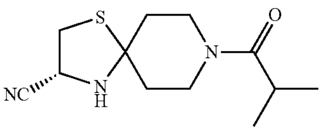
A-317
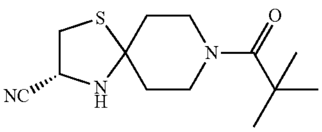
A-318
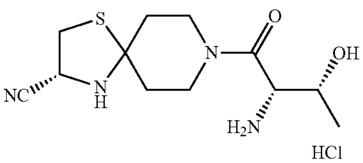
A-319
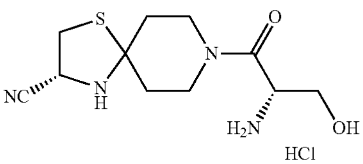
A-320
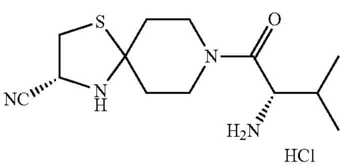
A-322
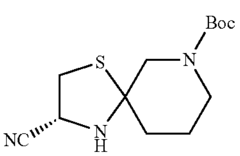
A-323
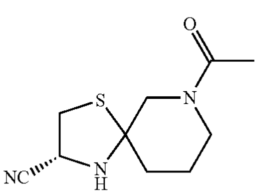
A-324
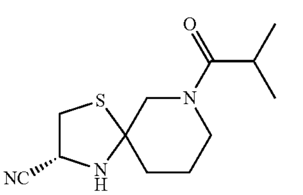
A-325
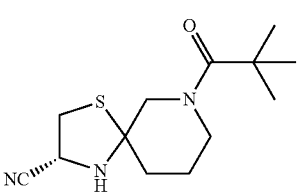
-continued
A-326
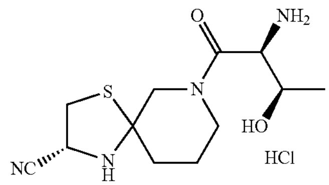
A-327
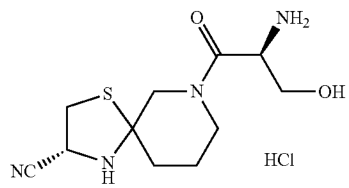
A-328
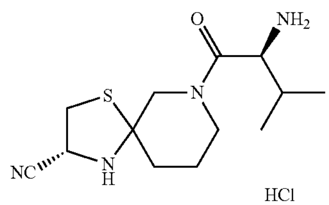
A-329
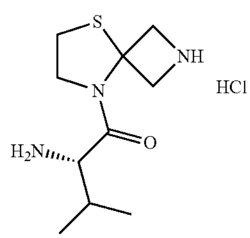
A-330
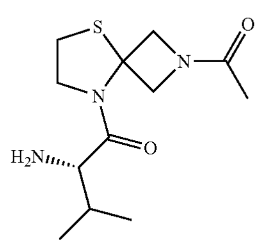
A-331
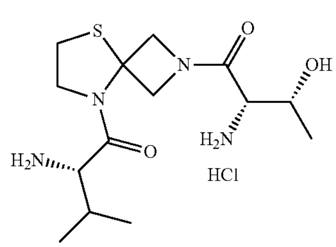
A-332
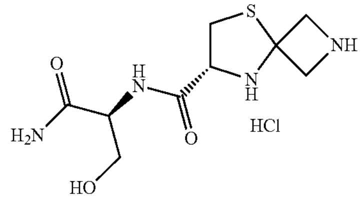

-continued
A-333
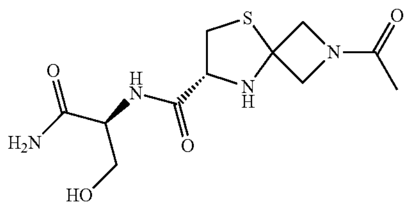
A-334
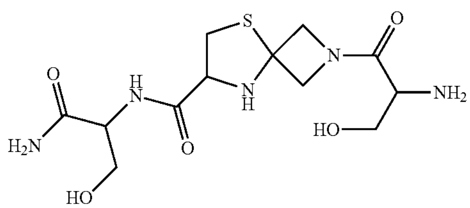
A-335
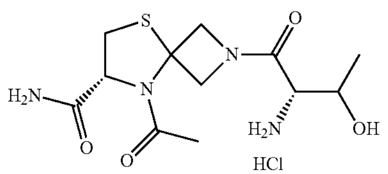
A-336
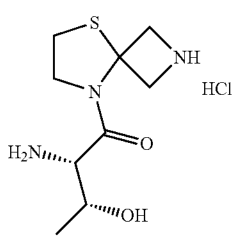
A-337
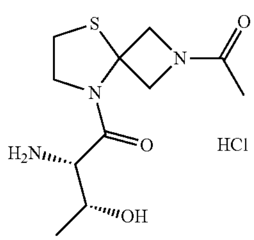
A-338
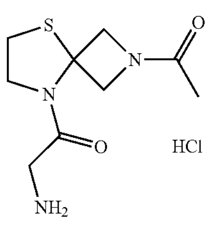
A-339
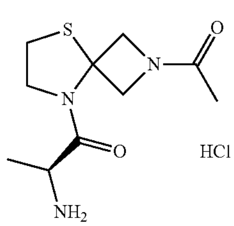
-continued
A-340
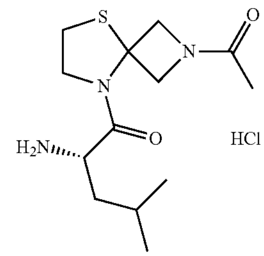
A-341
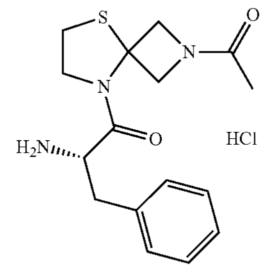
A-342
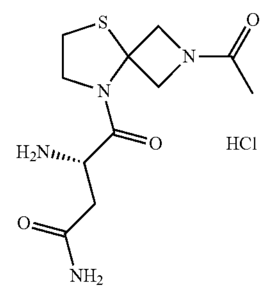
A-343
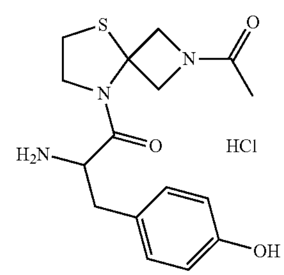
A-344
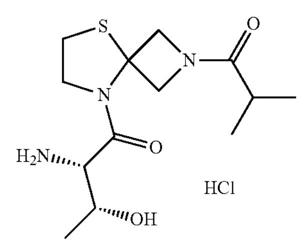
A-345
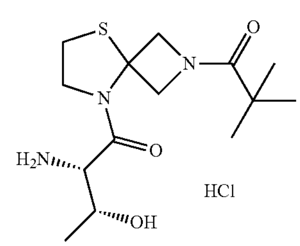

-continued
A-346
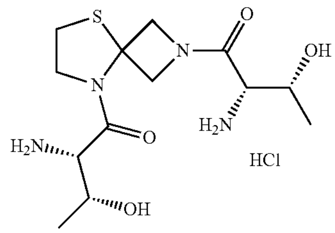
A-347
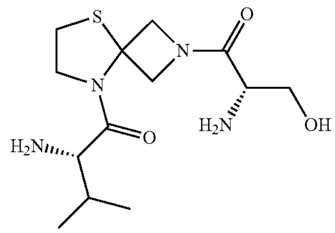
A-348
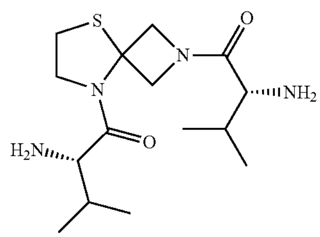
A-350
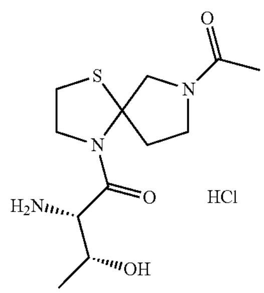
A-351
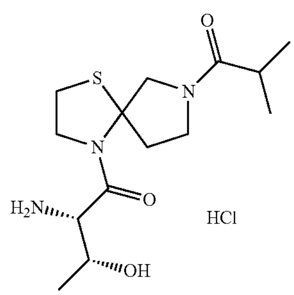
A-352
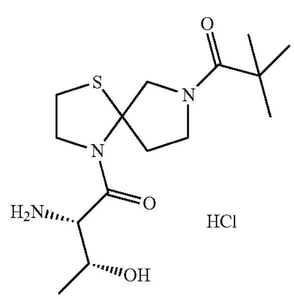
-continued
A-353
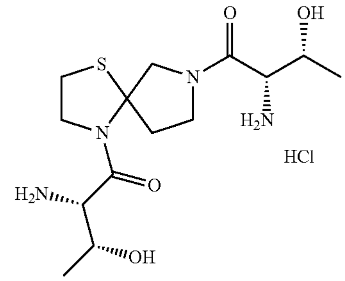
A-354
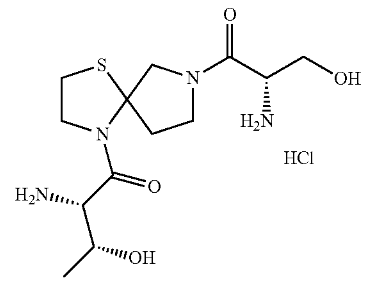
A-355
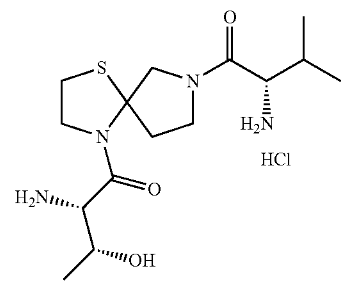
A-357
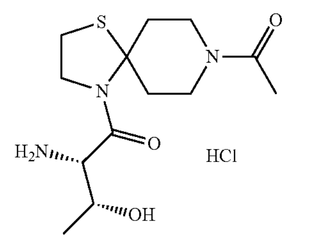
A-358
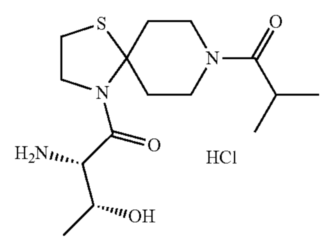
A-359
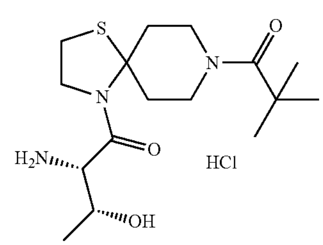

A-360
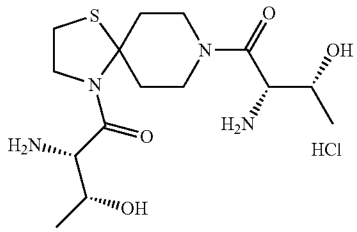
A-361
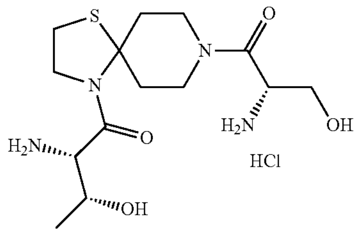
A-362
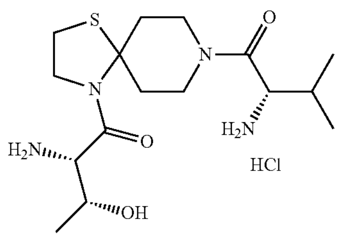
A-364
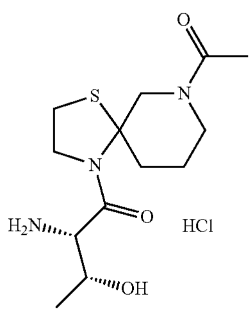
A-365
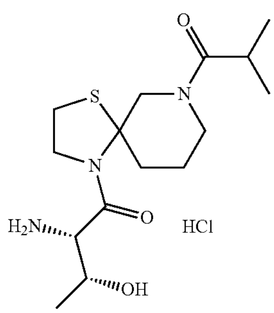
A-366
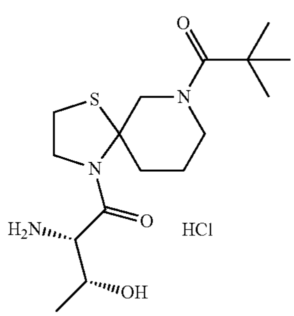
A-367
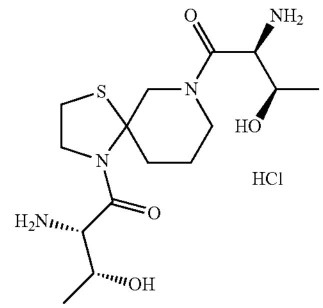
A-368
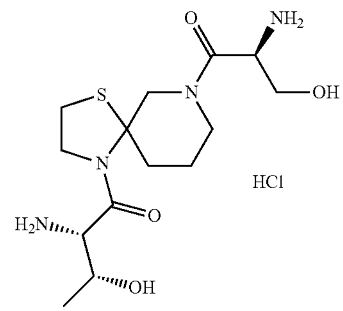
A-369
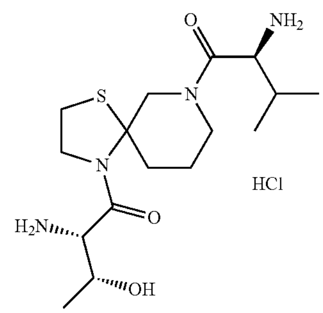
A-370
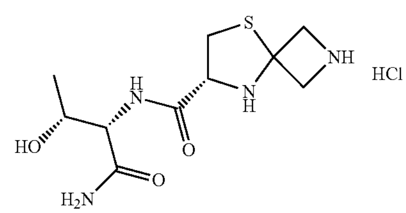
A-371
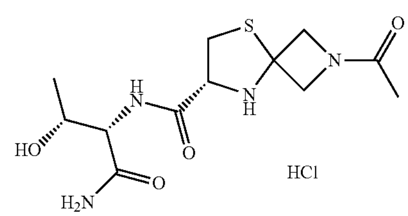
A-372
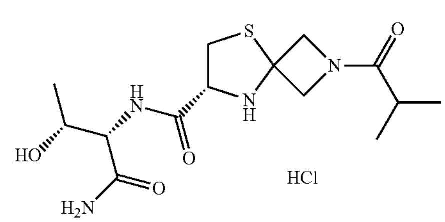

-continued
A-373
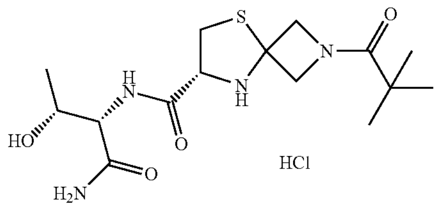
A-374
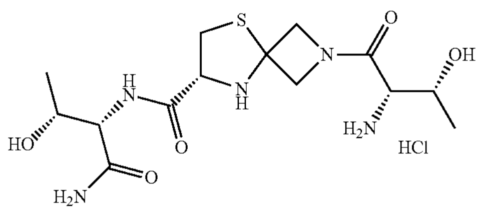
A-375
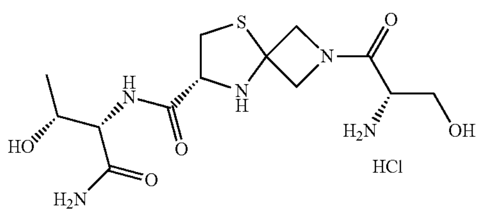
A-376
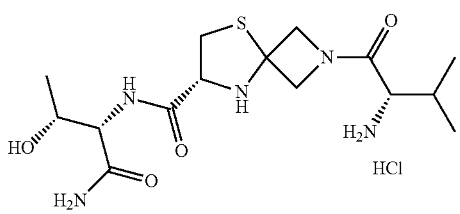
A-377
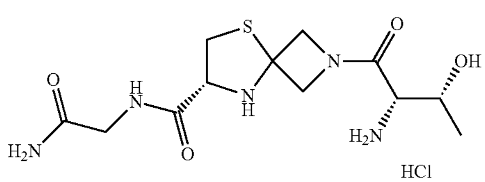
A-378
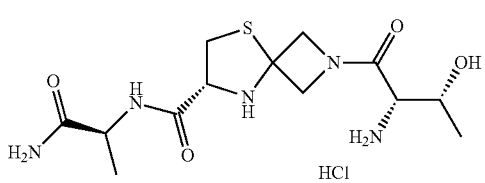
A-379
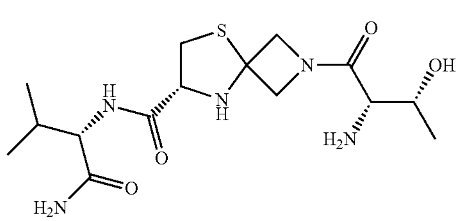
-continued
A-380
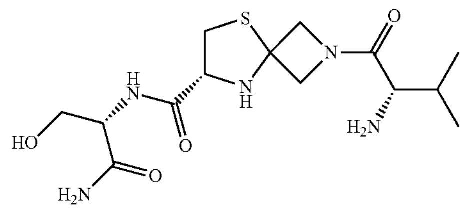
A-381
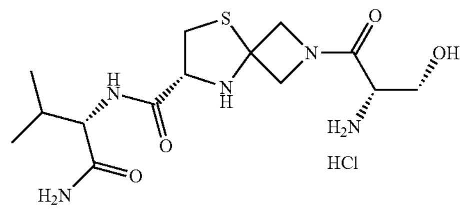
A-382
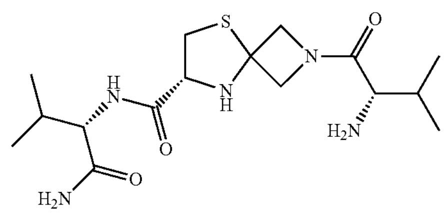
A-384
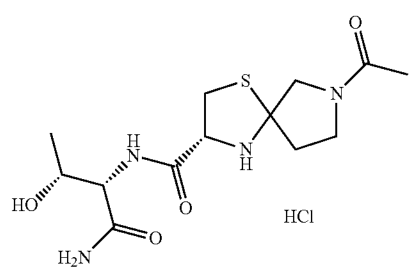
A-385
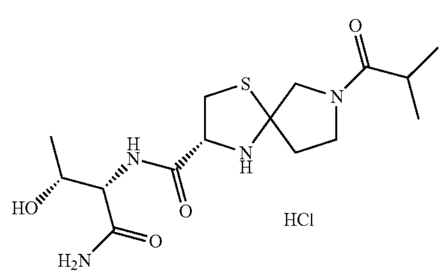
A-386
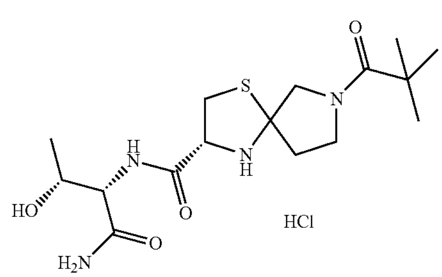

-continued
A-387
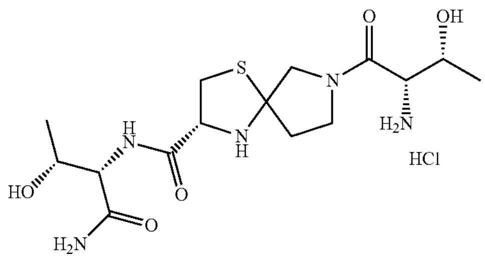
A-388
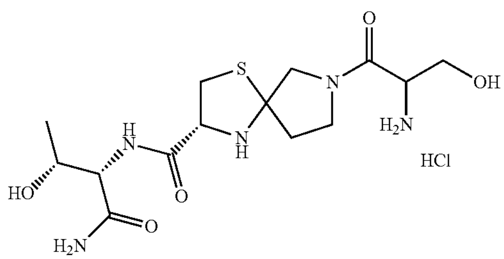
A-389
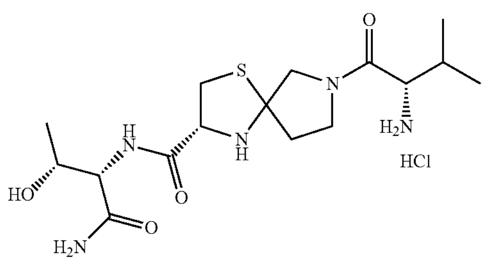
A-391
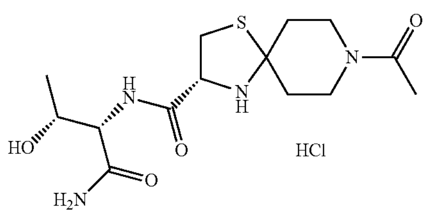
A-392
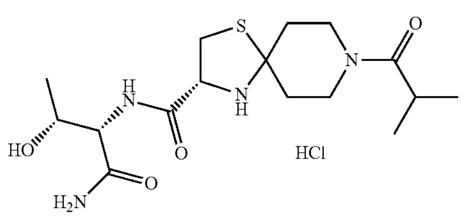
A-393
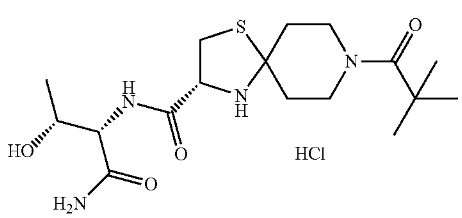
-continued
A-394
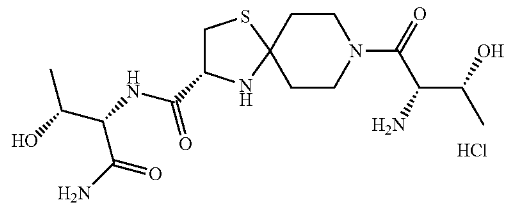
A-395
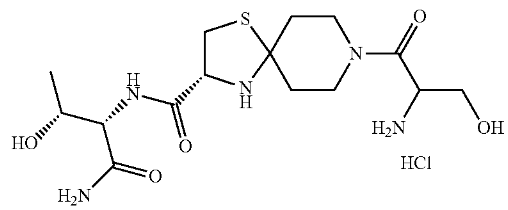
A-396
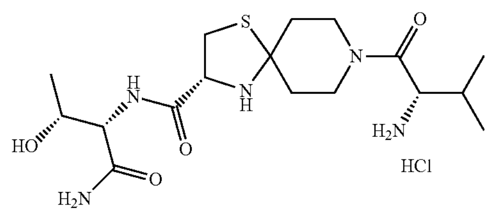
A-398
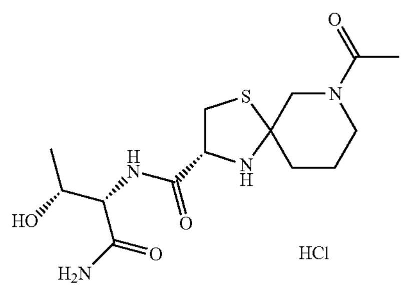
A-399
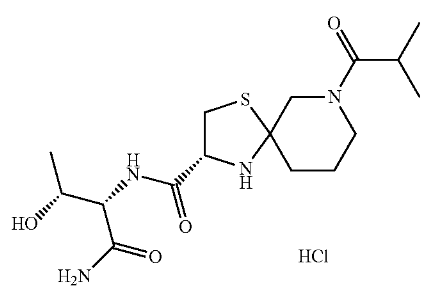
A-400
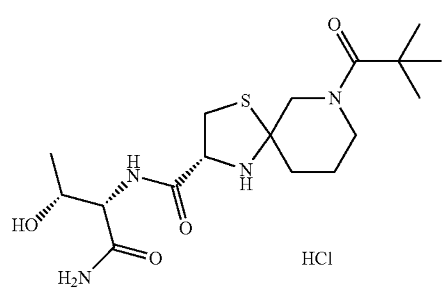

-continued
A-401
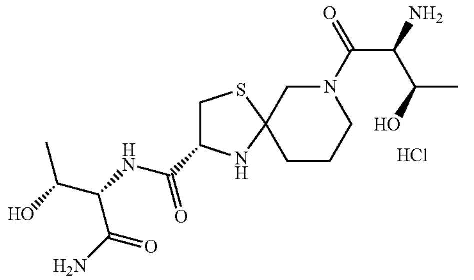
A-402
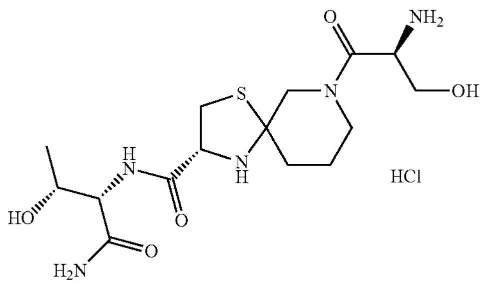
A-403
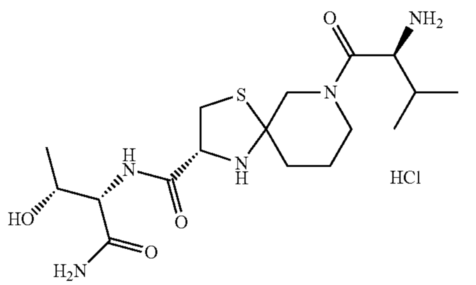
A-404
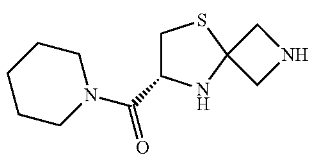
A-405
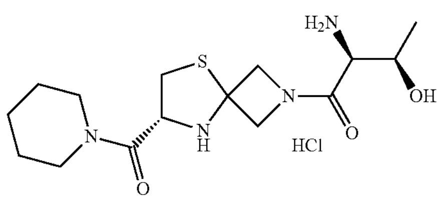
A-406
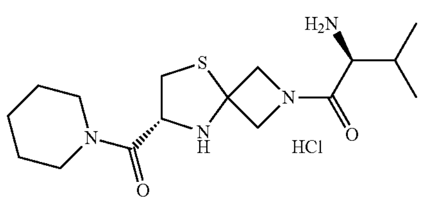
A-407
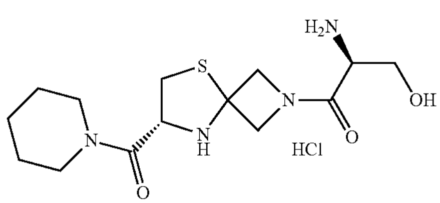
-continued
A-408
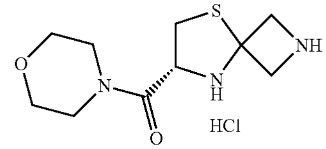
A-409
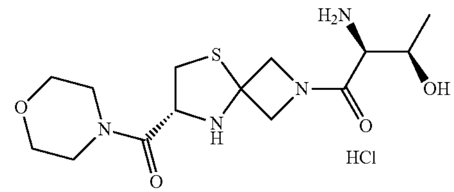
A-410
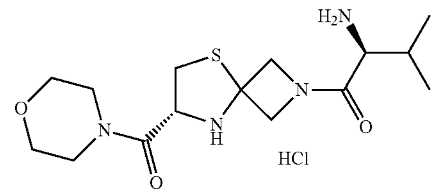
A-411
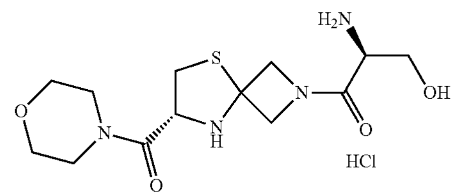
A-412
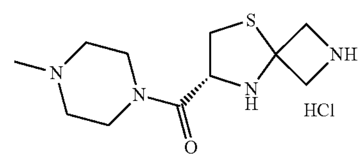
A-413
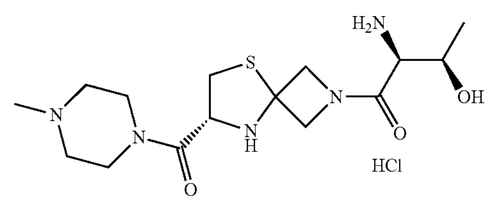
A-414
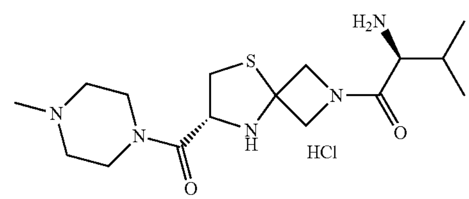
A-415
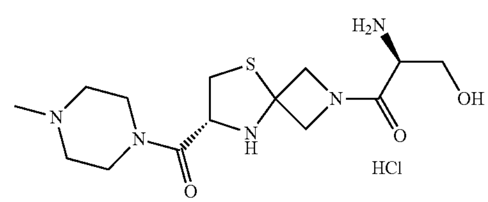

-continued
A-416
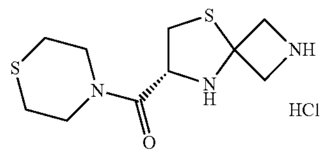
A-417
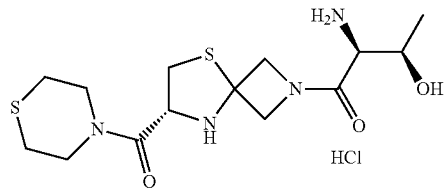
A-418
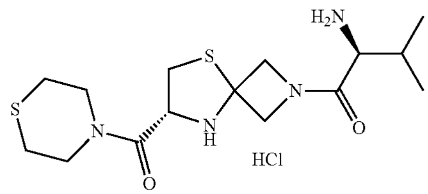
A-419
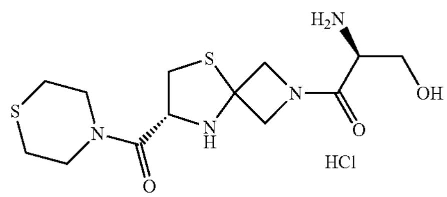
A-421
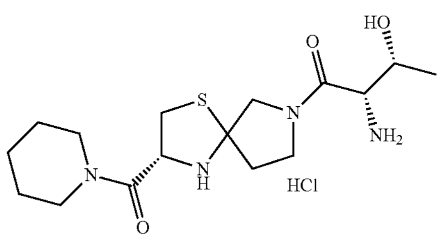
A-422
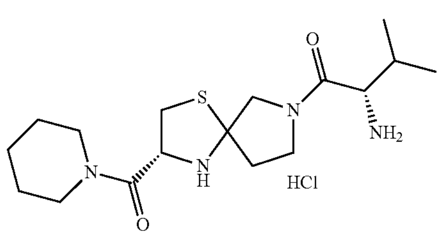
A-423
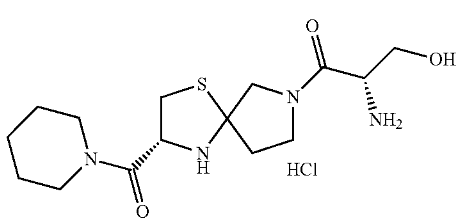
-continued
A-425
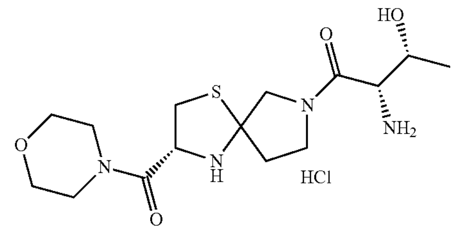
A-426
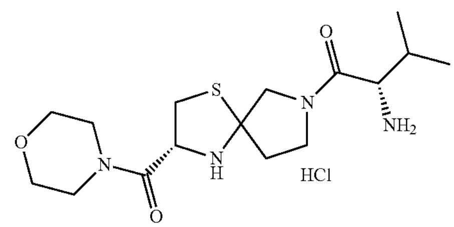
A-427
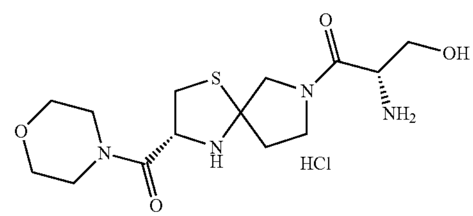
A-429
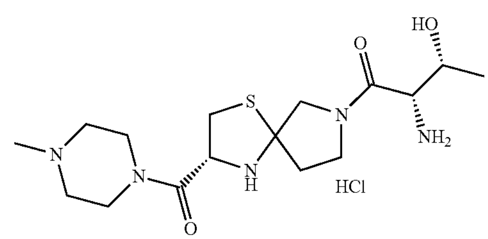
A-430
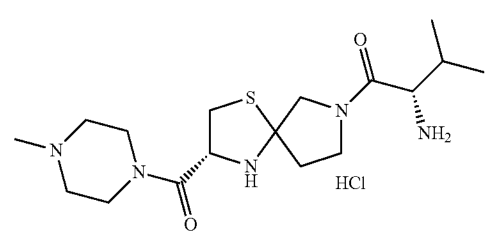
A-431
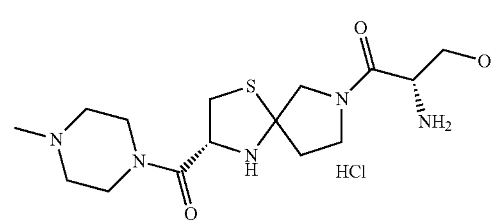

-continued
A-433
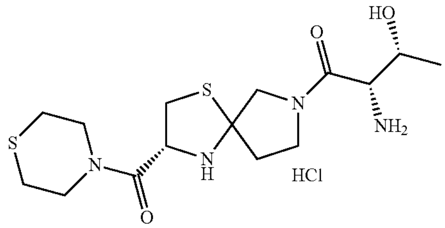
A-434
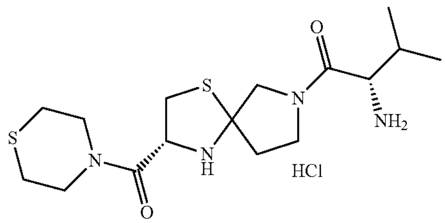
A-435
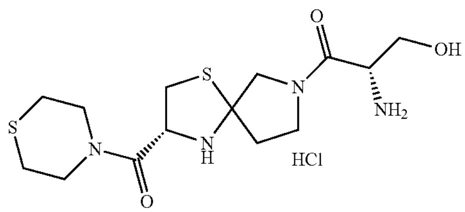
A-437
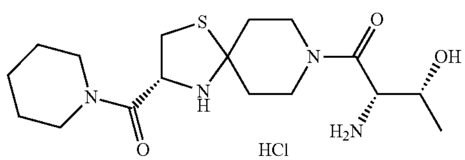
A-438
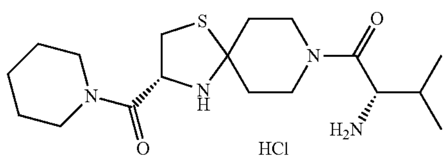
A-439
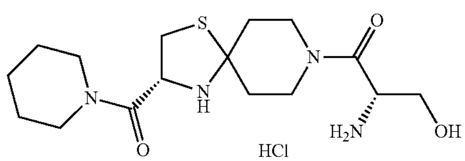
A-441
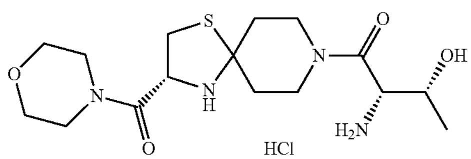
A-442
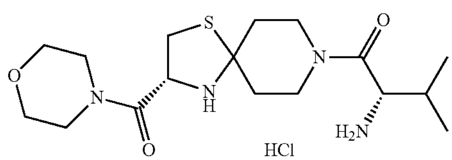
-continued
A-443
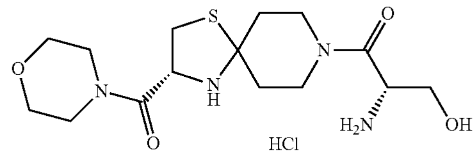
A-445
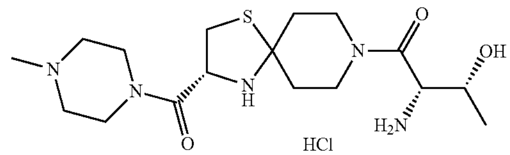
A-446
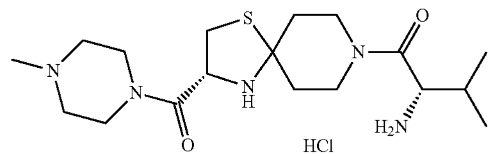
A-447
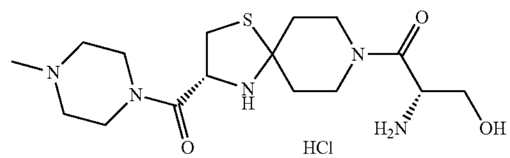
A-449
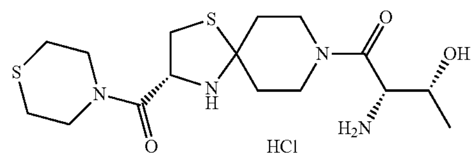
A-450
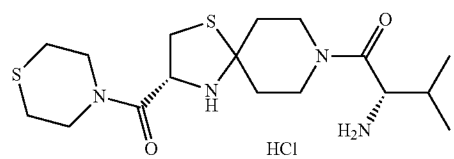
A-451
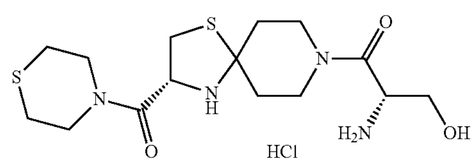
A-453
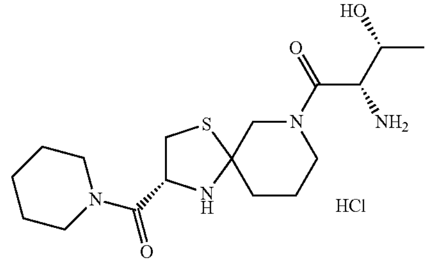

-continued
A-454
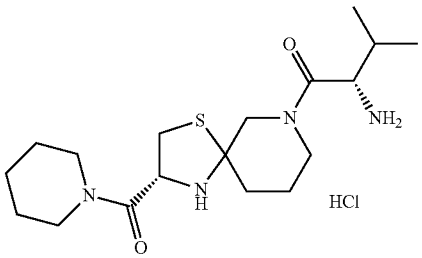
A-455
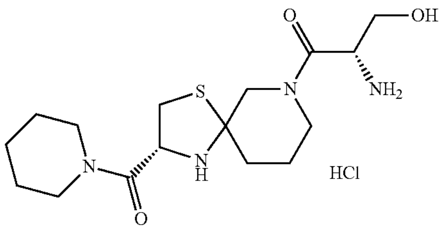
A-457
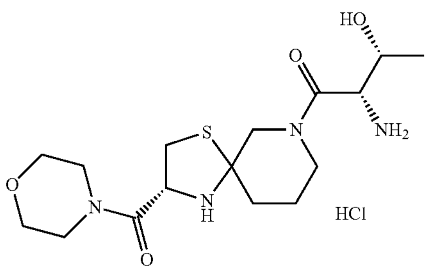
A-458
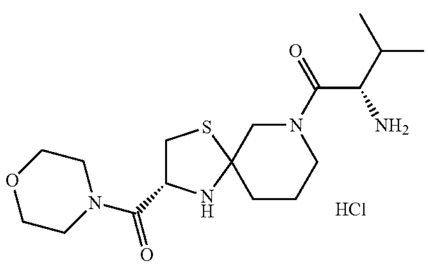
A-459
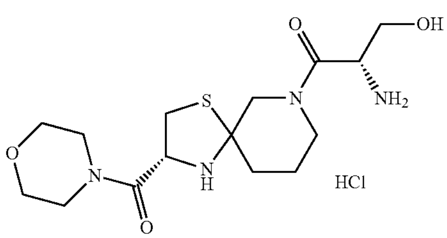
A-461
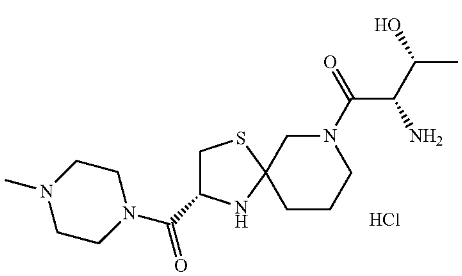
-continued
A-462
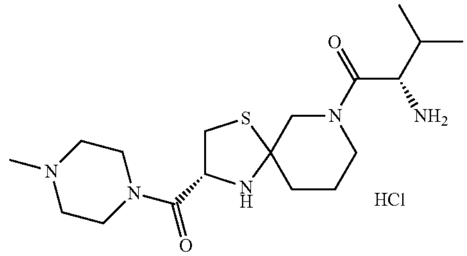
A-463
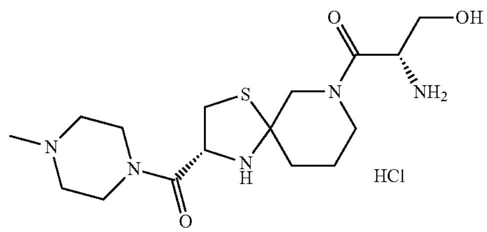
A-465
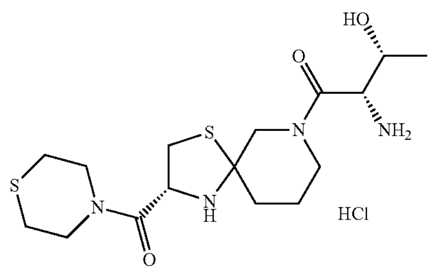
A-466
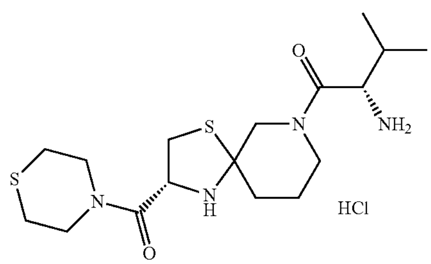
A-467
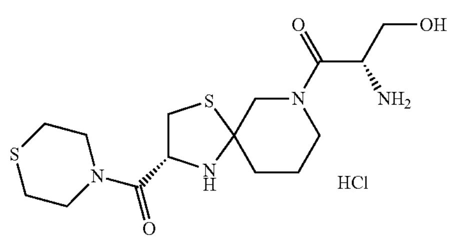
A-468
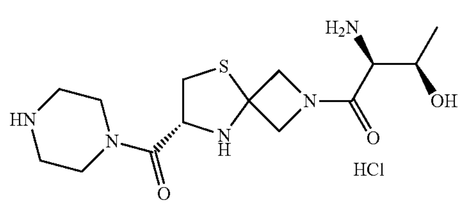

-continued

A-469

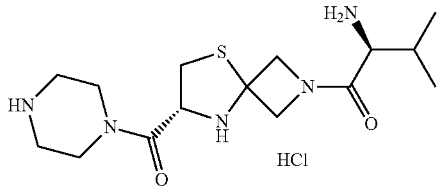

A-470

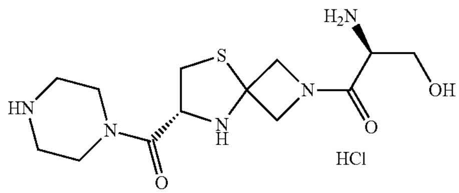

A-471

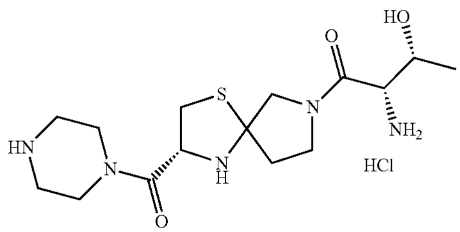

A-472

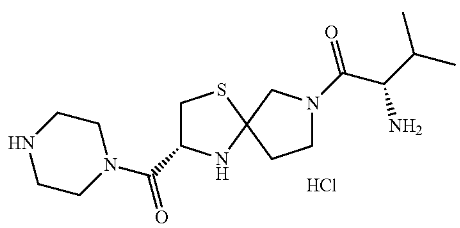

A-473

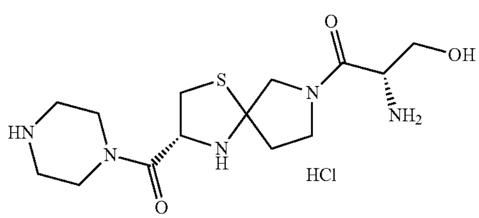

A-474

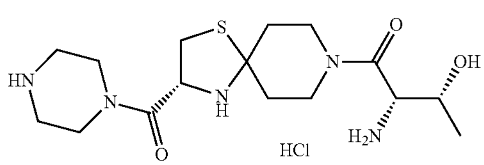

A-475

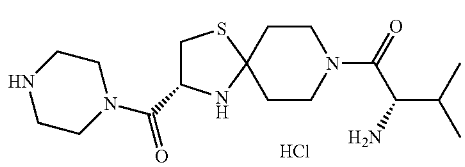

A-476

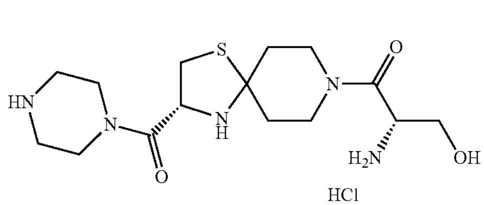

-continued

A-477

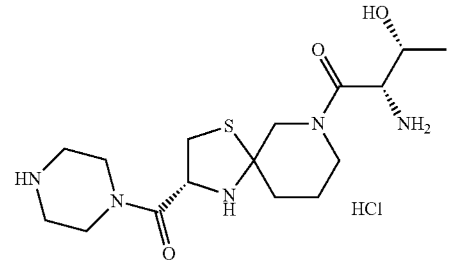

A-478

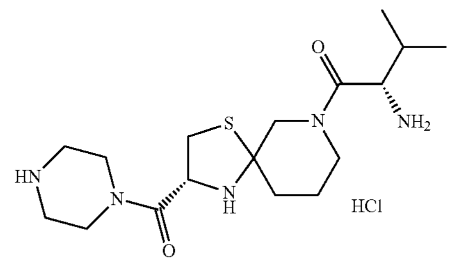

A-479

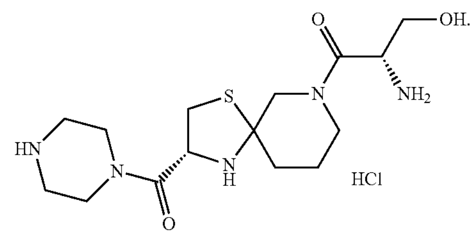

8. A pharmaceutical composition comprising an effective amount of the compound of the formula I according to claim 1, a pharmaceutically acceptable salt, ester, or stereoisomer thereof.

9. A method for treating depression, anxiety, stroke, Huntington's disease, Alzheimer's disease, neuralgia or schizophrenia in subjects, including administering an effective amount of the compound, pharmaceutically acceptable salt, ester, or stereoisomer of claim 1 to a subject in need thereof.

10. A method for regulating activity of NMDA receptor in vivo or in vitro, including providing a subject, a mammalian cell or an NMDA receptor with an effective amount of the compound, pharmaceutically acceptable salt, ester, or stereoisomer of claim 1.

11. The compound according to claim 1, or a pharmaceutically acceptable salt, ester, or stereoisomer thereof, wherein $R_1$ is selected from H, C1-C6 alkyl, and C2-C6 acyl.

12. The compound according to claim 1, or a pharmaceutically acceptable salt, ester, or stereoisomer thereof, wherein $R_1$ is selected from H, acetyl, methyl,

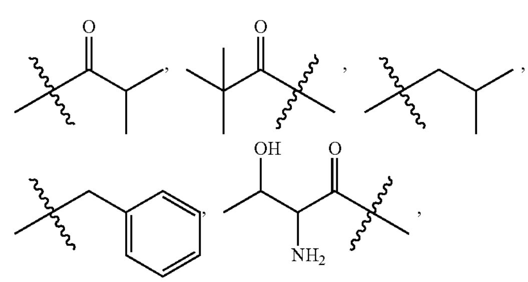

-continued

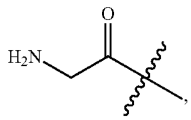,
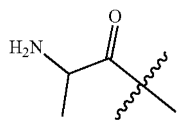,

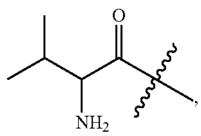,
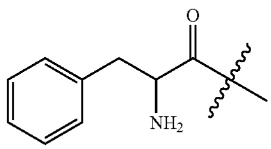,

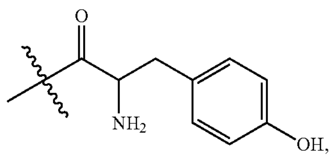

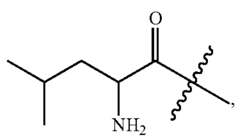, and

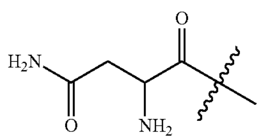

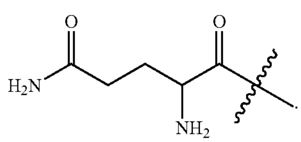.

13. The compound according to claim 1, or a pharmaceutically acceptable salt, ester, or stereoisomer thereof, wherein:

when Ring A is

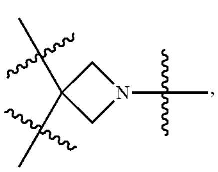 [SMILES: *N1CC(*)(*)C1], $R_2$ is selected from H, C1-C4 alkoxycarbonyl, C2-C6 acyl, and carboxyl residues of the natural amino acids;

when Ring A is

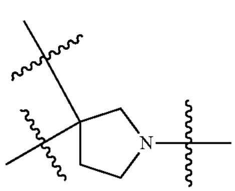,
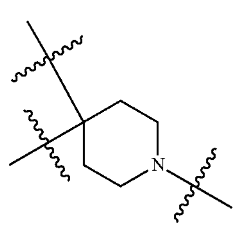,

-continued

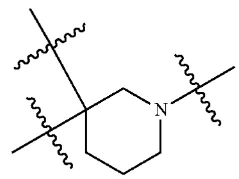,
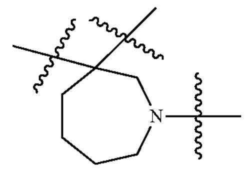

and

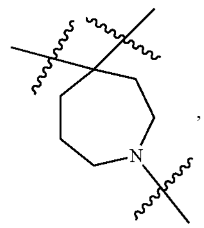, $R_2$ is selected from C1-C4 alkoxycarbonyl, C2-C6 acyl, and carboxyl residues of the natural amino acids.

14. The compound according to claim 1, or a pharmaceutically acceptable salt, ester, or stereoisomer thereof, wherein:

when Ring A is

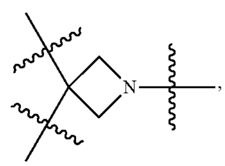 [SMILES: *N1CC(*)(*)C1], $R_2$ is selected from H, methyl, ethyl, propyl, butyl, tert-butoxycarbonyl, acetyl,

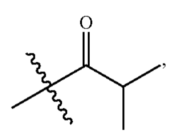,
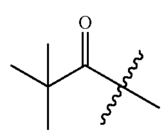,

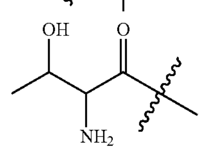,
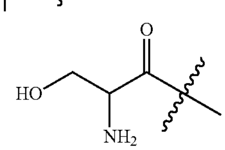,

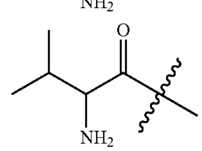,
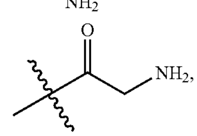

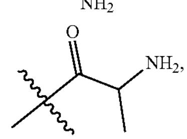
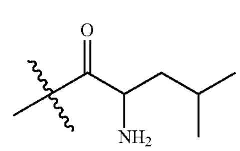.

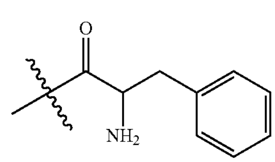,

-continued

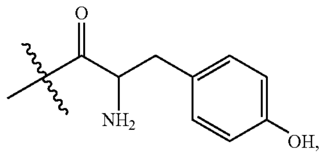

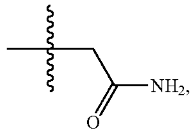

and

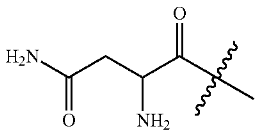

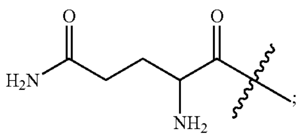

;

when Ring A is

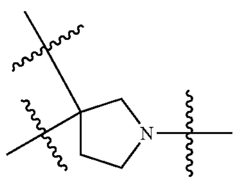

,

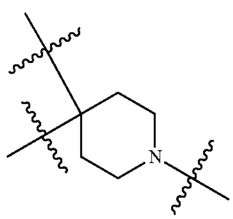

,

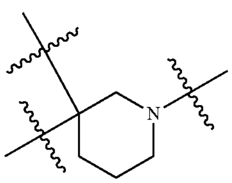

,

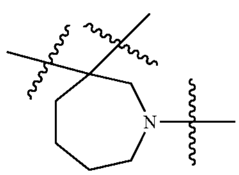

and

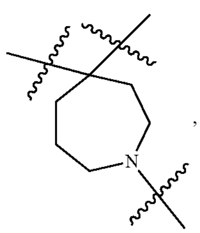

, $R_2$ is selected from tert-butoxycarbonyl, acetyl,

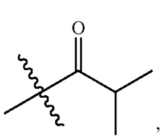

,

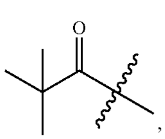

,

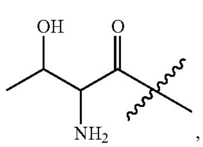

,

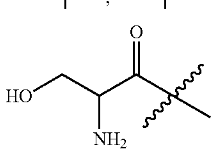

,

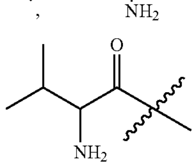

,

-continued

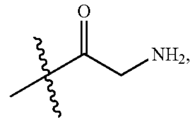

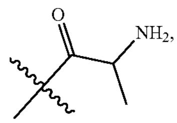

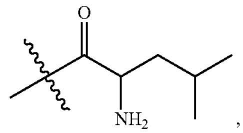

,

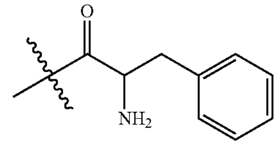

,

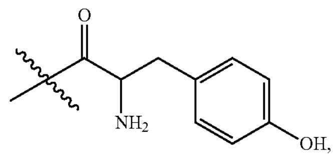

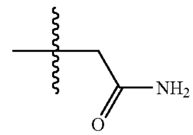

,

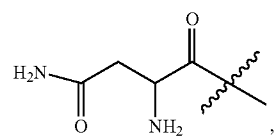

, and

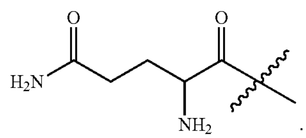

.

15. The compound according to claim 1, or a pharmaceutically acceptable salt, ester, or stereoisomer thereof, wherein $R_3$ is selected from H, cyano, 5- to 7-membered nitrogen-containing aliphatic heterocycle-C1-C3 acyl, C1-C4 alkoxycarbonyl, and —$CONHR_4$; $R_4$ is selected from H, natural amino acid fragments and amide derivatives of the said natural amino acid fragments.

16. The compound according to claim 1, or a pharmaceutically acceptable salt, ester, or stereoisomer thereof, wherein $R_3$ is selected from H, cyano,

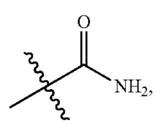

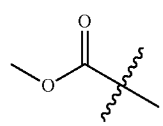

,

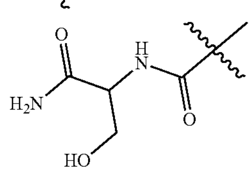

,

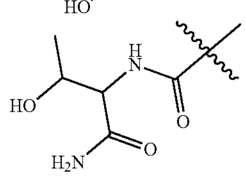

,

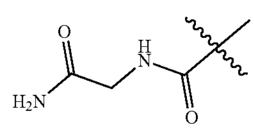

,

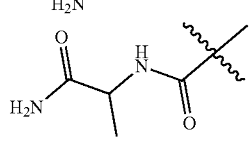

,

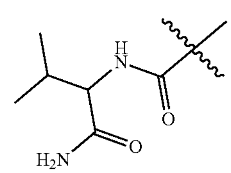

,

-continued
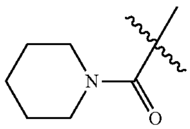, 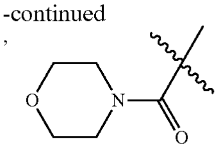, 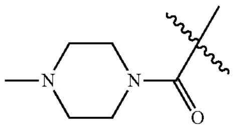, 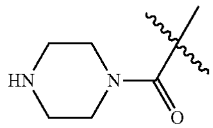 and 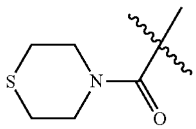.
17. The pharmaceutical composition according to claim 8, wherein, the pharmaceutical composition also comprises one or more pharmaceutically acceptable excipients.
18. The compound of claim 1 or a pharmaceutically acceptable salt or stereoisomer thereof.
* * * * *